US007939069B2

(12) United States Patent
Brophy et al.

(10) Patent No.: US 7,939,069 B2
(45) Date of Patent: May 10, 2011

(54) HUMAN BNP IMMUNOSPECIFIC ANTIBODIES

(75) Inventors: Susan E. Brophy, Lindenhurst, IL (US); Joan D. Tyner, Beach Park, IL (US); Bryan C. Tieman, Elmhurst, IL (US)

(73) Assignee: Abbott Laboratories, Abbott Park, IL (US)

( * ) Notice: Subject to any disclaimer, the term of this patent is extended or adjusted under 35 U.S.C. 154(b) by 426 days.

(21) Appl. No.: 11/745,963

(22) Filed: May 8, 2007

(65) Prior Publication Data

US 2008/0124811 A1 May 29, 2008

Related U.S. Application Data

(63) Continuation-in-part of application No. 11/595,625, filed on Nov. 9, 2006, now abandoned.

(60) Provisional application No. 60/734,964, filed on Nov. 9, 2005.

(51) Int. Cl.
*A61K 39/395* (2006.01)
*C12N 5/10* (2006.01)
*G01N 33/53* (2006.01)

(52) U.S. Cl. ............... 424/133.1; 424/135.1; 424/139.1; 424/141.1; 424/142.1; 424/145.1; 435/328; 435/331; 435/336; 435/358; 435/975

(58) Field of Classification Search ........................ None
See application file for complete search history.

(56) References Cited

U.S. PATENT DOCUMENTS

| | | | |
|---|---|---|---|
| 4,399,216 A | 8/1983 | Axel et al. |
| 4,510,245 A | 4/1985 | Cousens et al. |
| 4,607,023 A | 8/1986 | Thibault et al. |
| 4,634,665 A | 1/1987 | Axel et al. |
| 4,816,397 A | 3/1989 | Boss et al. |
| 4,816,567 A | 3/1989 | Cabilly et al. |
| 4,968,615 A | 11/1990 | Koszinowski et al. |
| 5,114,923 A | 5/1992 | Seilhamer et al. |
| 5,168,062 A | 12/1992 | Stinski |
| 5,179,017 A | 1/1993 | Axel et al. |
| 5,468,646 A | 11/1995 | Mattingly et al. |
| 5,545,806 A | 8/1996 | Lonberg et al. |
| 5,674,710 A | 10/1997 | Seilhamer et al. |
| 6,090,382 A | 7/2000 | Salfeld et al. |
| 6,117,644 A | 9/2000 | DeBold |
| 6,124,430 A | 9/2000 | Mischak et al. |
| 6,162,902 A | 12/2000 | Mischak et al. |
| 6,376,207 B1 | 4/2002 | Mischak et al. |
| 6,461,828 B1 | 10/2002 | Stanton et al. |
| 6,677,124 B2 | 1/2004 | Tsuji et al. |
| 6,770,740 B1 | 8/2004 | Rice et al. |
| 7,341,838 B2 | 3/2008 | Buechler et al. |
| 7,351,586 B2 | 4/2008 | Friese et al. |
| 2003/0022235 A1 | 1/2003 | Dahlen et al. |
| 2003/0162710 A1 | 8/2003 | Sudoh et al. |
| 2003/0199000 A1 | 10/2003 | Valkirs et al. |
| 2004/0132013 A1 | 7/2004 | De Bold |
| 2004/0175379 A1 | 9/2004 | DeVries et al. |
| 2004/0180396 A1 | 9/2004 | Bergmann et al. |
| 2004/0209307 A1 | 10/2004 | Valkirs et al. |
| 2004/0219509 A1 | 11/2004 | Valkirs et al. |
| 2004/0243010 A1 | 12/2004 | Zoghbi et al. |
| 2004/0253655 A1 | 12/2004 | Tsuji et al. |
| 2004/0265926 A1 | 12/2004 | Ng |
| 2005/0014287 A1 | 1/2005 | Friese et al. |
| 2005/0064511 A1 | 3/2005 | Buechler et al. |
| 2006/0121042 A1 | 6/2006 | Dall'Acqua et al. |
| 2006/0121242 A1 | 6/2006 | Pesovic et al. |
| 2006/0183154 A1 | 8/2006 | Shih et al. |
| 2007/0207152 A1 | 9/2007 | Brophy et al. |

FOREIGN PATENT DOCUMENTS

| | | |
|---|---|---|
| EP | 0 384 176 | 8/1990 |
| EP | 0 418 308 | 3/1991 |
| EP | 0 542 255 | 5/1993 |
| EP | 0 914 344 | 5/1999 |
| EP | 1 016 867 | 7/2000 |
| EP | 1 030 177 | 8/2000 |
| JP | 3297392 | 12/1991 |
| JP | 2676144 | 11/1997 |
| WO | 2004/094460 | 11/2004 |

OTHER PUBLICATIONS

Abbott Axysm® System, BNP package insert, REF 8G82-20 Abbott Diagnostics Division, Feb. 2004.
Apple, et al., "Quality Specifications for B-Type Natriuretic Peptide Assays," *Clin. Chem.*, 51(3):486-493 (2005).
Ausubel, et al., *Curr. Protocols in Molec. Biol.*, Section 2.10 (Terry Brown) and Section 6.3 (William W. Strauss)(1997).
Belenky, et al., "The effect of class-specific protease inhibitors on the stabilization of B-type natriuretic peptide in human plasma," *Clinica Chimica Acta*, 340:163-172 (2004).
Benjamini, et al., S., *Immunology, A Short Course*, Immunogens and Antigens, 2nd Ed., pp. 37-40 (1991).
Berzofsky, et al., "Antigen-Antibody Interactions and Monoclonal Antibodies," *Fund. Immunol.*, 2:315-336 (1989).
Bird, et al., "Single-Chain Antigen-Binding Proteins," *Science*, 242:423-426 (1988).
Bluestein, "Comparing BNP ASSAYS, Factors Impacting Analytical Method Comparison," *Bayer Healthcare Diagnostics Division Publ.*, (2004).
Boder, et al., "Directed evolution of antibody fragments with monovalent femtomolar antigen-affinity," *PNAS*, 97(20): 10701-10705, (2000).
Boder, et al., "Optimal Screening of Surface-Displayed Polypeptide Libraries," *Biotechnol. Prog.*, 14:55-62 (1998).

(Continued)

*Primary Examiner* — Jeffrey Stucker
*Assistant Examiner* — Stephen Gucker
(74) *Attorney, Agent, or Firm* — Audrey L. Bartnicki; Lisa V. Mueller; Polsinelli Shughart

(57) ABSTRACT

The present invention relates to antibodies that immunospecifically bind to human brain natriuretic peptide or a human brain natriuretic peptide fragment with a high binding affinity, methods for producing and selecting said antibodies, immunoassays for human brain natriuretic peptide or a human brain natriuretic peptide fragment that employ said antibodies and therapeutic compositions containing said antibodies.

22 Claims, 53 Drawing Sheets

OTHER PUBLICATIONS

Boder, et al., "Yeast Surface Display for Directed Evolution of Protein Expression, Affinity, and Stability," *Meth. In Enzymol.*, 328:430-444 (2000).
Boder, et al., "Yeast surface display for screening combinatorial polypeptide libraries," *Nature Biotech.*, 15(6):553-557 (1997).
Bogan, et al., "Anatomy of Hot Spots in Protein Interfaces," *J. Mol. Biol.*, 280:1-9 (1998).
Boss, et al., "Genetically engineered antibodies," *Imunol. Today*, 6(1):12-13 (1985).
Brandt, et al., "Dipeptidyl-Peptidase IV Converts Intact B- Type Natriuretic Peptide into Its *des*-SerPro Form," *Clin. Chem.*, 52(1):82-87 (2006).
Buckley, et al., "Cardiac peptide stability, aprotinin and room temperature: importance for assessing cardiac function in clinical practice," *Clin. Sci.*, 97:689-695 (1999).
Cataliotti, et al., "Circulating Natriuretic Peptide Concentrations in Patients with End-Stage Renal Disease: Role of Brain Natriuretic Peptide as a Biomarker for Ventricular Remodeling," *Mayo Clin. Proc.*, 76:1111-1119 (2001).
Davidson, et al., "Brain natriuretic peptide," *J. of Hypertension*, 12:329-336 (1994).
Diagnostic Automation/Cortez Diagnostics, Inc., "Nt-proBNP ELISA Quantitative dertermination of Nt-proBNP in biological fluids," (Cat. No. 2852-7), pp. 1-8 (1997).
Galfre, et al., "Antibodies to major histocompatibility antigens produced by hybrid cell lines," *Nature*, 266:550-552 (1977).
Gutkowska, et al., "Atrial Natriuretic Factor in Human Plasma," *Biochem. & Biophys. Res. Comm.*, 139(1):287-295 (1986).
Holmes, et al., "Renal, Endocrine, and Hemodynamic Effects of Human Brain Natriuretic Peptide in Normal Man," *J. of Clin. Endocrin. & Metab.*, 76(1):91-96 (1993).
Huston, et al., "Protein engineering of antibody binding sites: Recovery of specific activity in an anti-digoxin single-chain Fv analogue produced in *Escherichia coli*," *PNAS*, 85:5879-5883 (1988).
Itoh, et al., "Preparation of Monoclonal Antibodies against Brain Natriuretic Peptide and Their Application to Radioimmunoassay and Passive Immunization," *Endocrinology*, 127(3):1292-1300 (1990).
Kaufman, et al, "Amplification and Expression of Sequences cotransfected with a Modular Dihydrofolate Reductase Complementary DNA Gene," *J. Mol. Biol.*, 159:601-621 (1982).
Kenny, et al., "Hydrolysis of human and pig brain natriuretic peptides, urodilatin, C-type natriuretic peptide and some C-receptor ligands by endopeptidase-24.11," *Biochem. J.*, 291:83-88 (1993).
Ma, et al., "Protein-protein interactions: Structurally conserved residues distinguish between binding sites and exposed protein surfaces," *PNAS*, 100(10):5772-5777 (2003).
McCafferty, et al., "Phage antibodies: filamentous phage displaying antibody variable domains," *Nature*, 348:552-554 (1990).
Mizushima, et al., "pEF-BOS, a powerful mammalian expression vector," *Nucl. Acids Res.*, 18(17):5322 (1990).
Morrison, et al., "Chimeric human antibody molecules: Mouse antigen-binding domains with human constant region domains," *PNAS*, 81:6851-6855 (1984).
Motwani, et al., "Plasma brain natriuretic peptide as an indicator for angiotensin-converting-enzyme inhibition after myocardial infarction," *The Lancet*, 341:1109-1113 (1993).
Mukoyama, et al., "Brain Natriuretic Peptide as a Novel Cardiac Hormone in Humans," *J. Clin. Invest.*, 87:1402-1412 (1991).
Murdoch, et al., "Brain natriuretic peptide is stable in whole blood and can be measured using a simple rapid assay: implications for clinical practice," *Heart*, 78:594-597 (1997).
Nordin, et al., "Kinetic studies of small molecule interactions with protein kinases using biosensor technology," *Analytical Biochem.*, 340:359-368 (2005).
Rajpal, et al., "A general method for greatly improving the affinity of antibodies by using combinatorial libraries," *PNAS*, 102 (24):8466-8471 (2005).
Sanz, et al., "Comparison of BNP and NT-proBNP Assays in the Approach to the Emergency Diagnosis of Actue Dyspnea," *J. of Clin. Lab. Analysis*, 20:227-232 (2006).
Schiestl, et al., "High efficiency transformation of intact yeast cells using single stranded nucleic acids as a carrier," *Curr. Genet.*, 16:339-346 (1989).
Shimizu, et al., "Degradation of human brain natriuretic peptide (BNP) by contact activation of blood coagulation system," *Clinica Chimica Acta*, 305:181-186 (2001).
Shimizu, et al., "Molecular forms of human brain natriuretic peptide in plasma," *Clinica Chimica Acta*, 316:129-135 (2002).
Tetin, et al., "Interactions of Two Monclonal Antibodies with BNP High Resolution Epitope Mapping Using Fluorescence Correlation Spectroscopy," *Biochem.*, 45:14155-14165 (2006).
Thorpe, et al., "Clonal Analysis of a Human Antimouse Antibody (HAMA) Response," *Scandinavian J. of Immunol.*, 57:85-92 (2003).
Urlaub, et al., "Isolation of Chinese hamster cell mutants deficient in dihydrofolate reductase activity," *PNAS.*, 77(7):4216-4220 (1980).
Valli, et al., "Review of 10 years of the clinical use of brain natriuretic peptide in cardiology," *J. Lab. Clin. Med.*, 134(5):437-444 (1999).
Von Mehren, et al., "Monoclonal antibody-based therapy," *Current Opinion in Oncology*, 8:493-498, 1996.
Walther, et al., "Biochemical analysis of netural endopeptidase activity reveals independent catabolism of atrial and brain natriuretic peptide," *Biol. Chem.*, 385:179-184 (2004).
Watanabe, et al., "Prognostic Value of Plasma Brain Natriuretic Peptide Combined With Left Ventricular Dimensions in Predicting Sudden Death of Patients With Chronic Heart Failure," *J. of Cardiac Failure*, 11(1):50-55 (2005).
Yandle, "Biochemistry of natriuretic peptides," *J. of Int. Med.*, 235:561-576 (1994).
Zahnd, et al., "Directed in Vitro Evolution and Crystallographic Analysis of a Peptide-binding Single Chain Antibody Fragment (scFv) with Low Picomolar Affinity," *J. of Biol. Chem.*, 279(18):18870-18877 (2004).
Colucci, et al., "Intravenous nesiritide, a natriuretic peptide, in the treatment of decompensated congestive heart failure", N. Engl. Med, 2000, 343 (34), 246-253.
Kabat, E.A. et al., "Sequence of Proteins of Immunological Interest, Fifth Edition, US. Department of Health and Human Services, NIH Publication No. 91-3242," 1992, Table of Contents (pp. iii-xi).
PCT International Application No. PCT/US2006/0043608, Transmittal of the International Search Report and the Written Opinion of the International Searching Authority, Mailed Mar. 27, 2007 (13 pages).
PCT International Application No. PCT/US08/62973, Transmittal of the International Search Report and the Written Opinion of the International Searching Authority, Mailed Sep. 2, 2008 (10 pages).
Thorpe, et al., "Enhanced Chemiluminescent Reactions Catalyzed by Horseradish Peroxidase," Methods in Enzymology, 1986,133,333-353.
Tsutamoto, et al., "Attenuation of Compensation of Endogenous Cardiac Natriuretic Peptide System in Chronic Heart Failure," 1997, 96, 509-516.
Yoshibayashi, et al., Attenuation of Compensation of Endogenous Cardiac Natriuretic Peptide System in Chronic Heart Failure, The New England Journal of Medicine, 329(6):433-434 (1993).

FIGURE 3A

```
   1    ACGGATTAGAAG  CCGCCGAGCGGG  TGACAGCCCTCC
  37    GAAGGAAGACTC  TCCTCCGTGCGT  CCTCGTCCTCAC
  73    CGGTCGCGTTCC  TGAAACGCAGAT  GTGCCTCGCGCC
 109    GCACTGCTCCGA  ACAATAAAGATT  CTACAATACTAG
 145    CTTTTATGGTTA  TGAAGAGGAAAA  ATTGGCAGTAAC
 181    CTGGCCCCACAA  ACCTTCAAATGA  ACGAATCAAATT
 217    AACAACCATAGG  ATGATAATGCGA  TTAGTTTTTTAG
 253    CCTTATTTCTGG  GGTAATTAATCA  GCGAAGCGATGA
 289    TTTTTGATCTAT  TAACAGATATAT  AAATGCAAAAAC
 325    TGCATTAACCAC  TTTAACTAATAC  TTTCAACATTTT
 361    CGGTTTGTATTA  CTTCTTATTCAA  ATGTAATAAAAG
 397    TATCAACAAAAA  ATTGTTAATATA  CCTCTATACTTT
 433    AACGTCAAGGAG  AAAAAACCCCGG  ATCGGACTACTA
 469    GCAGCTGTAATA  CGACTCACTATA  GGGAATATTAAG
                                               AGA2
 505    CTAATTCTACTT  CATACATTTTCA  ATTAAGATGCAG
        ----------------AGA2----------------
 541    TTACTTCGCTGT  TTTTCAATATTT  TCTGTTATTGCT
        ----------------AGA2----------------
 577    TCAGTTTTAGCA  CAGGAACTGACA  ACTATATGCGAG
        ----------------AGA2----------------
 613    CAAATCCCCTCA  CCAACTTTAGAA  TCGACGCCGTAC
        ----------------AGA2----------------
 649    TCTTTGTCAACG  ACTACTATTTTG  GCCAACGGGAAG
        ----------------AGA2----------------
 685    GCAATGCAAGGA  GTTTTTGAATAT  TACAAATCAGTA
        ----------------AGA2----------------
 721    ACGTTTGTCAGT  AATTGCGGTTCT  CACCCCTCAACA
        ----------------AGA2----------------
 757    ACTAGCAAAGGC  AGCCCCATAAAC  ACACAGTATGTT
        ---                       Tether 41-------
 793    TTTAAGCTTCTG  CAGGCTAGTGGT  GAGAACAAGGTG
        --------------------------Tether41
 829    GAGTACGCGCCG  GCGTTGATGGCC  TTGTCTGCTAGC
 865    ATGACTGGTGGA  CAGCAAATGGGT  CGGGATCTGTAC
 901    GACGATGACGAT  AAGGTACCAGGA  TCCAGTGTGGTG
                                                106.3
 937    GAATTCGCGGCC  CAGCCGGCCATG  GCCCAGATCCAG
        variable heavy----------------------
 973    TTGGTGCAGTCT  GGACCTGAGCTG  AGGAAGCCTGGA
        -------------------------------------
1009    GAGACAGTCAAG  ATCCTGCAAG    GGTTCTGGATAT
        -------------------------------------
```

FIGURE 3B

```
1045    ACCTTCACACAC TATGGAATAAAC TGGGTGAAGCAG
        ----------------------------------------
1081    ACTCCAAGAAAG GATTTAAAGTGG ATGGGCTGGATA
        ----------------------------------------
1117    AACACCCATACT GGAGAGCCAATA TATGCTGATGAC
        ----------------------------------------
1153    TTCAAGGGACGG TTTGCCTTCTCT TTGGAAACCTCT
        ----------------------------------------
1189    GCCAACACTGCC TATTTGCAAATC AACAACCTCAAC
        ----------------------------------------
1225    AATGGAGACATG GTACATATTTC TGTACAAGAAGT
        ----------------------------------------
1261    CACCGGTTTGGT TTGGACTACTGG GGTCAAGGTACC
        -------------VH end-Linker 40---------
1297    TCAGTCACCGTC TCGTCAGGTCCC GCCAAGGAGTTG
        -------------------------------106.3 ---
1333    ACGCCCCTGAAG GAGGCGAAGGTC TCTGACAATGTG
        Variable light-------------------------
1369    CTGACCCAATCT CCACCTTCTTTG GCTGTGTCTCTA
        ----------------------------------------
1405    GGGCAGAGGGCC ACCATCTCCTGC AAGGCCAGCCAA
        ----------------------------------------
1441    AGTGTTGATTAT AATGGTGATAGT TATCTGAACTGG
        ----------------------------------------
1477    TACCAACAGAAG CCAGGACAGCCA CCCAAATTCCTC
        ----------------------------------------
1513    ATCTATGCTGCA TCCAATCTAGAA TCTGGGATCCCA
        ----------------------------------------
1549    GCCAGGTTTAGT GGCAGTGGGTCT GGGACAGACTTC
        ----------------------------------------
1585    AACCTCAACATC CATCCTGTGGAG GAGGAGGATGCT
        ----------------------------------------
1621    GCAACCTATTAC TGTCAGCAAAGT AATGAGGATCCA
        ----------------------------------------
1657    TTCACGTTCGGC TCGGGGACAAAG TTGGAAATAAAA
        end
1693    CGGGCGGCCGCC CTCGAGTCTAGA GGGCCCTTCGAA
        V5 Epitope-----------------------------
1729    GGTAAGCCTATC CCTAACCCTCTC CTCGGTCTCGAT
        ------           Six HIS tag-------STOP
1765    TCTACGCGTACC GGTCATCATCAC CATCACCATTGA
1801    GTTTAAACCCGC TGATCTGATAAC AACAGTGTAGAT
1837    GTAACAAAATCG ACTTTGTTCCCA CTGTACTTTTAG
```

FIGURE 3C

```
1873    CTCGTACAAAAT ACAATATACTTT TCATTTCTCCGT
1909    AAACAACATGTT TTCCCATGTAAT ATCCTTTTCTAT
1945    TTTTCGTTCGT TACCAACTTTAC ACATACTTTATA
1981    TAGCTATTCACT TCTATACACTAA AAAACTAAGACA
2017    ATTTTAATTTTG CTGCCTGCCATA TTTCAATTTGTT
2053    ATAAATTCCTAT AATTTATCCTAT TAGTAGCTAAAA
2089    AAAGATGAATGT GAATCGAATCCT AAGAGAATTGGG
2125    CAAGTGCACAAA CAATACTTAAAT AAATACTACTCA
                       end TRP1 ORF
2161    GTAATAACCTAT TTCTTAGCATTT TTGACGAAATT
2197    GCTATTTGTTA GAGTCTTTTACA CCATTTGTCTCC
2233    ACACCTCCGCTT ACATCAACACCA ATAACGCCATTT
2269    AATCTAAGCGCA TCACCAACATTT TCTGGCGTCAGT
2305    CCACCAGCTAAC ATAAAATGTAAG CTCTCGGGGCTC
2341    TCTTGCCTTCCA ACCCAGTCAGAA ATCGAGTTCCAA
2377    TCCAAAAGTTCA CCTGTCCCACCT GCTTCTGAATCA
2413    AACAAGGGAATA AACGAATGAGGT TTCTGTGAAGCT
2449    GCACTGAGTAGT ATGTTGCAGTCT TTTGGAAATACG
2485    AGTCTTTTAATA ACTGGCAAACCG AGGAACTCTTGG
2521    TATTCTTGCCAC GACTCATCTCCG TGCAGTTGGACG
2557    ATATCAATGCCG TAATCATTGACC AGAGCCAAAACA
2593    TCCTCCTTAGGT TGATTACGAAAC ACGCCAACCAAG
2629    TATTTCGGAGTG CCTGAACTATTT TTATATGCTTTT
2665    ACAAGACTTGAA ATTTTCCTTGCA ATAACCGGGTCA
2701    ATTGTTCTCTTT CTATTGGGCACA CATATAATACCC
2737    AGCAAGTCAGCA TCGGAATCTAGA GCACATTCTGCG
2773    GCCTCTGTGCTC TGCAAGCCGCAA ACTTTCACCAAT
2809    GGACCAGAACTA CCTGTGAAATTA ATAACAGACATA
                                       TRP1 ORF
2845    CTCCAAGCTGCC TTTGTGTGCTTA ATCACGTATACT
2881    CACGTGCTCAAT AGTCACCAATGC CCTCCCTCTTGG
2917    CCCTCTCCTTTT CTTTTTCGACC GAATTCTTGAA
2953    GACGAAAGGGCC TCGTGATACGCC TATTTTTATAGG
2989    TTAATGTCATGA TAATAATGGTTT CTTAGGACGGAT
3025    CGCTTGCCTGTA ACTTACACGCGC CTCGTATCTTTT
3061    AATGATGGAATA ATTTGGGAATTT ACTCTGTGTTTA
3097    TTTATTTTTATG TTTTGTATTTGG ATTTTAGAAAGT
3133    AAATAAAGAAGG TAGAAGAGTTAC GGAATGAAGAA
3169    AAAAAATAAACA AAGGTTTAAAAA ATTTCAACAAA
3205    AGCGTACTTTAC ATATATATTTAT TAGACAAGAAAA
3241    GCAGATTAAATA GATATACATTCG ATTAACGATAAG
3277    TAAAATGTAAAA TCACAGGATTTT CGTGTGTGGTCT
3313    TCTACACAGACA AGATGAAACAAT TCGGCATTAATA
3349    CCTGAGAGCAGG AAGAGCAAGATA AAAGGTAGTATT
3385    TGTTGGCGATCC CCCTAGAGTCTT TTACATCTTCGG
3421    AAAACAAAAACT ATTTTTTCTTTA ATTTCTTTTTTT
3457    ACTTTCTATTTT TAATTTATATAT TTATATTAAAAA
3493    ATTTAAATTATA ATTATTTTTATA GCACGTGATGAA
```

FIGURE 3D

```
3529  AAGGACCCAGGT  GGCACTTTTCGG  GGAAATGTGCGC
3565  GGAACCCCTATT  TGTTTATTTTTC  TAAATACATTCA
3601  AATATGTATCCG  CTCATGAGACAA  TAACCCTGATAA
                                         Amp Res---
3637  ATGCTTCAATAA  TATTGAAAAAGG  AAGAGTATGAGT
3673  ATTCAACATTTC  CGTGTCGCCCTT  ATTCCCTTTTTT
3709  GCGGCATTTTGC  CTTCCTGTTTTT  GCTCACCCAGAA
3745  ACGCTGGTGAAA  GTAAAAGATGCT  GAAGATCAGTTG
3781  GGTGCACGAGTG  GGTTACATCGAA  CTGGATCTCAAC
3817  AGCGGTAAGATC  CTTGAGAGTTTT  CGCCCCGAAGAA
3853  CGTTTTCCAATG  ATGAGCACTTTT  AAAGTTCTGCTA
3889  TGTGGCGCGGTA  TTATCCCGTGTT  GACGCCGGGCAA
3925  GAGCAACTCGGT  CGCCGCATACAC  TATTCTCAGAAT
3961  GACTTGGTTGAG  TACTCACCAGTC  ACAGAAAAGCAT
3997  CTTACGGATGGC  ATGACAGTAAGA  GAATTATGCAGT
4033  GCTGCCATAACC  ATGAGTGATAAC  ACTGCGGCCAAC
4069  TTACTTCTGACA  ACGATCGGAGGA  CCGAAGGAGCTA
4105  ACCGCTTTTTTG  CACAACATGGGG  GATCATGTAACT
4141  CGCCTTGATCGT  TGGGAACCGGAG  CTGAATGAAGCC
4177  ATACCAAACGAC  GAGCGTGACACC  ACGATGCCTGTA
4213  GCAATGGCAACA  ACGTTGCGCAAA  CTATTAACTGGC
4249  GAACTACTTACT  CTAGCTTCCCGG  CAACAATTAATA
4285  GACTGGATGGAG  GCGGATAAAGTT  GCAGGACCACTT
4321  CTGCGCTCGGCC  CTTCCGGCTGGC  TGGTTTATTGCT
4357  GATAAATCTGGA  GCCGGTGAGCGT  GGGTCTCGCGGT
4393  ATCATTGCAGCA  CTGGGGCCAGAT  GGTAAGCCCTCC
4429  CGTATCGTAGTT  ATCTACACGACG  GGCAGTCAGGCA
4465  ACTATGGATGAA  CGAAATAGACAG  ATCGCTGAGATA
           Amp Res end
4501  GGTGCCTCACTG  ATTAAGCATTGG  TAACTGTCAGAC
4537  CAAGTTTACTCA  TATATACTTTAG  ATTGATTTAAAA
4573  CTTCATTTTTAA  TTTAAAAGGATC  TAGGTGAAGATC
4609  CTTTTTGATAAT  CTCATGACCAAA  ATCCCTTAACGT
4645  GAGTTTTCGTTC  CACTGAGCGTCA  GACCCCGTAGAA
4681  AAGATCAAAGGA  TCTTCTTGAGAT  CCTTTTTTTCTG
4717  CGCGTAATCTGC  TGCTTGCAAACA  AAAAAACCACCG
4753  CTACCAGCGGTG  GTTTGTTTGCCG  GATCAAGAGCTA
4789  CCAACTCTTTTT  CCGAAGGTAACT  GGCTTCAGCAGA
4825  GCGCAGATACCA  AATACTGTCCTT  CTAGTGTAGCCG
4861  TAGTTAGGCCAC  CACTTCAAGAAC  TCTGTAGCACCG
4897  CCTACATACCTC  GCTCTGCTAATC  CTGTTACCAGTG
4933  GCTGCTGCCAGT  GGCGATAAGTCG  TGTCTTACCGGG
4969  TTGGACTCAAGA  CGATAGTTACCG  GATAAGGCGCAG
5005  CGGTCGGGCTGA  ACGGGGGGTTCG  TGCACACAGCCC
5041  AGCTTGGAGCGA  ACGACCTACACC  GAACTGAGATAC
5077  CTACAGCGTGAG  CATTGAGAAAGC  GCCACGCTTCCC
5113  GAAGGGAGAAAG  GCGGACAGGTAT  CCGGTAAGCGGC
```

FIGURE 3E

```
5149  AGGGTCGGAACA  GGAGAGCGCACG  AGGGAGCTTCCA
5185  GGGGGGAACGCC  TGGTATCTTTAT  AGTCCTGTCGGG
5221  TTTCGCCACCTC  TGACTTGAGCGT  CGATTTTTGTGA
5257  TGCTCGTCAGGG  GGGCCGAGCCTA  TGGAAAAACGCC
5293  AGCAACGCGGCC  TTTTACGGTTC   CTGGCCTTTTGC
5329  TGGCCTTTTGCT  CACATGTTCTTT  CCTGCGTTATCC
5365  CCTGATTCTGTG  GATAACCGTATT  ACCGCCTTTGAG
5401  TGAGCTGATACC  GCTCGCCGCAGC  CGAACGACCGAG
5437  CGCAGCGAGTCA  GTGAGCGAGGAA  GCGGAAGAGCGC
5473  CCAATACGCAAA  CCGCCTCTCCCC  GCGCGTTGGCCG
5509  ATTCATTAATGC  AGCTGGCACGAC  AGGTTTCCCGAC
5545  TGGAAAGCGGGC  AGTGAGCGCAAC  GCAATTAATGTG
5581  AGTTACCTCACT  CATTAGGCACCC  CAGGCTTTACAC
5617  TTTATGCTTCCG  GCTCCTATGTTG  TGTGGAATTGTG
5653  AGCGGATAACAA  TTTCACACAGGA  AACAGCTATGAC
5689  CATGATTACGCC  AAGCTCGGAATT  AACCCTCACTAA
5725  AGGGAACAAAAG  CTGGCTAGT
```

FIGURE 5

QLVQSGPELR KPGETVKISC KGSGYTFTHY GINWVKQTPR KDLKWMGWIN

THTGEPIYAD DFKGRFAFSL ETSANTAYLQ INNLNNGDMG TYFCTRSHRF

GLDYWGQGTS VTVSSGPAKE LTPLKEAKVS DNVLTQSPPS LAVSLGQRAT

ISCKASQSVD YNGDSYLNWY QQKPGQPPKF LIYAASNLES GIPARFSGSG

SGTDFNLNIH PVEEEDAATY YCQQSNEDPF TFGSGTKLEI KRAAALESRG

PFEGKPIPNP LLGLDSTRTG HHHHHH*

FIGURE 6A

```
                          106.3 Variable heavy
946                       CAGATCCAG TTGGTGCAG TCTGGACCT
                          GTCTAGGTC AACCACGTC AGACCTGGA 106.3 Variable heavy
991    GAGCTGAGG AAGCCTGGA GAGACAGTC AAGATCTCC TGCAAGGGT
       CTCGACTCC TTCGGACCT CTCTGTCAG TTCTAGAGG ACGTTCCCA CDR H1----------------------(10)
                 106.3 Variable heavy
1036   TCTGGATAT ACCTTCACA CACTATGGA ATAAACTGG GTGAAGCAG
       AGACCTATA TGGAAGTGT GTGATACCT TATTTGACC CACTTCGTC CDR H2----------
                 106.3 Variable heavy
1081   ACTCCAAGA AAGGATTTA AAGTGGATG GGCTGGATA AACACCCAT
       TGAGGTTCT TTCCTAAAT TTCACCTAC CCGACCTAT TTGTGGGTA H2--------------------------------(17)
                 106.3 Variable heavy
1126   ACTGGAGAG CCAATATAT GCTGATGAC TTCAAGGGA CGGTTTGCC
       TGACCTCTC GGTTATATA CGACTACTG AAGTTCCCT GCCAAACGG 106.3 Variable heavy
1171   TTCTCTTTG GAAACCTCT GCCAACACT GCCTATTTG CAAATCAAC
       AAGAGAAAC CTTTGGAGA CGGTTGTGA CGGATAAAC GTTTAGTTG CDR H3
                 106.3 Variable heavy
1216   AACCTCAAC AATGGAGAC ATGGGTACA TATTTCTGT ACAAGAAGT
       TTGGAGTTG TTACCTCTG TACCCATGT ATAAAGACA TGTTCTTCA H3----------------(8)
                 106.3 Variable heavy
1261   CACCGGTTT GGTTTGGAC TACTGGGGT CAAGGTACC TCAGTCACC
       GTGGCCAAA CCAAACCTG ATGACCCCA GTTCCATGG AGTCAGTGG 106.3 Vh
                 Linker 40----------------------------
1306   GTCTCGTCA GGTCCCGCC AAGGAGTTG ACGCCCCTG AAGGAGGCG
       CAGAGCAGT CCAGGGCGG TTCCTCAAC TGCGGGGAC TTCCTCCGC 106.3 Variable light
           Linker 40
1351   AAGGTCTCT GACAATGTG CTGACCCAA TCTCCACCT TCTTTGGCT
       TTCCAGAGA CTGTTACAC GACTGGGTT AGAGGTGGA AGAAACCGA CDR L1-------
                 106.3 Variable light
1396   GTGTCTCTA GGGCAGAGG GCCACCATC TCCTGCAAG GCCAGCCAA
       CACAGAGAT CCCGTCTCC CGGTGGTAG AGGACGTTC CGGTCGGTT CDR L1-------------------------(15)
                 106.3 Variable light
1441   AGTGTTGAT TATAATGGT GATAGTTAT CTGAACTGG TACCAACAG
       TCACAACTA ATATTACCA CTATCAATA GACTTGACC ATGGTTGTC
```

FIGURE 6B

```
                                                    CDR L2-------
               106.3 Variable light
1486   AAGCCAGGA CAGCCACCC AAATTCCTC ATCTATGCT GCATCCAAT
       TTCGGTCCT GTCGGTGGG TTTAAGGAG TAGATACGA CGTAGGTTA ------(7)
               106.3 Variable light
1531   CTAGAATCT GGGATCCCA GCCAGGTTT AGTGGCAGT GGGTCTGGG
       GATCTTAGA CCCTAGGGT CGGTCCAAA TCACCGTCA CCCAGACCC 106.3 Variable light
1576   ACAGACTTC AACCTCAAC ATCCATCCT GTGGAGGAG GAGGATGCT
       TGTCTGAAG TTGGAGTTG TAGGTAGGA CACCTCCTC CTCCTACGA CDR L3-------------------- (9)
               106.3 Variable light
1621   GCAACCTAT TACTGTCAG CAAAGTAAT GAGGATCCA TTCACGTTC
       CGTTGGATA ATGACAGTC GTTTCATTA CTCCTAGGT AAGTGCAAG 106.3 Variable light
                                   end   NotI
1666   GGCTCGGGG ACAAAGTTG GAAATAAAA *CGGGCGGCC* GCCCTCGAG
       CCGAGCCCC TGTTTCAAC CTTTATTTT GCCCGCCGG CGGGAGCTC V5 Epitope
1711   TCTAGAGGG CCCTTCGAA GGTAAGCCT ATCCCTAAC CCTCTCCTC
       AGATCTCCC GGGAAGCTT CCATTCGGA TAGGGATTG GGAGAGGAG V5 Epitope                        poly HIS
1756   GGTCTCGAT TCTACGCGT ACCGGTCAT CATCACCAT CACCATTGA
       CCAGAGCTA AGATGCGCA TGGCCAGTA GTAGTGGTA GTGGTAACT
```

FIGURE 11

| Name | $k_{off}$ (sec$^{-1}$) | Fold Improvement |
|---|---|---|
| 106.3 wt | 8.4E-05 | ----- |
| H2 288 | 3.7E-05 | 2.3 |
| L1 B4 | 7.3E-06 | 11.5 |
| L1 B9 | 3.1E-05 | 2.7 |
| L1 9b | 1.3E-05 | 6.4 |
| L1 B12 | 7.6E-06 | 11.0 |
| L1 B15 | 8.6E-06 | 9.7 |
| L1 16 | 8.7E-06 | 9.6 |
| L1 B24 | 6.7E-06 | 12.5 |
| L2 6 | 3.2E-05 | 2.7 |
| L2 21 | 4.0E-05 | 2.1 |

FIGURE 12A

| Name | CDR H2 Pos 56 | CDR H2 Pos 57 | CDR H2 Pos 58 |
|---|---|---|---|
| 106.3 wt | Glu (GAG) | Pro (CCA) | Ile (ATA) |
| H2 288 | Glu (GAG) | Ala (GCG) | Tyr (TAC) |

FIGURE 12B

| Name | CDR L1 Pos 26 | CDR L1 Pos 27 | CDR L1 Pos 27A | Other Mutations |
|---|---|---|---|---|
| 106.3 wt | Ser (AGC) | Gln (CAA) | Ser (AGT) | |
| L1 B4 | Gln (CAG) | Phe (TTC) | Ala (GCG) | |
| L1 B9 | Tyr (TAC) | Ala (GCG) | Ser (AGT) | |
| L1 9b | Gln (CAG) | Trp (TGG) | Gly (GGC) | R42S |
| L1 B12 | Thr (ACC) | Trp (TGG) | Asp (GAC) | |
| L1 B15 | Arg (AGG) | Trp (TGG) | Pro (CCG) | |
| L1 16 | Ala (GCG) | Tyr (TAC) | Gly (GGC) | |
| L1 B24 | Asn (AAC) | Trp (TGG) | Pro (CCC) | R42S |

FIGURE 12C

| Name | CDR L2 Pos 53 | CDR L2 Pos 54 | CDR L2 Pos 55 |
|---|---|---|---|
| 106.3 wt | Asn (AAT) | Leu (CTA) | Glu (GAA) |
| L2 6 | Cys (TGC) | Gly (GGG) | Trp (TGG) |
| L2 21 | Cys (TGC) | Ala (GCG) | Pro (CCG) |

FIGURE 13

| Clone Name | Antibody Type | $k_{on}$ (M$^{-1}$sec$^{-1}$) | $k_{off}$ (sec$^{-1}$) | $K_D$ (pM) |
|---|---|---|---|---|
| 106.3 wt | Mouse IgG1 | 1.2E+07 | 2.2E-04 | 18 |
| 106.3 wt | Mouse-Human IgG1 | 7.8E+06 | 1.5E-04 | 19 |
| 106.3 AM1 | Mouse-Human IgG1 | 1.3E+07 | 2.4E-05 | 1.9 |

FIGURE 14A

Degenerate Oligonucleotides:
N= A, G, C, T; S = G, C

CDR H3 Degenerate Oligonucleotides

| System | Code | CDR | Library name | Length(ntd) |
|---|---|---|---|---|
| 106.3 | Oligo1 | H3 | H3-1 | 105 |
| 106.3 | Oligo 2 | H3 | H3-2 | 105 |
| 106.3 | Oligo 3 | H3 | H3-3 | 105 |
| 106.3 | Oligo 4 | H3 | H3-4 | 105 |
| 106.3 | Oligo 5 | H3 | H3-5 | 105 |
| 106.3 | Oligo 6 | H3 | H3-6 | 99 |

Oligo1
   AAC CTC AAC AAT GGA GAC ATG GGT ACA TAT TTC TGT ACA AGA NNS NNS NNS TTT GGT TTG GAC TAC TGG GGT CAA GGT ACC TCA GTC ACC GTC TCG TCA GGT CCC Oligo2
   AAC CTC AAC AAT GGA GAC ATG GGT ACA TAT TTC TGT ACA AGA AGT NNS NNS NNS GGT TTG GAC TAC TGG GGT CAA GGT ACC TCA GTC ACC GTC TCG TCA GGT CCC Oligo3
   AAC CTC AAC AAT GGA GAC ATG GGT ACA TAT TTC TGT ACA AGA AGT CAC NNS NNS NNS TTG GAC TAC TGG GGT CAA GGT ACC TCA GTC ACC GTC TCG TCA GGT CCC Oligo 4
   AAC CTC AAC AAT GGA GAC ATG GGT ACA TAT TTC TGT ACA AGA AGT CAC CGG NNS NNS NNS GAC TAC TGG GGT CAA GGT ACC TCA GTC ACC GTC TCG TCA GGT CCC Oligo 5
   AAC CTC AAC AAT GGA GAC ATG GGT ACA TAT TTC TGT ACA AGA AGT CAC CGG TTT NNS NNS NNS TAC TGG GGT CAA GGT ACC TCA GTC ACC GTC TCG TCA GGT CCC Oligo 6
   GAC ATG GGT ACA TAT TTC TGT ACA AGA AGT CAC CGG TTT GGT NNS NNS NNS TGG GGT CAA GGT ACC TCA GTC ACC GTC TCG TCA GGT CCC GCC GCC AAG

FIGURE 14B

H2 Degenerate Oligonucleotides

| System | Code | CDR | Library name | Length(ntd) |
|---|---|---|---|---|
| 106.3 | Oligo 7 | H2 | H2-1 | 105 |
| 106.3 | Oligo 8 | H2 | H2-2 | 105 |
| 106.3 | Oligo 9 | H2 | H2-3 | 105 |
| 106.3 | Oligo10 | H2 | H2-4 | 105 |
| 106.3 | Oligo11 | H2 | H2-5 | 105 |
| 106.3 | Oligo12 | H2 | H2-6 | 105 |
| 106.3 | Oligo 13 | H2 | H2-7 | 105 |
| 106.3 | Oligo 14 | H2 | H2-8 | 105 |
| 106.3 | Oligo 15 | H2 | H2-9 | 105 |
| 106.3 | Oligo 16 | H2 | H2-10 | 105 |
| 106.3 | Oligo 17 | H2 | H2-11 | 105 |
| 106.3 | Oligo 18 | H2 | H2-12 | 105 |
| 106.3 | Oligo 19 | H2 | H2-13 | 105 |
| 106.3 | Oligo 20 | H2 | H2-14 | 105 |
| 106.3 | Oligo 21 | H2 | H2-15 | 105 |

Oligo 7
   TGG GTG AAG CAG ACT CCA AGA AAG GAT TTA AAG TGG ATG GGC NNS NNS NNS ACC CAT ACT GGA GAG CCA ATA TAT GCT GAT GAC TTC AAG GGA CGG TTT GCC TTC Oligo 8
   TGG GTG AAG CAG ACT CCA AGA AAG GAT TTA AAG TGG ATG GGC TGG NNS NNS NNS CAT ACT GGA GAG CCA ATA TAT GCT GAT GAC TTC AAG GGA CGG TTT GCC TTC Oligo 9
   TGG GTG AAG CAG ACT CCA AGA AAG GAT TTA AAG TGG ATG GGC TGG ATA NNS NNS NNS ACT GGA GAG CCA ATA TAT GCT GAT GAC TTC AAG GGA CGG TTT GCC TTC Oligo 10
   TGG GTG AAG CAG ACT CCA AGA AAG GAT TTA AAG TGG ATG GGC TGG ATA AAC NNS NNS NNS GGA GAG CCA ATA TAT GCT GAT GAC TTC AAG GGA CGG TTT GCC TTC Oligo 11
   TGG GTG AAG CAG ACT CCA AGA AAG GAT TTA AAG TGG ATG GGC TGG ATA AAC ACC NNS NNS NNS GAG CCA ATA TAT GCT GAT GAC TTC AAG GGA CGG TTT GCC TTC Oligo 12
   CCA AGA AAG GAT TTA AAG TGG ATG GGC TGG ATA AAC ACC CAT NNS NNS NNS CCA ATA TAT GCT GAT GAC TTC AAG GGA CGG TTT GCC TTC TCT TTG AAA ACC TCT

FIGURE 14C

Oligo 13
   CCA AGA AAG GAT TTA AAG TGG ATG GGC **TGG ATA AAC ACC CAT ACT
NNS NNS NNS ATA TAT GCT GAT GAC TTC AAG GGA** CGG TTT GCC TTC
TCT TTG GAA ACC TCT Oligo 14
   CCA AGA AAG GAT TTA AAG TGG ATG GGC **TGG ATA AAC ACC CAT ACT
GGA NNS NNS NNS TAT GCT GAT GAC TTC AAG GGA** CGG TTT GCC TTC
TCT TTG GAA ACC TCT Oligo15
   CCA AGA AAG GAT TTA AAG TGG ATG GGC **TGG ATA AAC ACC CAT ACT
GGA GAG NNS NNS NNS GCT GAT GAC TTC AAG GGA** CGG TTT GCC TTC
TCT TTG GAA ACC TCT Oligo16
   CCA AGA AAG GAT TTA AAG TGG ATG GGC **TGG ATA AAC ACC CAT ACT
GGA GAG CCA NNS NNS NNS GAT GAC TTC AAG GGA** CGG TTT GCC TTC
TCT TTG GAA ACC TCT Oligo17
   AAG TGG ATG GGC **TGG ATA AAC ACC CAT ACT GGA GAG CCA ATA NNS
NNS NNS GAC TTC AAG GGA** CGG TTT GCC TTC TCT TTG GAA ACC TCT
GCC AAC ACT GCC TAT Oligo18
   AAG TGG ATG GGC **TGG ATA AAC ACC CAT ACT GGA GAG CCA ATA TAT
NNS NNS NNS TTC AAG GGA** CGG TTT GCC TTC TCT TTG GAA ACC TCT
GCC AAC ACT GCC TAT Oligo19
   AAG TGG ATG GGC **TGG ATA AAC ACC CAT ACT GGA GAG CCA ATA TAT
GCT NNS NNS NNS AAG GGA** CGG TTT GCC TTC TCT TTG GAA ACC TCT
GCC AAC ACT GCC TAT Oligo20
   AAG TGG ATG GGC **TGG ATA AAC ACC CAT ACT GGA GAG CCA ATA TAT
GCT GAT NNS NNS NNS GGA** CGG TTT GCC TTC TCT TTG GAA ACC TCT
GCC AAC ACT GCC TAT Oligo21
   AAG TGG ATG GGC **TGG ATA AAC ACC CAT ACT GGA GAG CCA ATA TAT
GCT GAT GAC NNS NNS NNS** CGG TTT GCC TTC TCT TTG GAA ACC TCT
GCC AAC ACT GCC TAT

FIGURE 14D

CDR H1 Degenerate Oligonucleotides

| System | Code | CDR | Library name | Length(ntd) |
|---|---|---|---|---|
| 106.3 | Oligo22 | H1 | H1-1 | 105 |
| 106.3 | Oligo23 | H1 | H1-2 | 105 |
| 106.3 | Oligo24 | H1 | H1-3 | 105 |
| 106.3 | Oligo25 | H1 | H1-4 | 105 |
| 106.3 | Oligo26 | H1 | H1-5 | 105 |
| 106.3 | Oligo27 | H1 | H1-6 | 99 |
| 106.3 | Oligo28 | H1 | H1-7 | 99 |
| 106.3 | Oligo29 | H1 | H1-8 | 99 |

Oligo22
   AGG AAG CCT GGA GAG ACA GTC AAG ATC TCC TGC AAG GGT TCT NNS NNS NNS TTC ACA CAC TAT GGA ATA AAC TGG GTG AAG CAG ACT CCA AGA AAG GAT TTA AAG Oligo23
   AGG AAG CCT GGA GAG ACA GTC AAG ATC TCC TGC AAG GGT TCT GGA NNS NNS NNS ACA CAC TAT GGA ATA AAC TGG GTG AAG CAG ACT CCA AGA AAG GAT TTA AAG Oligo24
   AGG AAG CCT GGA GAG ACA GTC AAG ATC TCC TGC AAG GGT TCT GGA TAT NNS NNS NNS CAC TAT GGA ATA AAC TGG GTG AAG CAG ACT CCA AGA AAG GAT TTA AAG Oligo25
   AGG AAG CCT GGA GAG ACA GTC AAG ATC TCC TGC AAG GGT TCT GGA TAT ACC NNS NNS NNS TAT GGA ATA AAC TGG GTG AAG CAG ACT CCA AGA AAG GAT TTA AAG Oligo26
   AGG AAG CCT GGA GAG ACA GTC AAG ATC TCC TGC AAG GGT TCT GGA TAT ACC TTC NNS NNS NNS GGA ATA AAC TGG GTG AAG CAG ACT CCA AGA AAG GAT TTA AAG Oligo27
   ACA GTC AAG ATC TCC TGC AAG GGT TCT GGA TAT ACC TTC ACA NNS NNS NNS ATA AAC TGG GTG AAG CAG ACT CCA AGA AAG GAT TTA AAG TGG ATG GGC Oligo28
   ACA GTC AAG ATC TCC TGC AAG GGT TCT GGA TAT ACC TTC ACA CAC NNS NNS NNS AAC TGG GTG AAG CAG ACT CCA AGA AAG GAT TTA AAG TGG ATG GGC Oligo29
   ACA GTC AAG ATC TCC TGC AAG GGT TCT GGA TAT ACC TTC ACA CAC TAT NNS NNS NNS TGG GTG AAG CAG ACT CCA AGA AAG GAT TTA AAG TGG ATG GGC

FIGURE 14E

CDR L1 Degenerate Oligonucleotides (13)

| System | Code | CDR | Library name | Length(ntd) |
|---|---|---|---|---|
| 106.3 | Oligo30 | L1 | L1-1 | 99 |
| 106.3 | Oligo31 | L1 | L1-2 | 99 |
| 106.3 | Oligo32 | L1 | L1-3 | 99 |
| 106.3 | Oligo33 | L1 | L1-4 | 99 |
| 106.3 | Oligo34 | L1 | L1-5 | 99 |
| 106.3 | Oligo35 | L1 | L1-6 | 99 |
| 106.3 | Oligo36 | L1 | L1-7 | 99 |
| 106.3 | Oligo37 | L1 | L1-8 | 99 |
| 106.3 | Oligo38 | L1 | L1-9 | 99 |
| 106.3 | Oligo39 | L1 | L1-10 | 99 |
| 106.3 | Oligo40 | L1 | L1-11 | 99 |
| 106.3 | Oligo41 | L1 | L1-12 | 93 |
| 106.3 | Oligo42 | L1 | L1-13 | 93 |

Oligo 30
  TTG GCT GTG TCT CTA GGG CAG AGG GCC ACC ATC TCC TGC NNS NNS NNS CAA AGT GTT GAT TAT AAT GGT GAT AGT TAT CTG AAC TGG TAC CAA CAG AAG Oligo 31
  TTG GCT GTG TCT CTA GGG CAG AGG GCC ACC ATC TCC TGC AAG NNS NNS NNS AGT GTT GAT TAT AAT GGT GAT AGT TAT CTG AAC TGG TAC CAA CAG AAG Oligo 32
  TTG GCT GTG TCT CTA GGG CAG AGG GCC ACC ATC TCC TGC AAG GCC NNS NNS NNS GTT GAT TAT AAT GGT GAT AGT TAT CTG AAC TGG TAC CAA CAG AAG Oligo 33
  TTG GCT GTG TCT CTA GGG CAG AGG GCC ACC ATC TCC TGC AAG GCC AGC NNS NNS NNS GAT TAT AAT GGT GAT AGT TAT CTG AAC TGG TAC CAA CAG AAG Oligo 34
  TTG GCT GTG TCT CTA GGG CAG AGG GCC ACC ATC TCC TGC AAG GCC AGC CAA NNS NNS NNS TAT AAT GGT GAT AGT TAT CTG AAC TGG TAC CAA CAG AAG Oligo 35
  GGG CAG AGG GCC ACC ATC TCC TGC AAG GCC AGC CAA AGT NNS NNS NNS AAT GGT GAT AGT TAT CTG AAC TGG TAC CAA CAG AAG CCA GGA CAG CCA CCC

FIGURE 14F

Oligo 36
  GGG CAG AGG GCC ACC ATC TCC TGC AAG GCC AGC CAA AGT GTT NNS NNS NNS GGT GAT AGT TAT CTG AAC TGG TAC CAA CAG AAG CCA GGA CAG CCA CCC Oligo 37
  GGG CAG AGG GCC ACC ATC TCC TGC AAG GCC AGC CAA AGT GTT GAT NNS NNS NNS GAT AGT TAT CTG AAC TGG TAC CAA CAG AAG CCA GGA CAG CCA CCC Oligo38
  GGG CAG AGG GCC ACC ATC TCC TGC AAG GCC AGC CAA AGT GTT GAT TAT NNS NNS NNS AGT TAT CTG AAC TGG TAC CAA CAG AAG CCA GGA CAG CCA CCC Oligo39
  GGG CAG AGG GCC ACC ATC TCC TGC AAG GCC AGC CAA AGT GTT GAT TAT AAT NNS NNS NNS TAT CTG AAC TGG TAC CAA CAG AAG CCA GGA CAG CCA CCC Oligo40
  ATC TCC TGC AAG GCC AGC CAA AGT GTT GAT TAT AAT GGT NNS NNS NNS CTG AAC TGG TAC CAA CAG AAG CCA GGA CAG CCA CCC AAA TTC CTC Oligo41
  ATC TCC TGC AAG GCC AGC CAA AGT GTT GAT TAT AAT GGT GAT NNS NNS NNS AAC TGG TAC CAA CAG AAG CCA GGA CAG CCA CCC AAA TTC CTC Oligo42
  ATC TCC TGC AAG GCC AGC CAA AGT GTT GAT TAT AAT GGT GAT AGT NNS NNS NNS TGG TAC CAA CAG AAG CCA GGA CAG CCA CCC AAA TTC CTC CDR L2 Degenerate Oligonucleotides (5)

| System | Code | CDR | Library name | Length(ntd) |
|---|---|---|---|---|
| 106.3 | Oligo43 | L2 | L2-1 | 99 |
| 106.3 | Oligo44 | L2 | L2-2 | 99 |
| 106.3 | Oligo45 | L2 | L2-3 | 99 |
| 106.3 | Oligo46 | L2 | L2-4 | 99 |
| 106.3 | Oligo47 | L2 | L2-5 | 99 |

Oligo43
  CAA CAG AAG CCA GGA CAG CCA CCC AAA TTC CTC ATC TAT NNS NNS NNS AAT CTA GAA TCT GGG ATC CCA GCC AGG TTT AGT GGC AGT GGG TCT GGG ACA Oligo44
  CAA CAG AAG CCA GGA CAG CCA CCC AAA TTC CTC ATC TAT GCT NNS NNS NNS CTA GAA TCT GGG ATC CCA GCC AGG TTT AGT GGC AGT GGG TCT GGG ACA

FIGURE 14G

Oligo45
CAA CAG AAG CCA GGA CAG CCA CCC AAA TTC CTC ATC TAT GCT GCA NNS NNS NNS GAA TCT GGG ATC CCA GCC AGG TTT AGT GGC AGT GGG TCT GGG ACA Oligo46
CAA CAG AAG CCA GGA CAG CCA CCC AAA TTC CTC ATC TAT GCT GCA TCC NNS NNS NNS TCT GGG ATC CCA GCC AGG TTT AGT GGC AGT GGG TCT GGG ACA Oligo47
CAA CAG AAG CCA GGA CAG CCA CCC AAA TTC CTC ATC TAT GCT GCA TCC AAT NNS NNS NNS GGG ATC CCA GCC AGG TTT AGT GGC AGT GGG TCT GGG ACA

CDR L3 Degenerate Oligonucleotides (7)

| System | Code | CDR | Library name | Length(ntd) |
|---|---|---|---|---|
| 106.3 | Oligo48 | L3 | L3-1 | 99 |
| 106.3 | Oligo49 | L3 | L3-2 | 99 |
| 106.3 | Oligo50 | L3 | L3-3 | 99 |
| 106.3 | Oligo51 | L3 | L3-4 | 99 |
| 106.3 | Oligo52 | L3 | L3-5 | 99 |
| 106.3 | Oligo53 | L3 | L3-6 | 93 |
| 106.3 | Oligo54 | L3 | L3-7 | 93 |

Oligo48
CAT CCT GTG GAG GAG GAG GAT GCT GCA ACC TAT TAC TGT NNS NNS NNS AAT GAG GAT CCA TTC ACG TTC GGC TCG GGG ACA AAG TTG GAA ATA AAA CGG Oligo49
CAT CCT GTG GAG GAG GAG GAT GCT GCA ACC TAT TAC TGT CAG NNS NNS NNS GAG GAT CCA TTC ACG TTC GGC TCG GGG ACA AAG TTG GAA ATA AAA CGG Oligo50
CAT CCT GTG GAG GAG GAG GAT GCT GCA ACC TAT TAC TGT CAG CAA NNS NNS NNS GAT CCA TTC ACG TTC GGC TCG GGG ACA AAG TTG GAA ATA AAA CGG Oligo51
CAT CCT GTG GAG GAG GAG GAT GCT GCA ACC TAT TAC TGT CAG CAA AGT NNS NNS NNS CCA TTC ACG TTC GGC TCG GGG ACA AAG TTG GAA ATA AAA CGG Oligo52
CAT CCT GTG GAG GAG GAG GAT GCT GCA ACC TAT TAC TGT CAG CAA AGT AAT NNS NNS NNS TTC ACG TTC GGC TCG GGG ACA AAG TTG GAA ATA AAA CGG

FIGURE 14H

Oligo53
    GAG GAT GCT GCA ACC TAT TAC TGT CAG CAA AGT AAT GAG NNS NNS NNS ACG TTC GGC TCG GGG ACA AAG TTG GAA ATA AAA CGG GCG GCC GCC Oligo54
    GAG GAT GCT GCA ACC TAT TAC TGT CAG CAA AGT AAT GAG GAT NNS NNS NNS TTC GGC TCG GGG ACA AAG TTG GAA ATA AAA CGG GCG GCC GCC

FIGURE 22A

```
      GAL1 promoter
   1  ACGGATTAGAAGCCG CCGAGCGGGTGACAG CCCTCCGAAGGAAGA CTCTCCTCCGTGCGT
  61  CCTCGTCCTCACCGG TCGCGTTCCTGAAAC GCAGATGTGCCTCGC GCCGCACTGCTCCGA
 121  ACAATAAAGATTCTA CAATACTAGCTTTTA TGGTTATGAAGAGGA AAAATTGGCAGTAAC
 181  CTGGCCCCACAAACC TTCAAATGAACGAAT CAAATTAACAACCAT AGGATGATAATGCGA
 241  TTAGTTTTTTAGCCT TATTTCTGGGGTAAT TAATCAGCGAAGCGA TGATTTTGATCTAT
 301  TAACAGATATATAAA TGCAAAAACTGCATT AACCACTTTAACTAA TACTTTCAACATTTT
 361  CGGTTTGTATTACTT CTTATTCAAATGTAA TAAAAGTATCAACAA AAAATTGTTAATATA
 421  CCTCTATACTTTAAC GTCAAGGAGAAAAAA CCCCGGATCGGACTA CTAGCAGCTGTAATA
                                                                 AGA2
                                                                 ~~~~~~
 481  CGACTCACTATAGGG AATATTAAGCTAATT CTACTTCATACATTT TCAATTAAGATGCAG
                                 AGA2
      ~~~~~~~~~~~~~~~~~~~~~~~~~~~~~~~~~~~~~~~~~~~~~~~~~~~~~~~~~~~~~~~
 541  TTACTTCGCTGTTTT TCAATATTTTCTGTT ATTGCTTCAGTTTTA GCACAGGAACTGACA
                                 AGA2
      ~~~~~~~~~~~~~~~~~~~~~~~~~~~~~~~~~~~~~~~~~~~~~~~~~~~~~~~~~~~~~~~
 601  ACTATATGCGAGCAA ATCCCCTCACCAACT TTAGAATCGACGCCG TACTCTTTGTCAACG
                                 AGA2
      ~~~~~~~~~~~~~~~~~~~~~~~~~~~~~~~~~~~~~~~~~~~~~~~~~~~~~~~~~~~~~~~
 661  ACTACTATTTTGGCC AACGGGAAGGCAATG CAAGGAGTTTTTGAA TATTACAAATCAGTA
                                 AGA2
      ~~~~~~~~~~~~~~~~~~~~~~~~~~~~~~~~~~~~~~~~~~~~~~~~~~~~~~~~~~~~~~~
 721  ACGTTTGTCAGTAAT TGCGGTTCTCACCCC TCAACAACTAGCAAA GGCAGCCCCATAAAC
                 AGA2                                     Tether41
      ~~~~~~~~~~~~~~~~                             ~~~~~~~~~~~~~~~~~~~~~
 781  ACACAGTATGTTTTT AAGCTTCTGCAGGCT AGTGGTGAGAACAAG GTGGAGTACGCGCCG
           Tether41
      ~~~~~~~~~~~~~~~~~~~~
 841  GCGTTGATGGCCTTG TCTGCTAGCATGACT GGTGGACAGCAAATG GGTCGGGATCTGTAC
                                                                SfiI
                                                        ~~~~~~~~~~~~~~
 901  GACGATGACGATAAG GTACCAGGATCCAGT GTGGTGGAATTCGCG GCCCAGCCGGCCATG
                                                        3-631-436 VH
                                                     ~~~~~~~~~~~~~~~~~~
 961  GCCCAGGTCCAACTG CAGCAGCCTGGGGCT GAGCTGGTGAGGCCT GGGGCTTCAGTGAAG
                                 3-631-436 VH
      ~~~~~~~~~~~~~~~~~~~~~~~~~~~~~~~~~~~~~~~~~~~~~~~~~~~~~~~~~~~~~~~
1021  CTGTCCTGCAAGGCT TCTGGCTACACGTTC ACCAGTTACTGGATG AACTGGGTTAAACAG
                                 3-631-436 VH
      ~~~~~~~~~~~~~~~~~~~~~~~~~~~~~~~~~~~~~~~~~~~~~~~~~~~~~~~~~~~~~~~
1081  AGGCCTGAGCAAGGC CTTGAGTGGATTGGA AGGATTGATCCTTAC GATAGTGAAACTCAC
                                 3-631-436 VH
      ~~~~~~~~~~~~~~~~~~~~~~~~~~~~~~~~~~~~~~~~~~~~~~~~~~~~~~~~~~~~~~~
1141  TACAATCAAAAGTTC AAGGACAAGGCCATT TTGACTGTAGACAAA TCCTCCAGCACAGCC
                                 3-631-436 VH
      ~~~~~~~~~~~~~~~~~~~~~~~~~~~~~~~~~~~~~~~~~~~~~~~~~~~~~~~~~~~~~~~
1201  TTCGTGCAACTCACC AGCCTGACATCTGAG GACTCTGCGGTCTAT TATTGCGTCTCTGAT
                       3-631-436 VH                          Linker 40
                 ~~~~~~~~~~~~~~~~~~~~~~~~~~~~~~~~~~ ~~~~~~~~~~~~~~~~~~
1261  GGTTACTGGGGCGCA GGGACCACGGTCACC GTCTCCTCAGGTCCC GCCAAGGAGTTGACG
               Linker 40                                 3-631-436 VL
           ~~~~~~~~~~~~~~~~                        ~~~~~~~~~~~~~~~~~~~~
1321  CCCCTGAAGGAGGCG AAGGTCTCTGATGTT GTTATGACTCAGACA CCACTCACTTTGTCG
```

FIGURE 22B

```
                                     3-631-436 VL
      ~~~~~~~~~~~~~~~~~~~~~~~~~~~~~~~~~~~~~~~~~~~~~~~~~~~~~~~~~~~~~~~~~
1381  GTTACCACTGGACAA CCAGCTTCCATCTCT TGCAAGTCAAGTCAG AGCCTCTTAGATAGT
                                     3-631-436 VL
      ~~~~~~~~~~~~~~~~~~~~~~~~~~~~~~~~~~~~~~~~~~~~~~~~~~~~~~~~~~~~~~~~~
1441  GATGGAAAAACCTAT TTAAATTGGTTATTC CAGAGGCCAGGCGAG TCTCCAAAGCTCCTA 3-631-436 VL
      ~~~~~~~~~~~~~~~~~~~~~~~~~~~~~~~~~~~~~~~~~~~~~~~~~~~~~~~~~~~~~~~~~
1501  ATCTATGTGGTGTCT AAACTGGAGTCTGGA GTCCCTGACAGGTTC ACTGGCAGTGGATCA
                                     3-631-436 VL
      ~~~~~~~~~~~~~~~~~~~~~~~~~~~~~~~~~~~~~~~~~~~~~~~~~~~~~~~~~~~~~~~~~
1561  GGGACAGATTTCACA CTGAAAATCAGCAGA GTGGAGGCTGAGGAT TTGGGAGTTTATTAC 3-631-436 VL
      ~~~~~~~~~~~~~~~~~~~~~~~~~~~~~~~~~~~~~~~~~~~~~~~~~~~~~~~~~~~~~~~~~
1621  TGCTTGCAAGCTACA CATTTTCCGTGGACG TTCGGTGGAGGCACC AAGCTGGAAATCAAA
            NotI                                      V5 Epitope
          ~~~~~~~~                              ~~~~~~~~~~~~~~~~~~~~~~~~~
1681  CGGGCGGCCGCCCTC GAGTCTAGAGGGCCC TTCGAAGGTAAGCCT ATCCCTAACCCTCTC
            V5 Epitope                          poly HIS
         ~~~~~~~~~~~~~~~~~~                   ~~~~~~~~~~~~~~~~~~~~
1741  CTCGGTCTCGATTCT ACGCGTACCGGTCAT CATCACCATCACCAT TGAGTTTAAACCCGC
1801  TGATCTGATAACAAC AGTGTAGATGTAACA AAATCGACTTTGTTC CCACTGTACTTTTAG
1861  CTCGTACAAAATACA ATATACTTTTCATTT CTCCGTAAACAACAT GTTTTCCCATGTAAT
1921  ATCCTTTTCTATTTT TCGTTCCGTTACCAA CTTTACACATACTTT ATATAGCTATTCACT
1981  TCTATACACTAAAAA ACTAAGACAATTTTA ATTTTGCTGCCTGCC ATATTTCAATTTGTT
2041  ATAAATTCCTATAAT TTATCCTATTAGTAG CTAAAAAAGATGAA TGTGAATCGAATCCT
2101  AAGAGAATTGGGCAA GTGCACAAACAATAC TTAAATAAATACTAC TCAGTAATAACCTAT
                                                                       ~
2161  TTCTTAGCATTTTTG ACGAAATTTGCTATT TTGTTAGAGTCTTTT ACACCATTTGTCTCC
      ~~~~~~~~~~~~~~~~~~~~~~~~~~~~~~~~~~~~~~~~~~~~~~~~~~~~~~~~~~~~~~~~~
                                      TRP1 ORF
2221  ACACCTCCGCTTACA TCAACACCAATAACG CCATTTAATCTAAGC GCATCACCAACATTT
      ~~~~~~~~~~~~~~~~~~~~~~~~~~~~~~~~~~~~~~~~~~~~~~~~~~~~~~~~~~~~~~~~~
                                      TRP1 ORF
2281  TCTGGCGTCAGTCCA CCAGCTAACATAAAA TGTAAGCTCTCGGGG CTCTCTTGCCTTCCA
      ~~~~~~~~~~~~~~~~~~~~~~~~~~~~~~~~~~~~~~~~~~~~~~~~~~~~~~~~~~~~~~~~~
                                      TRP1 ORF
2341  ACCCAGTCAGAAATC GAGTTCCAATCCAAA AGTTCACCTGTCCCA CCTGCTTCTGAATCA
      ~~~~~~~~~~~~~~~~~~~~~~~~~~~~~~~~~~~~~~~~~~~~~~~~~~~~~~~~~~~~~~~~~
                                      TRP1 ORF
2401  AACAAGGGAATAAAC GAATGAGGTTTCTGT GAAGCTGCACTGAGT AGTATGTTGCAGTCT
      ~~~~~~~~~~~~~~~~~~~~~~~~~~~~~~~~~~~~~~~~~~~~~~~~~~~~~~~~~~~~~~~~~
                                      TRP1 ORF
2461  TTTGGAAATACGAGT CTTTTAATAACTGGC AAACCGAGGAACTCT TGGTATTCTTGCCAC
      ~~~~~~~~~~~~~~~~~~~~~~~~~~~~~~~~~~~~~~~~~~~~~~~~~~~~~~~~~~~~~~~~~
                                      TRP1 ORF
2521  GACTCATCTCCGTGC AGTTGGACGATATCA ATGCCGTAATCATTG ACCAGAGCCAAAACA
      ~~~~~~~~~~~~~~~~~~~~~~~~~~~~~~~~~~~~~~~~~~~~~~~~~~~~~~~~~~~~~~~~~
                                      TRP1 ORF
2581  TCCTCCTTAGGTTGA TTACGAAACACGCCA ACCAAGTATTTCGGA GTGCCTGAACTATTT
      ~~~~~~~~~~~~~~~~~~~~~~~~~~~~~~~~~~~~~~~~~~~~~~~~~~~~~~~~~~~~~~~~~
```

FIGURE 22C

```
                                    TRP1 ORF
2641    TTATATGCTTTTACA AGACTTGAAATTTTC CTTGCAATAACCGGG TCAATTGTTCTCTTT
        ~~~~~~~~~~~~~~~~~~~~~~~~~~~~~~~~~~~~~~~~~~~~~~~~~~~~~~~~~~~~~~
                                    TRP1 ORF
2701    CTATTGGGCACACAT ATAATACCCAGCAAG TCAGCATCGGAATCT AGAGCACATTCTGCG
        ~~~~~~~~~~~~~~~~~~~~~~~~~~~~~~~~~~~~~~~~~~~~~~~~~~~~~~~~~~~~~~
                                    TRP1 ORF
2761    GCCTCTGTGCTCTGC AAGCCGCAAACTTTC ACCAATGGACCAGAA CTACCTGTGAAATTA
        ~~~~~~~~~~~~~~~~~~~~~~~~~~~~~~~~~~~~~~~~~~~~~~~~~~~~~~~~~~~~~~
                                    TRP1 ORF
2821    ATAACAGACATACTC CAAGCTGCCTTTGTG TGCTTAATCACGTAT ACTCACGTGCTCAAT
        ~~~~~~~~~~~~
          TRP1 ORF
2881    AGTCACCAATGCCCT CCCTCTTGGCCCTCT CCTTTTCTTTTTTCG ACCGAATTTCTTGAA
2941    GACGAAAGGGCCTCG TGATACGCCTATTTT TATAGGTTAATGTCA TGATAATAATGGTTT
3001    CTTAGGACGGATCGC TTGCCTGTAACTTAC ACGCGCCTCGTATCT TTTAATGATGGAATA
3061    ATTTGGGAATTTACT CTGTGTTTATTTATT TTTATGTTTTGTATT TGGATTTTAGAAAGT
3121    AAATAAAGAAGGTAG AAGAGTTACGGAATG AAGAAAAAAAATAA ACAAAGGTTTAAAAA
3181    ATTTCAACAAAAAGC GTACTTTACATATAT ATTTATTAGACAAGA AAAGCAGATTAAATA
3241    GATATACATTCGATT AACGATAAGTAAAAT GTAAAATCACAGGAT TTTCGTGTGTGGTCT
3301    TCTACACAGACAAGA TGAAACAATTCGGCA TTAATACCTGAGAGC AGGAAGAGCAAGATA
3361    AAAGGTAGTATTTGT TGGCGATCCCCCTAG AGTCTTTTACATCTT CGGAAAACAAAAACT
3421    ATTTTTTCTTTAATT TCTTTTTTTACTTTC TATTTTAATTTATA TATTTATATTAAAAA
3481    ATTTAAATTATAATT ATTTTTATAGCACGT GATGAAAAGGACCCA GGTGGCACTTTTCGG
3541    GGAAATGTGCGCGGA ACCCCTATTTGTTTA TTTTTCTAAATACAT TCAAATATGTATCCG
                                                                   ~~~~~
3601    CTCATGAGACAATAA CCCTGATAAATGCTT CAATAATATTGAAAA AGGAAGAGTATGAGT
                                Ampicillin Resistence
        ~~~~~~~~~~~~~~~~~~~~~~~~~~~~~~~~~~~~~~~~~~~~~~~~~~~~~~~~~~~~~~
3661    ATTCAACATTTCCGT GTCGCCCTTATTCCC TTTTTTGCGGCATTT TGCCTTCCTGTTTTT
                                Ampicillin Resistence
        ~~~~~~~~~~~~~~~~~~~~~~~~~~~~~~~~~~~~~~~~~~~~~~~~~~~~~~~~~~~~~~
3721    GCTCACCCAGAAACG CTGGTGAAAGTAAAA GATGCTGAAGATCAG TTGGGTGCACGAGTG
                                Ampicillin Resistence
        ~~~~~~~~~~~~~~~~~~~~~~~~~~~~~~~~~~~~~~~~~~~~~~~~~~~~~~~~~~~~~~
3781    GGTTACATCGAACTG GATCTCAACAGCGGT AAGATCCTTGAGAGT TTTCGCCCCGAAGAA
                                Ampicillin Resistence
        ~~~~~~~~~~~~~~~~~~~~~~~~~~~~~~~~~~~~~~~~~~~~~~~~~~~~~~~~~~~~~~
3841    CGTTTTCCAATGATG AGCACTTTTAAAGTT CTGCTATGTGGCGCG GTATTATCCCGTGTT
                                Ampicillin Resistence
        ~~~~~~~~~~~~~~~~~~~~~~~~~~~~~~~~~~~~~~~~~~~~~~~~~~~~~~~~~~~~~~
3901    GACGCCGGGCAAGAG CAACTCGGTCGCCGC ATACACTATTCTCAG AATGACTTGGTTGAG
                                Ampicillin Resistence
        ~~~~~~~~~~~~~~~~~~~~~~~~~~~~~~~~~~~~~~~~~~~~~~~~~~~~~~~~~~~~~~
3961    TACTCACCAGTCACA GAAAAGCATCTTACG GATGGCATGACAGTA AGAGAATTATGCAGT
                                Ampicillin Resistence
        ~~~~~~~~~~~~~~~~~~~~~~~~~~~~~~~~~~~~~~~~~~~~~~~~~~~~~~~~~~~~~~
4021    GCTGCCATAACCATG AGTGATAACACTGCG GCCAACTTACTTCTG ACAACGATCGGAGGA
                                Ampicillin Resistence
        ~~~~~~~~~~~~~~~~~~~~~~~~~~~~~~~~~~~~~~~~~~~~~~~~~~~~~~~~~~~~~~
4081    CCGAAGGAGCTAACC GCTTTTTTGCACAAC ATGGGGGATCATGTA ACTCGCCTTGATCGT
                                Ampicillin Resistence
        ~~~~~~~~~~~~~~~~~~~~~~~~~~~~~~~~~~~~~~~~~~~~~~~~~~~~~~~~~~~~~~
4141    TGGGAACCGGAGCTG AATGAAGCCATACCA AACGACGAGCGTGAC ACCACGATGCCTGTA
```

FIGURE 22D

```
           Ampicillin Resistence
           ~~~~~~~~~~~~~~~~~~~~~~~~~~~~~~~~~~~~~~~~~~~~~~~~~~~~~~~~~~
 4201      GCAATGGCAACAACG TTGCGCAAACTATTA ACTGGCGAACTACTT ACTCTAGCTTCCCGG
                           Ampicillin Resistence
           ~~~~~~~~~~~~~~~~~~~~~~~~~~~~~~~~~~~~~~~~~~~~~~~~~~~~~~~~~~
 4261      CAACAATTAATAGAC TGGATGGAGGCGGAT AAAGTTGCAGGACCA CTTCTGCGCTCGGCC
                           Ampicillin Resistence
           ~~~~~~~~~~~~~~~~~~~~~~~~~~~~~~~~~~~~~~~~~~~~~~~~~~~~~~~~~~
 4321      CTTCCGGCTGGCTGG TTTATTGCTGATAAA TCTGGAGCCGGTGAG CGTGGGTCTCGCGGT
                           Ampicillin Resistence
           ~~~~~~~~~~~~~~~~~~~~~~~~~~~~~~~~~~~~~~~~~~~~~~~~~~~~~~~~~~
 4381      ATCATTGCAGCACTG GGGCCAGATGGTAAG CCCTCCCGTATCGTA GTTATCTACACGACG
                           Ampicillin Resistence
           ~~~~~~~~~~~~~~~~~~~~~~~~~~~~~~~~~~~~~~~~~~~~~~~~~~~~~~~~~~
 4441      GGCAGTCAGGCAACT ATGGATGAACGAAAT AGACAGATCGCTGAG ATAGGTGCCTCACTG
           Ampicillin Resistence
           ~~~~~~~~~~~~~
 4501      ATTAAGCATTGGTAA CTGTCAGACCAAGTT TACTCATATATACTT TAGATTGATTTAAAA
 4561      CTTCATTTTTAATTT AAAAGGATCTAGGTG AAGATCCTTTTTGAT AATCTCATGACCAAA
 4621      ATCCCTTAACGTGAG TTTTCGTTCCACTGA GCGTCAGACCCCGTA GAAAAGATCAAAGGA
 4681      TCTTCTTGAGATCCT TTTTTTCTGCGCGTA ATCTGCTGCTTGCAA ACAAAAAAACCACCG
 4741      CTACCAGCGGTGGTT TGTTTGCCGGATCAA GAGCTACCAACTCTT TTTCCGAAGGTAACT
 4801      GGCTTCAGCAGAGCG CAGATACCAAATACT GTCCTTCTAGTGTAG CCGTAGTTAGGCCAC
 4861      CACTTCAAGAACTCT GTAGCACCGCCTACA TACCTCGCTCTGCTA ATCCTGTTACCAGTG
 4921      GCTGCTGCCAGTGGC GATAAGTCGTGTCTT ACCGGGTTGGACTCA AGACGATAGTTACCG
 4981      GATAAGGCGCAGCGG TCGGGCTGAACGGGG GGTTCGTGCACACAG CCCAGCTTGGAGCGA
 5041      ACGACCTACACCGAA CTGAGATACCTACAG CGTGAGCATTGAGAA AGCGCCACGCTTCCC
 5101      GAAGGGAGAAAGGCG GACAGGTATCCGGTA AGCGGCAGGGTCGGA ACAGGAGAGCGCACG
 5161      AGGGAGCTTCCAGGG GGGAACGCCTGGTAT CTTTATAGTCCTGTC GGGTTTCGCCACCTC
 5221      TGACTTGAGCGTCGA TTTTTGTGATGCTCG TCAGGGGGGCCGAGC CTATGGAAAAACGCC
 5281      AGCAACGCGGCCTTT TTACGGTTCCTGGCC TTTTGCTGGCCTTTT GCTCACATGTTCTTT
 5341      CCTGCGTTATCCCCT GATTCTGTGGATAAC CGTATTACCGCCTTT GAGTGAGCTGATACC
 5401      GCTCGCCGCAGCCGA ACGACCGAGCGCAGC GAGTCAGTGAGCGAG GAAGCGGAAGAGCGC
 5461      CCAATACGCAAACCG CCTCTCCCCGCGCGT TGGCCGATTCATTAA TGCAGCTGGCACGAC
 5521      AGGTTTCCCGACTGG AAAGCGGGCAGTGAG CGCAACGCAATTAAT GTGAGTTACCTCACT
 5581      CATTAGGCACCCCAG GCTTTACACTTTATG CTTCCGGCTCCTATG TTGTGTGGAATTGTG
 5641      AGCGGATAACAATTT CACACAGGAAACAGC TATGACCATGATTAC GCCAAGCTCGGAATT
 5701      AACCCTCACTAAAGG GAACAAAAGCTGGCT AGT
```

FIGURE 24

```
1    QVQLQQPGAE LVRPGASVKL SCKASGYTFT SYWMNWVKQR PEQGLEWIGR
51   IDPYDSETHY NQKFKDKAIL TVDKSSSTAF VQLTSLTSED SAVYYCVSDG
101  YWGAGTTVTV SSGPAKELTP LKEAKVSDVV MTQTPLTLSV TTGQPASISC
151  KSSQSLLDSD GKTYLNWLFQ RPGESPKLLI YVVSKLESGV PDRFTGSGSG
201  TDFTLKISRV EAEDLGVYYC LQATHFPWTF GGGTKLEIKR AAALESRGPF
251  EGKPIPNPLL GLDSTRTGHH HHHH (SEQ ID NO:91)
```

1    GGCCCAGCCG GCCATGGCCC AGGTCCAACT GCAGCAGCCT GGGGCTGAGC
       CCGGGTCGGC CGGTACCGGG TCCAGGTTGA CGTCGTCGGA CCCCGACTCG 3-631-436 VH
       ~~~~~~~~~~~~~~~~~~~~~~~~~~~~~~~~~~~~~~~~~~~~~~~~~~~
                                                     CDR H1
 51    TGGTGAGGCC TGGGGCTTCA GTGAAGCTGT CCTGCAAGGC TTCTGGCTAC
       ACCACTCCGG ACCCCGAAGT CACTTCGACA GGACGTTCCG AAGACCGATG
                          3-631-436 VH
       ~~~~~~~~~~~~~~~~~~~~~~~~~~~~~~~~~~~~~~~~~~~~~~~~~~~
       ----------------------(10)
101    ACGTTCACCA GTTACTGGAT GAACTGGGTT AAACAGAGGC CTGAGCAAGG
       TGCAAGTGGT CAATGACCTA CTTGACCCAA TTTGTCTCCG GACTCGTTCC
                          3-631-436 VH
       ~~~~~~~~~~~~~~~~~~~~~~~~~~~~~~~~~~~~~~~~~~~~~~~~~~~
                  CDR H2-----------------------------

151    CCTTGAGTGG ATTGGAAGGA TTGATCCTTA CGATAGTGAA ACTCACTACA
       GGAACTCACC TAACCTTCCT AACTAGGAAT GCTATCACTT TGAGTGATGT
                          3-631-436 VH
       ~~~~~~~~~~~~~~~~~~~~~~~~~~~~~~~~~~~~~~~~~~~~~~~~~~~
       ---------------(17)
201    ATCAAAAGTT CAAGGACAAG GCCATTTGA CTGTAGACAA ATCCTCCAGC
       TAGTTTTCAA GTTCCTGTTC CGGTAAAACT GACATCTGTT TAGGAGGTCG
                          3-631-436 VH
       ~~~~~~~~~~~~~~~~~~~~~~~~~~~~~~~~~~~~~~~~~~~~~~~~~~~
251    ACAGCCTTCG TGCAACTCAC CAGCCTGACA TCTGAGGACT CTGCGGTCTA
       TGTCGGAAGC ACGTTGAGTG GTCGGACTGT AGACTCCTGA GACGCCAGAT
                          3-631-436 VH
       ~~~~~~~~~~~~~~~~~~~~~~~~~~~~~~~~~~~~~~~~~~~~~~~~~~~
                 CDR H3-(3)
301    TTATTGCGTC TCTGATGGTT ACTGGGGCGC AGGGACCACG GTCACCGTCT
       AATAACGCAG AGACTACCAA TGACCCCGCG TCCCTGGTGC CAGTGGCAGA
                           Linker 40
            ~~~~~~~~~~~~~~~~~~~~~~~~~~~~~~~~~~~~~~~~~~~~~~
       VH
       ~~~~~
351    CCTCAGGTCC CGCCAAGGAG TTGACGCCCC TGAAGGAGGC GAAGGTCTCT
       GGAGTCCAGG GCGGTTCCTC AACTGCGGGG ACTTCCTCCG CTTCCAGAGA
                          3-631-436 VL
       ~~~~~~~~~~~~~~~~~~~~~~~~~~~~~~~~~~~~~~~~~~~~~~~~~~~
401    GATGTTGTTA TGACTCAGAC ACCACTCACT TTGTCGGTTA CCACTGGACA
       CTACAACAAT ACTGAGTCTG TGGTGAGTGA AACAGCCAAT GGTGACCTGT
                          3-631-436 VL
       ~~~~~~~~~~~~~~~~~~~~~~~~~~~~~~~~~~~~~~~~~~~~~~~~~~~
                                 CDR L1----------------------
451    ACCAGCTTCC ATCTCTTGCA AGTCAAGTCA GAGCCTCTTA GATAGTGATG
       TGGTCGAAGG TAGAGAACGT TCAGTTCAGT CTCGGAGAAT CTATCACTAC
                          3-631-436 VL
       ~~~~~~~~~~~~~~~~~~~~~~~~~~~~~~~~~~~~~~~~~~~~~~~~~~~
       ---------------(16)
```

FIGURE 25B

```
501    GAAAAACCTA TTTAAATTGG TTATTCCAGA GGCCAGGCGA GTCTCCAAAG
       CTTTTTGGAT AAATTTAACC AATAAGGTCT CCGGTCCGCT CAGAGGTTTC
                              3-631-436 VL
       ~~~~~~~~~~~~~~~~~~~~~~~~~~~~~~~~~~~~~~~~~~~~~~~~~~
                  CDR L2-------------(7)
551    CTCCTAATCT ATGTGGTGTC TAAACTGGAG TCTGGAGTCC CTGACAGGTT
       GAGGATTAGA TACACCACAG ATTTGACCTC AGACCTCAGG GACTGTCCAA 3-631-436 VL
       ~~~~~~~~~~~~~~~~~~~~~~~~~~~~~~~~~~~~~~~~~~~~~~~~~~
601    CACTGGCAGT GGATCAGGGA CAGATTTCAC ACTGAAAATC AGCAGAGTGG
       GTGACCGTCA CCTAGTCCCT GTCTAAAGTG TGACTTTTAG TCGTCTCACC
                              3-631-436 VL
       ~~~~~~~~~~~~~~~~~~~~~~~~~~~~~~~~~~~~~~~~~~~~~~~~~~
                                CDR L3-------------(7)
651    AGGCTGAGGA TTTGGGAGTT TATTACTGCT TGCAAGCTAC ACATTTTCCG
       TCCGACTCCT AAACCCTCAA ATAATGACGA ACGTTCGATG TGTAAAAGGC
                         3631VL
       ~~~~~~~~~~~~~~~~~~~~~~~~~~~~~~~~~~~~~~~~
701    TGGACGTTCG GTGGAGGCAC CAAGCTGGAA ATCAAACGGG CGGCCGCCCT
       ACCTGCAAGC CACCTCCGTG GTTCGACCTT TAGTTTGCCC GCCGGCGGGA
                                                    V5 Epitope
                                             ~~~~~~~~~~~~~~~~~~~~~~~~~~
751    CGAGTCTAGA GGGCCCTTCG AAGGTAAGCC TATCCCTAAC CCTCTCCTCG
       GCTCAGATCT CCCGGGAAGC TTCCATTCGG ATAGGGATTG GGAGAGGAGC V5 Epitope                         poly HIS
       ~~~~~~~~~~~~~~~                   ~~~~~~~~~~~~~~~~~~
801    GTCTCGATTC TACGCGTACC GGTCATCATC ACCATCACCA T
       CAGAGCTAAG ATGCGCATGG CCAGTAGTAG TGGTAGTGGT A
```

FIGURE 26
FIGURE 26A
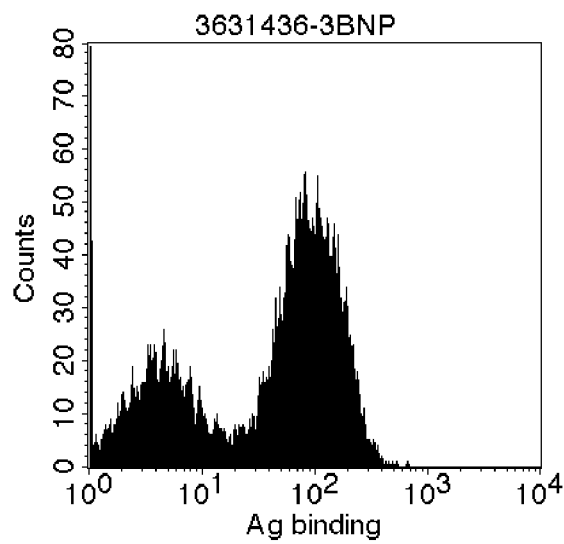
FIGURE 26B
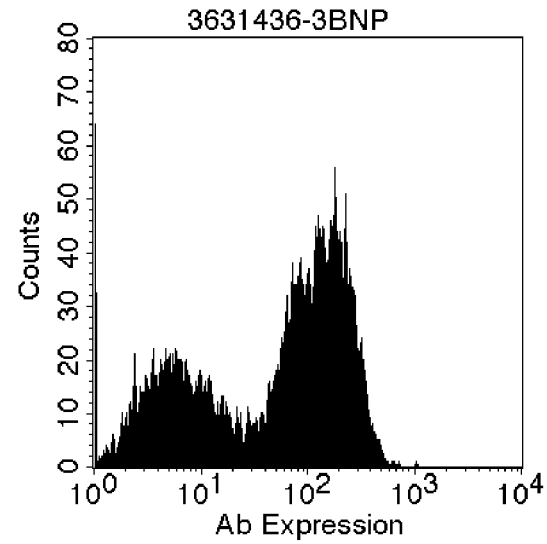

FIGURE 28

| Selection Strategy | Clone Name | koff (sec$^{-1}$) | Fold Improvement |
|---|---|---|---|
| N/A | 3-631-436 | 4.8E-03 | ----- |
| Equilibrium | L2 1 | 2.5E-04 | 19 |
| Equilibrium | L2 4 | 1.4E-03 | 4 |
| Equilibrium | L2 7 | 1.5E-04 | 32 |
| Equilibrium | L2 8 | 1.7E-04 | 28 |
| Off-rate | L2 9 | 5.0E-04 | 10 |
| Off-rate | L2 10 | 1.9E-03 | 3 |
| On/Off-rate | 500-1 | 5.3E-04 | 9 |
| On/Off-rate | 500-2 | 3.2E-04 | 15 |
| On/Off-rate | 500-5 | 1.7E-04 | 28 |
| On/Off-rate | 500-10 | 4.9E-04 | 10 |

FIGURE 29

| Clone Name | Position 50 | Position 51 | Position 52 | Position 53 |
|---|---|---|---|---|
| 3-631-436 | Val (GTG) | Val (GTG) | Ser (TCT) | Lys (AAA) |
| L2 1 | Gln (CAG) | Asn (AAC) | Thr (ACG) | Lys (AAA) |
| L2 4 | His (CAC) | Thr (ACG) | Thr (ACG) | Lys (AAA) |
| L2 7 | Trp (TGG) | Met (ATG) | Thr (ACC) | Lys (AAA) |
| L2 8 | Trp (TGG) | Met (ATG) | Asn (AAC) | Lys (AAA) |
| L2 9 | Val (GTG) | Thr (ACC) | Asp (GAC) | Lys (AAG) |
| L2 10 | Arg (CGC) | Thr (ACG) | Asn (AAC) | Lys (AAA) |
| 500-1 | Trp (TGG) | Met (ATG) | Asp (GAC) | Lys (AAA) |
| 500-2 | Trp (TGG) | Thr (ACG) | Thr (ACG) | Lys (AAA) |
| 500-10 | Val (GTG) | Thr (ACG) | Asp (GAC) | Ile (ATC) |

FIGURE 30

| Clone Name | Isotype | IgG name | KinExA (pM) | Biacore (pM) | Biacore kon (M$^{-1}$sec$^{-1}$) | Biacore koff (sec$^{-1}$) |
|---|---|---|---|---|---|---|
| 3-631-436 | mIgG2aκ |  | 286 | 375 | 6.7E+06 | 2.5E-03 |
| 3-631-436 | mIgG2bκ | AM1 | ND | 363 | 8.4E+06 | 2.9E-03 |
| L2 1 | mIgG2bκ | AM2 | 94 | 155 | 3.6E+06 | 5.6E-04 |
| L2 7 | mIgG2bκ | AM3 | 156 | 213 | 5.8E+06 | 1.6E-03 |
| L2 8 | mIgG2bκ | AM4 | 101 | 371 | 1.6E+06 | 6.0E-04 |
| L2 9 | mIgG2bκ | AM5 | 218 | 144 | 7.9E+06 | 1.1E-03 |
| 500-2 | mIgG2bκ | AM6 | 203 | 280 | 1.5E+06 | 4.1E-04 |
| 500-10 | mIgG2bκ | AM8 | 41 | 101 | 8.1E+06 | 8.2E-04 |

FIGURE 31A

Degenerate Oligonucleotides: N=A, G, C, T; S=G, C

CDR H1 Degenerate Oligonucleotides (8)

| System | Code | CDR | Library name | Length (nucleotide, "ntd") |
|---|---|---|---|---|
| 3-631-436 | 1-1h | H1 | H1-1 | 102 |
| 3-631-436 | 1-2h | H1 | H1-2 | 102 |
| 3-631-436 | 1-3h | H1 | H1-3 | 102 |
| 3-631-436 | 1-4h | H1 | H1-4 | 102 |
| 3-631-436 | 1-5h | H1 | H1-5 | 102 |
| 3-631-436 | 1-6h | H1 | H1-6 | 102 |
| 3-631-436 | 1-7h | H1 | H1-7 | 102 |
| 3-631-436 | 1-8h | H1 | H1-8 | 102 |

Oligo 1-1h
```
CCT GGG GCT TCA GTG AAG CTG TCC TGC AAG GCT TCT NNS NNS NNS TTC ACC AGT TAC TGG ATG
AAC TGG GTT AAA CAG AGG CCT GAG CAA GGC CTT GAG TGG (SEQ ID NO:93)
```

Oligo 1-2h
```
CCT GGG GCT TCA GTG AAG CTG TCC TGC AAG GCT TCT GGC NNS NNS NNS ACC AGT TAC TGG ATG
AAC TGG GTT AAA CAG AGG CCT GAG CAA GGC CTT GAG TGG (SEQ ID NO:94)
```

Oligo 1-3h
```
CCT GGG GCT TCA GTG AAG CTG TCC TGC AAG GCT TCT GGC TAC NNS NNS NNS AGT TAC TGG ATG
AAC TGG GTT AAA CAG AGG CCT GAG CAA GGC CTT GAG TGG (SEQ ID NO:95)
```

Oligo 1-4h
```
CCT GGG GCT TCA GTG AAG CTG TCC TGC AAG GCT TCT GGC TAC ACG NNS NNS NNS TAC TGG ATG
AAC TGG GTT AAA CAG AGG CCT GAG CAA GGC CTT GAG TGG (SEQ ID NO:96)
```

Oligo 1-5h
```
CCT GGG GCT TCA GTG AAG CTG TCC TGC AAG GCT TCT GGC TAC ACG TTC NNS NNS NNS TGG ATG
AAC TGG GTT AAA CAG AGG CCT GAG CAA GGC CTT GAG TGG (SEQ ID NO:97)
```

Oligo 1-6h
```
CCT GGG GCT TCA GTG AAG CTG TCC TGC AAG GCT TCT GGC TAC ACG TTC ACC NNS NNS NSS ATG
AAC TGG GTT AAA CAG AGG CCT GAG CAA GGC CTT GAG TGG (SEQ ID NO:98)
```

Oligo 1-7h
```
CCT GGG GCT TCA GTG AAG CTG TCC TGC AAG GCT TCT GGC TAC ACG TTC ACC AGT NNS NNS NNS
AAC TGG GTT AAA CAG AGG CCT GAG CAA GGC CTT GAG TGG (SEQ ID NO:99)
```

Oligo 1-8h
```
CCT GGG GCT TCA GTG AAG CTG TCC TGC AAG GCT TCT GGC TAC ACG TTC ACC AGT TAC NNS NNS
NNS TGG GTT AAA CAG AGG CCT GAG CAA GGC CTT GAG TGG (SEQ ID NO:100)
```

FIGURE 31B

CDR H2 Degenerate Oligonucleotides (15)

| System | Code | CDR | Library name | Length (ntd) |
|---|---|---|---|---|
| 3-631-436 | 2-1-1h | H2 | H2-1-1 | 102 |
| 3-631-436 | 2-1-2h | H2 | H2-1-2 | 102 |
| 3-631-436 | 2-1-3h | H2 | H2-1-3 | 102 |
| 3-631-436 | 2-1-4h | H2 | H2-1-4 | 102 |
| 3-631-436 | 2-1-5h | H2 | H2-1-5 | 102 |
| 3-631-436 | 2-1-6h | H2 | H2-1-6 | 102 |
| 3-631-436 | 2-1-7h | H2 | H2-1-7 | 102 |
| 3-631-436 | 2-1-8h | H2 | H2-1-8 | 102 |
| 3-631-436 | 2-2-1h | H2 | H2-2-1 | 99 |
| 3-631-436 | 2-2-2h | H2 | H2-2-2 | 99 |
| 3-631-436 | 2-2-3h | H2 | H2-2-3 | 99 |
| 3-631-436 | 2-2-4h | H2 | H2-2-4 | 99 |
| 3-631-436 | 2-2-5h | H2 | H2-2-5 | 99 |
| 3-631-436 | 2-2-6h | H2 | H2-2-6 | 99 |
| 3-631-436 | 2-2-7h | H2 | H2-2-7 | 99 |

Oligo 2-1-1h
AAA CAG AGG CCT GAG CAA GGC CTT GAG TGG ATT GGA **NNS NNS NNS CCT TAC GAT AGT GAA ACT
CAC** TAC AAT CAA AAG TTC AAG GAC AAG GCC ATT TTG ACT (SEQ ID NO:101)

Oligo 2-1-2h
AAA CAG AGG CCT GAG CAA GGC CTT GAG TGG ATT GGA **AGG NNS NNS NNS TAC GAT AGT GAA ACT
CAC** TAC AAT CAA AAG TTC AAG GAC AAG GCC ATT TTG ACT (SEQ ID NO:102)

Oligo 2-1-3h
AAA CAG AGG CCT GAG CAA GGC CTT GAG TGG ATT GGA **AGG ATT NNS NNS NNS GAT AGT GAA ACT
CAC** TAC AAT CAA AAG TTC AAG GAC AAG GCC ATT TTG ACT (SEQ ID NO:103)

Oligo 2-1-4h
AAA CAG AGG CCT GAG CAA GGC CTT GAG TGG ATT GGA **AGG ATT GAT NNS NNS NNS AGT GAA ACT
CAC** TAC AAT CAA AAG TTC AAG GAC AAG GCC ATT TTG ACT (SEQ ID NO:104)

Oligo 2-1-5h
AAA CAG AGG CCT GAG CAA GGC CTT GAG TGG ATT GGA **AGG ATT GAT CCT NNS NNS NNS GAA ACT
CAC** TAC AAT CAA AAG TTC AAG GAC AAG GCC ATT TTG ACT (SEQ ID NO:105)

Oligo 2-1-6h
AAA CAG AGG CCT GAG CAA GGC CTT GAG TGG ATT GGA **AGG ATT GAT CCT TAC NNS NNS NNS ACT
CAC** TAC AAT CAA AAG TTC AAG GAC AAG GCC ATT TTG ACT (SEQ ID NO:106)

Oligo 2-1-7h
AAA CAG AGG CCT GAG CAA GGC CTT GAG TGG ATT GGA **AGG ATT GAT CCT TAC GAT NNS NNS NNS
CAC** TAC AAT CAA AAG TTC AAG GAC AAG GCC ATT TTG ACT (SEQ ID NO:107)

Oligo 2-1-8h
AAA CAG AGG CCT GAG CAA GGC CTT GAG TGG ATT GGA **AGG ATT GAT CCT TAC GAT AGT NNS NNS
NNS** TAC AAT CAA AAG TTC AAG GAC AAG GCC ATT TTG ACT (SEQ ID NO:108)

FIGURE 31C

Oligo 2-2-1h
GAG TGG ATT GGA AGG ATT GAT CCT TAC GAT AGT GAA NNS NNS NNS AAT CAA AAG TTC AAG GAC
AAG GCC ATT TTG ACT GTA GAC AAA TCC TCC AGC ACA (SEQ ID NO:109)

Oligo 2-2-2h
GAG TGG ATT GGA AGG ATT GAT CCT TAC GAT AGT GAA ACT NNS NNS NNS CAA AAG TTC AAG GAC
AAG GCC ATT TTG ACT GTA GAC AAA TCC TCC AGC ACA (SEQ ID NO:110)

Oligo 2-2-3h
GAG TGG ATT GGA AGG ATT GAT CCT TAC GAT AGT GAA ACT CAC NNS NNS NNS AAG TTC AAG GAC
AAG GCC ATT TTG ACT GTA GAC AAA TCC TCC AGC ACA (SEQ ID NO:111)

Oligo 2-2-4h
GAG TGG ATT GGA AGG ATT GAT CCT TAC GAT AGT GAA ACT CAC TAC NNS NNS NNS TTC AAG GAC
AAG GCC ATT TTG ACT GTA GAC AAA TCC TCC AGC ACA (SEQ ID NO:112)

Oligo 2-2-5h
GAG TGG ATT GGA AGG ATT GAT CCT TAC GAT AGT GAA ACT CAC TAC AAT NNS NNS NNS AAG GAC
AAG GCC ATT TTG ACT GTA GAC AAA TCC TCC AGC ACA (SEQ ID NO:113)

Oligo 2-2-6h
GAG TGG ATT GGA AGG ATT GAT CCT TAC GAT AGT GAA ACT CAC TAC AAT CAA NNS NNS NNS GAC
AAG GCC ATT TTG ACT GTA GAC AAA TCC TCC AGC ACA (SEQ ID NO:114)

Oligo 2-2-7h
GAG TGG ATT GGA AGG ATT GAT CCT TAC GAT AGT GAA ACT CAC TAC AAT CAA AAG NNS NNS NNS
AAG GCC ATT TTG ACT GTA GAC AAA TCC TCC AGC ACA (SEQ ID NO:115)

CDR H3 Degenerate Oligonucleotides (1)

| System | Code | CDR | Library name | Length (ntd) |
|---|---|---|---|---|
| 3-631-436 | 3-1h | H3 | H3-1 | 93 |

Oligo 3-1h
AGC CTG ACA TCT GAG GAC TCT GCG GTC TAT TAT TGC GTC TCT NNS NNS NNS TGG GGC GCA GGG
ACC ACG GTC ACC GTC TCC TCA GGT CCC GCC (SEQ ID NO:116)

FIGURE 31D

CDR L1 Degenerate Oligonucleotides (14)

| System | Code | CDR | Library name | Length (ntd) |
|---|---|---|---|---|
| 3-631-436 | 1-1-1L | L1 | L1-1 | 102 |
| 3-631-436 | 1-1-2L | L1 | L1-2 | 102 |
| 3-631-436 | 1-1-3L | L1 | L1-3 | 102 |
| 3-631-436 | 1-1-4L | L1 | L1-4 | 102 |
| 3-631-436 | 1-1-5L | L1 | L1-5 | 102 |
| 3-631-436 | 1-1-6L | L1 | L1-6 | 102 |
| 3-631-436 | 1-1-7L | L1 | L1-7 | 102 |
| 3-631-436 | 1-1-8L | L1 | L1-8 | 102 |
| 3-631-436 | 1-2-1L | L1 | L1-2-1 | 96 |
| 3-631-436 | 1-2-2L | L1 | L1-2-2 | 96 |
| 3-631-436 | 1-2-3L | L1 | L1-2-3 | 96 |
| 3-631-436 | 1-2-4L | L1 | L1-2-4 | 96 |
| 3-631-436 | 1-2-5L | L1 | L1-2-5 | 96 |
| 3-631-436 | 1-2-6L | L1 | L1-2-6 | 96 |

Oligo 1-1-1L
TCG GTT ACC ACT GGA CAA CCA GCT TCC ATC TCT TGC NNS NNS NNS CAG AGC CTC TTA GAT AGT
GAT GGA AAA ACC TAT TTA AAT TGG TTA TTC CAG AGG CCA (SEQ ID NO:117)

Oligo 1-1-2L
TCG GTT ACC ACT GGA CAA CCA GCT TCC ATC TCT TGC AAG NNS NNS NNS AGC CTC TTA GAT AGT
GAT GGA AAA ACC TAT TTA AAT TGG TTA TTC CAG AGG CCA (SEQ ID NO:118)

Oligo 1-1-3L
TCG GTT ACC ACT GGA CAA CCA GCT TCC ATC TCT TGC AAG TCA NNS NNS NNS CTC TTA GAT AGT
GAT GGA AAA ACC TAT TTA AAT TGG TTA TTC CAG AGG CCA (SEQ ID NO:119)

Oligo 1-1-4L
TCG GTT ACC ACT GGA CAA CCA GCT TCC ATC TCT TGC AAG TCA AGT NNS NNS NNS TTA GAT AGT
GAT GGA AAA ACC TAT TTA AAT TGG TTA TTC CAG AGG CCA (SEQ ID NO:120)

Oligo 1-1-5L
TCG GTT ACC ACT GGA CAA CCA GCT TCC ATC TCT TGC AAG TCA AGT CAG NNS NNS NNS GAT AGT
GAT GGA AAA ACC TAT TTA AAT TGG TTA TTC CAG AGG CCA (SEQ ID NO:121)

Oligo 1-1-6L
TCG GTT ACC ACT GGA CAA CCA GCT TCC ATC TCT TGC AAG TCA AGT CAG AGC NNS NNS NNS AGT
GAT GGA AAA ACC TAT TTA AAT TGG TTA TTC CAG AGG CCA (SEQ ID NO:122)

Oligo 1-1-7L
TCG GTT ACC ACT GGA CAA CCA GCT TCC ATC TCT TGC AAG TCA AGT CAG AGC CTC NNS NNS NNS
GAT GGA AAA ACC TAT TTA AAT TGG TTA TTC CAG AGG CCA (SEQ ID NO:123)

Oligo 1-1-8L
TCG GTT ACC ACT GGA CAA CCA GCT TCC ATC TCT TGC **AAG TCA AGT CAG AGC CTC TTA NNS NNS
NNS** GGA AAA ACC TAT TTA AAT TGG TTA TTC CAG AGG CCA (SEQ ID NO:124)

FIGURE 31E

Oligo 1-2-1L
TCC ATC TCT TGC AAG TCA AGT CAG AGC CTC TTA GAT NNS NNS NNS AAA ACC TAT TTA AAT TGG
TTA TTC CAG AGG CCA GGC GAG TCT CCA AAG CTC (SEQ ID NO: 125)

Oligo 1-2-2L
TCC ATC TCT TGC AAG TCA AGT CAG AGC CTC TTA GAT AGT NNS NNS NNS ACC TAT TTA AAT TGG
TTA TTC CAG AGG CCA GGC GAG TCT CCA AAG CTC (SEQ ID NO:126)

Oligo 1-2-3L
TCC ATC TCT TGC AAG TCA AGT CAG AGC CTC TTA GAT AGT GAT NNS NNS NNS TAT TTA AAT TGG
TTA TTC CAG AGG CCA GGC GAG TCT CCA AAG CTC (SEQ ID NO:127)

Oligo 1-2-4L
TCC ATC TCT TGC AAG TCA AGT CAG AGC CTC TTA GAT AGT GAT GGA NNS NNS NNS TTA AAT TGG
TTA TTC CAG AGG CCA GGC GAG TCT CCA AAG CTC (SEQ ID NO:128)

Oligo 1-2-5L
TCC ATC TCT TGC AAG TCA AGT CAG AGC CTC TTA GAT AGT GAT GGA AAA NNS NNS NNS AAT TGG
TTA TTC CAG AGG CCA GGC GAG TCT CCA AAG CTC (SEQ ID NO: 129)

Oligo 1-2-6L
TCC ATC TCT TGC AAG TCA AGT CAG AGC CTC TTA GAT AGT GAT GGA AAA ACC NNS NNS NNS TGG
TTA TTC CAG AGG CCA GGC GAG TCT CCA AAG CTC (SEQ ID NO: 130)

CDR L2 Degenerate Oligonucleotides (5)

| System | Code | CDR | Library name | Length (ntd) |
|---|---|---|---|---|
| 3-631-436 | 2-1L | L2 | L2-1 | 93 |
| 3-631-436 | 2-2L | L2 | L2-2 | 93 |
| 3-631-436 | 2-3L | L2 | L2-3 | 93 |
| 3-631-436 | 2-4L | L2 | L2-4 | 93 |
| 3-631-436 | 2-5L | L2 | L2-5 | 93 |

Oligo 2-1L
CAG AGG CCA GGC GAG TCT CCA AAG CTC CTA ATC TAT NNS NNS NNS AAA CTG GAG TCT GGA GTC
CCT GAC AGG TTC ACT GGC AGT GGA TCA GGG (SEQ ID NO:131)

Oligo 2-2L
CAG AGG CCA GGC GAG TCT CCA AAG CTC CTA ATC TAT GTG NNS NNS NNS CTG GAG TCT GGA GTC
CCT GAC AGG TTC ACT GGC AGT GGA TCA GGG (SEQ ID NO:132)

Oligo 2-3L
CAG AGG CCA GGC GAG TCT CCA AAG CTC CTA ATC TAT GTG GTG NNS NNS NNS GAG TCT GGA GTC
CCT GAC AGG TTC ACT GGC AGT GGA TCA GGG (SEQ ID NO:133)

Oligo 2-4L
CAG AGG CCA GGC GAG TCT CCA AAG CTC CTA ATC TAT GTG GTG TCT NNS NNS NNS TCT GGA GTC
CCT GAC AGG TTC ACT GGC AGT GGA TCA GGG (SEQ ID NO:134)

FIGURE 31F

Oligo 2-5L
CAG AGG CCA GGC GAG TCT CCA AAG CTC CTA ATC TAT GTG GTG TCT AAA NNS NNS NNS GGA GTC
CCT GAC AGG TTC ACT GGC AGT GGA TCA GGG (SEQ ID NO:135)

CDR L3 Degenerate Oligonucleotides (7)

| System | Code | CDR | Library name | Length (ntd) |
|---|---|---|---|---|
| 3-631-436 | 3-1L | L3 | L3-1 | 99 |
| 3-631-436 | 3-2L | L3 | L3-2 | 99 |
| 3-631-436 | 3-3L | L3 | L3-3 | 99 |
| 3-631-436 | 3-4L | L3 | L3-4 | 99 |
| 3-631-436 | 3-5L | L3 | L3-5 | 99 |
| 3-631-436 | 3-6L | L3 | L3-6 | 99 |
| 3-631-436 | 3-7L | L3 | L3-7 | 99 |

Oligo 3-1L
AGA GTG GAG GCT GAG GAT TTG GGA GTT TAT TAC TGC NNS NNS NNS ACA CAT TTT CCG TGG ACG
TTC GGT GGA GGC ACC AAG CTG AAA ATC AAA CGG GCG (SEQ ID NO:136)

Oligo 3-2L
AGA GTG GAG GCT GAG GAT TTG GGA GTT TAT TAC TGC TTG NNS NNS NNS CAT TTT CCG TGG ACG
TTC GGT GGA GGC ACC AAG CTG AAA ATC AAA CGG GCG (SEQ ID NO:137)

Oligo 3-3L
 AGA GTG GAG GCT GAG GAT TTG GGA GTT TAT TAC TGC **TTG CAA NNS NNS NNS TTT CCG TGG
ACG** TTC GGT GGA GGC ACC AAG CTG AAA ATC AAA CGG GCG (SEQ ID NO:138)

Oligo 3-4L
AGA GTG GAG GCT GAG GAT TTG GGA GTT TAT TAC TGC TTG CAA GCT NNS NNS NNS CCG TGG ACG
TTC GGT GGA GGC ACC AAG CTG AAA ATC AAA CGG GCG (SEQ ID NO:139)

Oligo 3-5L
AGA GTG GAG GCT GAG GAT TTG GGA GTT TAT TAC TGC TTG CAA GCT ACA NNS NNS NNS TGG ACG
TTC GGT GGA GGC ACC AAG CTG AAA ATC AAA CGG GCG (SEQ ID NO:140)

Oligo 3-6L
AGA GTG GAG GCT GAG GAT TTG GGA GTT TAT TAC TGC TTG CAA GCT ACA CAT NNS NNS NNS ACG
TTC GGT GGA GGC ACC AAG CTG AAA ATC AAA CGG GCG (SEQ ID NO:141)

Oligo 3-7L
AGA GTG GAG GCT GAG GAT TTG GGA GTT TAT TAC TGC TTG CAA GCT ACA CAT TTT NNS NNS NNS
TTC GGT GGA GGC ACC AAG CTG AAA ATC AAA CGG GCG (SEQ ID NO:142)

HUMAN BNP IMMUNOSPECIFIC ANTIBODIES

RELATED APPLICATION INFORMATION

This application is a continuation-in-part of U.S. application Ser. No. 11/595,625, filed on Nov. 9, 2006 now abandonded, which claims the benefit of U.S. Application No. 60/734,964, filed Nov. 9, 2005, which is incorporated herein by reference in its entirety.

SEQUENCE LISTING

The instant application contains a Sequence Listing which has been submitted via EFS-Web and is hereby incorporated by reference in its entirety. Said ASCII copy, created on Dec. 4, 2009, is named 8022USP1.txt, and is 93,298 bytes in size.

FIELD OF THE INVENTION

The present invention relates to antibodies that immunospecifically bind to human brain natriuretic peptide or a human brain natriuretic peptide fragment with a high binding affinity, methods for producing and selecting said antibodies, immunoassays for human brain natriuretic peptide or a human brain natriuretic peptide fragment that employ said antibodies and therapeutic compositions containing said antibodies.

BACKGROUND OF THE INVENTION

Atrial natriuretic peptide (hereinafter referred to as "ANP"), brain natriuretic peptide (hereinafter referred to as "BNP"), C-type natriuretic peptide (hereinafter referred to as "CNP") and Dendroaspis natriuretic peptide (hereinafter referred to as "DNP") are each members of a family of hormones known as "natriuretic peptides". ANP and BNP share a wide spectrum of biological properties and belong to the cardiac natriuretic system. Both ANP and BNP are of myocardial cell origin while CNP is of endothelial cell origin. DNP was isolated from the venom of the green mamba snake and possesses structural similarity to ANP, BNP and CNP.

BNP received its name because it was first isolated from porcine brain, thus "BNP" stood for "brain natriuretic peptide". However, because BNP belongs to the cardiac natriuretic system, "brain" has been changed to "B-type". Therefore, "BNP" now refers to "B-type natriuretic peptide".

ANP is secreted by the heart in the atria. BNP is secreted by the heart through the coronary sinus, predominantly from the cardiac ventricles. BNP is secreted as a 108 amino acid polypeptide precursor (See Valli et al., *J. Lab. Clin. Med.*, 134(5):437-444 (November 1999)). The mature form of BNP is made up of 32 amino acids (representing amino acids 77-108 of the 108 amino acid polypeptide precursor) with a 17 amino acid ring closed by a disulfide bond between two cysteine residues, an amino-terminal tail of 9 amino acids, and a carboxyl-terminal tail of 6 amino acids. ANP and CNP also have a 17 amino acid ring closed by a disulfide bond between two cysteine residues. Eleven of the seventeen amino acids in the ring are conserved between the three molecules. In addition to the 17 amino acid ring structure, ANP has an amino-terminal tail of 6 amino acids and a carboxy-terminal tail of 5 amino acids. ANP is produced as a 126 amino acid pro-ANP form that is the major storage form of ANP. After proteolytic cleavage between amino acids 98 and 99, the mature 28 amino acid peptide ANP is found in coronary sinus plasma (See Yandle, *J. Internal Med.*, 235:561-576 (1994)).

CNP is found in the brain and cerebral spinal fluid and is the most prevalent of the three peptides in the central nervous system. Little if any CNP is present in the heart. Pro-CNP is a 103 amino acid peptide that is processed into either CNP-53 (amino acids 51 to 103) or CNP-22 (amino acids 82 to 103) that are the active peptides. In addition the 17 amino acid ring structure, CNP-22 has an amino-terminal tail of 5 amino acids and contains no carboxy-terminal tail. CNP-53 is identical to CNP-22 except for a 31 amino acid extension at the amino terminal end.

As mentioned previously, DNP was isolated from the venom of the green mamba snake. The mature form of DNP is made up of 38 amino acids. DNP-like immunoreactivity (DNP-L1) has been reported in human plasma and the plasma concentration of DNP-L1 has been found to be elevated in patients with congestive heart failure (See, Cataliotti, et al., *Mayo Clin. Proc.*, 76:111-1119 (2001)). Additionally, it is also known that the infusion of synthetic DNP results in marked natriuresis and diuresis in association with increased plasma and urinary cyclic guanosine monophosphate. Id.

One of the problems with natural human natriuretic peptides is that they are unstable in plasma and serum. Specifically, enzymes, such as proteases, cleave these peptides. For example, proteases cleave BNP (natural and synthetic) at various locations along its amino acid chain. For example, protease cleavage is known to occur at the amino terminus of BNP between amino acids 2-3 (Shimizu et al., *Clinica Chimica Acta*, 316:129-135 (2002)) and at its carboxy terminus between amino acids 30-32. Moreover, endopeptidase cleavage of BNP is also known in the art (Davidson and Struthers, *J. Hypertension*, 12:329-336 (1994)).

The measurement of mature BNP (i.e., the 32 amino acid molecule (amino acids 77-108 of the precursor polypeptide of BNP)) in humans (hereinafter referred to has "hBNP"), in the general population has been found to reflect cardiac diseases, such as congestive heart failure, ischemic heart diseases, atrial fibrillation and renal dysfunction. In fact, elevated levels of BNP in human plasma have been reported in heart disease, following acute myocardial infarction and during symptomless or subclinical ventricular dysfunction (See Mukoyama et al., *J. Clin. Invest.*, 87:11402-11412 (1991), Motwani et al., *Lancet*, 341:1109-1113 (1993), Yoshibayashi et al., *New Eng. J. Med.*, 327:434 (1992)). Increased circulating levels of ANP are seen in congestive heart failure, chronic renal failure and in severe hypertension. The presence of CNP in human plasma remains controversial with reports of its absence or presence as CNP-22 (See Yandle, *J. Internal Med.*, 235:561-576 (1994)).

A ligand binding assay is an analytical technique for measuring concentrations of substances commonly referred to as ligands that react selectively with specific binding proteins. Immunoassays that measure the concentrations of antigens that react selectively with specific antibodies are an example of a class of ligand binding assays.

Ligand binding assays, such as immunoassays, for measuring human natriuretic peptides in plasma, particularly hBNP, are well-known in the art and are commercially available. These immunoassays require the use of at least one or two specific antibodies as well as at least one calibrator and, ideally, at least one control. In addition to the calibrators and controls, immunoassays require the use of at least one test sample. Test samples are normally biological samples derived from serum, plasma, whole blood or other bodily fluids (normally from a human patient). The levels of at least one human natriuretic peptide in the test sample is quantified in the immunoassay.

For example, U.S. Pat. No. 6,162,902 (hereinafter referred to as the "'902 patent") discloses isolated antibodies that are monospecifically reactive to epitopes 1-10, 5-13 and 15-25 of hBNP. More particularly, the '902 patent describes two isolated monoclonal antibodies. The first monoclonal antibody is produced by hybridoma cell line 106.3 (A.T.C.C. Accession No. HB-12044) and is monospecifically reactive to epitopes 5-13 of hBNP. The second monoclonal antibody is produced by hybridoma cell line 201.3 (A.T.C.C. Accession No. HB 12045) and is monospecifically reactive to epitopes 1-10 of hBNP. The '902 patent also describes the use of the above antibodies in immunoassays for the purpose of quantifying the amount of hBNP in a biological sample. U.S. Pat. No. 6,677,124 (hereinafter referred to as the "'124 patent") discloses a monoclonal antibody that binds to an epitope having the amino acid sequence of LYS-VAL-LEU-ARG-ARG-HIS (SEQ ID NO: 159) that is found in the C-terminal region of hBNP, namely epitopes 27-32. More particularly, the '124 patent describes a monoclonal antibody produced by hybridoma cell line BC203 (FERM BP-3515). The '124 patent also describes immunoassays for hBNP using this monoclonal antibody.

It is generally known in the art that the specificity and sensitivity of the antibodies used in immunoassays, such as hBNP immunoassays, are very important. One way in which to increase both the specificity and sensitivity of one or more antibodies is to improve the binding affinity of an antibody for its intended target (i.e., an antigen). Antibodies having an improved binding affinity for their intended targets should exhibit increased specificity and sensitivity. Therefore, there is a need in the art for new antibodies that specifically bind to human BNP with a high binding affinity and thus exhibit high specificity and sensitivity when used in said hBNP immunoassays.

BRIEF SUMMARY OF THE INVENTION

In one aspect, the present invention relates to an isolated antibody which immunospecifically binds to an epitope comprising amino acid residues 5 through 13 of human brain natriuretic peptide ("hBNP") with at least about a two fold improvement in its equilibrium dissociation constant ($K_D$) when compared with an antibody produced by hybridoma cell line 106.3, said cell line having A.T.C.C. Accession No. HB-12044. More specifically, the antibody of the present invention exhibits at least about a three fold improvement, at least about a five fold improvement, at least about a ten fold improvement, at least about a fifteen fold improvement, at least about a twenty fold improvement or at least about a twenty-five fold improvement in its $K_D$ when compared with an antibody produced by hybridoma cell line 106.3. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

In another aspect, the present invention relates to an isolated antibody which immunospecifically binds to hBNP, wherein said antibody has an association rate ($k_a$) of between about $5.0 \times 10^4$ and about $1.0 \times 10^8$ $M^{-1}s^{-1}$ More specifically, the antibody of the present invention has an association rate of between about $3.3 \times 10^4$ and about $1.0 \times 10^9$ $M^{-1}s^{-1}$, between about $2.5 \times 10^4$ and about $1.0 \times 10^8$ $M^{-1}s^{-1}$ or between about $2.4 \times 10^4$ and about $1.35 \times 10^7$ $M^{-1}s^{-1}$ The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Additionally, this isolated antibody immunospecifically binds to an epitope comprising amino acid residues 5 through 13 of hBNP.

In another aspect, the present invention relates to an isolated antibody which immunospecifically binds to hBNP, wherein said antibody has a dissociation rate ($k_d$) of between about $1.0 \times 10^{-3}$ and about $1.0 \times 10^{-6} \cdot s^{-1}$. More specifically, the antibody of the present invention has a dissociation rate of between about $1.0 \times 10^{-3}$ and about $1.0 \times 10^{-5}$ $s^{-1}$ or between about $1.0 \times 10^{-3}$ and about $1.0 \times 10^{-4} \cdot s^{-1}$. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Additionally, this isolated antibody immunospecifically binds to an epitope comprising amino acid residues 5 through 13 of hBNP.

In another aspect, the present invention relates to an isolated antibody which immunospecifically binds to hBNP wherein said antibody has an equilibrium dissociation constant ($K_D$) of between about $4.2 \times 10^{-11}$ M and about $1 \times 10^{-15}$ M. More specifically, the antibody of the present invention has an equilibrium dissociation constant of between about $4.0 \times 10^{-11}$ M and about $1.0 \times 10^{-14}$ M, between about $3.0 \times 10^{-11}$ M and about $1.0 \times 10^{-13}$ M between about $2.0 \times 10^{-11}$ M and about $8.0 \times 10^{-13}$ M, or between about $1.0 \times 10^{-12}$ M and about $7.4 \times 10^{-13}$ M. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Additionally, this isolated antibody immunospecifically binds to an epitope comprising amino acid residues 5 through 13 of hBNP.

In still another aspect, the present invention relates to a Chinese hamster ovary ("CHO") cell line 106.3 AM1 having A.T.C.C. Accession No. PTA-6987.

In still yet another aspect, the present invention relates to an antibody made from DNA extracted from CHO cell line 106.3 AM1 having A.T.C.C. Accession No. PTA-6987.

In yet another aspect, the present invention relates to a chimeric antibody or a hBNP-epitope binding fragment thereof produced by CHO cell line 106.3 AM1, wherein said cell line has A.T.C.C. Accession No. PTA-6987.

In still a further aspect, the present invention relates to an isolated antibody which immunospecifically binds to hBNP, wherein said antibody has a variable heavy domain and a variable light domain, the variable heavy domain comprising a heavy chain complementary determining region ("CDR") 1, a heavy chain CDR 2 and a heavy chain CDR 3, the variable light domain comprising a light chain CDR 1, a light chain CDR 2 and a light chain CDR 3, wherein (a) the Heavy Chain CDR 1 has an amino acid sequence of: Gly-Tyr-Thr-Phe-Thr-His-Tyr-Gly-Ile-Asn (SEQ ID NO:6);

(b) the Heavy Chain CDR 2 has an amino acid sequence having a formula of:

```
                                              (SEQ ID NO: 12)
Trp-Ile-Asn-Thr-His-Thr-Gly-Glu-Xaa₁-Xaa₂-Tyr-Ala-

Asp-Asp-Phe-Lys-Gly
``` wherein $Xaa_1$ is selected from the group consisting of proline and alanine;

wherein $Xaa_2$ is selected from the group consisting of isoleucine and tyrosine;

(c) the Heavy Chain CDR 3 has an amino acid sequence of: Ser-His-Arg-Phe-Gly-Leu-Asp-Tyr (SEQ ID NO:8);

(d) the Light Chain CDR 1 has an amino acid sequence having a formula of:

```
                                              (SEQ ID NO: 13)
Lys-Ala-Xaa₃-Xaa₄-Xaa₅-Val-Asp-Tyr-Asn-Gly-Asp-

Ser-Tyr-Leu-Asn
``` wherein $Xaa_3$ is selected from the group consisting of: serine, alanine, asparagine, glutamine, tyrosine, threonine and arginine;

wherein $Xaa_4$ is selected from the group consisting of: glutamine, tyrosine, tryptophan, alanine and phenylalanine;

wherein $Xaa_5$ is selected from the group consisting of: serine, glycine, proline, alanine and aspartic acid;

(e) the Light Chain CDR 2 has an amino acid sequence having the formula of:

```
                                              (SEQ ID NO: 14)
        Ala-Ala-Ser-Xaa₆-Xaa₇-Xaa₈-Ser
``` wherein $Xaa_6$ is selected from the group consisting of: asparagine and cysteine;

wherein $Xaa_7$ is selected from the group consisting of: leucine, glycine and alanine;

wherein $Xaa_8$ is selected from the group consisting of glutamic acid, tryptophan and proline; and (f) the Light Chain CDR 3 has an amino acid sequence of: Gln-Gln-Ser-Asn-Glu-Asp-Pro-Phe-Thr (SEQ ID NO:11), wherein the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO:10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO:10), or the light chain CDR 2 has an amino acid sequence other than Ala-Ala-Ser-Asn-Leu-Glu-Ser (SEQ ID NO:10) when the heavy chain CDR 2 has the amino acid sequence of Trp-Ile-Asn-Thr-His-Thr-Gly-Glu-Pro-Ile-Tyr-Ala-Asp-Asp-Phe-Lys-Gly (SEQ ID NO:7) and the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9).

More specifically, in the above-described isolated antibody:

$Xaa_1$ can be alanine;
$Xaa_2$ can be tyrosine;
$Xaa_3$ can be serine;
$Xaa_4$ can be glutamine;
$Xaa_5$ can be serine;
$Xaa_6$ can be asparagine;
$Xaa_7$ can be leucine; and
$Xaa_8$ can be glutamic acid (SEQ ID NO: 160); or In the above-described isolated antibody:
$Xaa_1$ can be proline;
$Xaa_2$ can be isoleucine;
$Xaa_3$ can be glutamine;
$Xaa_4$ can be phenylalanine;
$Xaa_5$ can be alanine;
$Xaa_6$ can be asparagine;
$Xaa_7$ can be leucine; and
$Xaa_8$ can be glutamic acid (SEQ ID NO: 161); or In the above-described isolated antibody:
$Xaa_1$ can be proline;
$Xaa_2$ can isoleucine;
$Xaa_3$ can be tyrosine;
$Xaa_4$ can be alanine;
$Xaa_5$ can be serine;
$Xaa_6$ can be asparagine;
$Xaa_7$ can be leucine; and
$Xaa_8$ can be glutamic acid (SEQ ID NO: 162); or In the above-described isolated antibody
$Xaa_1$ can be proline;
$Xaa_2$ can be isoleucine;
$Xaa_3$ can be glutamine;
$Xaa_4$ can be tryptophan;
$Xaa_5$ can be glycine;
$Xaa_6$ can be asparagine;
$Xaa_7$ can be leucine; and
$Xaa_8$ can be glutamic acid (SEQ ID NO: 163); or In the above-described isolated antibody:
$Xaa_1$ can be proline;
$Xaa_2$ can be isoleucine;
$Xaa_3$ can be threonine;
$Xaa_4$ can be tryptophan;
$Xaa_5$ can be aspartic acid;
$Xaa_6$ can be asparagine;
$Xaa_7$ can be leucine; and
$Xaa_8$ can be glutamic acid (SEQ ID NO: 164); or In the above-described isolated antibody:
$Xaa_1$ can be proline;
$Xaa_2$ can be isoleucine;
$Xaa_3$ can be arginine;
$Xaa_4$ can be tryptophan;
$Xaa_5$ can be proline;
$Xaa_6$ can be asparagine;
$Xaa_7$ can be leucine; and $Xaa_8$ can be glutamic acid (SEQ ID NO: 165); or In the above-described isolated antibody:
$Xaa_1$ can be proline;
$Xaa_2$ can be isoleucine;
$Xaa_3$ can be alanine;
$Xaa_4$ can be tyrosine;
$Xaa_5$ can be glycine;
$Xaa_6$ can be asparagine;
$Xaa_7$ can be leucine; and
$Xaa_8$ can be glutamic acid (SEQ ID NO: 166); or In the above-described isolated antibody:
$Xaa_1$ can be prolin
$Xaa_2$ can be isoleucine;

Xaa$_3$ can be asparagine;
Xaa$_4$ can be tryptophan;
Xaa$_5$ can be proline;
Xaa$_6$ can be asparagine;
Xaa$_7$ can be leucine; and
Xaa$_8$ can be glutamic acid (SEQ ID NO: 167); or
In the above-described isolated antibody:
Xaa$_1$ can be proline;
Xaa$_2$ can be isoleucine;
Xaa$_3$ can be serine;
Xaa$_4$ can be glutamine;
Xaa$_5$ can be serine;
Xaa$_6$ can be cysteine;
Xaa$_7$ can be glycine; and
Xaa$_8$ can be tryptophan (SEQ ID NO: 168); or
In the above-described isolated antibody:
Xaa$_1$ can be proline;
Xaa$_2$ can be isoleucine;
Xaa$_3$ can be serine;
Xaa$_4$ can be glutamine;
Xaa$_5$ can be serine;
Xaa$_6$ can be cysteine;
Xaa$_7$ can be alanine; and
Xaa$_8$ can be proline (SEQ ID NO: 169).

The above-described antibody can have an equilibrium dissociation constant ($K_D$) of between about $4.2 \times 10^{-11}$ M and about $1.0 \times 10^{-15}$ M, between about $4.0 \times 10^{-11}$ M and about $1.0 \times 10^{-14}$ M, between about $3.0 \times 10^{-11}$ M and about $1.0 \times 10^{-13}$ M, between about $2.0 \times 10^{-11}$ M and about $8.0 \times 10^{-13}$ M, or between about $1.0 \times 10^{-12}$ M and about $7.4 \times 10^{-13}$ M. Additionally, the above-described antibody can have an association rate ($k_a$) of between about $5.0 \times 10^4$ and about $1.0 \times 10^8$ M$^{-1}$s$^{-1}$ Furthermore, the above-described antibody can have a dissociation rate ($k_d$) of between about $1.0 \times 10^{-3}$ and $1.0 \times 10^{-6}$ s$^{-1}$. Furthermore, the above-described antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. Finally, the above-described antibody can immunospecifically bind to an epitope comprising amino acid residues 5 through 13 of hBNP.

In another aspect, the present invention relates to an immunoassay for hBNP or hBNP fragment, wherein said immunoassay comprises any one of the hereinbefore described antibodies of the present invention. More specifically, said immunoassay may comprise only a single antibody that immunospecifically binds to hBNP or hBNP fragment. Moreover, said immunoassay may further comprise an additional specific binding partner for hBNP or hBNP fragment.

In another aspect, the present invention relates to a pharmaceutical composition comprising a therapeutically effective amount of any of the hereinbefore described antibodies of the present invention and a pharmaceutically acceptable carrier or excipient.

In yet still another aspect, the present invention relates to an isolated antibody which immunospecifically binds to an epitope comprising at least three (3) amino acids of amino acid residues 5 through 18 of human brain natriuretic peptide ("hBNP") with at least about a two fold improvement in its equilibrium dissociation constant ($K_D$) when compared with at least one of (1) an antibody produced by hybridoma cell line 106.3, said cell line having A.T.C.C. Accession No. HB-12044; and (2) an antibody produced by hybridoma cell line 3-631-436 having A.T.C.C. Accession No. PTA-6476. More specifically, the antibody of the present invention exhibits at least about a two fold improvement in its $K_D$ when compared with an antibody produced by hybridoma cell line 106.3, at least about a two fold improvement in its $K_D$ when compared with an antibody produced by hybridoma cell line 3-631-436, at least about a two fold improvement in its $K_D$ when compared with an antibody produced by hybridoma cell line 106.3 and an antibody produced by hybridoma cell line 3-631-436, at least about a five fold improvement in its $K_D$ when compared with an antibody produced by hybridoma cell line 106.3, at least about a five fold improved in its $K_D$ when compared with an antibody produced by hybridoma cell line 3-631-436 or at least about a five fold improvement in its $K_D$ when compared with an antibody produced by hybridoma cell line 106.3 and an antibody produced by hybridoma cell line 3-631-436. Moreover, the antibody of the present invention immunospecifically binds to an epitope comprising amino acid residues 5 through 13 of hBNP. Alternatively, the antibody of the present invention immunospecifically binds to an epitope comprising amino acid residues 13 through 18 of hBNP. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

In yet still a further aspect, the present invention relates to an isolated antibody which immunospecifically binds to an epitope comprising at least three (3) amino acids of amino acid residues 13 through 18 of human brain natriuretic peptide ("hBNP") with at least about a two fold improvement in its equilibrium dissociation constant ($K_D$) when compared with an antibody produced by hybridoma cell line 3-631-436 having A.T.C.C. Accession No. PTA-6476. More specifically, the antibody of the present invention exhibits at least about a five fold improvement in its $K_D$ when compared with an antibody produced by hybridoma cell line 3-631-436, at least about a ten fold improvement in its $K_D$ when compared with an antibody produced by hybridoma cell line 3-631-436, at least about a fifteen fold improvement in its $K_D$ when compared with an antibody produced by hybridoma cell line 3-631-436, at least about a twenty fold improvement in its $K_D$ when compared with an antibody produced by hybridoma cell line 3-631-436 or at least about a twenty-five fold improvement in its $K_D$ when compared with an antibody produced by hybridoma cell line 3-631-436. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

In yet still a further aspect, the present invention relates to an isolated antibody which immunospecifically binds to hBNP, wherein said antibody has an association rate ($k_a$) of between about $1.5 \times 10^6$ M$^{-1}$s$^{-1}$ to about $1.0 \times 10^8$ M$^{-1}$s$^{-1}$, with the proviso that if the $k_a$ is $1.6 \times 10^6$ M$^{-1}$s$^{-1}$ then the $k_d$ is not $5.4 \times 10^4$ s$^{-1}$ or $6.5 \times 10^{-4}$ s$^{-1}$, if the $k_a$ is $6.7 \times 10^6$ M$^{-1}$s$^{-1}$ then the $k_d$ is not $2.5 \times 10^{-3}$ s$^{-1}$, if the $k_a$ is $8.4 \times 10^6$ M$^{-1}$s$^{-1}$ then the $k_d$ is not $2.9 \times 10^{-3}$ s$^{-1}$, if the $k_a$ is $8.4 \times 10^6$ M$^{-1}$s$^{-1}$ then the $k_d$ is not $2.9 \times 10^{-3}$ s$^{-1}$, if the $k_a$ is $5.8 \times 10^6$ M$^{-1}$s$^{-1}$ then the $k_d$ is not $1.6 \times 10^{-3}$ s$^{-1}$ or if the $k_a$ is $1.5 \times 10^6$ M$^{-1}$s$^{-1}$ then the $k_d$ is not $4.1 \times 10^{-4}$ s$^{-1}$. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. The isolated antibody of the present invention immunospecifically binds to an epitope comprising amino acid residues 13 through 18 of hBNP.

In yet still another aspect, the present invention relates to an isolated antibody which immunospecifically binds to hBNP, wherein said antibody has a dissociation rate ($k_d$) of between about $2.0 \times 10^{-3}$ s$^{-1}$ to about $1.0 \times 10^{-6}$ s$^{-1}$. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. The isolated antibody of the present invention immunospecifically binds to an epitope comprising amino acid residues 13 through 18 of hBNP.

In yet another aspect, the present invention relates to an isolated antibody which immunospecifically binds to hBNP wherein said antibody has an equilibrium dissociation constant ($K_D$) of between about $3.5 \times 10^{-10}$ M to about $1.0 \times 10^{-13}$ M. The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. The isolated antibody of the present invention immunospecifically binds to an epitope comprising amino acid residues 13 through 18 of hBNP.

In yet another aspect, the present invention relates to a chinese hamster ovary ("CHO") cell line 3-631-436 AM5 having A.T.C.C. Accession No. PTA-8369.

In yet another aspect, the present invention relates to an antibody made from DNA extracted from the CHO cell line 3-631-436 AM5 having A.T.C.C. Accession No. PTA-8369.

In still yet another aspect, the present invention relates to a chimeric antibody or a hBNP-epitope binding fragment thereof produced by CHO cell line 3-631-436 AM5, wherein said cell line has A.T.C.C. Accession No. PTA-8369.

In still yet another aspect, the present invention relates to a chinese hamster ovary ("CHO") cell line 3-631-436 AM8 having A.T.C.C. Accession No. PTA-8368.

In still yet another aspect, the present invention relates to an antibody made from DNA extracted from the CHO cell line 3-631-436 AM8 having A.T.C.C. Accession No. PTA-8368.

In still yet another aspect, the present invention relates to a chimeric antibody or a hBNP-epitope binding fragment thereof produced by CHO cell line 3-631-436 AM8, wherein said cell line has A.T.C.C. Accession No. PTA-8368.

In still yet another aspect, the present invention relates to an isolated antibody which immunospecifically binds to hBNP, wherein said antibody has a variable heavy domain and a variable light domain, the variable heavy domain comprising a heavy chain complementarity determining region ("CDR") 1, a heavy chain CDR 2 and a heavy chain CDR 3, the variable light domain comprising a light chain CDR 1, a light chain CDR 2 and a light chain CDR 3, wherein (a) Heavy Chain CDR 1 having an amino acid sequence of:

```
                                      (SEQ ID NO: 84)
    Gly-Tyr-Thr-Phe-Thr-Ser-Tyr-Trp-Met-Asn;
```

(b) Heavy Chain CDR 2 having an amino acid sequence of:

```
                                      (SEQ ID NO: 85)
Arg-Ile-Asp-Pro-Tyr-Asp-Ser-Glu-Thr-His-Tyr-Asn-

Gln-Lys-Phe-Lys-Asp;
```

(c) Heavy Chain CDR 3 having an amino acid sequence of:

```
    Asp-Gly-Tyr;           (SEQ ID NO: 86)
```

(d) Light Chain CDR 1 having an amino acid sequence of:

```
                                      (SEQ ID NO: 87)
Lys-Ser-Ser-Gln-Ser-Leu-Leu-Asp-Ser-Asp-Gly-Lys-

Thr-Tyr-Leu-Asn;
```

(e) Light Chain CDR 2 having an amino acid sequence having the formula of:

```
                                      (SEQ ID NO: 83)
    Xaa9-Xaa10-Xaa11-Xaa12-Leu-Glu-Ser;
``` where $Xaa_9$ is selected from the group consisting of valine, glutamine, histidine, tryptophan and arginine;

where $Xaa_{10}$ is selected from the group consisting of valine, asparagine, threonine and methionine;

where $Xaa_{11}$ is selected from the group consisting of serine, threonine, asparagine and aspartic acid;

where $Xaa_{12}$ is selected from the group consisting of lysine and isoleucine;

provided that $Xaa_9$ is other than valine if $Xaa_{10}$ is Valine, $Xaa_{11}$ is serine and $Xaa_{12}$ is Lysine; and (f) Light Chain CDR 3 having an amino acid sequence of:

```
                                      (SEQ ID NO: 89)
    Leu-Gln-Ala-Thr-His-Phe-Pro.
```

More specifically, in the above-described isolated antibody:

$Xaa_9$ is Glutamine;
$Xaa_{10}$ is Asparagine;
$Xaa_{11}$ is Threonine; and
$Xaa_{12}$ is Lysine (SEQ ID NO: 143).

More specifically, in the above-described isolated antibody:

$Xaa_9$ is Histidine;
$Xaa_{10}$ is Threonine;
$Xaa_{11}$ is Threonine; and
$Xaa_{12}$ is Lysine (SEQ ID NO: 144).

More specifically, in the above-described isolated antibody:

$Xaa_9$ is Tryptophan;
$Xaa_{10}$ is Methionine;
$Xaa_{11}$ is Threonine; and
$Xaa_{12}$ is Lysine (SEQ ID NO: 145).

More specifically, in the above-described isolated antibody:
Xaa$_9$ is Tryptophan;
Xaa$_{10}$ is Methionine;
Xaa$_{11}$ is Asparagine; and
Xaa$_{12}$ is Lysine (SEQ ID NO: 146).
More specifically, in the above-described isolated antibody:
Xaa$_9$ is Valine;
Xaa$_{10}$ is Threonine;
Xaa$_{11}$ is Aspartic Acid; and
Xaa$_{12}$ is Lysine (SEQ ID NO: 147).
More specifically, in the above-described isolated antibody:
Xaa$_9$ is Arginine;
Xaa$_{10}$ is Threonine;
Xaa$_{11}$ is Asparagine; and
Xaa$_{12}$ is Lysine (SEQ ID NO: 148).
More specifically, in the above-described isolated antibody:
Xaa$_9$ is Tryptophan;
Xaa$_{10}$ is Methionine;
Xaa$_{11}$ is Aspartic Acid; and
Xaa$_{12}$ is Lysine (SEQ ID NO: 149).
More specifically, in the above-described isolated antibody:
Xaa$_9$ is Tryptophan;
Xaa$_{11}$ is Threonine;
Xaa$_{11}$ is Threonine; and
Xaa$_{12}$ is Lysine (SEQ ID NO: 150).
More specifically, in the above-described isolated antibody:
Xaa$_9$ is Tryptophan;
Xaa$_{11}$ is Methionine;
Xaa$_{11}$ is Asparagine; and
Xaa$_{12}$ is Lysine (SEQ ID NO: 146).
More specifically, in the above-described isolated antibody:
Xaa$_9$ is Valine;
Xaa$_{11}$ is Threonine;
Xaa$_{11}$ is Aspartic Acid; and
Xaa$_{12}$ is Isoleucine (SEQ ID NO: 151).

The isolated antibody of the present invention can be a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof. The isolated antibody of the present invention immunospecifically binds to an epitope comprising amino acid residues 13 through 18 of hBNP.

In yet another aspect, the present invention relates to an immunoassay for hBNP or hBNP fragment, wherein said immunoassay comprises any one of the hereinbefore described antibodies of the present invention. More specifically, said immunoassay may comprise only a single antibody that immunospecifically binds to hBNP or hBNP fragment. Moreover, said immunoassay may further comprise an additional specific binding partner for hBNP or hBNP fragment.

In another aspect, the present invention relates to a pharmaceutical composition comprising a therapeutically effective amount of any of the hereinbefore described antibodies of the present invention and a pharmaceutically acceptable carrier or excipient.

BRIEF DESCRIPTION OF THE FIGURES

FIGS. 3A-3E are the nucleotide sequence (SEQ ID NO: 1) of the vector shown in FIG. 2. Six His tag disclosed as SEQ ID NO: 156.

FIG. 5 shows the amino acid sequence of the 106.3 single-chain variable fragment ("scFv") (SEQ ID NO: 3). The solid underlined sequence represents the variable heavy chain sequence ("VH"), the double underlined sequence the linker, and the stippled underline sequence the variable light chain sequence ("VL"). Italicized and bold type indicates the complementary determining regions (CDR).

FIGS. 6A-6B show the nucleotide sequence of the 106.3 scFv (SEQ ID NO: 157).

FIG. 11 is a summary showing that 106.3scFv variants isolated from CDR mutagenic libraries exhibited improvements in off-rate (namely, said variants had a slower k$_{off}$).

FIGS. 12A-C show the sequence characterization of scFv 106.3 variants. More specifically, plasmid DNA was isolated from 106.3 variants and scFv genes were sequenced.

FIG. 13 shows affinity measurements of selected 106.3 engineered, human-mouse chimeric antibodies and mouse 106.3 mAb using surface plasmon resonance using BIAcore.

FIGS. 14A-H show the fifty-four (54) oligonucleotides 1 (SEQ ID NOS 25-78, respectively, in order of appearance) that were used to create the pYD41 vector discussed in Example.

FIGS. 22A-22D are the nucleotide sequence of the vector shown in FIG. 21 (SEQ ID NO:90).

FIG. 24 shows the amino acid sequence of the 3-631-436 scFv (SEQ ID NO:91). The solid underlined sequence represents the variable heavy chain sequence ("VH"), the double underlined sequence the linker, and the stippled underline sequence the variable light chain sequence ("VL"). Italicized and bold type indicates the complementary determining regions (CDR).

FIGS. 25A-25B show the nucleotide sequence of the 3-631-436 scFv (SEQ ID NO:92). The double-stranded sequence is depicted.

FIGS. 26A-26B show that yeast expressing full-length 3-631-436 scFv bind to cyclic BNP (SEQ ID NO:5). More specifically, this figure shows that 3-631-436 scFv expressing yeast were incubated with cyclic BNP (1-32c) (SEQ ID NO:5) or anti-V5 followed by secondary reagents streptavidin phycoerythrin (SA:PE) (FIG. 26A) and goat anti mouse-FITC (GAM:FITC) (FIG. 26B). The flow cytometry histograms illustrate the full-length expression of 3-631-436 scFv as detected by anti-V5 and the ability of 3-631-436 scFv to bind to cyclic BNP peptide (1-32) (SEQ ID NO:5). Antigen (Ag) binding or PE-A units (abscissa): 100, 101, 102, and $10^3$ and $10^4$. Count units (ordinate): 0, 10, 20, 30, 40, 50, 60, 70, 80 (FIG. 26A); Antibody (Ab) expression or FITC-A units (abscissa) $10^0$, $10^1$, $10^2$, and $10^3$ and $10^4$: 0, 10, 20, 30, 40, 50, 60, 70, 80 (FIG. 26B).

FIG. 28 is a summary showing that 3-631-436 scFv variants isolated from CDR mutagenic libraries exhibited improvements in off-rate (namely, said variants had a slower $k_{off}$).

FIG. 29 shows the sequence characterization of scFv 3-631-436 variants. More specifically, plasmid DNA was isolated from 3-631-436 variants and scFv genes were sequenced (SEQ ID NOS 158 and 143-151, respectively, in order of appearance).

FIG. 30 shows affinity measurements of selected 3-631-436 engineered, mouse-mouse chimeric antibodies and wild-type mouse 3-631-436 mAb (IgG2a kappa) using surface plasmon resonance Biacore and using KinExA.

FIGS. 31A-31F show the fifty (50) oligonucleotides (SEQ ID NOS:93-142) that were used to create the pYD1-41-40-3-631-436 vector discussed in Example 5.

DETAILED DESCRIPTION OF THE INVENTION

I. Introduction

Figure 1:
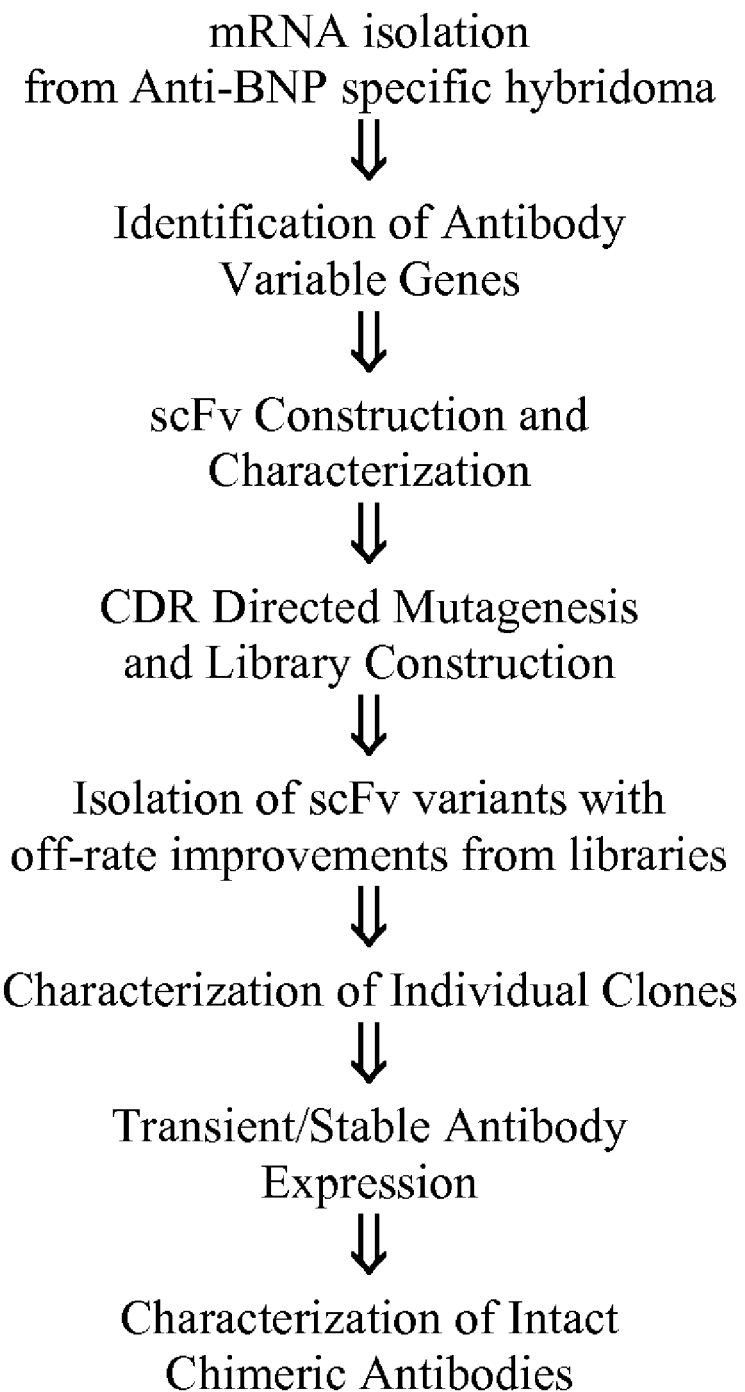
FIG. 1 is a flow chart showing the steps used to identify and create antibodies that immunospecifically bind to human BNP with a high binding affinity.

The present invention relates to novel antibodies that immunospecifically bind to human brain natriuretic peptide with a high binding affinity. The antibodies of the present invention are highly sensitive reagents and are useful in the qualitative and/or quantitative detection of hBNP or hBNP fragments in test samples. In another embodiment, the present invention relates to immunoassays that employ the antibodies of the present invention. In yet still a further embodiment, the present invention relates to therapeutic compositions comprising the antibodies of the present invention.

DEFINITIONS

As used herein, the terms "antibody" and "antibodies" refer to monoclonal antibodies, multispecific antibodies, human antibodies, humanized antibodies (fully or partially humanized), animal antibodies (in one aspect, a bird (for example, a duck or goose), in another aspect, a shark or whale, in yet another aspect, a mammal, including a non-primate (for example, a cow, pig, camel, llama, horse, goat, rabbit, sheep, hamsters, guinea pig, cat, dog, rat, mouse, etc) and a non-human primate (for example, a monkey, such as a cynomologous monkey, a chimpanzee, etc), recombinant antibodies, chimeric antibodies, single-chain Fvs (scFv), single chain antibodies, single domain antibodies, Fab fragments, F(ab')$_2$ fragments, disulfide-linked Fv (sdFv), and anti-idiotypic (anti-Id) antibodies (including, for example, anti-Id antibodies to antibodies of the present invention), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$, and IgA$_2$) or subclass.

As used herein, the term "association rate", "$k_{on}$" or "$k_a$" as used interchangeably herein, refers to the value indicating the binding strength (degree) of an antibody to its target antigen or the rate of complex formation between mAb and antigen as shown by the below:

Antibody (Ab)+Antigen (Ag)→Ab–Ag

Methods for determining association constants ($k_a$) are well known in the art. For example, a Biacore® (Sweden) assay can be used. Additionally, a KinExA® (Kinetic Exclusion Assay) assay, available from Sapidyne Instruments (Boise, Id.) can also be used.

As used herein, the term "dissociation rate", "$k_{off}$" or "$k_d$" as used interchangeably herein, refers to the value indicating the dissociation strength (degree) of an antibody from its target antigen or separation of Ab–Ag complex over time into free mAb and antigen as shown by the below:

Antibody (Ab)+Antigen (Ag)←Ab–Ag

Methods for determining dissociation constants ($k_d$) are well known in the art. For example, a Biacore® (Sweden) assay can be used. Additionally, a KinExA® (Kinetic Exclusion Assay) assay, available from Sapidyne Instruments (Boise, Id.) can also be used.

As used herein, the term "epitope" or "epitopes" refers to sites or fragments of a polypeptide or protein having antigenic or immunogenic activity in a subject. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to those skilled in the art, for example by immunoassays.

As used herein, the term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

As used herein, the term "human brain natriuretic peptide", "human BNP", "hBNP", "hBNP peptide", "B-type natriuretic peptide", "hBNP polypeptide" hBNP 1-32 refers to a 32 amino acid molecule representing amino acids 77-108 of the 108 amino acid precursor molecule of human brain natriuretic peptide. The sequence of human brain natiuretic peptide is shown in SEQ ID NO: 155.

As used herein, the term "hBNP fragment" or "hBNP peptide fragment" as used herein refers to a polypeptide that comprises at least about five contiguous amino acids of amino acids 77-108 of the 108 amino acid BNP precursor molecule (See, SEQ ID NO: 155). In one aspect, a hBNP fragment or hBNP peptide fragment refers to a polypeptide that comprises at least about ten contiguous amino acids residues of amino acids 77-108 of the 108 amino acid BNP precursor molecule; at least about fifteen contiguous amino acids residues of amino acids 77-108 of the 108 amino acid BNP precursor molecule; at least about 20 contiguous amino acids residues of amino acids 77-108 of the 108 amino acid BNP precursor molecule; at least about 25 contiguous amino acids residues of amino acids 77-108 of the 108 amino acid BNP precursor molecule, or at least about 30 contiguous amino acid residues of amino acids 77-108 of the 108 amino acid BNP precursor molecule. Examples of hBNP fragments or hBNP peptide fragments include, but are not limited to, amino acid sequences containing amino acids residues 1-31, 1-30, 1-29, 1-28, 1-27, 1-26, 1-25, 1-24, 1-23, 1-22, 1-21, 1-20, 1-19, 1-18, 1-17, 1-16, 1-15, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 3-14, 3-13, 3-12, 3-11, 3-10, 3-9, 3-8, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 6-14, 6-13, 6-12, 6-11, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 7-14, 7-13, 7-12, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 9-14, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 11-32, 11-31, 11-30, 11-29, 11-28, 11-27, 11-26, 11-25, 11-24, 11-23, 11-22, 11-21, 11-20, 11-19, 11-18, 11-17 or 11-16 of hBNP.

As used herein, the term "humanized" antibody refers to an immunoglobulin variant or fragment thereof, which is capable of binding to a predetermined antigen and which comprises framework regions having substantially the amino acid sequence of a human immunoglobulin and CDRs having substantially the amino acid sequence of a non-human immunoglobulin. Ordinarily, a humanized antibody has one or more amino acid residues introduced into it from a source that is non-human. In general, the humanized antibody will include substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally comprises at least a portion of an immunoglobulin constant region (Fc), typically that of a human immunoglobulin. Generally, the antibody will contain both the light chain as well as at least the variable domain of a heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. The humanized antibody may comprise sequences from more than one class or isotype, and selecting particular constant domains to optimize desired effector functions is within those skilled in the art.

As used herein, the phrase "immunospecifically binds to a human brain natriuretic peptide", "immunospecifically binds to hBNP", "immunospecifically binds to human brain natriuretic peptide fragment" or "immunospecifically binds to hBNP fragment" and analogous terms thereof refer to peptides, polypeptides, proteins, fusion proteins and antibodies that specifically bind to hBNP or hBNP fragment and do not specifically bind to other peptides. A peptide, polypeptide, protein, or antibody that immunospecifically binds to hBNP or hBNP fragment may bind to other peptides, polypeptides, or proteins with lower binding affinity as determined by, for example, immunoassays, BIAcore, or other assays known in the art. Antibodies or antibody fragments that immunospecifically bind to hBNP or hBNP fragment can be identified, for example, by immunoassays, BIAcore, or other techniques known to those of skill in the art. An antibody binds immunospecifically to a hBNP peptide or hBNP fragment when it binds to hBNP or hBNP fragment with a higher binding affinity than to any cross-reactive antigen as determined using experimental techniques, such as, but not limited to, radioimmunoassays (RIA) and enzyme-linked immunosorbent assays (ELISAs) (See, for example, Paul, ed., *Fundamental Immunology*, 2nd ed., Raven Press, New York, pages 332-336 (1989) for a discussion regarding antibody specificity.). In one aspect of the present invention, an antibody binds immunospecifically to hBNP or hBNP fragment (such as amino acids 5-13) when it has an equilibrium dissociation constant ($K_D$) for the hBNP or hBNP fragment of at least about $2.0 \times 10^{-11}$ M as determined by a BIAcore assay under standard assay conditions, and in particular the BIAcore assay described in Example 1. In another aspect of the present invention, an antibody binds immunospecifically to hBNP or hBNP fragment (such as amino acids 13-18) when it has an equilibrium dissociation constant ($K_D$) for the hBNP or hBNP fragment of at least about $3.5 \times 10^{-10}$ M as determined by a BIAcore assay under standard assay conditions, and in particular the BIAcore assay described in Example 5.

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In one aspect, nucleic acid molecules are isolated. In another aspect, a nucleic acid molecule encoding an antibody of the invention is isolated.

As used herein, the term "stringent conditions" refers to hybridization to filter-bound DNA in 6× sodium chloride/sodium citrate (SSC) at about 45° C. followed by one or more washes in 0.2×SSC/0.1% SDS at about 50-65° C. The term "under highly stringent conditions", refers to hybridization to filter-bound nucleic acid in 6×SSC at about 45° C. followed by one or more washes in 0.1×SSC/0.2% SDS at about 68° C., or under other stringent hybridization conditions which are known to those skilled in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

As used herein, the terms "subject" and "patient" are used interchangeably. As used herein, the terms "subject" and "subjects" refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomolgous monkey, chimpanzee, and a human).

As used herein, the term "test sample" refers to a biological sample derived from serum, plasma, whole blood, lymph, CNS fluid, urine or other bodily fluids of a subject. The test sample can be prepared using routine techniques known to those skilled in the art.

As used herein, the term "therapeutically effective amount" or "pharmaceutically effective amount" means an amount of antibody or antibody portion effective, at dosages and for periods of time necessary, to achieve the desired therapeutic result. The exact dose will be ascertainable by one skilled in the art. As known in the art, adjustments based on age, body weight, sex, race, diet, time of administration, drug interaction and severity of condition may be necessary and will be ascertainable with routine experimentation by those skilled in the art. A therapeutically effective amount is also one in which the therapeutically beneficial effects outweigh any toxic or detrimental effects of the antibody or antibody fragment. A "prophylactically effective amount" refers to an amount effective, at dosages and for periods of time necessary to achieve the desired prophylactic result. Typically, since a prophylactic dose is used in subjects prior to or at an earlier stage of disease, the prophylactically effective amount will be less than the therapeutically effective amount.

II. Antibodies of the Present Invention

The present invention provides antibodies that immunospecifically bind to hBNP or hBNP fragment. In particular, the present invention provides for antibodies that have a high binding affinity for hBNP or hBNP fragment. More specifically, in one aspect, the present invention relates to isolated antibodies which immunospecifically bind to an epitope comprising at least three (3) amino acids of amino acid residues 5 through 18 of human brain natriuretic peptide ("hBNP") (such as, but not limited, an epitope comprising amino acids 5 through 13 or amino acids 13 through 18 of hBNP) and which exhibit at least about a two fold improvement in its equilibrium dissociation constant ($K_D$) when compared with at least one of (1) an antibody produced by hybridoma cell line 106.3, said cell line having A.T.C.C. Accession No. HB-12044; and (2) an antibody produced by hybridoma cell line 3-631-436 having A.T.C.C. Accession No. PTA-6476. More specifically, the antibodies of the present invention immunospecifically bind to an epitope comprising at least (3) amino acid residues of amino acid residues 5 through 18 of hBNP (such as, but not limited, an epitope comprising amino acids 5 through 13 or amino acids 13 through 18 of hBNP) or hBNP fragment thereof with at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3 (the wildtype), an antibody produced by hybridoma cell line 3-631-436 (wildtype) having A.T.C.C. Accession No. PTA-6476 or both an antibody produced by hybridoma cell line 106.3 (the wildtype), an antibody produced by hybridoma cell line 3-631-436 (wildtype) having A.T.C.C. Accession No. PTA-6476.

106.3 AM1 Antibodies

Specifically, in another aspect, the present invention relates to an antibody that immunospecifically binds to an epitope comprising at least three (3) amino acids of amino acid residues 5 through 13 of hBNP or hBNP fragment with at least about a two fold improvement in its equilibrium dissociation constant ($K_D$) when compared with an antibody produced by hybridoma cell line 106.3, said cell line having A.T.C.C. Accession No. HB-12044 (which is also referred to herein as the "wildtype" or "106.3 wildtype"). More specifically, the antibodies of the present invention immunospecifically bind to an epitope comprising amino acid residues 5 through 13 of hBNP or a hBNP fragment thereof with at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3 (the wildtype).

In another aspect, the present invention relates to an antibody that immunospecifically binds to hBNP or hBNP fragment and has a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, of at least about $1.25 \times 10^7$ $M^{-1}s^{-1}$ of at least about $1.35 \times 10^7$ $M^{-1}$-1, of at least about $1.0 \times 10^8$ $M^{-1}s^{-1}$, of at least about $1.0 \times 10^9$ $M^{-1}s^{-1}$, or has a $k_{on}$ (or $k_a$) ranging from about $5.0 \times 10^4$ $M^{-1}s^{-1}$ to about $1.0 \times 10^8$ $M^{-1}s^{-1}$, from about $3.3 \times 10^4$ $M^{-1}s^{-1}$ to about $1.0 \times 10^9$ $M^{-1}s^{-1}$, from about $2.5 \times 10^4$ $M^{-1}s^{-1}$ to about $1.25 \times 10^7$ $M^{-1}s^{-1}$, from about $2.4 \times 10^4$ $M^{-1}s^{-1}$ to about $1.35 \times 10^7$ $M^{-1}s^{-1}$.

In another aspect, an antibody of the present invention immunospecifically binds to the amino acid residues 5 through 13 of human BNP or hBNP fragment at a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, of at least about $1.25 \times 10^7$ $M^{-1}s^{-1}$ of at least about $1.35 \times 10^7$ $M^{-1}s^{-1}$, of at least about $1.0 \times 10^8$ $M^{-1}s^{-1}$, of at least about $1.0 \times 10^9$ $M^{-1}s^{-1}$, or has a $k_{on}$ (or $k_a$) ranging from about $5.0 \times 10^4$ $M^{-1}s^{-1}$ to about $1.0 \times 10^8$ $M^{-1}s^{-1}$, from about $3.3 \times 10^4$ $M^{-1}s^{-1}$ to about $1.0 \times 10^9$ $M^{-1}s^{-1}$, from about $2.5 \times 10^4$ $M^{-1}s^{-1}$ to about $1.25 \times 10^7$ $M^{-1}s^{-1}$, from about $2.4 \times 10^4$ $M^{-1}s^{-1}$ to about $1.35 \times 10^7$ $M^{-1}s^{-1}$.

In another aspect, the present invention provides antibodies produced by Chinese hamster ovary cell line 106.3 AM1 (also known as 106.3 L1 B24/H2288). Antibodies produced by this cell line bind to amino acid residues 5 thorough 13 of hBNP or hBNP fragment at a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, of at least about $1.25 \times 10^7$ $M^{-1}s^{-1}$ of at least about $1.35 \times 10^7$ $M^{-1}s^{-1}$, of at least about $1.0 \times 10^8$ $M^{-1}s^{-1}$, of at least about $1.0 \times 10^9$ $M^{-1}s^{-1}$, or has a $k_{on}$ (or $k_a$) ranging from about $5.0 \times 10^4$ $M^{-1}s^{-1}$ to about $1.0 \times 10^8$ $M^{-1}s^{-1}$, from about $3.3 \times 10^4$ $M^{-1}s^{-1}$ to about $1.0 \times 10^9$ $M^{-1}s^{-1}$, from about $2.5 \times 10^4$ $M^{-1}s^{-1}$ to about $1.25 \times 10^7$ $M^{-1}s^{-1}$, from about $2.4 \times 10^4$ $M^{-1}s^{-1}$ to about $1.35 \times 10^7$ $M^{-1}s^{-1}$.

The present invention provides antibodies that immunospecifically bind to hBNP or hBNP fragment. In particular, the present invention provides for antibodies that have a high binding affinity for hBNP or hBNP fragment. More specifically, in one aspect, an antibody that immunospecifically binds to hBNP or hBNP fragment and has a $k_{off}$ (or $k_d$) of at least about $1.0 \times 10^{-3}$ $s^{-1}$, of at least about $1.0 \times 10^{-4}$ $s^{-1}$, of at least about $1.0 \times 10^{-5}$ $s^{-1}$, of at least about $1.0 \times 10^{-6}$ $s^{-1}$ or has a $k_{off}$ (or $k_d$) ranging from about $1.0 \times 10^{-3}$ $s^{-1}$ to about $1.0 \times 10^{-6}$ $s^{-1}$, from about $1.0 \times 10^{-3}$ $s^{-1}$ to about $1.0 \times 10^{-5}$ $s^{-1}$ or from about $1.0 \times 10^{-3}$ $s^{-1}$ to about $1.0 \times 10^{-4}$ $s^{-1}$.

In another aspect, an antibody of the present invention immunospecifically binds to the amino acid residues 5 through 13 of human BNP or hBNP fragment at a $k_{off}$ (or $k_{off}$) of at least about $1.0 \times 10^{-3}$ $s^{-1}$, of at least about $1.0 \times 10^4$ $s^{-1}$, of at least about $1.0 \times 10^{-5}$ $s^{-1}$, of at least about $1.0 \times 10^{-6}$ $s^{-1}$ or has a $k_{off}$ (or $k_d$) ranging from about $1.0 \times 10^{-3}$ $s^{-1}$ to about $1.0 \times 10^{-6}$ $s^{-1}$, from about $1.0 \times 10^{-3}$ $s^{-1}$ to about $1.0 \times 10^{-5}$ $s^{-1}$ or from about $1.0 \times 10^{-3}$ $s^{-1}$ to about $1.0 \times 10^{-4}$ $s^{-1}$.

In another aspect, the present invention provides antibodies produced by Chinese hamster ovary cell line 106.3 AM1. Antibodies produced by this cell line bind to amino acid residues 5 thorough 13 of hBNP or hBNP fragment at a $k_{off}$ (or $k_d$) of at least about $1.0 \times 10^{-3}$ $s^{-1}$, of at least about $1.0 \times 10^{-4}$ $s^{-1}$, of at least about $1.0 \times 10^{-5}$ $s^{-1}$, of at least about $1.0 \times 10^{-6}$ $s^{-1}$ or has a $k_{off}$ (or $k_d$) ranging from about $1.0 \times 10^{-3}$ $s^{-1}$ to about $1.0 \times 10^{-6}$ $s^{-1}$, from about $1.0 \times 10^{-3}$ $s^{-1}$ to about $1.0 \times 10^{-5}$ $s^{-1}$ or from about $1.0 \times 10^{-3}$ $s^{-1}$ to about $1.0 \times 10^{-4}$ $s^{-1}$ The present invention provides antibodies that immunospecifically bind to hBNP or hBNP fragment. In particular, the present invention provides for antibodies that have a high binding affinity for hBNP or hBNP fragment. More specifically, in one aspect, the present invention relates to an antibody that immunospecifically binds to hBNP or hBNP fragment and has a $K_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a $K_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M.

In another aspect, an antibody of the present invention immunospecifically binds to the amino acid residues 5 through 13 of human BNP at a $K_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a $K_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$. M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M.

In another aspect, the present invention provides antibodies produced by Chinese hamster ovary (CHO) cell line 106.3 AM1. Antibodies produced by this cell line bind to amino acid residues 5 thorough 13 of hBNP or hBNP fragment at a $K_D$ of from $4.2 \times 10^{-11}$ M to $7.4 \times 10^{-13}$ M.

In another aspect, the antibodies of the present invention are derivatives or variants of the antibodies produced by hybridoma cell line 106.3 (A.T.C.C. Accession No. HB-12044). More specifically, the inventors of the present invention have discovered that antibodies that are derivatives or variants of the antibodies produced by hybridoma cell line 106.3 can be produced which exhibit a high binding affinity to hBNP or hBNP fragment. More specifically, the antibodies of the present invention exhibit a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, of at least about $1.25 \times 10^7$ $M^{-1}s^{-1}$ of at least about $1.35 \times 10^7$ $M^{-1}s^{-1}$, of at least about $1.0 \times 10^8$ $M^{-1}s^{-1}$, of at least about $1.0 \times 10^9$ $M^{-1}s^{-1}$, or have a $k_{on}$ (or $k_a$) ranging from about $5.0 \times 10^4 M^{-1}s^{-1}$ to about $1.0 \times 10^8 M^{-1}s^{-1}$, from about $3.3 \times 10^4$ $M^{-1}s^{-1}$ to about $1.0 \times 10^9$ $M^{-1}s^{-1}$, from about $2.5 \times 10^4 M^{-1}s^{-1}$ to about $1.25 \times 10^7$ $M^{-1}s^{-1}$, from about $2.4 \times 10^4$ $M^{-1}s^{-1}$ to about $1.35 \times 10^7 M^{-1}s^{-1}$, a $k_{off}$ (or $k_d$) of at least about $1.0 \times 10^{-3}$ $s^{-1}$, of at least about $1.0 \times 10^4$ $s^{-1}$, of at least about $1.0 \times 10^{-5}$ $s^{-1}$, of at least about $1.0 \times 10^{-6}$ $s^{-1}$ or have a $k_{off}$ (or $k_d$) ranging from about $1.0 \times 10^{-3}$ $s^{-1}$ to about $1.0 \times 10^{-6}$ $s^{-1}$, from about $1.0 \times 10^{-3}$ $s^{-1}$ to about $1.0 \times 10^{-5}$ $s^{-1}$ or from about $1.0 \times 10^{-3}$ $s^{-1}$ to about $1.0 \times 10^{-4}$ $s^{-1}$ and a $K_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a $K_D$ ranging from $4.2 \times 10^{-11}$ M to $1.0 \times 10^{-15}$ M, from $4.0 \times 10^{-11}$ M to $1.0 \times 10^{14}$ M, from $3 \times 10^{-1}$ M to $1.0 \times 10^{-13}$ M, from $2 \times 10^{-1}$ M to $8.0 \times 10^{13}$ M, or from $1.0 \times 10^{-12}$ M to $7.4 \times 10^{-13}$ M. The derived or variant antibodies of the present invention comprise at least one mutation (such as deletions, additions and/or substitutions) in at least one of the heavy chain complementary determining ("CDR") regions (for example, the heavy chain CDR 1, heavy chain CDR 2 and/or heavy chain CDR 3), and/or at least one mutation (such as deletions, additions and/or substitutions) in the light chain CDR regions (for example, the light chain CDR 1, light chain CDR 2, and/or light chain CDR 3) when compared to the amino acid sequence of the antibody produced by hybridoma cell line 106.3 (also referred to herein as the "wildtype"). Moreover, the antibodies of the present invention may also contain one or more other mutations (such as deletions, additions and/or substitutions) in a part or portion of the antibody other than the CDR, such as, but not limited to, the framework region of an antibody. Methods for creating such derivatives are well known in the art and include the use of site-directed mutagenesis and PCR-mediated mutagenesis, which will be discussed in more detail infra.

More specifically, in another aspect, the antibody of the present invention immunospecifically binds to hBNP or hBNP fragment and comprises a heavy chain CDR 2 having an amino acid sequence of the formula of:

```
                                            (SEQ ID NO: 12)
Trp-Ile-Asn-Thr-His-Thr-Gly-Glu-Xaa1-Xaa2-Tyr-Ala-

Asp-Asp-Phe-Lys-Gly
``` where $Xaa_1$ is selected from the group consisting of proline and alanine and $Xaa_2$ is selected from the group consisting of isoleucine and tyrosine, provided that when $Xaa_1$ is proline, $Xaa_2$ is not isoleucine.

In yet a further aspect, the antibody of the present invention immunospecifically binds to hBNP or hBNP fragment and comprises a heavy chain CDR 2 having the amino acid sequence shown in SEQ ID NO: 15. In another aspect, the present invention relates to an antibody that immunospecifically binds to hBNP or hBNP fragment that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NO: 15.

In yet another aspect, the antibody of the present invention immunospecifically binds to hBNP or hBNP fragment and comprises a light chain CDR 1 that has an amino acid sequence having a formula of:

```
                                            (SEQ ID NO: 13)
Lys-Ala-Xaa3-Xaa4-Xaa5-Val-Asp-Tyr-Asn-Gly-Asp-

Ser-Tyr-Leu-Asn
``` where $Xaa_3$ is selected from the group consisting of: serine, alanine, asparagine, glutamine, tyrosine, threonine and arginine; where $Xaa_4$ is selected from the group consisting of: glutamine, tyrosine, tryptophan, alanine and phenylalanine and where $Xaa_5$ is selected from the group consisting of: serine, glycine, proline, alanine and aspartic acid, provided that $Xaa_3$ is not serine when $Xaa_4$ is glutamine and $Xaa_5$ is serine.

In yet a further aspect, the antibody immunospecifically binds to hBNP or hBNP fragment and has a light chain CDR 1 having the amino acid sequence of SEQ ID NO:16, SEQ ID NO: 17, SEQ ID NO:18, SEQ ID NO:19, SEQ ID NO:20, SEQ ID NO: 21 or SEQ ID NO:22. In another aspect, the present invention relates to an antibody that immunospecifically binds to hBNP or hBNP fragment that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NO:16, SEQ ID NO: 17, SEQ ID NO:18, SEQ ID NO:19, SEQ ID NO:20, SEQ ID NO: 21 or SEQ ID NO:22.

In yet another aspect, the antibody of the present invention immunospecifically binds to hBNP or hBNP fragment and comprises a light chain CDR 2 that has an amino acid sequence having a formula of:

```
                                            (SEQ ID NO: 14)
          Ala-Ala-Ser-Xaa6-Xaa7-Xaa8-Ser
``` where $Xaa_6$ is selected from the group consisting of: asparagine and cysteine, where $Xaa_7$ is selected from the group consisting of: leucine, glycine and alanine and where $Xaa_8$ is selected from the group consisting of glutamic acid, tryptophan and proline, provided that $Xaa_6$ is not asparagine when $Xaa_7$ is leucine and $Xaa_8$ is glutamic acid.

In yet a further aspect, the antibody immunospecifically binds to hBNP or hBNP fragment and has a light chain CDR 2 having the amino acid sequence of SEQ ID NO:23 or SEQ ID NO: 24. In another aspect, the present invention relates to an antibody that immunospecifically binds to hBNP or hBNP fragment that comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to an amino acid sequence of SEQ ID NO:23 or SEQ ID NO:24.

In yet a further aspect, the antibody of the present invention immunospecifically binds to hBNP or hBNP fragment and has a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 having an amino acid sequence of: Gly-Tyr-Thr-Phe-Thr-His-Tyr-Gly-Ile-Asn (SEQ ID NO:6);

(b) Heavy Chain CDR 2 having an amino acid sequence having a formula of:

Trp-Ile-Asn-Thr-His-Thr-Gly-Glu-Xaa$_1$-Xaa$_2$-Tyr-Ala-Asp-Asp-Phe-Lys-Gly                    (SEQ ID NO: 12)

where Xaa$_1$ is selected from the group consisting of proline and alanine; where Xaa$_2$ is selected from the group consisting of isoleucine and tyrosine;

(c) Heavy Chain CDR 3 having an amino acid sequence of: Ser-His-Arg-Phe-Gly-Leu-Asp-Tyr (SEQ ID NO:8);

(d) Light Chain CDR 1 having an amino acid sequence having a formula of:

Lys-Ala-Xaa$_3$-Xaa$_4$-Xaa$_5$-Val-Asp-Tyr-Asn-Gly-Asp-Ser-Tyr-Leu-Asn                    (SEQ ID NO: 13)

where Xaa$_3$ is selected from the group consisting of: serine, alanine, asparagine, glutamine, tyrosine, threonine and arginine;

where Xaa$_4$ is selected from the group consisting of: glutamine, tyrosine, tryptophan, alanine and phenylalanine;

where Xaa$_5$ is selected from the group consisting of: serine, glycine, proline, alanine and aspartic acid;

(e) Light Chain CDR 2 has an amino acid sequence having the formula of:

Ala-Ala-Ser-Xaa$_6$-Xaa$_7$-Xaa$_8$-Ser                    (SEQ ID NO: 14)

where Xaa$_6$ is selected from the group consisting of: asparagine and cysteine;

where Xaa$_7$ is selected from the group consisting of: leucine, glycine and alanine;

where Xaa$_8$ is selected from the group consisting of glutamic acid, tryptophan and proline; and (f) Light Chain CDR 3 has an amino acid sequence of: Gln-Gln-Ser-Asn-Glu-Asp-Pro-Phe-Thr (SEQ ID NO:11), where the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO:10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO:10), or the light chain CDR 2 has an amino acid sequence other than Ala-Ala-Ser-Asn-Leu-Glu-Ser (SEQ ID NO:10) when the heavy chain CDR 2 has the amino acid sequence of Trp-Ile-Asn-Thr-His-Thr-Gly-Glu-Pro-Ile-Tyr-Ala-Asp-Asp-Phe-Lys-Gly (SEQ ID NO:7) and the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9).

Preferably, the antibodies having the above-described formulas comprise a heavy chain CDR 1, heavy chain CDR 2, heavy chain CDR 3, light chain CDR 1, light chain CDR 2 and light chain CDR 3 where Xaa$_1$-Xaa$_8$ in the above described formulas have the amino acid residues shown below in Table 1.

TABLE 1

| Xaa$_1$ | Xaa$_2$ | Xaa$_3$ | Xaa$_4$ | Xaa$_5$ | Xaa$_6$ | Xaa$_7$ | Xaa$_8$ |
| --- | --- | --- | --- | --- | --- | --- | --- |
| Alanine | Tyrosine | Serine | Glutamine | Serine | Asparagines | Leucine | Glutamic Acid |
| Proline | Isoleucine | Glutamine | Phenylalanine | Alanine | Asparagines | Leucine | Glutamic Acid |
| Proline | Isoleucine | Tyrosine | Alanine | Serine | Asparagines | Leucine | Glutamic Acid |
| Proline | Isoleucine | Glutamine | Tryptophan | Glycine | Asparagines | Leucine | Glutamic Acid |
| Proline | Isoleucine | Threonine | Tryptophan | Aspartic Acid | Asparagines | Leucine | Glutamic Acid |
| Proline | Isoleucine | Arginine | Tryptophan | Proline | Asparagines | Leucine | Glutamic Acid |
| Proline | Isoleucine | Alanine | Tyrosine | Glycine | Asparagines | Leucine | Glutamic Acid |
| Proline | Isoleucine | Asparagine | Tryptophan | Proline | Asparagines | Leucine | Glutamic Acid |
| Proline | Isoleucine | Serine | Glutamine | Serine | Cysteine | Glycine | Tryptophan |
| Proline | Isoleucine | Serine | Glutamine | Serine | Cysteine | Alanine | Proline |

3-631-436 AM5 and 3-631-436 AM8 Antibodies

In another aspect, the present invention relates to an antibody that immunospecifically binds to an epitope comprising at least three (3) amino acids of amino acid residues 13 through 18 of hBNP or a hBNP fragment with at least about a two fold improvement in its equilibrium dissociation constant ($K_D$) when compared with an antibody produced by 3-631-436 which was deposited with the American Type Culture Collection (A.T.C.C.) on Dec. 21, 2004 and assigned A.T.C.C. Accession No. PTA-6476 and is described in U.S. Patent Publication 2006/0183154 published on Aug. 17, 2006 (which is also referred to herein as the "wildtype" and "3-631-436"). More specifically, the antibodies of the present invention immunospecifically bind to an epitope comprising amino acid residues 13 through 18 of hBNP or a hBNP fragment thereof with at least about a two fold improvement, at least about a three fold improvement, at least about a four fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 3-631-436.

In another aspect, the present invention relates to an antibody that immunospecifically binds to hBNP or hBNP fragment and has a $k_{on}$ (or $k_a$) of at least about $1.5 \times 10^6$ $M^{-1}s^{-1}$, of at least about $3.5 \times 10^6$ $M^{-1}s^{-1}$, of at least about $7.8 \times 10^6$ $M^{-1}s^{-1}$, of at least about $8.0 \times 10^6$ $M^{-1}s^{-1}$ of at least about $1.0 \times 10^7$ $M^{-1}s^{-1}$, of at least about $2.0 \times 10^7$ $M^{-1}s^{-1}$, of at least about $5.0 \times 10^7$ $M^{-1}s^{-1}$, of at least about $7.5 \times 10^7$ $M^{-1}s^{-1}$, of at least about $1.0 \times 10^8$ $M^{-1}s^{-1}$, or has a $k_{on}$ (or $k_a$) ranging from about $1.5 \times 10^6$ $M^{-1}s^{-1}$ to about $1.0 \times 10^8$ $M^{-1}s^{-1}$, from about $1.95 \times 10^6$ $M^{-1}s^{-1}$ to about $1.0 \times 10^7$ $M^{-1}s^{-1}$, from about $2.70 \times 10^6$ $M^{-1}s^{-1}$ to about $9.0 \times 10^6$ $M^{-1}s^{-1}$, or from about $7.0 \times 10^6$ $M^{-1}s^{-1}$ to about $9.0 \times 10^6$ $M^{-1}s^{-1}$ with the proviso that if the $k_{on}$ is $1.6 \times 10^6$ $M^{-1}s^{-1}$ then the $k_{off}$ is not $5.4 \times 10^{-4}$ $s^{-1}$ or $6.5 \times 10^{-4}$ $s^{-1}$, if the $k_{on}$ is $6.7 \times 10^6$ $M^{-1}s^{-1}$ then the $k_{off}$ is not $2.5 \times 10^{-3}$ $s^{-1}$, if the $k_{on}$ is $8.4 \times 10^6$ $M^{-1}s^{-1}$ then the $k_{off}$ is not $2.9 \times 10^{-3}$ $s^{-1}$, if the $k_{on}$ is $8.4 \times 10^6$ $M^{-1}s^{-1}$ then the $k_{off}$ is not $2.9 \times 10^{-3}$ $s^{-1}$, if the $k_{on}$ is $5.8 \times 10^6$ $M^{-1}s^{-1}$ then the $k_{off}$ is not $1.6 \times 10^{-3}$ $s^{-1}$ or if the $k_{on}$ is $1.5 \times 10^6$ $M^{-1}s^{-1}$ then the $k_{off}$ is not $4.1 \times 10^{-4}$ $s^{-1}$.

In another aspect, an antibody of the present invention immunospecifically binds to at least three (3) amino acid residues of amino acid residues 13 through 18 of human BNP or hBNP fragment at a $k_{on}$ (or $k_a$) of at least about $1.5 \times 10^6$ $M^{-1}s^{-1}$, of at least about $3.5 \times 10^6$ $M^{-1}s^{-1}$, of at least about $7.8 \times 10^6$ $M^{-1}s^{-1}$, of at least about $8.0 \times 10^6$ $M^{-1}s^{-1}$ of at least about $1.0 \times 10^7$ $M^{-1}s^{-1}$, of at least about $2.0 \times 10^7$ $M^{-1}s^{-1}$, of at least about $5.0 \times 10^7$ $M^{-1}s^{-1}$, of at least about $7.5 \times 10^7$ $M^{-1}s^{-1}$, of at least about $1.0 \times 10^8$ $M^{-1}s^{-1}$, or has a $k_{on}$ (or $k_a$) ranging from about $1.5 \times 10^6$ $M^{-1}s^{-1}$ to about $1.0 \times 10^8$ $M^{-1}s^{-1}$, from about $1.95 \times 10^6$ $M^{-1}s^{-1}$ to about $1.0 \times 10^7$ $M^{-1}s^{-1}$, from about $2.70 \times 10^6$ $M^{-1}s^{-1}$ to about $9.0 \times 10^6$ $M^{-1}s^{-1}$, or from about $7.0 \times 10^6$ $M^{-1}s^{-1}$ to about $9.0 \times 10^6$ $M^{-1}s^{-1}$ with the proviso that if the $k_{on}$ is $1.6 \times 10^6$ $M^{-1}s^{-1}$ then the $k_{off}$ is not $5.4 \times 10^{-4}$ $s^{-1}$ or $6.5 \times 10^{-4}$ $s^{-1}$, if the $k_{on}$ is $6.7 \times 10^6$ $M^{-1}s^{-1}$ then the $k_{off}$ is not $2.5 \times 10^{-3}$ $s^{-1}$, if the $k_{on}$ is $8.4 \times 10^6$ $M^{-1}s^{-1}$ then the $k_{off}$ is not $2.9 \times 10^{-3}$ $s^{-1}$, if the $k_{on}$ is $8.4 \times 10^6$ $M^{-1}s^{-1}$ then the $k_{off}$ is not $2.9 \times 10^{-3}$ $s^{-1}$, if the $k_{on}$ is $5.8 \times 10^6$ $M^{-1}s^{-1}$ then the $k_{off}$ is not $1.6 \times 10^{-3}$ $s^{-1}$ or if the $k_{on}$ is $1.5 \times 10^6$ $M^{-1}s^{-1}$ then the $k_{off}$ is not $4.1 \times 10^{-4}$ $s^{-1}$.

In another aspect, the present invention provides antibodies produced by Chinese hamster ovary cell line 3-631-436 AM5 (also known as BNP3-631-436AM5CHO893-214), Chinese hamster ovary cell line 3-631-436 AM8 (also known as BNP3-631-436AM8CHO974-211) or a combination of antibodies produced by Chinese hamster ovary cell line 3-631-436 AM5 and Chinese hamster ovary cell line 3-631-436 AM8. Antibodies produced by the CHO cell line 3-631-436 AM5 bind to amino acid residues 13 thorough 18 of hBNP or hBNP fragment having a $k_{on}$ (or $k_a$) of at least about $7.6 \times 10^6$ $M^{-1}s^{-1}$, of at least about $7.7 \times 10^6$ $M^{-1}s^{-1}$, of at least about $7.8 \times 10^6$ $M^{-1}s^{-1}$, of at least about $7.9 \times 10^6$ $M^{-1}s^{-1}$ or have a $k_{on}$ (or $k_a$) ranging from about $7.6 \times 10^6$ $M^{-1}s^{-1}$ to about $7.9 \times 10^6$ $M^{-1}s^{-1}$. Antibodies produced by the CHO cell line 3-631-436 AM8 bind to amino acid residues 13 thorough 18 of hBNP or hBNP fragment having a $k_{on}$ (or $k_a$), of at least about $8.0 \times 10^6$ $M^{-1}s^{-1}$, of at least about $8.1 \times 10^6$ $M^{-1}s^{-1}$, of at least about $8.2 \times 10^6$ $M^{-1}s^{-1}$, of at least about $8.3 \times 10^6$ $M^{-1}s^{-1}$, of at least about $8.4 \times 10^6$ $M^{-1}s^{-1}$, or has a $k_{on}$ (or $k_a$) ranging from about $8.0 \times 10^6$ $M^{-1}s^{-1}$ to about $8.4 \times 10^6$ $M^{-1}s^{-1}$.

The present invention provides antibodies that immunospecifically bind to hBNP or hBNP fragment. In particular, the present invention provides for antibodies that have a high binding affinity for hBNP or hBNP fragment. More specifically, in one aspect, an antibody that immunospecifically binds to hBNP or hBNP fragment and has a $k_{off}$ (or $k_d$) of at least about $1.0 \times 10^{-3}$ $s^{-1}$, of at least about $6.5 \times 10^{-4}$ $s^{-1}$, of at least about $5.0 \times 10^{-4}$ $s^{-1}$, of at least about $4.0 \times 10^{-4}$ $s^{-1}$, of at least about $1.0 \times 10^{-4}$ $s^{-1}$, of at least about $7.5 \times 10^{-5}$ $s^{-1}$, $5.0 \times 10^{-5}$ $s^{-1}$, of at least about $2.0 \times 10^{-5}$ $s^{-1}$, of at least about $1 \times 10^{-5}$ $s^{-1}$, of at least about $1.0 \times 10^{-6}$ $s^{-1}$ or has a $k_{off}$ (or $k_d$) ranging from $2.0 \times 10^{-3}$ $s^{-1}$ to $1.0 \times 10^{-6}$ $s^{-1}$, from $1.0 \times 10^{-3}$ $s^{-1}$ to $1.0 \times 10^{-5}$ $s^{-1}$ or from $1.0 \times 10^{-3}$ $s^{-1}$ to $8.5 \times 10^4$ $s^{-1}$.

In another aspect, an antibody of the present invention immunospecifically binds to at least three amino acid residues of amino acid residues 13 through 18 of human BNP or hBNP fragment at a $k_{off}$ (or $k_{off}$) $k_{off}$ (or $k_d$) of at least about $1.0 \times 10^{-3}$ $s^{-1}$, of at least about $6.5 \times 10^{-4}$ $s^{-1}$, of at least about $5.0 \times 10^{-4}$ $s^{-1}$, of at least about $4.0 \times 10^{-4}$ $s^{-1}$, of at least about $1.0 \times 10^{-4}$ $s^{-1}$, of at least about $7.5 \times 10^{-5}$ $s^{-1}$, $5.0 \times 10^{-5}$ $s^{-1}$, of at least about $2.0 \times 10^{-5}$ $s^{-1}$, of at least about $1 \times 10^{-5}$ $s^{-1}$, of at least about $1.0 \times 10^{-6}$ $s^{-1}$ or has a $k_{off}$ (or $k_d$) ranging from $2.0 \times 10^{-3}$ $s^{-1}$ to $1.0 \times 10^{-6}$ $s^{-1}$, from $1.0 \times 10^{-3}$ $s^{-1}$ to $1.0 \times 10^{-5}$ $s^{-1}$ or from $1.0 \times 10^{-3}$ $s^{-1}$ to $8.5 \times 10^{-4}$ $s^{-1}$.

In another aspect, the present invention provides antibodies produced by Chinese hamster ovary cell line 3-631-436 AM5. Antibodies produced by this cell line bind to amino acid residues 13 thorough 18 of hBNP or hBNP fragment at a $k_{off}$ (or $k_d$) of at least about $1.5 \times 10^{-3}$ $s^{-1}$, of at least about $1.2 \times 10^{-3}$ $s^{-1}$, of at least about $1.1 \times 10^{-3}$ $s^{-1}$, or of at least about $1.0 \times 10^{-3}$ $s^{-1}$ or has a $k_{off}$ (or $k_d$) ranging from about $1.0 \times 10^{-3}$ $s^{-1}$ to about $1.5 \times 10^{-3}$ $s^{-1}$ or from about $1.1 \times 10^{-3}$ $s^{-1}$ to about $1.3 \times 10^{-3}$ $s^{-1}$.

In another aspect, the present invention provides antibodies produced by Chinese hamster ovary cell line 3-631-436 AM8. Antibodies produced by this cell line bind to amino acid residues 13 thorough 18 of hBNP or hBNP fragment at a $k_{off}$ (or $k_d$) of at least about $8.5 \times 10^{-4}$ $s^{-1}$, of at least about $8.2 \times 10^4$ $s^{-1}$, of at least about $8.1 \times 10^{-4}$ $s^{-1}$, or of at least about $8.0 \times 10^{-4}$ $s^{-1}$ or has a $k_{off}$ (or $k_d$) ranging from about $8.0 \times 10^{-4}$ $s^{-1}$ to about $8.5 \times 10^{-4}$ $s^{-1}$ or from about $8.2 \times 10^{-4}$ $s^{-1}$ to about $8.4 \times 10^{-4}$ $s^{-1}$.

The present invention provides antibodies that immunospecifically bind to hBNP or hBNP fragment. In particular, the present invention provides for antibodies that have a high binding affinity for hBNP or hBNP fragment. More specifically, in one aspect, the present invention relates to an antibody that immunospecifically binds to hBNP or hBNP fragment and has a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.6 \times 10^{-10}$ M to about $1.0 \times 10^{-10}$ M.

In another aspect, an antibody of the present invention immunospecifically binds to at least three (3) amino acid residues of the amino acid residues 13 through 18 of human BNP at a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.6 \times 10^{-10}$ M to about $1.0 \times 10^{-10}$ M.

In another aspect, the present invention provides antibodies produced by Chinese hamster ovary (CHO) cell line 3-631-436 AM5. Antibodies produced by this cell line bind to at least three (3) amino acid residues of amino acid residues 13 thorough 18 of hBNP or hBNP fragment at a $K_D$ of from $1.6 \times 10^{-10}$ M to $1.2 \times 10^{-10}$ M.

In another aspect, the present invention provides antibodies produced by Chinese hamster ovary (CHO) cell line 3-631-436 AM8. Antibodies produced by this cell line bind to at least three (3) amino acid residues of amino acid residues 13 thorough 18 of hBNP or hBNP fragment at a $K_D$ of from $1.2\times10^{-10}$ M to $1.0\times10^{-10}$ M.

In another aspect, the antibodies of the present invention are derivatives or variants of the antibodies produced by hybridoma cell line 3-631-436 (A.T.C.C. Accession No. PTA-6476). More specifically, the inventors of the present invention have discovered that antibodies that are derivatives or variants of the antibodies produced by hybridoma cell line 3-631-436 can be produced which exhibit a high binding affinity to hBNP or hBNP fragment. More specifically, the antibodies of the present invention exhibit a $k_{on}$ (or $k_a$) of at least about $1.5\times10^6$ M$^{-1}$s$^{-1}$, of at least about $3.5\times10^6$ M$^{-1}$s$^{-1}$, of at least about $7.8\times10^6$ M$^{-1}$s$^{-1}$, of at least about $8.0\times10^6$ M$^{-1}$s$^{-1}$, of at least about $1.0\times10^7$ M$^{-1}$s$^{-1}$, of at least about $2.0\times10^7$ M$^{-1}$s$^{-1}$, of at least about $5.0\times10^7$ M$^{-1}$s$^{-1}$, of at least about $7.5\times10^7$ M$^{-1}$s$^{-1}$, of at least about $1.0\times10^8$ M$^{-1}$s$^{-1}$, or has a $k_{on}$ (or $k_a$) ranging from about $1.5\times10^6$ M$^{-1}$s$^{-1}$ to about $1.0\times10^8$ M$^{-1}$s$^{-1}$, from about $1.95\times10^6$ M$^{-1}$s$^{-1}$ to about $1.0\times10^7$ M$^{-1}$s$^{-1}$, from about $2.70\times10^6$ M$^{-1}$s$^{-1}$ to about $9.0\times10^6$ M$^{-1}$s$^{-1}$, or from about $7.0\times10^6$ M$^{-1}$s$^{-1}$ to about $9.0\times10^6$ M$^{-1}$s$^{-1}$ with the proviso that if the $k_{on}$ is $1.6\times10^6$ M$^{-1}$s$^{-1}$ then the $k_{off}$ is not $5.4\times10^{-4}$ s$^{-1}$ or $6.5\times10^{-4}$ s$^{-1}$, if the $k_{on}$ is $6.7\times10^6$ M$^{-1}$s$^{-1}$ then the $k_{off}$ is not $2.5\times10^{-3}$ s$^{-1}$, if the $k_{on}$ is $8.4\times10^6$ M$^{-1}$s$^{-1}$ then the $k_{off}$ is not $2.9\times10^{-3}$ s$^{-1}$, if the $k_{on}$ is $8.4\times10^6$ M$^{-1}$s$^{-1}$ then the $k_{off}$ is not $2.9\times10^{-3}$ s$^{-1}$, if the $k_{on}$ is $5.8\times10^6$ M$^{-1}$s$^{-1}$ then the $k_{off}$ is not $1.6\times10^{-3}$-1 or if the $k_{on}$ is $1.5\times10^6$ M$^{-1}$s$^{-1}$ then the $k_{off}$ is not $4.1\times10^{-4}$ s$^{-1}$, or has a $k_{off}$ (or $k_d$) of at least about $1.0\times10^{-3}$s$^{-1}$, of at least about $6.5\times10^{-4}$s$^{-1}$, of at least about $5.0\times10^{-4}$ s$^{-1}$ of at least about $4.0\times10^{-4}$ s$^{-1}$, of at least about $1.0\times10^{-4}$ s$^{-1}$, of at least about $7.5\times10^{-5}$ s$^{-1}$, of least about $5.0\times10^{-5}$ s$^{-1}$, of at least about $2.0\times10^{-5}$ s$^{-1}$, of at least about $1.0\times10^{-5}$ s$^{-1}$, of at least about $1.0\times10^{-6}$ s$^{-1}$ or has a $k_{off}$ (or $k_d$) ranging from $2.0\times10^{-3}$ s$^{-1}$ to $1.0\times10^{-6}$ s$^{-1}$, from $1.0\times10^{-3}$ s$^{-1}$ to $1.0\times10^{-5}$ s$^{-1}$ or from $1.0\times10^{-3}$ s$^{-1}$ to $8.5\times10^{-4}$s$^{-1}$ or has a $K_D$ ranging from about $3.5\times10^{-10}$ M to about $1.0\times10^{-13}$ M, from about $2.8\times10^{-10}$ M to about $1.0\times10^{-12}$ M, from about $2.15\times10^{-10}$ M to about $1.0\times10^{-11}$ M or from about $1.6\times10^{-10}$ M to about $1.0\times10^{-10}$ M.

The derived or variant antibodies of the present invention comprise at least one mutation (such as deletions, additions and/or substitutions) in at least one of the heavy chain complementary determining ("CDR") regions (for example, the heavy chain CDR 1, heavy chain CDR 2 and/or heavy chain CDR 3), and/or at least one mutation (such as deletions, additions and/or substitutions) in the light chain CDR regions (for example, the light chain CDR 1, light chain CDR 2, and/or light chain CDR 3) when compared to the amino acid sequence of the antibody produced by hybridoma cell line 3-631-436 (also referred to herein as the "wildtype" and "3-631-436"). Moreover, the antibodies of the present invention may also contain one or more other mutations (such as deletions, additions and/or substitutions) in a part or portion of the antibody other than the CDR, such as, but not limited to, the framework region of an antibody. Methods for creating such derivatives are well known in the art and include the use of site-directed mutagenesis and PCR-mediated mutagenesis, which will be discussed in more detail infra.

More specifically, in another aspect, the antibody of the present invention immunospecifically binds to hBNP or hBNP fragment and comprises a light chain CDR 2 having an amino acid sequence of the formula of:

$Xaa_9$-$Xaa_{10}$-$Xaa_{11}$-$Xaa_{12}$-Leu-Glu-Ser (SEQ ID NO:83)
where $Xaa_9$ is selected from the group consisting of valine, glutamine, histidine, tryptophan and arginine;
where $Xaa_{10}$ is selected from the group consisting of valine, asparagine, threonine and methionine;
where $Xaa_{11}$ is selected from the group consisting of serine, threonine, asparagine and aspartic acid;
where $Xaa_{12}$ is selected from the group consisting of lysine and isoleucine;
provided that $Xaa_9$ is other than valine if $Xaa_{10}$ is Valine, $Xaa_1$ is serine and $Xaa_{12}$ is lysine.

In yet a further aspect, the antibody of the present invention immunospecifically binds to hBNP or hBNP fragment and comprises a light chain CDR 2 having the amino acid sequence shown in SEQ ID NO:83. In another aspect, the present invention relates to an antibody that immunospecifically binds to hBNP or hBNP fragment that comprises an amino acid sequence that is at least about 35%, preferably at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% identical to an amino acid sequence of SEQ ID NO:83.

In yet a further aspect, the antibody immunospecifically binds to hBNP or hBNP fragment and has a light chain CDR 2 having the amino acid sequence of SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 149, SEQ ID NO:150 or SEQ ID NO: 151. In another aspect, the present invention relates to an antibody that immunospecifically binds to hBNP or hBNP fragment that comprises an amino acid sequence that is at least about 35%, preferably at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% identical to an amino acid sequence of SEQ ID NO: 143, SEQ ID NO: 144, SEQ ID NO: 145, SEQ ID NO: 146, SEQ ID NO:147, SEQ ID NO: 148, SEQ ID NO:149, SEQ ID NO:149, SEQ ID NO:150 or SEQ ID NO: 151.

In yet a further aspect, the antibody of the present invention immunospecifically binds to hBNP or hBNP fragment and has a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 having an amino acid sequence of:

```
                                         (SEQ ID NO: 84)
       Gly-Tyr-Thr-Phe-Thr-Ser-Tyr-Trp-Met-Asn;
```

(b) Heavy Chain CDR 2 having an amino acid sequence having an amino acid sequence of:

```
                                         (SEQ ID NO: 85)
Arg-Ile-Asp-Pro-Tyr-Asp-Ser-Glu-Thr-His-Tyr-Asn-

Gln-Lys-Phe-Lys-Asp;
```

(c) Heavy Chain CDR 3 having an amino acid sequence of:

```
                                         (SEQ ID NO: 86)
                     Asp-Gly-Tyr
```

(d) Light Chain CDR 1 having an amino acid sequence having an amino acid sequence of:

```
                                         (SEQ ID NO: 87)
Lys-Ser-Ser-Gln-Ser-Leu-Leu-Asp-Ser-Asp-Gly-Lys-

Thr-Tyr-Leu-Asn
```

(e) Light Chain CDR 2 has an amino acid sequence having the formula of:

(SEQ ID NO: 83)
Xaa$_9$-Xaa$_{10}$-Xaa$_{11}$-Xaa$_{12}$-Leu-Glu-Ser where Xaa$_9$ is selected from the group consisting of valine, glutamine, histidine, tryptophan and arginine;
where Xaa$_{10}$ is selected from the group consisting of valine, asparagine, threonine and methionine;
where Xaa$_{11}$ is selected from the group consisting of serine, threonine, asparagine and aspartic acid;
where Xaa$_{12}$ is selected from the group consisting of lysine and isoleucine;
provided that Xaa$_9$ is other than valine if Xaa$_{10}$ is Valine, Xaa$_{11}$ is serine and Xaa$_{12}$ is Lysine,
(f) Light Chain CDR 3 has an amino acid sequence of:

(SEQ ID NO: 89)
Leu-Gln-Ala-Thr-His-Phe-Pro.

Preferably, the antibodies having the above-described formulas comprise a heavy chain CDR 1, heavy chain CDR 2, heavy chain CDR 3, light chain CDR 1, light chain CDR 2 and light chain CDR 3 where Xaa$_9$-Xaa$_{12}$ in the above described formulas have the amino acid residues shown below in Table 2.

TABLE 2

| Xaa$_9$ | Xaa$_{10}$ | Xaa$_{11}$ | Xaa$_{12}$ |
|---|---|---|---|
| Glutamine | Asparagine | Threonine | Lysine |
| Histidine | Threonine | Threonine | Lysine |
| Tryptophan | Methionine | Threonine | Lysine |
| Tryptophan | Methionine | Asparagine | Lysine |
| Valine | Threonine | Aspartic Acid | Lysine |
| Arginine | Threonine | Asparagine | Lysine |
| Tryptophan | Methionine | Aspartic Acid | Lysine |
| Tryptophan | Threonine | Threonine | Lysine |
| Tryptophan | Methionine | Asparagine | Lysine |
| Valine | Threonine | Aspartic Acid | Isoleucine |

III. Nucleic Acid Molecules

The present invention provides for a nucleic acid molecule, generally isolated, encoding an antibody of the present invention that immunospecifically binds to hBNP or hBNP fragment.

106.3 AM1 Nucleic Acid Molecules

In one aspect, the invention provides an isolated nucleic acid molecule encoding an antibody that binds to an epitope comprising amino acid residues 5 through 13 of hBNP or a hBNP fragment thereof with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant (K$_D$) when compared with an antibody produced by hybridoma cell line 106.3, said cell line having A.T.C.C. Accession No. HB-12044. The present invention also provides an isolated nucleic acid molecule that comprises a nucleotide sequence that hybridizes, under stringent conditions, to the nucleic acid molecule described herein that encodes an antibody that binds to an epitope comprising amino acid residues 5 through 13 of hBNP or hBNP fragment with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant (K$_D$) when compared with an antibody produced by hybridoma cell line 106.3, said cell line having A.T.C.C. Accession No. HB-12044.

In another aspect, the invention provides an isolated nucleic acid molecule encoding an antibody that immunospecifically binds to hBNP or hBNP fragment and that has a K$_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a K$_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{13}$ M, from $2 \times 10^{-11}$ M to $8.0 \times 10^{13}$ M, or from $1.0 \times 10^{-12}$ M to $7.4 \times 10^{-13}$ M. The present invention also provides an isolated nucleic acid molecule that comprises a nucleotide sequence that hybridizes, under stringent conditions, to the nucleic acid molecule described herein that encodes an antibody that immunospecifically binds to hBNP or hBNP fragment and that has a K$_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a K$_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M.

In another aspect, an isolated nucleic acid molecule encodes an antibody that immunospecifically binds to amino acid residues 5 through 13 of human BNP or hBNP fragment at a K$_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a K$_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M. The present invention also provides an isolated nucleic acid molecule that comprises a nucleotide sequence that hybridizes, under stringent conditions, to the nucleic acid molecule described herein that encodes an antibody that immunospecifically binds to amino acid residues 5 through 13 of hBNP or hBNP fragment at a K$_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a $K_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M.

In yet another aspect, the invention provides an isolated nucleic acid molecule encoding an antibody that immunospecifically binds to amino acid residues 5 through 13 of hBNP or hBNP fragment at a $K_D$ of from $4.2 \times 10^{-11}$ M to $7.4 \times 10^{-13}$ M, wherein said nucleic acid molecule comprises the nucleotide sequence of antibody produced by CHO cell line 106.3 AM1. The present invention also provides an isolated nucleic acid molecule that comprises a nucleotide sequence that hybridizes, under stringent conditions, to the nucleic acid molecule described herein that encodes an antibody that immunospecifically binds to amino acid residues 5 through 13 of hBNP or hBNP fragment at a $K_D$ of from $4.2 \times 10^{-11}$ M to $7.4 \times 10^{-13}$ M, wherein said nucleic acid molecule comprises the nucleotide sequence of antibody produced by CHO cell line 106.3 AM1.

In another aspect, the present invention provides an isolated nucleic acid molecule that encodes antibodies that immunospecifically bind to hBNP or hBNP fragment, wherein said antibodies comprise derivatives or variants of antibodies produced by hybridoma cell line 106.3 (A.T.C.C. Accession No. HB-12044). As discussed previously herein, the inventors of the present invention have discovered that antibodies that are derivatives or variants of the antibodies produced by hybridoma cell line 106.3 can be produced which exhibit a high binding affinity, specifically a $k_{on}$ (or $k_a$) of at least about $2.4 \times 10^4$ M$^{-1}$s$^{-1}$, of at least about $2.5 \times 10^4$ M$^{-1}$s$^{-1}$, of at least about $3.3 \times 10^4$ M$^{-1}$s$^{-1}$, of at least about $5.0 \times 10^4$ M$^{-1}$s$^{-1}$, of at least about $1.25 \times 10^7$ M$^{-1}$s$^{-1}$ of at least about $1.35 \times 10^7$ M$^{-1}$s$^{-1}$, of at least about $1.0 \times 10^8$ M$^1$s$^1$, of at least about $1.0 \times 10^9$ M$^{-1}$s$^1$, or have a $k_{on}$ (or $k_a$) ranging from about $5.0 \times 10^4$ M$^{-1}$s$^{-1}$ to about $1.0 \times 10^8$ M$^{-1}$s$^1$, from about $3.3 \times 10^4$ M$^{-1}$s$^{-1}$ to about $1.0 \times 10^9$ M$^{-1}$s$^{-1}$, from about $2.5 \times 10^4$ M$^{-1}$s$^{-1}$ to about $1.25 \times 10^7$ M$^{-1}$s$^{-1}$, from about $2.4 \times 10^4$ M$^{-1}$s$^{-1}$ to about $1.35 \times 10^7$ M$^{-1}$s$^{-1}$, a $k_{off}$ (or $k_d$) of at least about $1.0 \times 10^{-3}$ s$^{-1}$, of at least about $1.0 \times 10^{-4}$ s$^{-1}$, of at least about $1.0 \times 10^{-5}$ s$^{-1}$, of at least about $1.0 \times 10^{-6}$ s$^{-1}$ or have a $k_{off}$ (or $k_d$) ranging from about $1.0 \times 10^{-3}$ s$^{-1}$ to about $1.0 \times 10^{-6}$ s$^{-1}$, from about $1.0 \times 10^{-3}$ s$^{-1}$ to about $1.0 \times 10^{-5}$ s$^{-1}$ or from about $1.0 \times 10^{-3}$ s$^{-1}$ to about $1.0 \times 10^{-4}$ s$^{-1}$ and a $K_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a $K_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M. The derived or variant antibodies of the present invention comprises at least one mutation (such as deletions, additions and/or substitutions) in at least one of the heavy chain complementary determining ("CDR") regions (for example, the heavy chain CDR 1, heavy chain CDR 2, or heavy chain CDR 3), at least one mutation (such as deletions, additions and/or substitutions) in the light chain CDR regions (for example, the light chain CDR 1, light chain CDR 2, or light chain CDR 3) when compared to the amino acid sequence of the antibody produced by hybridoma cell line 106.3. Standard techniques known to those of skill in the art can be used to introduce mutations (such as deletions, additions, and/or substitutions) in the nucleic acid molecule encoding an antibody of the present invention, including, for example, site-directed mutagenesis and PCR-mediated mutagenesis which results in amino acid substitutions. In one aspect, the derivatives include less than 10 amino acid substitutions, less than 5 amino acid substitutions, less than 4 amino acid substitutions, less than 3 amino acid substitutions, or less than 2 amino acid substitutions relative to the original antibody produced by hybridoma cell line 106.3. In one aspect, the derivatives have conservative amino acid substitutions are made at one or more predicted non-essential amino acid residues (i.e., amino acid residues which are not critical for the antibody to immunospecifically bind to hBNP or hBNP fragment). A "conservative amino acid substitution" is one in which the amino acid residue is replaced with the amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that exhibit enhanced binding affinity to hBNP or hBNP fragment. Following mutagenesis, the encoded antibody can be expressed and the activity of the antibody can be determined.

In another aspect, the present invention provides an isolated nucleic acid molecule encoding an antibody that immunospecifically binds to hBNP or hBNP fragment, said antibody having a heavy chain CDR 2 having an amino acid sequence of the formula of:

(SEQ ID NO: 12)
Trp-Ile-Asn-Thr-His-Thr-Gly-Glu-Xaa$_1$-Xaa$_2$-Tyr-Ala-

Asp-Asp-Phe-Lys-Gly where Xaa$_1$ is selected from the group consisting of proline and alanine and Xaa$_2$ is selected from the group consisting of isoleucine and tyrosine, provided that when Xaa$_1$ is proline, Xaa$_2$ is not isoleucine. The present invention also provides an isolated nucleic acid molecule that comprises a nucleotide sequence that hybridizes, under stringent conditions, to the nucleic acid molecule described herein that encodes an antibody having a heavy chain CDR 2 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a heavy chain CDR 2 having an amino acid sequence of SEQ ID NO: 15. The present invention also provides an isolated nucleic acid molecule that comprises a nucleotide sequence that hybridizes, under stringent conditions, to the nucleic acid molecule described herein that encodes an antibody comprising a heavy chain CDR 2 having the amino acid sequence of SEQ ID NO:15.

In another aspect, the present invention provides an isolated nucleic acid molecule encoding an antibody that immunospecifically binds to hBNP or hBNP fragment, said antibody having a light chain CDR 1 that has an amino acid sequence having a formula of:

Lys-Ala-Xaa$_3$-Xaa$_4$-Xaa$_5$-Val-Asp-Tyr-Asn-Gly-Asp-Ser-Tyr-Leu-Asn (SEQ ID NO: 13)

where Xaa$_3$ is selected from the group consisting of: serine, alanine, asparagine, glutamine, tyrosine, threonine and arginine; where Xaa$_4$ is selected from the group consisting of: glutamine, tyrosine, tryptophan, alanine and phenylalanine and where Xaa$_5$ is selected from the group consisting of: serine, glycine, proline, alanine and aspartic acid, provided that Xaa$_3$ is not serine when Xaa$_4$ is glutamine and Xaa$_5$ is serine. The present invention also provides an isolated nucleic acid molecule that comprises a nucleotide sequence that hybridizes, under stringent conditions, to the nucleic acid molecule described herein that encodes an antibody having a light chain CDR 1 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a light chain CDR 1 having an amino acid sequence of SEQ ID NO:16, SEQ ID NO: 17, SEQ ID NO:18, SEQ ID NO:19, SEQ ID NO:20, SEQ ID NO:21 or SEQ ID NO:22. The present invention also provides an isolated nucleic acid molecule that comprises a nucleotide sequence that hybridizes, under stringent conditions, to the nucleic acid molecule described herein that encodes an antibody comprising a light chain CDR 1 having the amino acid sequence of SEQ ID NO:16, SEQ ID NO: 17, SEQ ID NO:18, SEQ ID NO:19, SEQ ID NO:20, SEQ ID NO:21 or SEQ ID NO:22.

In another aspect, the present invention provides an isolated nucleic acid molecule encoding an antibody that immunospecifically binds to hBNP or hBNP fragment, said antibody having a light chain CDR 2 that has an amino acid sequence having a formula of:

Ala-Ala-Ser-Xaa$_6$-Xaa$_7$-Xaa$_8$-Ser (SEQ ID NO: 14)

where Xaa$_6$ is selected from the group consisting of: asparagine and cysteine, where Xaa$_7$ is selected from the group consisting of: leucine, glycine and alanine and where Xaa$_8$ is selected from the group consisting of glutamic acid, tryptophan and proline, provided that Xaa$_6$ is not asparagine when Xaa$_7$ is leucine and Xaa$_8$ is glutamic acid. The present invention also provides an isolated nucleic acid molecule that comprises a nucleotide sequence that hybridizes, under stringent conditions, to the nucleic acid molecule described herein that encodes an antibody having a light chain CDR 2 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a light chain CDR 2 having an amino acid sequence of SEQ ID NO:23 or SEQ ID NO:24. The present invention also provides an isolated nucleic acid molecule that comprises a nucleotide sequence that hybridizes, under stringent conditions, to the nucleic acid molecule described herein that encodes an antibody comprising a light chain CDR 2 having the amino acid sequence of SEQ ID NO:23 or SEQ ID NO:24.

In another aspect, the invention provides an isolated nucleic acid molecule that encodes an antibody that immunospecifically binds to hBNP or hBNP fragment, said antibody comprising (alternatively, consisting) a heavy chain CDR 2 having an amino acid sequence of SEQ ID NO: 15, a light chain CDR 1 having an amino acid sequence of SEQ ID NO:16, SEQ ID NO: 17, SEQ ID NO:18, SEQ ID NO:19, SEQ ID NO:20, SEQ ID NO:21 or SEQ ID NO:22, a light chain CDR 2 having an amino acid sequence of SEQ ID NO:23 or SEQ ID NO:24 or any combinations these amino acid sequences. The present invention also provides an isolated nucleic acid molecule that comprises a nucleotide sequence that hybridizes, under stringent conditions, to the nucleic acid molecule described herein that encodes an antibody comprising a heavy chain CDR 2 having an amino acid sequence of SEQ ID NO: 15, a light chain CDR 1 having an amino acid sequence of SEQ ID NO:16, SEQ ID NO: 17, SEQ ID NO:18, SEQ ID NO:19, SEQ ID NO:20, SEQ ID NO:21 or SEQ ID NO:22, a light chain CDR 2 having an amino acid sequence of SEQ ID NO:23 or SEQ ID NO:24 or any combinations these amino acid sequences.

In another aspect, the present invention provides an isolated nucleic acid molecule encoding an antibody that immunospecifically binds to hBNP or hBNP fragment, said antibody having a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 having an amino acid sequence of: Gly-Tyr-Thr-Phe-Thr-His-Tyr-Gly-Ile-Asn (SEQ ID NO:6);

(b) Heavy Chain CDR 2 having an amino acid sequence having a formula of:

Trp-Ile-Asn-Thr-His-Thr-Gly-Glu-Xaa$_1$-Xaa$_2$-Tyr-Ala-Asp-Asp-Phe-Lys-Gly (SEQ ID NO: 12)

where Xaa$_1$ is selected from the group consisting of proline and alanine;

where Xaa$_2$ is selected from the group consisting of isoleucine and tyrosine;

(c) Heavy Chain CDR 3 having an amino acid sequence of: Ser-His-Arg-Phe-Gly-Leu-Asp-Tyr (SEQ ID NO:8);

(d) Light Chain CDR 1 having an amino acid sequence having a formula of:

Lys-Ala-Xaa$_3$-Xaa$_4$-Xaa$_5$-Val-Asp-Tyr-Asn-Gly-Asp-Ser-Tyr-Leu-Asn (SEQ ID NO: 13)

where Xaa$_3$ is selected from the group consisting of: serine, alanine, asparagine, glutamine, tyrosine, threonine and arginine;

where Xaa$_4$ is selected from the group consisting of: glutamine, tyrosine, tryptophan, alanine and phenylalanine;

where Xaa$_5$ is selected from the group consisting of: serine, glycine, proline, alanine and aspartic acid;

(e) Light Chain CDR 2 has an amino acid sequence having the formula of:

Ala-Ala-Ser-Xaa$_6$-Xaa$_7$-Xaa$_8$-Ser (SEQ ID NO: 14)

where Xaa$_6$ is selected from the group consisting of: asparagine and cysteine;

where Xaa₇ is selected from the group consisting of: leucine, glycine and alanine;
where Xaa₈ is selected from the group consisting of glutamic acid, tryptophan and proline; and
(f) Light Chain CDR 3 has an amino acid sequence of: Gln-Gln-Ser-Asn-Glu-Asp-Pro-Phe-Thr (SEQ ID NO:11),
where the heavy chain CDR 2 has an amino acid sequence other than Trp-Ile-Asn-Thr-His-Thr-Gly-Glu-Pro-Ile-Tyr-Ala-Asp-Asp-Phe-Lys-Gly (SEQ ID NO:7) when the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9) and the light chain CDR 2 has the amino acid sequence of Ala-Ala-Ser-Asn-Leu-Glu-Ser (SEQ ID NO:10), the light chain CDR 1 has an amino acid sequence other than Lys-Ala-Ser-Gln-Ser-Val-Asp-Tyr-Asn-Gly-Asp-Ser-Tyr-Leu-Asn (SEQ ID NO:9) when the heavy chain CDR 2 has the amino acid sequence Trp-Ile-Asn-Thr-His-Thr-Gly-Glu-Pro-Ile-Tyr-Ala-Asp-Asp-Phe-Lys-Gly (SEQ ID NO:7) and the light chain CDR 2 has the amino acid sequence Ala-Ala-Ser-Asn-Leu-Glu-Ser (SEQ ID NO:10), or the light chain CDR 2 has an amino acid sequence other than Ala-Ala-Ser-Asn-Leu-Glu-Ser (SEQ ID NO:10) when the heavy chain CDR 2 has the amino acid sequence of Trp-Ile-Asn-Thr-His-Thr-Gly-Glu-Pro-Ile-Tyr-Ala- Asp-Asp-Phe-Lys-Gly (SEQ ID NO:7) and the light chain CDR 1 has the amino acid sequence of Lys-Ala-Ser-Gln-Ser-Val-Asp-Tyr-Asn-Gly-Asp-Ser-Tyr-Leu-Asn (SEQ ID NO:9). The present invention also provides an isolated nucleic acid molecule that comprises a nucleotide sequence that hybridizes, under stringent conditions, to the nucleic acid molecule described herein that encodes an antibody having a heavy chain CDR 1 region, a heavy chain CDR 2 region, a heavy chain CDR 3 region, a light chain CDR 1 region, a light chain CDR 2 region and a light chain CDR 3 region having the amino acid sequences pursuant to the above-described formula.

In yet another aspect, the present invention provides an isolated nucleic acid molecule encoding an antibody that immunospecifically binds to hBNP or hBNP fragment, wherein said antibody is produced by CHO cell line 106.3 AM1. The present invention also provides an isolated nucleic acid molecule that comprises a nucleotide sequence that hybridizes, under stringent conditions, to the nucleic acid molecule that encodes an antibody that immunospecifically binds to hBNP or hBNP fragment, wherein said antibody is produced by CHO cell line 106.3 AM1.

3-631-436 AM5 and 3-631-436 AM8 Nucleic Acid Molecules

In another aspect, the invention provides an isolated nucleic acid molecule encoding an antibody that binds to an epitope comprising at least three (3) amino acid residues of amino acid residues 13 through 18 of hBNP or a hBNP fragment thereof with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by cell line 3-631-436 which was deposited with the American Type Culture Collection (A.T.C.C.) on Dec. 21, 2004 and assigned A.T.C.C. Accession No. PTA-6476 and is described in U.S. Patent Publication 2006/0183154 published on Aug. 17, 2006 (which is also referred to herein as the "wildtype" and "3-631-436"). The present invention also provides an isolated nucleic acid molecule that comprises a nucleotide sequence that hybridizes, under stringent conditions, to the nucleic acid molecule described herein that encodes an antibody that binds to an epitope comprising at least three (3) amino acid residues of amino acid residues 13 through 15 of hBNP or hBNP fragment with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by 3-631-436 which was deposited with the American Type Culture Collection (A.T.C.C.) on Dec. 21, 2004 and assigned A.T.C.C. Accession No. PTA-6476 and is described in U.S. Patent Publication 2006/0183154 published on Aug. 17, 2006 (which is also referred to herein as the "3-631-436").

In another aspect, the invention provides an isolated nucleic acid molecule encoding an antibody that immunospecifically binds to hBNP or hBNP fragment and that has a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.60 \times 10^{-10}$ M to about $1.0 \times 10^{-10}$ M.

The present invention also provides an isolated nucleic acid molecule that comprises a nucleotide sequence that hybridizes, under stringent conditions, to the nucleic acid molecule described herein that encodes an antibody that immunospecifically binds to hBNP or hBNP fragment and that has a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.6 \times 10^{-10}$ M to about $1.0 \times 10^{-10}$ M.

In another aspect, an isolated nucleic acid molecule encodes an antibody that immunospecifically binds to amino acid residues 13 through 18 of human BNP or hBNP fragment at a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.6 \times 10^{-10}$ M to about $1.0 \times 10^{-10}$ M. The present invention also provides an isolated nucleic acid molecule that comprises a nucleotide sequence that hybridizes, under stringent conditions, to the nucleic acid molecule described herein that encodes an antibody that immunospecifically binds to amino acid residues 13 through 18 of hBNP or hBNP fragment at a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.6 \times 10^{-10}$ M to about $1.0 \times 10^{-10}$ M.

In yet another aspect, the invention provides an isolated nucleic acid molecule encoding an antibody that immunospecifically binds to amino acid residues 13 through 18 of hBNP or hBNP fragment at a $K_D$ from about $1.2 \times 10^{-10}$ M to about $1.6 \times 10^{-10}$ M, wherein said nucleic acid molecule comprises the nucleotide sequence of antibody produced by CHO cell line 3-631-436 AM5. The present invention also provides an isolated nucleic acid molecule that comprises a nucleotide sequence that hybridizes, under stringent conditions, to the nucleic acid molecule described herein that encodes an antibody that immunospecifically binds to amino acid residues 13 through 18 of hBNP or hBNP fragment at a $K_D$ of from about $1.2 \times 10^{-10}$ M to about $1.6 \times 10^{-10}$ M, wherein said nucleic acid molecule comprises the nucleotide sequence of antibody produced by CHO cell line 3-631-436 AM5.

In yet another aspect, the invention provides an isolated nucleic acid molecule encoding an antibody that immunospecifically binds to amino acid residues 13 through 18 of hBNP or hBNP fragment at a $K_D$ of from about $1.0 \times 10^{-10}$ M to about $1.2 \times 10^{-10}$ M, wherein said nucleic acid molecule comprises the nucleotide sequence of antibody produced by CHO cell line 3-631-436 AM8. The present invention also provides an isolated nucleic acid molecule that comprises a nucleotide sequence that hybridizes, under stringent conditions, to the nucleic acid molecule described herein that encodes an antibody that immunospecifically binds to amino acid residues 13 through 18 of hBNP or hBNP fragment at a $K_D$ of from about $1.0 \times 10^{-10}$ M to about $1.2 \times 10^{-10}$ M, wherein said nucleic acid molecule comprises the nucleotide sequence of antibody produced by CHO cell line 3-631-436 AM8.

In another aspect, the present invention provides an isolated nucleic acid molecule that encodes antibodies that immunospecifically bind to hBNP or hBNP fragment, wherein said antibodies comprise derivatives or variants of antibodies produced by hybridoma cell line 3-631-436 AM5 (A.T.C.C. Accession No. PTA-8369). As discussed previously herein, the inventors of the present invention have discovered that antibodies that are derivatives or variants of the antibodies produced by hybridoma cell lines 3-631-436 AM5 or 3-631-436 AM8 can be produced which exhibit a high binding affinity, specifically a $k_{on}$ (or $k_a$) of at least about $1.5 \times 10^6$ $M^{-1}s^{-1}$, of at least about $3.5 \times 10^6$ $M^{-1}s^{-1}$, of at least about $7.8 \times 10^6$ $M^{-1}s^{-1}$, of at least about $8.0 \times 10^6$ $M^{-1}s^{-1}$ of at least about $1.0 \times 10^7$ $M^{-1}s^{-1}$, of at least about $2.0 \times 10^7$ $M^{-1}s^{-1}$, of at least about $5.0 \times 10^7$ $M^{-1}s^{-1}$, of at least about $7.5 \times 10^7$ $M^{-1}s^{-1}$, of at least about $1.0 \times 10^8$ $M^{-1}s^{-1}$, or has a $k_{on}$ (or $k_a$) ranging from about $1.5 \times 10^6$ $M^{-1}s^{-1}$ to about $1.0 \times 10^8$ $M^{-1}s^{-1}$, from about $1.95 \times 10^6$ $M^{-1}s^{-1}$ to about $1.0 \times 10^7$ $M^{-1}s^{-1}$, from about $2.70 \times 10^6$ $M^{-1}s^{-1}$ to about $9.0 \times 10^6$ $M^{-1}s^{-1}$, or from about $7.0 \times 10^6$ $M^{-1}s^{-1}$ to about $9.0 \times 10^6$ $M^{-1}s^{-1}$ with the proviso that if the $k_{on}$ is $1.6 \times 10^6$ $M^{-1}s^{-1}$ then the $k_{off}$ is not $5.4 \times 10^{-4}$ $s^{-1}$ or $6.5 \times 10^{-4}$ $s^{-1}$, if the $k_{on}$ is $6.7 \times 10^6$ $M^{-1}s^{-1}$ then the $k_{off}$ is not $2.5 \times 10^{-3}$ $s^{-1}$, if the $k_{on}$ is $8.4 \times 10^6$ $M^{-1}s^{-1}$ then the $k_{off}$ is not $2.9 \times 10^{-3}$ $s^{-1}$, if the $k_{on}$ is $8.4 \times 10^6$ $M^{-1}s^{-1}$ then the $k_{off}$ is not $2.9 \times 10^{-3}$ $s^{-1}$, if the $k_{on}$ is $5.8 \times 10^6$ $M^{-1}s^{-1}$ then the $k_{off}$ is not $1.6 \times 10^{-3}$ $s^{-1}$ or if the $k_{on}$ is $1.5 \times 10^6$ $M^{-1}s^{-1}$ then the $k_{off}$ is not $4.1 \times 10^{-4}$ $s^{-1}$, or has a $k_{off}$ (or $k_d$) of at least about $1.0 \times 10^{-3}$ $s^{-1}$, of at least about $6.5 \times 10^{-4}$ $s^{-1}$, of at least about $5.0 \times 10^{-4}$ $s^{-1}$, of at least about $4.0 \times 10^4$ $s^{-1}$, of at least about $1.0 \times 10^{-4}$ $s^{-1}$, of at least about $7.5 \times 10^{-5}$ $s^{-1}$, of at least about $5.0 \times 10^{-5}$ $s^{-1}$, of at least about $2.0 \times 10^{-5}$ $s^{-1}$, of at least about $1.0 \times 10^{-5}$ $s^{-1}$, of at least about $1.0 \times 10^{-6}$ $s^{-1}$ or has a $k_{off}$ (or $k_d$) ranging from $2.0 \times 10^{-3}$ $s^{-1}$ to $1.0 \times 10^{-6}$ $s^{-1}$, from $1.0 \times 10^{-3}$ $s^{-1}$ to $1.0 \times 10^{-5}$ $s^{-1}$ or from $1.0 \times 10^{-3}$ $s^{-1}$ to $8.5 \times 10^4$ $s^{-1}$ or has a $K_D$ ranging from about $3.5 \times 10^{-10}$ M to about $1.0 \times 10^{-13}$ M, from about $2.8 \times 10^{-10}$ M to about $1.0 \times 10^{-12}$ M, from about $2.15 \times 10^{-10}$ M to about $1.0 \times 10^{-11}$ M or from about $1.6 \times 10^{-10}$ M to about $1.0 \times 10^{-10}$ M.

The derived or variant antibodies of the present invention comprises at least one mutation (such as deletions, additions and/or substitutions) in at least one of the light chain complementary determining ("CDR") region (for example, the light chain CDR 2) when compared to the amino acid sequence of the antibody produced by hybridoma cell line 3-631-436 (having A.T.C.C. Accession No. PTA-6476). Standard techniques known to those of skill in the art can be used to introduce mutations (such as deletions, additions, and/or substitutions) in the nucleic acid molecule encoding an antibody of the present invention, including, for example, site-directed mutagenesis and PCR-mediated mutagenesis which results in amino acid substitutions. In one aspect, the derivatives include less than 10 amino acid substitutions, less than 5 amino acid substitutions, less than 4 amino acid substitutions, less than 3 amino acid substitutions, or less than 2 amino acid substitutions relative to the original antibody produced by hybridoma cell line 3-631-436 (having A.T.C.C. Accession No. PTA-6476). In one aspect, the derivatives have conservative amino acid substitutions are made at one or more predicted non-essential amino acid residues (i.e., amino acid residues which are not critical for the antibody to immunospecifically bind to hBNP or hBNP fragment). A "conservative amino acid substitution" is one in which the amino acid residue is replaced with the amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that exhibit enhanced binding affinity to hBNP or hBNP fragment. Following mutagenesis, the encoded antibody can be expressed and the activity of the antibody can be determined.

In another aspect, the present invention provides an isolated nucleic acid molecule encoding an antibody that immunospecifically binds to hBNP or hBNP fragment, said antibody having a light chain CDR 2 having an amino acid sequence of the formula of:

```
                                        (SEQ ID NO: 83)
        Xaa9-Xaa10-Xaa11-Xaa12-Leu-Glu-Ser
``` where $Xaa_9$ is selected from the group consisting of valine, glutamine, histidine, tryptophan and arginine;

where $Xaa_{10}$ is selected from the group consisting of valine, asparagine, threonine and methionine;

where $Xaa_{11}$ is selected from the group consisting of serine, threonine, asparagine and aspartic acid;

where $Xaa_{12}$ is selected from the group consisting of lysine and isoleucine;

provided that $Xaa_9$ is other than valine if $Xaa_{10}$ is Valine, $Xaa_{11}$ is serine and $Xaa_{12}$ is Lysine.

The present invention also provides an isolated nucleic acid molecule that comprises a nucleotide sequence that hybridizes, under stringent conditions, to the nucleic acid molecule described herein that encodes an antibody having a light chain CDR 2 having an amino acid sequence of the above-described formula.

In another aspect, the invention provides an isolated nucleic acid molecule encoding an antibody that immunospecifically binds to hBNP or hBNP fragment, said antibody comprising (alternatively, consisting of) a light chain CDR 2 having an amino acid sequence of SEQ ID NO:143, SEQ ID NO:144, SEQ ID NO:145, SEQ ID NO:146, SEQ ID NO:147, SEQ ID NO: 148, SEQ ID NO:149, SEQ ID NO:149, SEQ ID NO:150 or SEQ ID NO: 151. The present invention also provides an isolated nucleic acid molecule that comprises a nucleotide sequence that hybridizes, under stringent conditions, to the nucleic acid molecule described herein that encodes an antibody comprising a light chain CDR 2 having the amino acid sequence of SEQ ID NO:143, SEQ ID NO:144, SEQ ID NO:145, SEQ ID NO:146, SEQ ID NO:147, SEQ ID NO: 148, SEQ ID NO:149, SEQ ID NO:149, SEQ ID NO 150 or SEQ ID NO: 151.

In another aspect, the present invention provides an isolated nucleic acid molecule encoding an antibody that immunospecifically binds to hBNP or hBNP fragment, said antibody having a heavy chain CDR 1, heavy chain CDR 2, heavy chain CDR 3, a light chain CDR 1, a light chain CDR 2 and a light variable CDR 3 comprising the following amino acid sequences:

(a) Heavy Chain CDR 1 having an amino acid sequence of:

(SEQ ID NO: 84)
Gly-Tyr-Thr-Phe-Thr-Ser-Tyr-Trp-Met-Asn;

(b) Heavy Chain CDR 2 having an amino acid sequence having a formula of:

(SEQ ID NO: 85)
Arg-Ile-Asp-Pro-Tyr-Asp-Ser-Glu-Thr-His-Tyr-Asn-

Gln-Lys-Phe-Lys-Asp;

(c) Heavy Chain CDR 3 having an amino acid sequence of:

(SEQ ID NO: 86)
Asp-Gly-Tyr (d) Light Chain CDR 1 having an amino acid sequence having a formula of:

(SEQ ID NO: 87)
Lys-Ser-Ser-Gln-Ser-Leu-Leu-Asp-Ser-Asp-Gly-Lys-

Thr-Tyr-Leu-Asn (e) Light Chain CDR 2 has an amino acid sequence having the formula of:

(SEQ ID NO: 83)
Xaa$_9$-Xaa$_{10}$-Xaa$_{11}$-Xaa$_{12}$-Leu-Glu-Ser where Xaa$_9$ is selected from the group consisting of valine, glutamine, histidine, tryptophan and arginine;
where Xaa$_{10}$ is selected from the group consisting of valine, asparagine, threonine and methionine;
where Xaa$_{11}$ is selected from the group consisting of serine, threonine, asparagine and aspartic acid;
where Xaa$_{12}$ is selected from the group consisting of lysine and isoleucine;
provided that Xaa$_9$ is other than valine if Xaa$_{10}$ is Valine, Xaa$_{11}$ is serine and Xaa$_{12}$ is Lysine, (f) Light Chain CDR 3 has an amino acid sequence of:

(SEQ ID NO: 89)
Leu-Gln-Ala-Thr-His-Phe-Pro.

In yet another aspect, the present invention provides an isolated nucleic acid molecule encoding an antibody that immunospecifically binds to hBNP or hBNP fragment, wherein said antibody is produced by CHO cell line 3-631-436 AM5 or 3-631-436 AM8. The present invention also provides an isolated nucleic acid molecule that comprises a nucleotide sequence that hybridizes, under stringent conditions, to the nucleic acid molecule that encodes an antibody that immunospecifically binds to hBNP or hBNP fragment, wherein said antibody is produced by CHO cell line 3-631-436 AM5 or 3-631-436 AM8.

IV. Methods for Preparing the Antibodies of the Present Invention

The antibodies of the present invention can be prepared using routine techniques known to those skilled in the art.

In one aspect, the antibodies of the present invention can be prepared by recombinant expression of immunoglobulin light and heavy chain genes in a host cell. To express an antibody recombinantly, a host cell is transfected with one or more recombinant expression vectors carrying nucleic acid molecules encoding the immunoglobulin light and heavy chains of the antibody such that the light and heavy chains are expressed in the host cell and, preferably, secreted into the medium in which the host cells are cultures, from which medium the antibodies can be recovered. Standard recombinant nucleic acid (DNA) methodologies are used to obtain antibody heavy and light chain genes, incorporate these genes into recombinant expressions vectors and introduce the vectors into host cells, such as those described in Sambrook, Fritsch and Maniatis (eds), *Molecular Cloning: A Laboratory Manual, Second Edition*, Cold Spring Harbor, New Your, (1989), Ausubel, F. M. et al. (eds.) *Current Protocols in Molecular Biology*, Greene Publishing Associates (1989) and in U.S. Pat. No. 4,816,397 by Boss et al.

To express the antibodies of the invention, nucleic acid molecules encoding the light and heavy chain regions are first obtained. These nucleic acid molecules may be obtained from a hybridoma cell line expressing monoclonal antibody 106.3 or a hybridoma cell line expressing monoclonal antibody 3-631-436 and modified by means well known in the art (such as site-directed mutagenesis) to generate antibodies of the present invention, including, for example, the antibodies produced by CHO cell line 106.3 AM1, CHO cell line 3-631-436 AM5, CHO cell line 3-631-436 AM8 or any combinations thereof. A hybridoma cell line expressing monoclonal antibody 106.3 was deposited with the American Type Culture Collection ("A.T.C.C."), 10801 University Boulevard, Manassas, Va. 20110 and was accorded accession number HB-12044. The nucleic acid sequence of monoclonal antibody 106.3 is shown in FIGS. 3A-3E and SEQ ID NO:1. A hybridoma cell line expressing monoclonal antibody 3-631-436 which was deposited with the American Type Culture Collection (A.T.C.C.) on Dec. 21, 2004 and assigned A.T.C.C. Accession No. PTA-6476 and is described in U.S. Patent Publication 2006/0183154 published on Aug. 17, 2006. The nucleic acid sequence of monoclonal antibody 3-631-436 is shown in FIGS. 25A-25B and SEQ ID NO: 92.

For example, once the 106.3 or 3-631-436 variable heavy (VH) and variable (VL) nucleic acid fragments are obtained, these sequences or specific regions within these sequences, such as the complementary determining ("CDR") regions, can be mutated to encode the 106.3 AM1, 3-631-436 AM5 or 3-631-436 AM8 or 106.3 AM1, 3-631-436 AM5 or 3-631-436 AM8-related amino acid sequences disclosed herein. The amino acid sequences encoded by the 106.3 or 3-631-436 VH and VL DNA sequences are compared to the 106.3 AM1, 3-631-436 AM5, 3-631-436 AM8 or 106.3 AM1, 3-631-436

AM5 or 3-631-436 AM8-related VH and VL amino acid sequences to identify amino acid residues in the 106.3 AM1, 3-631-436 AM5, 3-631-436 AM8 or 106.3 AM1, 3-631-436 AM5 or 3-631-436 AM8-related sequence that differ. The appropriate nucleotides of monoclonal antibody 106.3 or 3-631-436 are mutated such that the mutated sequence encodes the 106.3 AM1, 3-631-436 AM5, 3-631-436 AM8 or 106.3 AM1, 3-631-436 AM5 or 3-631-436 AM8-related amino acid sequence, using the genetic code to determine which nucleotide changes should be made. Mutagenesis of antibody 106.3 or 3-631-426 sequences can be carried out by standard methods, such as PCR-mediated mutagenesis (in which the mutated nucleotides are incorporated into the PCR primers such that the PCR product contains the mutations) or site-directed mutagenesis.

Alternatively, in another aspect, nucleic acid molecules encoding the VH and VL chains can be synthesized on a chemical synthesizer, using routine techniques known to those in the art. For example, the VH and VL chains from the nucleic acid molecules described in Section III can be chemically synthesized using routine techniques known in the art. Starting at the 3' terminal base which is attached to a support, nucleotides are coupled in a step-wise fashion. Following the addition of the most 5' nucleotide, the nucleotide is cleaved from the solid support and purified by desalting followed by polyacrylamide gel electrophoresis (PAGE) (Midland Certified Reagents, Midland, Tex., www.oligos.com).

Once nucleic acid fragments encoding 106.3 AM1, 3-631-436 AM5 or 3-631-436 AM8 or 106.3 AM1-, 3-631-436 AM5- or 3-631-436 AM8-related VH and VL segments are obtained (by amplification and mutagenesis of VH and VL genes, as described above), these nucleic acid fragments can be further manipulated by standard recombinant DNA techniques, for example to convert the variable region genes to an antibody (such as, but not limited to, a full-length antibody chain genes, to Fab fragment genes or to a scFv gene). In these manipulations, a VL- or VH-encoding nucleic acid fragment is operatively linked to another nucleic acid fragment encoding another protein, such as antibody constant region or a flexible linker. The term "operatively linked", as used in this context, is intended to mean that the two nucleic acid fragments are joined such that the amino acid sequences encoded by the two nucleic acid fragments remain in-frame.

In an alternative method, an scFv gene may be constructed with wildtype CDR regions (such as those of monoclonal antibody 106.3 or 3-631-426) and then mutated using techniques known in the art.

The isolated nucleic acid molecule encoding the VH region can be converted to a full-length heavy chain gene by operatively linking the VH-encoding nucleic acid molecule to another nucleic acid molecule encoding heavy chain constant regions ($CH_1$, $CH_2$ and $CH_3$). The sequences of human heavy chain constant region genes are known in the art (See for example, Kabat, E. A., et al., *Sequences of Proteins of Immunological Interest*, Fifth Edition, U.S. Department of Health and Human Services, NIH Publication No. 91-3242 (1991)). In another aspect, the present invention further encompasses all known human heavy chain constant regions, including but not limited to, all known allotypes of the human heavy chain constant region. Nucleic acid fragments encompassing these regions can be obtained by standard PCR amplification. The heavy chain constant region can be an IgG1, IgG2, IgG3, IgG4, IgA, IgE, IgM or IgD constant region.

The isolated nucleic acid molecule encoding the VL region can be converted to a full-length light chain gene (as well as a Fab light chain gene) by operatively linking the VL-encoding nucleic acid molecule to another nucleic acid molecule encoding the light chain constant region, CL. The sequences of human light chain constant region genes are known in the art (see e.g., Kabat, E. A., et al., *Sequences of Proteins of Immunological Interest*, Fifth Edition, U.S. Department of Health and Human Services, NIH Publication No. 91-3242 (1991)). The present invention encompasses all known human light chain constant regions, including but not limited to, all known allotypes of the human light chain constant region. Nucleic acid fragments encompassing these regions can be obtained by standard PCR amplification. The light chain constant region can be a kappa or lambda constant region, but most preferably is a kappa constant region.

It is to be understood that the specific designations of framework (FR) and CDR regions within a particular heavy or light chain region may vary depending on the convention or numbering system used to identify such regions (e.g. Chothia, Kabat, Oxford Molecular's AbM modeling software, all of which are known to those of ordinary skill in the art). For the purposes of the present invention, the Kabat numbering system is used.

To create a scFv gene, the VH- and VL-encoding nucleic acid fragments are operatively linked to another fragment encoding a flexible linker, such as, a linker that is encoded by the amino acid sequence GPAKELTPLKEAKVS (SEQ ID NO:4) (See, U.S. Patent Publication 2004-0175379 A1). Examples of other linker sequences that can be used in the present invention can be found in Bird et al., *Science* 242: 423-426 (1988), Huston et al., *Proc. Natl. Acad. Sci. USA* 85:5879-5883 (1988) and McCafferty et al., *Nature,* 348:552-554 (1990).

To express the antibodies, or antibody portions of the invention, nucleic acid molecules encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (for example, ligation of complementary restriction sites on the antibody gene fragment and vector, or blunt end ligation if no restriction sites are present). Prior to the insertion of the light or heavy chain sequences, the expression vector may already carry antibody constant region sequences. For example, one approach to converting the VH and VL sequences to full-length antibody genes is to insert them into expression vectors already encoding heavy chain constant and light chain constant regions, respectively, such that the VH segment is operatively linked to the CH "segment" within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The single peptide can be an immunoglobin signal peptide or a heterologous signal peptide (i.e., a signal peptide from a non-immunoglobulin protein).

In addition to the antibody chain genes, the recombinant expression vectors can carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology. Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of the expression of protein desired, etc. Preferred regulatory sequences for mammalian host cell expression include viral elements that direct high levels of protein expression in mammalian cells, such as promoters and/or enhancers derived from cytomegalovirus ("CMV") (such as the CMV promoter/enhancer), Simian Virus 40 ("SV40") (such as the SV40 promoter/enhancer), adenovirus, (such as the adenovirus major late promoter ("AdMLP")) and polyoma. For further description of viral regulatory elements, and sequences thereof, see for example, U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (See, for example, U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase ("DHFR") gene for use in dhfr-host cells with methotrexate selection/amplification and the neomycin ("neo") gene for G418 selection.

For expression of the light and heavy chains, the expression vector(s) encoding the heavy and light chains are transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active intact antibody. Prokaryotic expression of antibody genes has been reported to be ineffective for production of high yields of active antibody (See, Boss, M. A. and Wood, C. R., *Immunology Today* 6:12-13 (1985)).

Preferred mammalian host cells for expressing the recombinant antibodies of the invention include the Chinese Hamster Ovary ("CHO") cells (including dhfr-CHO cells, described in Urlaub and Chasin, *Proc. Natl. Acad. Sci. USA* 77:4216-4220 (1980), used with a DHFR selectable marker, for example, as described in R. J. Kaufman and P. A. Sharp, *Mol. Biol.* 159:601-621 (1982)), NSO myeloma cells, COS cells, and SP2/0 myeloma cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments, F(ab')$_2$ fragments or scFv molecules. It will be understood that variations on the above procedure are within the scope of the present invention. For example, it may be desirable to transfect a host cell with nucleic acid molecule encoding either the light chain or the heavy chain (but not both) of an antibody of the present invention. Recombinant DNA technology may also be used to remove some or all of the nucleic acid molecules encoding either or both of the light and heavy chains that are not necessary for binding to hBNP or hBNP fragment. The molecules expressed from such truncated nucleic acid molecules also are encompassed by the antibodies of the invention.

In a preferred system for recombinant expression of an antibody, or antigen binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector. Cells were cultured in medium without hypoxanthine and thymidine to obtain those CHO cells that have acquired the DHFR gene from the transfecting vector. Antigen specific screening methods were used to identify those clones that expressed the highest quantity of antibody. Those individual clones were expanded and were routinely re-screened. Cell lines were selected from 106.3 AM1, 3-631-436 AM5 and 3-631-436 AM8 transfections. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of forgoing, another aspect of the invention pertains to nucleic acid, vector and host cell compositions that can be used for recombinant expression of the antibodies and antibody portions of the invention. In one aspect, the amino acid sequence encoding the heavy chain CDR 2 region of 106.3 AM1 and variants thereof is shown in SEQ ID NO:15. The amino acid sequence encoding the 106.3 AM1 light chain CDR 1 region is shown in SEQ ID NO:22. The nucleic acid molecule encoding the heavy chain CDR 2 region of 106.3 AM1 is shown in SEQ ID NO:81. The nucleic acid molecule encoding the light chain CDR 1 region of 106.3 AM1 is shown in SEQ ID NO:82. In another aspect, the amino acid sequence encoding the light chain CDR 2 region of 3-631-436 AM5 and 3-631-436 AM8 and variants thereof is shown in SEQ ID NO:83. The nucleic acid molecule encoding the light chain CDR L2 of 3-631-436 AM5 and 3-631-436 AM8 is shown in SEQ ID NO: 154.

V. Selection of Recombinant Antibodies

The antibodies of the present invention, including the 106.3 AM1, 3-631-436 AM5, 3-631-436 AM8 or 106.3

AM1-, 3-631-436 AM5- or 3-631-436 AM8-related antibodies disclosed herein, can be isolated by screening of a combinatorial antibody library. Preferably, the combinatorial antibody library is a recombinant combinatorial library, preferably a scFv yeast display library, prepared using chimeric, humanized or human VL and VH cDNAs. Methodologies for preparing and screening such libraries are known in the art. In addition to commercially available vectors for generating yeast display libraries (such as, the pYD1 vector, Invitrogen, Carlsbad, Calif.) examples of methods and reagents particularly amenable for use in generating and screening antibody display libraries can be found in, for example, Boder E. T. and Wittrup K. D., Yeast surface display for directed evolution of protein expression, affinity, and stability, *Methods Enzymol.*, 328:430-44 (2000) and Boder E. T. and Wittrup K. D., Yeast surface display for screening combinatorial polypeptide libraries, *Nat. Biotechnol.* 15(6):553-7 (June 1997).

In a preferred embodiment, to isolate antibodies with high binding affinity, such as any of the antibodies described in Section II herein, an antibody that is known to immunospecifically bind to hBNP or hBNP fragment (such as, for example, monoclonal antibody 106.3 or monoclonal antibody 3-631-436) is first used to generate mouse heavy and light chain sequences expressed as scFvs on the surface of yeast (preferably, *Saccaromyces cerevisiae*). These antibody (Such as monoclonal antibody 106.3 or monoclonal antibody 3-631-426) scFvs are analyzed to determine the dissociation rate (namely, the $k_{off}$ or $k_d$) of these antibodies. Such constructs then are screened, preferably using biotinylated cyclic hBNP (1-32c). The dissociation rate data can then be plotted as mean fluorescence units ("MFU") versus time (in seconds). A first order decay equation can be used to fit the data. An example of such a formula that can be used is:

$$y = m1 * \exp(-m2 * M0) + m3$$

where m1 is the maximum fluorescence at time zero (*=multiply by and exp=exponential);

where m2 is the off-rate (the formula for determining off-rate is well known to those skilled in the art);

where M0 is time x (x being the time that is being measured); and where m3 is the background fluorescence being generated from the system.

The dissociation rate data can be used to identify off-rate improved antibodies of the present invention from mutagenic libraries.

Those scFv constructs having an improved dissociation rate are selected for subsequent mutagenesis of the heavy and light chain variable regions to generate CDR mutagenic libraries.

For 106.3 AM1 and 106.3 AM1-related antibodies, to further increase the binding affinity, the VH and VL segments of the preferred VH/VL pair(s) can be randomly mutated, preferably within the CDR2 region of VH, the CDR1 region and/or CDR2 region of VL in a process analogous to the in vivo somatic mutation process responsible for affinity maturation of antibodies during a natural immune response. This in vitro affinity maturation can be accomplished by replacing a portion of each CDR with a degenerate single-stranded oligonucleotide encoding three amino acids within the CDR being targeted. The replacement of a portion of each CDR with a new randomized sequence (up to 8000 possibilities) can be accomplished by homologous recombination in yeast (see, e.g. Example 1). These randomly mutated VH and VL segments can be analyzed for binding to hBNP or hBNP fragment in the context of an scFv; scFvs exhibiting an improved fluorescence and that (a) bind to an epitope comprising amino acid residues 5 through 13 of hBNP or a hBNP fragment thereof with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by hybridoma cell line 106.3, said cell line having A.T.C.C. Accession No. HB-12044, (b) exhibits a $k_{on}$ (or $k_a$) of at least about $2.4 \times 10^4$ $M^{-1}s^{-1}$, of at least about $2.5 \times 10^4$ $M^{-1}s^{-1}$, of at least about $3.3 \times 10^4$ $M^{-1}s^{-1}$, of at least about $5.0 \times 10^4$ $M^{-1}s^{-1}$, of at least about $1.25 \times 10^7$ $M^{-1}s^{-1}$ of at least about $1.35 \times 10^7$ $M^{-1}s^{-1}$, of at least about $1.0 \times 10^8$ $M^{-1}s^{1}$, of at least about $1.0 \times 10^9$ $M^{-1}s^{1}$, or have a $k_{on}$ (or $k_a$) ranging from about $5.0 \times 10^4$ $M^{-1}s^{-1}$ to about $1.0 \times 10^8$ $M^{-1}s^{1}$, from about $3.3 \times 10^4$ $M^{-1}s^{-1}$ to about $1.0 \times 10^9$ $M^{-1}s^{1}$, from about $2.5 \times 10^4$ $M^{-1}s^{-1}$ to about $1.25 \times 10^7$ $M^{-1}s^{-1}$, from about $2.4 \times 10^4$ $M^{-1}s^{-1}$ to about $1.35 \times 10^7$ $M^{-1}s^{-1}$, (c) exhibits a $k_{off}$ (or $k_d$) of at least about $1.0 \times 10^{-3}$ $s^{-1}$, of at least about $1.0 \times 10^{-4}$ $s^{-1}$, of at least about $1.0 \times 10^{-5}$ $s^{-1}$, of at least about $1.0 \times 10^{-6}$ $s^{-1}$ or have a $k_{off}$ (or $k_d$) ranging from about $1.0 \times 10^{-3}$ $s^{-1}$ to about $1.0 \times 10^{-6}$ $s^{-1}$, from about $1.0 \times 10^{-3}$ $s^{-1}$ to about $1.0 \times 10^{-5}$ $s^{-1}$ or from about $1.0 \times 10^{-3}$ $s^{-1}$ to about $1.0 \times 10^{-4}$ $s^{-1}$, or (d) exhibit a $K_D$ of at least about $4.2 \times 10^{-11}$ M, of at least about $4.0 \times 10^{-11}$ M, of at least about $3.0 \times 10^{-11}$ M, of at least about $2.0 \times 10^{-11}$ M, of at least about $1.0 \times 10^{-12}$ M of at least about $8.0 \times 10^{-13}$ M, of at least about $7.4 \times 10^{-13}$ M, of at least about $1.0 \times 10^{-13}$ M, of at least about $1.0 \times 10^{-14}$ M, of at least about $1.0 \times 10^{-15}$ M, or has a $K_D$ ranging from $4.2 \times 10^{-11}$ M to $1.0 \times 10^{-15}$ M, from $4.0 \times 10^{-11}$ M to $1.0 \times 10^{-14}$ M, from $3 \times 10^{-11}$ M to $1.0 \times 10^{-13}$ M, from $2 \times 10^{-11}$ M to $8.0 \times 10^{-13}$ M, or from $1.0 \times 10^{-12}$ M to $7.4 \times 10^{-13}$ M can then be isolated and the CDR mutation identified by sequencing.

Following screening of a recombinant scFv display library, clones having the desired characteristics are selected for conversion. Nucleic acid molecules encoding the selected antibody can be recovered from the display package (e.g., from the yeast expression vector) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section IV above.

For 3-631-436 AM5, 3-631-436 AM8 and 3-631-436 AM5- and 3-631-436 AM8-related antibodies, to further increase the binding affinity, the VH and VL segments of the preferred VH/VL pair(s) can be randomly mutated, preferably within the CDR2 region of VL in a process analogous to the in vivo somatic mutation process responsible for affinity maturation of antibodies during a natural immune response. This in vitro affinity maturation can be accomplished by replacing a portion of the VL CDR with a degenerate single-stranded oligonucleotide encoding three amino acids within the VL CDR being targeted. The replacement of a portion of the CDR with a new randomized sequence (up to 8000 possibilities) can be accomplished by homologous recombination in yeast (see, e.g. Example 5). The randomly mutated VL segments can be analyzed for binding to hBNP or hBNP fragment in the context of an scFv; scFvs exhibiting an improved fluorescence and that (a) bind to an epitope comprising at least three (3) amino acid residues of amino acid residues 13 through 18 of hBNP or a hBNP fragment thereof with at least about a two fold improvement, at least about a three fold improvement, at least about a five fold improvement, at least about a ten fold improvement, at least about a fifteen fold improvement, at least about a twenty fold improvement, at least about a twenty-five fold improvement, at least about a thirty fold improvement, at least about a thirty-five fold improvement, at least about a forty fold improvement, at least about a forty-five fold improvement, at least about a fifty fold improvement, at least about a fifty-five fold improvement, at least about a sixty fold improvement, at least about a seventy fold improvement or at least about a seventy-five fold improvement in its equilibrium dissociation constant ($K_D$) when compared with an antibody produced by 3-631-436 which was deposited with the A.T.C.C. on Dec. 21, 2004 and assigned A.T.C.C. Accession No. PTA-6476 and is described in U.S. Patent Publication 2006/0183154 published on Aug. 17, 2006, (b) exhibits a $k_{on}$ (or $k_a$) of at least about $1.5\times10^6$ $M^{-1}s^{-1}$, of at least about $3.5\times10^6$ $M^{-1}s^{-1}$, of at least about $7.8\times10^6$ $M^{-1}s^{-1}$, of at least about $8.0\times10^6$ $M^{-1}s^{-1}$ of at least about $1.0\times10^7$ $M^{-1}s^{-1}$, of at least about $2.0\times10^7$ $M^{-1}s^{-1}$, of at least about $5.0\times10^7$ $M^{-1}s^{-1}$, of at least about $7.5\times10^7$ $M^{-1}s^{-1}$, of at least about $1.0\times10^8$ $M^{-1}s^{-1}$, or has a $k_{on}$ (or $k_a$) ranging from about $1.5\times10^6$ $M^{-1}s^{-1}$ to about $1.0\times10^8$ $M^{-1}s^{-1}$, from about $1.95\times10^6$ $M^{-1}s^{-1}$ to about $1.0\times10^7$ $M^{-1}s^{-1}$, from about $2.70\times10^6$ $M^{-1}s^{-1}$ to about $9.0\times10^6$ $M^{-1}s^{-1}$, or from about $7.0\times10^6$ $M^{-1}s^{-1}$ to about $9.0\times10^6$ $M^{-1}s^{-1}$ with the proviso that if the $k_{on}$ is $1.6\times10^6$ $M^{-1}s^{-1}$ then the $k_{off}$ is not $5.4\times10^{-4}$ S-1 or $6.5\times10^4$ $s^{-1}$, if the $k_{on}$ is $6.7\times10^6$ $M^{-1}s^{-1}$ then the $k_{off}$ is not $2.5\times10^{-3}$ $s^{-1}$, if the $k_{on}$ is $8.4\times10^6$ $M^{-1}s^{-1}$ then the $k_{off}$ is not $2.9\times10^{-3}$ $s^{-1}$, if the $k_{on}$ is $8.4\times10^6$ $M^{-1}s^{-1}$ then the $k_{off}$ is not $2.9\times10^{-3}$ $s^{-1}$ if the $k_{on}$ is $5.8\times10^6$ $M^{-1}s^{-1}$ then the $k_{off}$ is not $1.6\times10^{-3}$ $s^{-1}$ or if the $k_{on}$ is $1.5\times10^6$ $M^{-1}s^{-1}$ then the $k_{off}$ is not $4.1\times10^4$ $s^{-1}$ or has a $k_{off}$ (or $k_d$) of at least about $1.0\times10^{-3}$ $s^{-1}$, of at least about $6.5\times10^4$ $s^{-1}$, of at least about $5.0\times10^{-4}$ $s^{-1}$, of at least about $4.0\times10^4$ $s^{-1}$, of at least about $1.0\times10^{-4}$ $s^{-1}$, of at least about $7.5\times10^{-5}$ $s^{-1}$, of at least about $5.0\times10^{-5}$ $s^{-1}$, of at least about $2.0\times10^{-5}$ $s^{-1}$, of at least about $1\times10^{-5}$ $s^{-1}$, of at least about $1.0\times10^{-6}$ $s^{-1}$ or has a $k_{off}$ (or $k_d$) ranging from $2.0\times10^{-3}$ $s^{-1}$ to $1.0\times10^{-6}$ $s^{-1}$, from $1.0\times10^{-3}$ $s^{-1}$ to $1.0\times10^{-5}$ $s^{-1}$ or from $1.0\times10^{-3}$ $s^{-1}$ to $8.5\times10^4$ $s^{-1}$ or has a $K_D$ ranging from about $3.5\times10^{-10}$ M to about $1.0\times10^{-13}$ M, from about $2.8\times10^{-10}$ M to about $1.0\times10^{-12}$ M, from about $2.15\times10^{-10}$ M to about $1.0\times10^{-11}$ M or from about $1.6\times10^{-10}$ M to about $1.0\times10^{-10}$ M can then be isolated and the CDR mutation identified by sequencing.

Following screening of a recombinant scFv display library, clones having the desired characteristics are selected for conversion. Nucleic acid molecules encoding the selected antibody can be recovered from the display package (e.g., from the yeast expression vector) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in Section IV above.

VI. Immunoassays

In another aspect, the present invention relates to immunoassays that can be used for the qualitative and/or quantitative detection of hBNP or hBNP fragment in a test sample. The immunoassays of the present invention can be conducted using any format known in the art, such as, but not limited to, a sandwich format, a competitive inhibition format (including both forward or reverse competitive inhibition assays) or in a fluorescence polarization format.

In immunoassays for the qualitative detection of hBNP or hBNP fragment in a test sample, at least one antibody that binds to certain epitopes of hBNP or a hBNP fragment thereof is contacted with at least one test sample suspected of containing or that is known to contain hBNP or hBNP fragment to form an antibody-hBNP immune complex. The antibodies described in Section II herein can be used in such immunoassays to form such antibody-hBNP immune complexes in at least one test sample. These immune complexes can then detected using routine techniques known to those skilled in the art. For example, the antibody of the present invention can be labeled with a detectable label to detect the presence of an antibody-hBNP complex. Alternatively, the hBNP or hBNP fragments in the test sample can be labeled with a detectable label and the resulting antibody-hBNP immune complexes detected using routine techniques known to those skilled in the art. Detectable labels and their attachment to antibodies are discussed in more detail infra.

Alternatively, a second antibody that binds to the hBNP or hBNP fragment and that contains a detectable label can be added to the test sample and used to detect the presence of the antibody-hBNP complex. Any detectable label known in the art can be used. Detectable labels and their attachment to antibodies are discussed in more detail infra.

In immunoassays for the quantitative detection of BNP, such as a sandwich type format, at least two antibodies are employed to separate and quantify hBNP or hBNP fragment in a test sample. More specifically, the immunoassay with at least two antibodies bind to certain epitopes of hBNP or hBNP fragment forming an immune complex which is referred to as a "sandwich". Generally, one or more antibodies can be used to capture the hBNP or hBNP fragment in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to their epitope are not diminished by the binding of any other antibody in the assay to its respective epitope. In other words, antibodies should be selected so that the one or more first antibodies brought into contact with a test sample suspected of containing hBNP or hBNP fragment do not bind to all or part of an epitope recognized by the second or subsequent antibodies, thereby interfering with the ability of the one or more second detection antibodies to bind to the hBNP or hBNP fragment.

The inventors have discovered that an excellent sandwich immunoassay can be performed using the antibodies of the present invention. More specifically, the antibodies of the present invention can be used as a first antibody in said immunoassay. Preferably, the antibody of the present invention immunospecifically bind to epitopes (a) comprising at least three (3) amino acids of 5-13 of hBNP or hBNP fragment with a $K_D$ of from about $4.2\times10^{-11}$ M to about $7.4\times10^{-13}$ M; (b) comprising at least three (3) amino acids of 13-18 of hBNP or hBNP fragment with a $K_D$ ranging from about $3.5\times10^{-10}$ M to about $1.0\times10^{-13}$ M, preferably from about $2.8\times10^{-10}$ M to about $1.0\times10^{-12}$ M, more preferably from about $2.15\times10^{-10}$ M to about $1.0\times10^{-11}$ M and even more preferably from about $1.6\times10^{-10}$ M to about $1.0\times10^{-10}$ M; or (c) any combination of (a) and (b). Optionally, in addition to the antibodies of the present invention, said immunoassay can comprise a second, third fourth or more antibodies, preferably one or more monoclonal antibodies, that immunospecifically binds to epitopes having an amino acid sequence comprising at least three (3) amino acids of amino acids 27-32 of hBNP. An example of a monoclonal antibody that immunospecifically binds to epitopes having an amino acid sequence containing amino acids 27-32 of hBNP is a monoclonal antibody produced by hybridoma cell line BC203.

In a preferred embodiment, the test sample suspected of containing hBNP or a hBNP fragment can be contacted with at least one first capture antibody (or antibodies) and at least one second detection antibodies either simultaneously or sequentially. In the sandwich assay format, a test sample suspected of containing hBNP or hBNP fragment is first brought into contact with at least one first capture antibody that specifically binds to a particular epitope under conditions which allow the formation of a first antibody-hBNP complex. If more than one capture antibody is used, a first multiple capture antibody-hBNP complex is formed. In a sandwich assay, the antibodies, preferably, at least one capture antibody, are used in molar excess amounts of the maximum amount of hBNP or hBNP fragment expected in the test sample. For example, from about 5 µg/mL to about 1 mg/mL of antibody per mL of microparticle coating buffer can be used.

Optionally, prior to contacting the test sample with at least one first capture antibody, the at least one first capture antibody can be bound to a solid support which facilitates the separation of the first antibody-hBNP complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind hBNP or hBNP fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing hBNP or an hBNP fragment is brought into contact with the at least one first capture antibody, the test sample is incubated in order to allow for the formation of a first capture antibody (or multiple antibody)-hBNP complex. The incubation can be carried out at a pH of from about 4.5 to about 10.0, at a temperature of from about 2° C. to about 45° C., and for a period from at least about one (1) minute to about eighteen (18) hours, preferably from about 2-6 minutes, most preferably from about 3-4 minutes.

After formation of the first/multiple capture antibody-hBNP complex, the complex is then contacted with at least one second detection antibody (under conditions which allow for the formation of a first/multiple antibody-hBNP-second antibody complex). If the first antibody-hBNP complex is contacted with more than one detection antibody, then a first/multiple capture antibody-hBNP-multiple antibody detection complex is formed. As with first antibody, when at least second (and subsequent) antibody is brought into contact with the first antibody-hBNP complex, a period of incubation under conditions similar to those described above is required for the formation of the first/multiple antibody-hBNP-second/multiple antibody complex. Preferably, at least one second antibody contains a detectable label. The detectable label can be bound to at least one second antibody prior to, simultaneously with or after the formation of the first/multiple antibody-hBNP-second/multiple antibody complex. Any detectable label known in the art can be used. For example, the detectable label can be a radioactive label, such as, $^{3}$H, $^{125}$I, $^{35}$S, $^{14}$C, $^{32}$P, $^{33}$P, an enzymatic label, such as horseradish peroxidase, alkaline peroxidase, glucose 6-phosphate dehydrogenase, etc., a chemiluminescent label, such as, acridinium esters, luminal, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemisty*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The first antibody/multiple-hBNP-second/multiple antibody complex can be, but does not have to be, separated from the remainder of the test sample prior to quantification of the label. For example, if at least first capture antibody is bound to a solid support, such as a well or a bead, separation can be accomplished by removing the fluid (from the test sample) from contact with the solid support. Alternatively, if at least first capture antibody is bound to a solid support it can be simultaneously contacted with the hBNP-containing sample and the at least one second detection antibody to form a first (multiple) antibody-hBNP-second (multiple) antibody complex, followed by removal of the fluid (test sample) from contact with the solid support. If at least first capture antibody is not bound to a solid support, then the first antibody/multiple-hBNP-second/multiple antibody complex does not have to be removed from the test sample for quantification of the amount of the label.

After formation of the labeled first antibody-hBNP-second antibody complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of hBNP or hBNP fragment in the test sample is determined by use of a standard curve that has been generated using serial dilutions of hBNP or hBNP fragment of known concentration. Other than using serial dilutions of hBNP or hBNP fragment, the standard curve can be generated gravimetrically, by mass spectroscopy and by other techniques known in the art.

In a forward competitive format, an aliquot of labeled hBNP, hBNP fragment or hBNP analogue thereof of a known concentration is used to compete with hBNP or hBNP fragment in a test sample for binding to hBNP antibody (such as an antibody of the present invention). Peptides of hBNP, hBNP fragments and hBNP analogues thereof and methods of making peptides of hBNP, hBNP fragments and hBNP analogues are known in the art (See, for example, U.S. Pat. No. 6,162,902). Moreover, as described in the Examples herein, cyclic hBNP (1-32) can also be used in said competitive formats.

In a forward competition assay, an immobilized antibody (such as an antibody of the present invention) can either be sequentially or simultaneously contacted with the test sample and a labeled hBNP, hBNP fragment or hBNP analogue thereof. The hBNP peptide, hBNP fragment or hBNP analogue can be labeled with any detectable label known to those skilled in the art, including those detectable labels discussed above in connection with the sandwich assay format. In this assay, the antibody of the present invention can be immobilized on to a solid support using the techniques discussed previously herein. Alternatively, the antibody of the present invention can be coupled to an antibody, such as an antispecies antibody, that has been immobilized on to a solid support, such as a microparticle (See Examples 3 and 7).

The labeled hBNP peptide, hBNP fragment or hBNP analogue, the test sample and the antibody are incubated under conditions similar to those described above in connection with the sandwich assay format. Two different species of antibody-hBNP complexes are then generated. Specifically, one of the antibody-hBNP complexes generated contains a detectable label while the other antibody-hBNP complex does not contain a detectable label. The antibody-hBNP complex can be, but does not have to be, separated from the remainder of the test sample prior to quantification of the detectable label. Regardless of whether the antibody-hBNP complex is separated from the remainder of the test sample, the amount of detectable label in the antibody-hBNP complex is then quantified. The concentration of hBNP or hBNP fragment in the test sample can then be determined by comparing the quantity of detectable label in the antibody-hBNP complex to a standard curve. The standard curve can be generated using serial dilutions of hBNP or hBNP fragment of known concentration, by mass spectroscopy, gravimetrically and by other techniques known in the art.

The antibody-hBNP complex can be separated from the test sample by binding the antibody to a solid support, such as the solid supports discussed above in connection with the sandwich assay format, and then removing the remainder of the test sample from contact with the solid support.

The labeled hBNP (or hBNP fragment or hBNP analogue thereof) that is used to compete with hBNP or a hBNP fragment in the test sample for binding to the antibody can be intact hBNP 1-32, any hBNP fragment thereof provided that said hBNP fragment comprises at least one amino acid sequence containing (meaning including and between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP) or any hBNP analogue provided that said hBNP peptide, hBNP fragment or hBNP analogue contains a sequence of amino acids that corresponds to an epitope that is recognized by the antibody. Preferably, the antibody employed specifically binds to an epitope (a) comprising at least three (3) amino acid residues of amino acid residues of 5-13 of hBNP (such as the antibody of the present invention, specifically, an antibody produced by CHO cell line 106.3 AM1) or specifically binds to an epitope having an amino acid sequence that contains (meaning that it includes and is between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP; (b) comprising at least three (3) amino acid residues of amino acid residues of 13-18 of hBNP (such as the antibody of the present invention, specifically, an antibody produced by CHO cell line 3-631-436 AM5 or 3-631-436 AM8) or specifically binds to an epitope having an amino acid sequence that contains (meaning that it includes and is between) amino acids 13-18, 13-17, 13-16, 13-15, 14-18, 14-17, 14-16, 15-18, 15-17 or 16-18 with a $K_D$ ranging from about $3.5 \times 10^{-10}$ M to about $1.0 \times 10^{-13}$ M, preferably from about $2.8 \times 10^{-10}$ M to about $1.0 \times 10^{-12}$ M, more preferably from about $2.15 \times 10^{-10}$ M to about $1.0 \times 10^{-11}$ M and even more preferably from about $1.6 \times 10^{-10}$ M to about $1.0 \times 10^{-10}$ M; or (c) any combination of (a) and (b). Examples of hBNP fragments that can be labeled and used in the present invention, include, but are not limited to, peptide fragments having an amino acid sequence containing amino acids 1-31, 1-30, 1-29, 1-28, 1-27, 1-26, 1-25, 1-24, 1-23, 1-22, 1-21, 1-20, 1-19, 1-18, 1-17, 1-16, 1-15, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 3-14, 3-13, 3-12, 3-11, 3-10, 3-9, 3-8, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 6-14, 6-13, 6-12, 6-11, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 7-14, 7-13, 7-12, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 8-14, 8-13, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 9-14, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 11-32, 11-31, 11-30, 11-29, 11-28, 11-27, 11-26, 11-25, 11-24, 11-23, 11-22, 11-21, 11-20, 11-19, 11-18, 11-17 or 11-16 of hBNP.

In a reverse competition assay, an immobilized hBNP peptide, hBNP fragment or hBNP analogue thereof can either be sequentially or simultaneously contacted with a test sample and at least one labeled antibody. Preferably, the antibody specifically binds to an epitope having an amino acid sequence (a) comprising at least three (3) amino acid residues of amino acid residues of 5-13 of hBNP (such as the antibody of the present invention, specifically, an antibody produced by CHO cell line 106.3 AM1) or specifically binds to an epitope having an amino acid sequence that contains (meaning that it includes and is between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP; (b) comprising at least three (3) amino acid residues of amino acid residues of 13-18 of hBNP (such as the antibody of the present invention, specifically, an antibody produced by CHO cell line 3-631-436 AM5 or 3-631-436 AM8) or specifically binds to an epitope having an amino acid sequence that contains (meaning that it includes and is between) amino acids 13-18, 13-17, 13-16, 13-15, 14-18, 14-17, 14-16, 15-18, 15-17 or 16-18 with a $K_D$ ranging from about $3.5 \times 10^{-10}$ M to about $1.0 \times 10^{-13}$ M, preferably from about $2.8 \times 10^{-10}$ M to about $1.0 \times 10^{-12}$ M, more preferably from about $2.15 \times 10^{-10}$ M to about $1.0 \times 10^{-11}$ M and even more preferably from about $1.6 \times 10^{-10}$ M to about $1.0 \times 10^{-10}$ M; or (c) any combination of (a) and (b). An example of an antibody that specifically binds to epitopes comprising at least three (3) amino acid residues of amino acid residues 5-13 of hBNP is an antibody produced by CHO cell line 106.3 AM1. An example of an antibody that specifically binds to epitopes comprising at least three (3) amino acid residues of amino acid residues 13-18 of hBNP is an antibody produced by CHO cell line 3-631-436 AM5 or 3-631-436 AM8. Any of these antibodies (106.3 AM1, 3-631-436 AM5 or 3-631-436 AM8) can be labeled with any detectable label known to those skilled in the art, including those detectable labels discussed above in connection with the sandwich assay format.

The hBNP peptide, hBNP fragment or hBNP analogue can be bound to a solid support, such as the solid supports discussed above in connection with the sandwich assay format. Preferably, the hBNP peptide fragment has an amino acid sequence that contains amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP.

The immobilized hBNP peptide, hBNP peptide fragment or hBNP analogue thereof, test sample and at least one labeled antibody are incubated under conditions similar to those described above in connection with the sandwich assay format. Two different species hBNP-antibody complexes are then generated. Specifically, one of the hBNP-antibody complexes generated is immobilized and contains a detectable label while the other hBNP-antibody complex is not immobilized and contains a detectable label. The non-immobilized hBNP-antibody complex and the remainder of the test sample are removed from the presence of the immobilized hBNP-antibody complex through techniques known in the art, such as washing. Once the non-immobilized hBNP antibody complex is removed, the amount of detectable label in the immobilized hBNP-antibody complex is then quantified. The concentration of hBNP or hBNP fragment in the test sample can then be determined by comparing the quantity of detectable label in the hBNP-complex to a standard curve. The standard curve can be generated using serial dilutions of hBNP or hBNP fragment of known concentration, by mass spectroscopy, gravimetrically and by other techniques known in the art.

In a fluorescence polarization assay, in one embodiment, an antibody or functionally active fragment thereof is first contacted with an unlabeled test sample suspected of containing hBNP or a hBNP fragment thereof to form an unlabeled hBNP-antibody complex. The unlabeled hBNP-antibody complex is then contacted with a fluorescently labeled hBNP, hBNP fragment or hBNP analogue thereof. The labeled hBNP, hBNP fragment or hBNP analogue competes with any unlabeled hBNP or hBNP fragment in the test sample for binding to the antibody or functionally active fragment thereof. The amount of labeled hBNP-antibody complex formed is determined and the amount of hBNP in the test sample determined via use of a standard curve.

Preferably, the antibody used in a fluorescence polarization assay specifically binds to an epitope having an amino acid sequence (a) comprising at least three (3) amino acid residues of amino acid residues of 5-13 of hBNP (such as the antibody of the present invention, specifically, an antibody produced by CHO cell line 106.3 AM1) or specifically binds to an epitope having an amino acid sequence that contains (meaning that it includes and is between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP; (b) comprising at least three (3) amino acid residues of amino acid residues of 13-18 of hBNP (such as the antibody of the present invention, specifically, an antibody produced by CHO cell line 3-631-436 AM5 or 3-631-436 AM8) or specifically binds to an epitope having an amino acid sequence that contains (meaning that it includes and is between) amino acids 13-18, 13-17, 13-16, 13-15, 14-18, 14-17, 14-16, 15-18, 15-17 or 16-18 with a $K_D$ ranging from about $3.5 \times 10^{-10}$ M to about $1.0 \times 10^{-13}$ M, preferably from about $2.8 \times 10^{-10}$ M to about $1.0 \times 10^{-12}$ M, more preferably from about $2.15 \times 10^{-10}$ M to about $1.0 \times 10^{-11}$ M and even more preferably from about $1.6 \times 10^{-10}$ M to about $1.0 \times 10^{-10}$ M; or (c) any combination of (a) and (b). An example of an antibody that specifically binds to epitopes comprising at least three (3) amino acid residues of amino acid residues of 5-13 hBNP is a monoclonal antibody produced by CHO cell line 106.3 AM1. An example of an antibody that specifically binds to epitopes comprising at least three (3) amino acid residues of amino acid residues 13-18 of hBNP is a monoclonal antibody produced by CHO cell line 3-631-436 AM5 or 3-631-436 AM8.

Preferably, the hBNP peptide fragment has an amino acid sequence that contains amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP. The antibody, labeled hBNP peptide, hBNP peptide fragment or hBNP analogue thereof and test sample and at least one labeled antibody are incubated under conditions similar to those described above in connection with the sandwich assay format.

Alternatively, in another embodiment, an antibody or functionally active fragment thereof is simultaneously contacted with a fluorescently labeled hBNP, hBNP fragment or hBNP analogue thereof and an unlabeled test sample suspected of containing hBNP or hBNP fragment thereof to form both labeled hBNP-antibody complexes and unlabeled hBNP-antibody complexes. The amount of labeled hBNP-antibody complex formed is determined and the amount of hBNP in the test sample determined via use of a standard curve. The antibody used in this immunoassay specifically binds to an epitope having an amino acid sequence (a) comprising at least three (3) amino acid residues of amino acid residues of 5-13 of hBNP (such as the antibody of the present invention, specifically, an antibody produced by CHO cell line 106.3 AM1) or specifically binds to an epitope having an amino acid sequence that contains (meaning that it includes and is between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP; (b) comprising at least three (3) amino acid residues of amino acid residues of 13-18 of hBNP (such as the antibody of the present invention, specifically, an antibody produced by CHO cell line 3-631-436 AM5 or 3-631-436 AM8) or specifically binds to an epitope having an amino acid sequence that contains (meaning that it includes and is between) amino acids 13-18, 13-17, 13-16, 13-15, 14-18, 14-17, 14-16, 15-18, 15-17 or 16-18 with a $K_D$ ranging from about $3.5 \times 10^{-10}$ M to about $1.0 \times 10^{-13}$ M, preferably from about $2.8 \times 10^{-10}$ M to about $1.0 \times 10^{-12}$ M, more preferably from about $2.15 \times 10^{-10}$ M to about $1.0 \times 10^{-11}$ M and even more preferably from about $1.6 \times 10^{-10}$ M to about $1.0 \times 10^{-10}$ M; or (c) any combination of (a) and (b). An example of an antibody that specifically binds to epitopes comprising at least three (3) amino acid residues of amino acid residues 5-13 of hBNP is a monoclonal antibody produced by CHO cell line 106.3 AM1. An example of an antibody that specifically binds to epitopes having an amino acid sequence comprising at least three (3) amino acid residues of amino acid residues 13-18 of hBNP is a monoclonal antibody produced by CHO cell line 3-631-436 AM5 or 3-631-436 AM8.

Alternatively, in yet another embodiment, an antibody (such as antibody of the present invention, such as an antibody produced by CHO cell line 106.3 AM1, CHO cell line 3-631-436 AM5, CHO cell line 3-631-436 AM8 or any combinations thereof) or functionally active fragment thereof is first contacted with a fluorescently labeled hBNP, hBNP fragment or hBNP analogue thereof to form a labeled hBNP-antibody complex. The labeled BNP-antibody complex is then contacted with an unlabeled test sample suspected of containing hBNP or a hBNP fragment thereof. Any unlabeled hBNP or hBNP fragment in the test sample competes with the labeled hBNP, hBNP fragment or hBNP analogue for binding to the antibody or functionally active fragment thereof. The amount of labeled hBNP-antibody complex formed is determined the amount of hBNP in the test sample determined via use of a standard curve. The antibody used in this immunoassay specifically binds to an epitope having an amino acid sequence (a) comprising at least three (3) amino acid residues of amino acid residues of 5-13 of hBNP (such as the antibody of the present invention, specifically, an antibody produced by CHO cell line 106.3 AM1) or specifically binds to an epitope having an amino acid sequence that contains (meaning that it includes and is between) amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of hBNP; (b) comprising at least three (3) amino acid residues of amino acid residues of 13-18 of hBNP (such as the antibody of the present invention, specifically, an antibody produced by CHO cell line 3-631-436 AM5 or 3-631-436 AM8) or specifically binds to an epitope having an amino acid sequence that contains (meaning that it includes and is between) amino acids 13-18, 13-17, 13-16, 13-15, 14-18, 14-17, 14-16, 15-18, 15-17 or 16-18 with a $K_D$ ranging from about $3.5 \times 10^{-10}$ M to about $1.0 \times 10^{-13}$ M, preferably from about $2.8 \times 10^{-10}$ M to about $1.0 \times 10^{-12}$ M, more preferably from about $2.15 \times 10^{-10}$ M to about $1.0 \times 10^{-11}$ M and even more preferably from about $1.6 \times 10^{-10}$ M to about $1.0 \times 10^{-10}$ M; or (c) any combination of (a) and (b). An example of an antibody that specifically binds to epitopes having an amino acid sequence comprising at least three (3) amino acid residues of amino acid residues 5-13 hBNP is a monoclonal antibody produced by CHO cell line 106.3 AM1. An example of an antibody that specifically binds to epitopes having an amino acid sequence comprising at least three (3) amino acid residues of amino acid residues 13-18 of hBNP is a monoclonal antibody produced by CHO cell in 3-631-436 AM5 or 3-631-436 AM8.

VII. Pharmaceutical Compositions and Pharmaceutical Administration

The antibodies of the present invention can be incorporated into pharmaceutical compositions suitable for administration to a subject. Typically, the pharmaceutical composition comprises a therapeutically or pharmaceutically effective amount of an antibody or the present invention along with a pharmaceutically acceptable carrier or excipient. As used herein, "pharmaceutically acceptable carrier" or "pharmaceutically acceptable excipient" includes any and all solvents, dispersion media, coating, antibacterial and antifungal agents, isotonic and absorption delaying agents, and the like that are physiologically compatible. Examples of pharmaceutically acceptable carriers or excipients include one or more of water, saline, phosphate buffered saline, dextrose, glycerol, ethanol and the like as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion also may be included. Optionally, disintegrating agents can be included, such as cross-linked polyvinyl pyrrolidone, agar, alginic acid or a salt thereof, such as sodium alginate and the like. In addition to the excipients, the pharmaceutical composition can include one or more of the following, carrier proteins such as serum albumin, buffers, binding agents, sweeteners and other flavoring agents; coloring agents and polyethylene glycol.

The compositions of this invention may be in a variety of forms. They include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody or antibody fragment is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e. antibody or antibody fragment) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the present invention can be administered by a variety of methods known in the art, although for many therapeutic applications, the preferred route/mode of administration is intravenous injection or infusion. As will be appreciated by those skilled in the art, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g. *Sustained and Controlled Release Drug Delivery Systems*, J. R. Robinson, ed., Marcel Dekker, Inc., New York, 1978).

In certain embodiments, an antibody of the present invention may be orally administered, for example, with an inert diluent or an assimilable edible carrier. The compound (and other ingredients if desired) may also be enclosed in a hard or soft shell gelatin capsule, compressed into tablets, buccal tablets, troches, capsules, elixirs, suspensions, syrups, wafers, and the like. To administer an antibody or antibody fragment of the invention by other than parenteral administration, it may be necessary to coat the compound with, or co-administer the compound with, a material to prevent its inactivation.

Supplementary active compounds also can be incorporated into the compositions. In certain embodiments, the antibody or antibody portion is co-formulated with and/or co-administered with one or more additional therapeutic agents. Such combination therapies may advantageously utilize lower dosages of the administered therapeutic agents, thus avoiding possible toxicities or complications associated with monotherapies or alternatively, act synergistically or additively to enhance the therapeutic effect.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be tested; each unit containing a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 0.5-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Now by way of example, and not of limitation, examples of the present invention shall now be given.

EXAMPLE 1

Identification of Immunoglobulin Genes

Messenger RNA was isolated from subcloned anti-BNP 106.3 hybridoma cells (hybridoma cell line 106.3 (A.T.C.C. Accession No. HB-12044) is described in U.S. Pat. No. 6,162,902). 106.3 mRNA was utilized in a reverse transcriptase-polymerase chain reaction using a mouse Ig primer set kit purchased from Novagen (Novagen (which is an Affiliate of Merck KGaA, Darmstadt, Germany), Cat No. 69831-3) with immunoglobulin gene specific primers contained in the kit. The resulting PCR products were sequenced and thus the immunoglobulin variable heavy and variable light chain genes were identified (See FIGS. 3A-3E and SEQ ID NO:1).

Cloning 106.3 Variable Region Genes into pYD41 Vector

Figure 2:
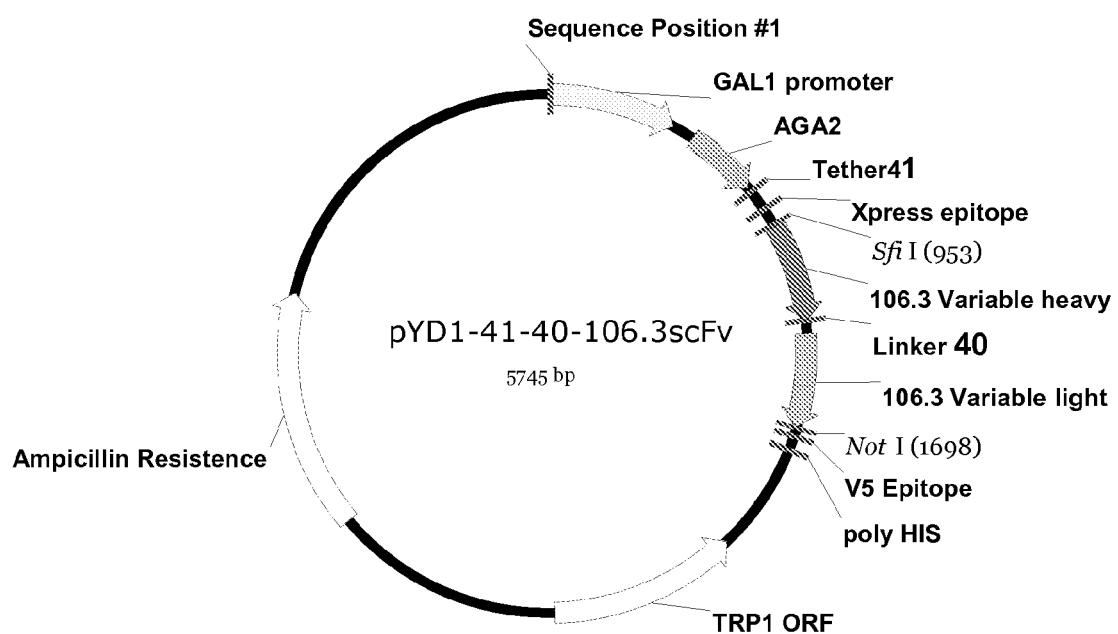
FIG. 2 is a plasmid map for vector pYD41-40 containing the 106.3 single-chain variable fragment shown in FIG. 4.

A yeast display system was used to express unmutated anti-BNP proteins (described herein infra) and a library of anti-BNP proteins on the yeast surface as a fusion to the yeast protein AGA2. A yeast display vector called pYD (Invitrogen, Carlsbad, Calif.), was used as it allows for cloning of the anti-BNP gene at the C-terminus of the AGA2 gene, a yeast mating factor (See, Boder and Wittrup, *Nature Biotechnology*, 15:553-557 (June 1997). Other critical features of the pYD vector include a galactose inducible promoter and an epitope tag, V5, on the C-terminus of the inserted anti-BNP gene (See, FIG. 2 and FIG. 6A-6B).

The yeast display platform utilizes an antibody format known as the single-chain variable fragment. In the scFv format, the variable heavy domain is connected to the variable light domain through a flexible linker (variable heavy domain—Linker GPAKELTPLKEAKVS (SEQ ID NO:4)—variable light domain) (See, U.S. Patent Publication 2004-0175379 A1).

Figure 4:
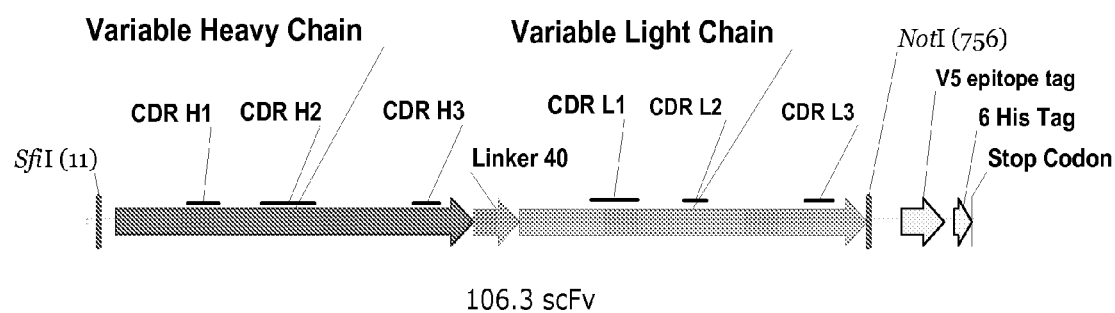
FIG. 4 is a diagram of the 106.3 single-chain variable fragment ("scFv"). Six His tag disclosed as SEQ ID NO: 156.

PCR single overlap extension (SOE) was used to combine the variable heavy (VH) and the variable light genes (VL) for the 106.3 scFv construct (See, e.g., FIGS. 4, 6A-6B, and SEQ ID NO:2). The 106.3 scFv DNA was cloned into the yeast display vector pYD41 using vector restriction sites SfiI and NotI. The pYD41-106.3scFv vector was transformed into DH5α *E. coli*. Plasmid DNA was then isolated from the *E. coli* and the 106.3 scFv insert was sequenced to ensure the scFv was cloned in frame with the AGA2 protein.

The cloning site for the scFv into the yeast display vector pYD41 is in an ORF that includes the following genes: AGA2-tether linker 41-X press epitope tag-106.3 variable heavy chain-Linker 40-106.3 variable light chain-V5 epitope tag - Six His tag (SEQ ID NO: 156). In addition, the yeast strain EBY100 is a tryptophan auxotroph and the pYDv41 vector encodes for tryptophan as the system's selectable marker. In addition, the yeast strain EBY100 is a tryptophan auxotroph and the pYD41 vector encodes for tryptophan as the system's selectable marker.

Transformation into *Saccharomyces cerevisiae* Strain EBY100

Figure 7A:
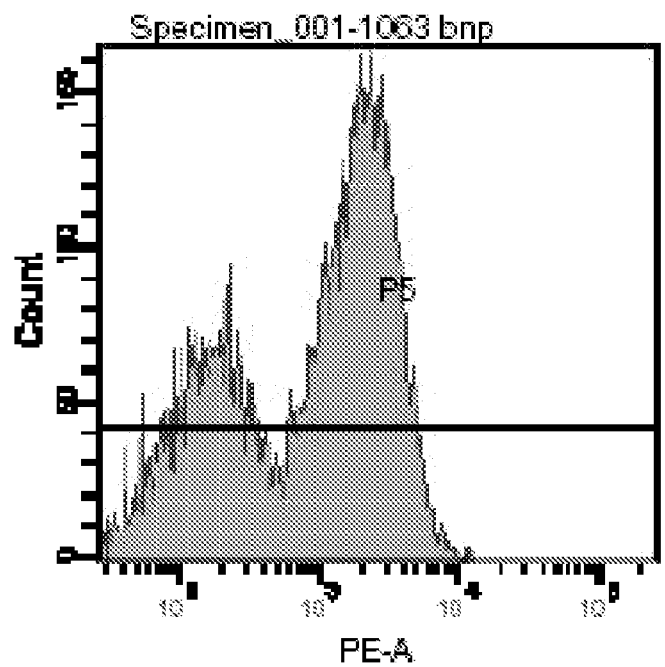
FIGS. 7A-7B show that yeast expressing full-length 106.3 single-chain variable fragment (scFv) bind to cyclic BNP (SEQ ID NO:5) More specifically, this figure shows that 106.3 scFv expressing yeast were incubated with cyclic BNP (1-32c) (SEQ ID NO:5) or anti-V5 followed by secondary reagents streptavidin phycoerythrin (SA:PE) (FIG. 7A) and goat anti mouse-phycoerythrin (GAM:PE) (FIG. 7B). The flow cytometry histograms illustrate the full-length expression of 106.3 scFv as detected by anti-V5 and the ability of 106.3 scFv to bind to cyclic BNP peptide (1-32) (SEQ ID NO:5). PE units (abscissa): $10^2$, $10^3$, $10^4$, and $10^5$. Count units (ordinate): 0, 50, 100, 150 (FIG. 7A); 0, 25, 50, 75, 100, 125 (FIG. 7B).
Figure 7B:
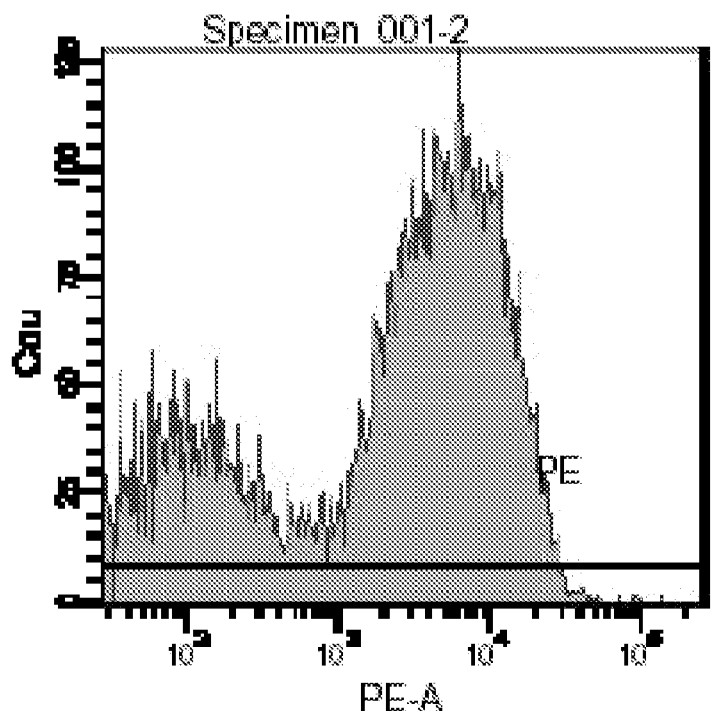

Yeast display plasmid, pYD41-106.3 scFv, was transformed into *S. cerevisiae* EBY100 using Gietz and Schiestl Method (See, Schiestl and Gietz, *Current Genetics,* 16(5-6):

339-46 (December 1989)). Dilutions of the transformation reaction were plated on selective glucose plates (2% glucose (0.67% yeast nitrogen base, 0.105% HSM -trp—ura, 1.8% bacterial agar, 18.2% sorbitol, 0.86% $NaH_2PO_4H_2O$, 1.02% $Na_2HPO_4$ $7H_2O$)) and incubated at 30° C. for 48-72 hours. Selective glucose media was inoculated with individual colonies and grown shaking at 30° C. for 16-20 hours. Protein expression was induced in colonies by transferring 0.5 OD600 of cells/mL (1e7cells/0.50D/mL) to selective galactose media. Colonies were shaken at 20° C. for 16-24 hours and then analyzed by the FACS Aria flow cytometer for binding to cyclic BNP (referred to as "1-32c") (SEQ ID NO:5) and anti-V5. For flow cytometry assays, yeast cells expressing 106.3 scFv were incubated with biotinylated: cyclic BNP (1-32c) (SEQ ID NO:5) or anti-V5 antibody followed by streptavidin: phycoerythrin (SA:PE, BD Pharmingen) or goat anti-mouse immunoglobulin-Alexa Fluora 633 (GAM:633, Molecular Probes (which is an Affiliate of Invitrogen, Carlsbad, Calif.)). The flow cytometry histograms as shown in FIGS. 7A-7B illustrate full-length surface expression of 106.3 scFv (anti-V5 binding) and binding of 106.3 scFv to cyclic BNP (1-32c) (SEQ ID NO:5).

Off-rate Analysis for 106.3 ScFv and 106.3 Variants on Yeast.

Figure 8:
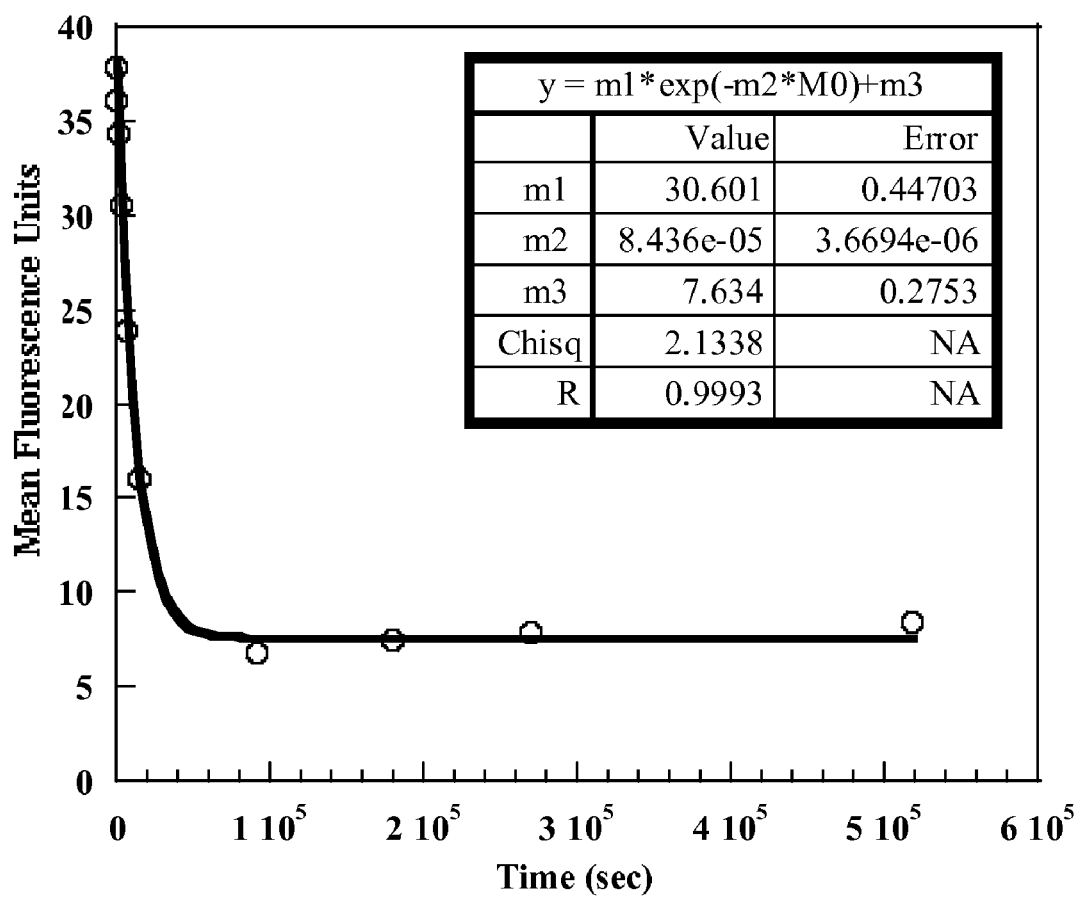
FIG. 8 shows the 106.3 scFv off-rate measurement. More specifically, yeast expressing 106.3 scFv were incubated with a saturating concentration of biotinylated cyclic BNP (1-32c) (SEQ ID NO:5). Cells were then washed and incubated with a saturating concentration of unlabelled BNP 1-32c (SEQ ID NO:5). At each time point, cells were transferred to ice, washed and incubated with SA:PE. After 30 minutes, cells were washed again and analyzed on the flow cytometer. A first order decay equation was used to fit the individual time points where m1 was the theoretical maximum mean fluorescence units ("MFU") at time 0, m2 was the off-rate ("koff"), m3 was the background MFU due to autofluorescence, and M0 was the time x (the x being the time that is being measured) that measurements are taken. The half-life ($t_{1/2}$) of 106.3 scFv binding to cyclic BNP (1-32c) was calculated using: $t_{1/2}$=ln 2/k$_{off}$. Three to five times the half-life was the time used to sort the 106.3 CDR mutagenic libraries.

Off-rate measurements of 106.3scFv and 106.3 variants on yeast were measured by incubating 0.05 OD yeast ($1\times10^6$ cells) with 100-fold molar excess of biotinylated-cyclic BNP 1-32c (~0.3 µM) (SEQ ID NO:5) and anti-V5 antibody (2.5 µg/mL) for 30-60 minutes at room temperature. Cells were then washed twice with blocking buffer containing phosphate buffered saline with 1% bovine serum albumin (PBS/BSA) and incubated at room temperature with 100-fold molar excess unlabelled cyclic BNP 1-32c (SEQ ID NO:5) for varying amounts of time (0, 0.25 hr, 0.5 hr, 1 hr, 2 hr, 4.25 hr, 25.5 hr, 50 hr 75 hr and 144 hr (See FIG. 8). At each individual time point, yeast cells were transferred to ice to halt the reaction. Cells were then washed twice with PBS/BSA and suspended in secondary staining reagents, specifically, SA:PE and GAM:633. Cells were incubated on ice for 30 minutes, washed twice and then analyzed on the FACS Aria flow cytometer. FIG. 8 shows the off-rate data plotted as mean fluorescence units ("MFU") versus time (in seconds). A first order decay equation was used to fit the data. The off-rate, m2 in the equation shown in FIG. 8, was fitted to $8.4^{-5}$ $sec^{-1}$ with and R value of 0.9993. The 106.3 scFv half-life ($t_{1/2}$) was 137 min ($t_{1/2}=ln\ 2/k_{off}$).

An off-rate sorting strategy was used to identify off-rate improved 106.3 variants from mutagenic libraries. Therefore, the 106.3 scFv, unmutated or wildtype ("wt"), half-life was used to determine the appropriate time to sort the mutagenic libraries. 106.3 mutagenic libraries were sorted approximately 3 hours after the addition of unlabelled cyclic BNP (1-32c) (SEQ ID NO:5) with the same assay conditions described for wt 106.3 scFv.

Generation of 106.3 CDR Directed Libraries

Figure 9:
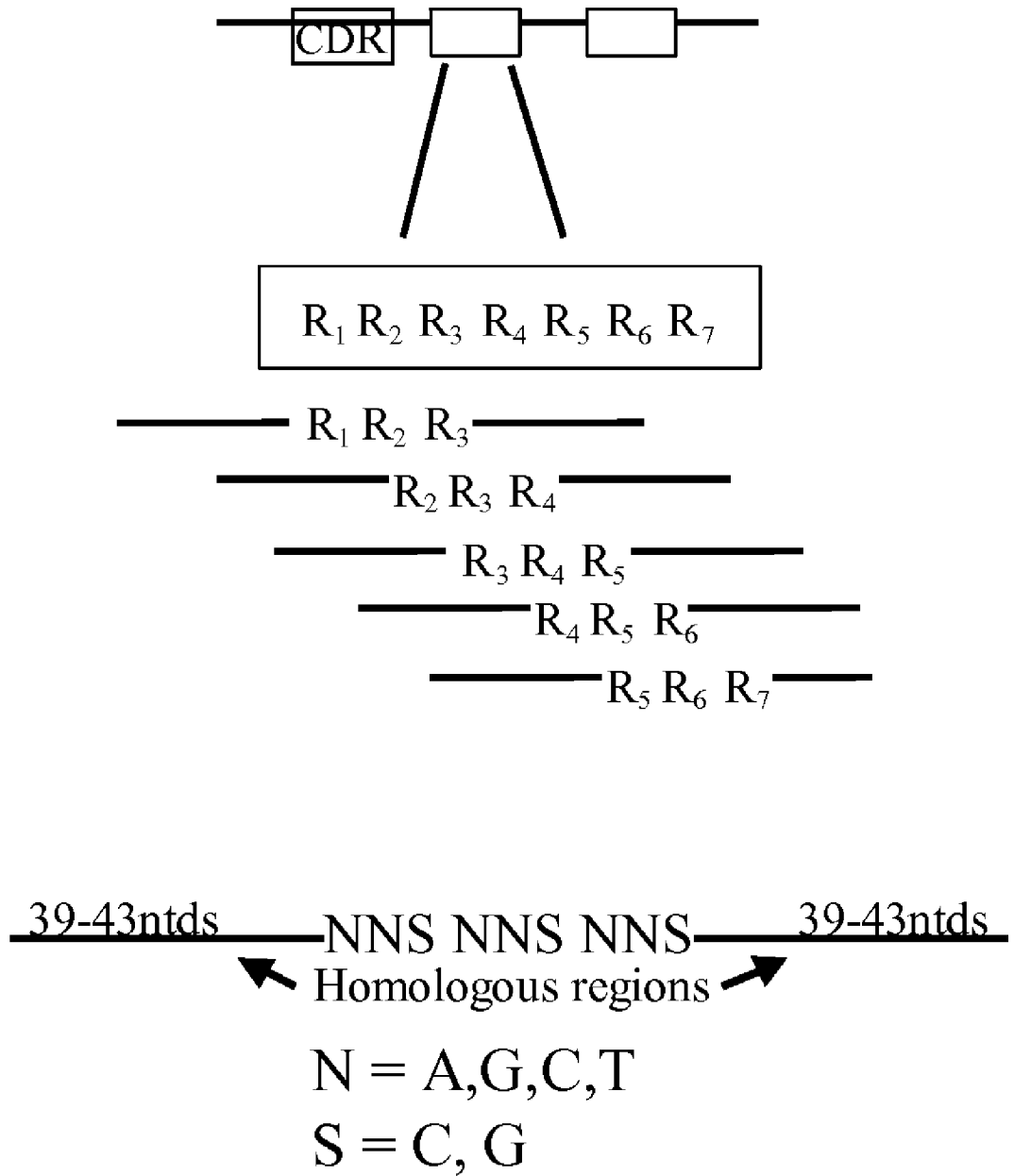
FIG. 9 is a schematic depiction which shows how degenerate oligonucleotides were designed so that three amino acid positions of the complementarity determining region (9 nucleotides) were randomly mutated per library.

Mutagenesis was directed to the three heavy and three light chain complementary determining regions (CDR) of antibody 106.3 (See, e.g., FIGS. 3-6 and SEQ ID NOS:6-11) since these loops are the major antigen contact sites. CDR loop lengths and numbering were defined using Kabat nomenclature. Individual libraries were composed that randomly mutated three amino acid positions of the CDR in a single library with the mutagenic window shifted by one amino acid per library (See, FIG. 9). The library diversity for an individual library totaled 203 or 8,000 possible variants with every amino acid sampled at every CDR position. For 106.3scFv, a total of 54 libraries were generated 29 variable heavy and 25 variable light libraries.

Figure 10:
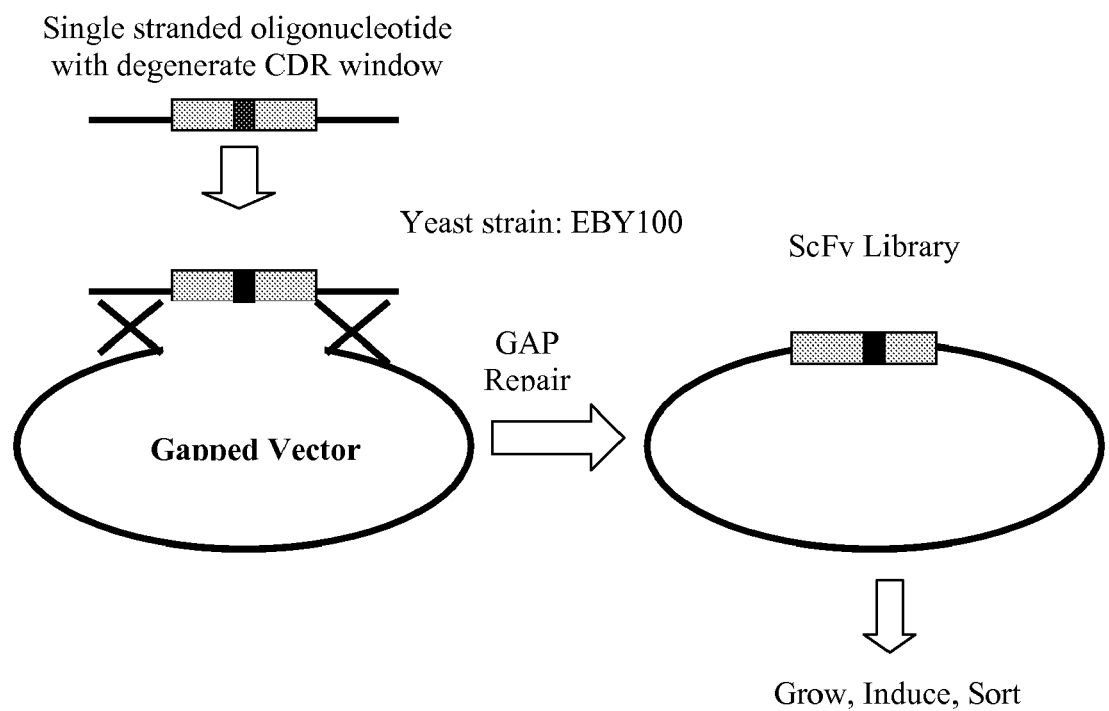
FIG. 10 is a schematic depiction which shows how the 106.3 scFv library was constructed using yeast homologous recombination. More specifically, gapped vectors were PCR generated to exclude those nucleotides that were being mutagenized in the library. The degenerate single stranded oligonucleotides were synthesized. Gapped vectors and single stranded degenerate oligonucleotides were transformed into S. cerevisiae strain EBY100. Transformed clones were selected in tryptophan deficient glucose media.

Libraries were generated by combining linearized gapped pYD41-106.3 vector and single stranded oligonucleotides with chemically competent EBY100 yeast (See, FIG. 10). The gapped pYD41 vector is a vector created by PCR that lacks a specific region of each CDR that is replaced in library construction by the single stranded degenerate oligonucleotide. Degenerate single-stranded oligonucleotides are 90-105 nucleotides long with 39-43 nucleotides of homology to the pYD41-106.3 scFv vector on each side of the nine degenerate nucleotide window. The oligonucleotides for each library, 54 total, were synthesized (See FIGS. 14A-H and SEQ ID NOS:25-78). Gapped vector (1 ug) and the degenerate oligonucleotide (16 ug) were combined with EBY100 yeast (3e8 cells) and transformed using the Gietz and Schiestl library transformation protocol (Schiestl and Gietz, *Current Genetics*, 16(5-6):339-46 (December 1989)). The degenerate oligonucleotide and the pYD41-106.3scFv gapped vector cyclize during transformation due to homologous recombination facilitated by the nucleotide overlap and the mechanism of yeast endogenous gap repair. Libraries were grown at 30° C. for 48-72 hours in selective glucose media and passed again in selective glucose media prior to induction of protein expression for library sorting.

106.3 Mutagenic CDR Libraries 106.3 libraries were sorted based on an off-rate sorting strategy. 106.3 CDR mutagenic libraries were induced in galactose expression media at 20° C. for 18-24 hours. At room temperature, 106.3 mutagenic libraries were washed with PBS/BSA, incubated with biotinylated cyclic BNP (1-32c) (SEQ ID NO:5) and anti-V5 antibody, washed twice and incubated with unlabelled cyclic BNP (1-32c) (SEQ ID NO:5). After three hours, mutagenic libraries were washed twice and incubated on ice with SA-PE (1:200 dilution) and GAM-633 (1:200 dilution) for 30 minutes. Finally, cells were washed, analyzed and sorted on the FACS Aria. Sort gates were set based on unmutated 106.3 binding at 3 hours with a gate set to sort full-length BNP binding clones. Each sort collected the top 0.1-0.5% of the BNP binding population. Sorted cells were grown in selective glucose media and grown 18-24 hours at 30° C. Sort 1 cells were induced and sorting was repeated for one or two additional rounds.

After the last sort, sorted cells were plated onto selective glucose plates and placed at 30° C. for 72 hours. Three libraries showed improvements relative to wt 106.3 scFv: heavy chain library H2 8, light chain library L1 (1-5 pool), and L2 (1-5 pool). Individual yeast colonies from these libraries were inoculated in selective glucose media, cryopreserved and induced in selective galactose media. Individual colonies were then characterized and ranked in an off-rate assay.

Analysis of Selected 106.3 Variants

Selected clones were initially characterized in the off-rate assay described above for wt 106.3 scFv. FIG. 11 shows the off-rate values determined from a first order decay curve for each improved 106.3 scFv variant evaluated. Overall, clones exhibited improvements in off-rate better than 2-fold that of the 106.3 scFv wt clone. The clone with the desired slowest off-rate was 106.3 L1 B24 scFv with an off rate of $6.7\times10^{-6}$ $sec^{-1}$.

Selected 106.3 scFv variants were sequenced to determine the amino acid mutations being expressed. Initially, plasmid DNA was isolated from yeast suspension cultures using a yeast mini-prep kit (Cat No. D2001, Zymo Research Orange, Calif.). In order to obtain sequencing grade plasmid DNA, plasmid from the yeast mini-prep kit was transformed into DH5α *E. coli*, and then purified from culture using *E. coli* mini-prep kits (Qiagen). Pure plasmid DNA was then sequenced using pYD41 vector specific primers (pYD41 for—TAGCATGACTGGTGGACAGC (SEQ ID NO:79) and pYD41rev-CGTAGAATCGAGACCGAG (SEQ ID NO:80)). Nucleotide and amino acid sequence data for 106.3 scFv variants is shown in FIGS. 12A-C. Position numbers refers to amino acid position in the respective CDR(H2 Pos 8 is 8th amino acid of CDR H2).

The sequence data for CDR L1 indicated a strong preference at position 4 for tryptophan or other bulky hydrophobic amino acids such as tyrosine or phenylalanine. A bulky amino acid residue at position 4 may be crucial for the substantial improvements in off-rate for the 106.3 scFv. The cyclic BNP (1-32c) peptide (SEQ ID NO:5) may become trapped by this bulky amino acid and thus slowing the off-rate. The L2 mutations both contain a cysteine at position 4.

Cloning and Soluble Expression of 106.3 Chimeric Antibodies in a Transient or Stable Expression System Selected 106.3 variants were converted to chimeric mouse-human IgG$_1$/human kappa antibodies through cloning of the 106.3 variable domains into the transient expression vector system called pBOS (Abbott Bioresearch Center, Worcester, Mass.) More specifically, PCR was used to amplify the variable heavy and variable light chain genes with restriction sites for cloning into separate pBOS vectors (Mizushima and Nagata, *Nucleic Acids Research,* 18:5322, (1990)). The variable heavy and variable light genes were ligated in digested/dephosphorylated vector and transformed into DH5α *E. coli.* Plasmid DNA was purified from *E. coli* and transfected into COS-7 cells and 293H cells using lipofectamine (Invitrogen, Carlsbad, Calif.) or electroporation. Transient antibody was expressed for the following 106.3 variants: wt chimeric, L1 B24 chimeric, L1 16 chimeric, L1 B24/H2 288 chimeric, and L1 16/H2 288 chimeric.

Using the pBOS-106.3 heavy and light vectors, a stable CHO cell line plasmid was created in a two step cloning procedure. First, variable heavy chain and variable light genes were ligated in frame to the human constant genes in pBV and pJV plasmids (Abbott Bioresearch Center, Worcester, Mass.), respectively, using the restriction enzymes SrfI/NotI. Ligation reactions were transformed into DH5α *E. coli* and plasmid DNA was subsequently isolated from individual colonies. The pBV-106.3 mouse variable heavy-human IgG1 and pJV-106.3 mouse variable light-human kappa were sequenced at the cloning sites.

The second cloning step involved combining the heavy chain IgG$_1$ genes and the light chain kappa genes into a single stable cell line vector. The pBV-106.3 and pJV-106.3 vectors were digested with AscI/PacI. The VL-human kappa constant and the VH-human IgG1 constant DNA fragments were gel purified and ligated to produce the stable cell line vector called pBJ-106.3. The pBJ-106.3 heavy/light chimeric plasmid was transformed into CHO cells using calcium phosphate protocol. Stable cell lines were subcloned from initial transformation. A stable CHO cell line has been developed for the clone 106.3 AM1 (also referred to as "BNP106.3sc128am1CHO1162-236" and "106.3 L1 B24/H2 288 chimeric") and deposited with the A.T.C.C. as described in Example 2 herein.

BIAcore Characterization of Engineered Chimeric 106.3 Variants

A high density Goat Anti-human Fc (GAHFc) antibody (Jackson ImmunoResearch Laboratories, West Grove, Pa.) (an antispecies antibody) surface plasma resonance (SPR) biosensor was prepared by immobilizing GAHFc to a preconditioned BIAcore CM5 chip (Uppsala, Sweden) by amine coupling (amino coupling is well known in the art, for example, see Nordin, H et al., *Analytical Biochemistry,* 340: 359-368 (2005)). The carboxymethyl-dextran biosensor is activated with an 8 minute injection of a 1:1 mixture of 0.4 M EDC and 0.1 NHS at 20 µL/minute. GAHFc in 10 mM sodium acetate (pH 5.0) is coupled to the activated surface with a 10 minute injection. The surface is then deactivated with 1 M ethanolamine pH 8.5 for 8 minutes followed by another 10 minute injection of GAHFc. This is followed with a biosensor conditioning of ten 20 second injection of 100 mM H$_3$PO$_4$ at a flow rate of 100 µL/min. ~10.5 kRU, resonance units, of GAHFc is coupled to the biosensor in each flow cell.

Purified anti-BNP chimeric antibodies ("cAb"): (1) stable 106.3 AM1 from CHO cells (described above and in Example 2), and (2) transient anti-BNP WT/WT from COS cells are diluted into SPR Running Buffer (BIAcore, Uppsala, Sweden) (degassed/vacuum-filtered HBS-EP (BIAcore, Sweden)) supplemented with 12 mg/mL BSA and 12 mg/mL carboxymethyl dextran sodium salt) to a concentration of 10 µg/mL of purified antibody. A frozen (−80° C.) aliquot of BNP in dH$_2$O at 100 µM is diluted into SPR Running Buffer to a concentration of 100 µM.

At 25° C., 30 µL of each anti-BNP cAbs are injected at 10 µL/min onto individual SPR flow cells with one flow cell left blank as a reference control. After loading each cAb onto the biosensor, all flow cells are allowed to equilibrate for 45 minutes with SPR running buffer at a flow rate of 100 µL/min before the running buffer bottle is substituted (in between syringe fills) for a sample solution of 100 µM BNP for ~16 hours. The sample solution is then switched back to SPR running buffer for another ~7 hours. The surface is then regenerated with three 33 second pulses of 100 mM phosphoric acid at a flow rate of 100 µL/min. A blank run is performed by running SPR running buffer over an anti-BNP cAb loaded sensor for ~23 hours.

The data was double-referenced corrected (the 100 µM BNP sample data was corrected by subtracting the reference data and then subtracting blank buffer data) and fitted to a 1:1 Langmuir Binding model (See, *BIA Evaluation* 3 Software Handbook, edition November 1999 (version AD) Copyright 1997-1999, Biacore AB) with considerations for mass transport and linear drift with BIAevaluation software (version 3.2).

Using BIAcore SPR, the equilibrium dissociation constant ($K_D$) of the wild-type 106.3 cAb was determined to be 1.9× $10^{-11}$ M with an on-rate of 7.8×$10^6$ M$^{-1}$sec$^{-1}$ and an off-rate of 1.5×$10^{-4}$sec$^{-1}$. The equilibrium dissociation constant ($K_D$) Of the 106.3 AM1 cAb was determined to be 1.9×$10^{-12}$M with an on-rate of 1.3×$10^7$ M$^{-1}$ sec$^{-1}$ and an off-rate of 2.4× $10^{-5}$sec$^{-1}$. Similar $K_D$ values were obtained for both 106.3 and 106.3 AM1, 1.7×$10^{-12}$ M and 9.3×$10^{-12}$M respectively, using Sapidyne's KinExA instrument that determines $K_D$ values in a solution phase measurement (Sapidyne, Boise, Id.).

Specificity of Engineered Chimeric 106.3 Variants

Anti-BNP 106.3 AM1 BNP Truncated BNP Peptide Displacement EIA

Figure 18:
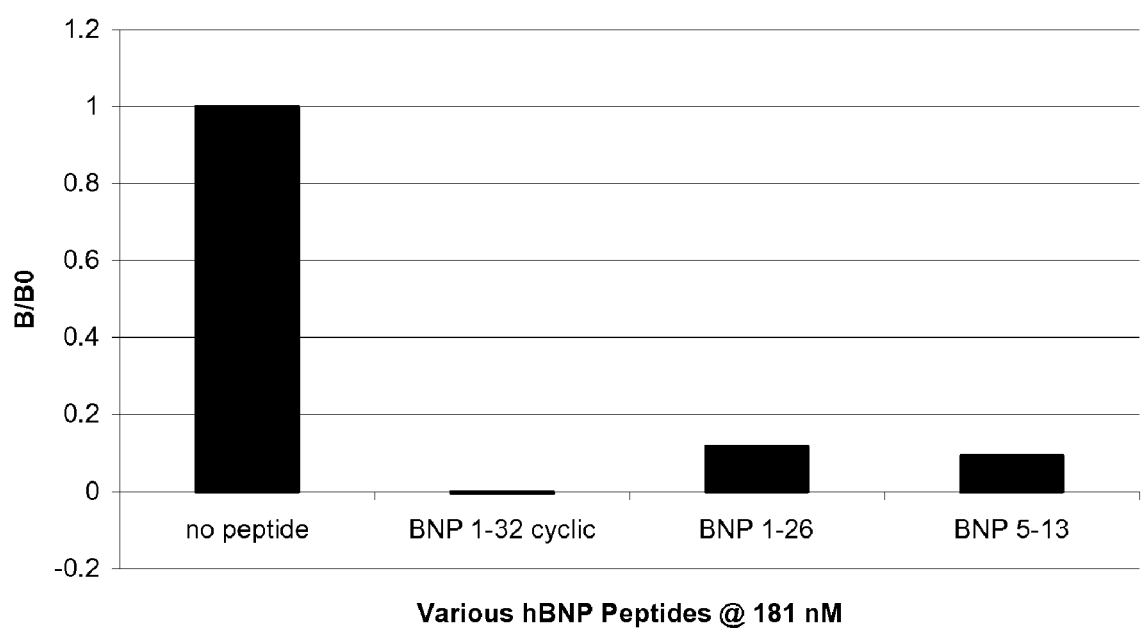
FIG. 18 shows the displacement of antibody 106.3 AM1 (used at about 0.01 μg/mL) with various hBNP peptides (used at about 181 nM).

The 106.3 AM1 mAb's ability to bind to truncated forms of hBNP, namely hBNP 1-26 and hBNP 5-13, was determined in a displacement microtiter CIA (See, FIG. 18). Blocked antispecies coated plates were incubated with mAb for 1 hour and washed. Serially diluted free, unconjugated hBNP 1-26 (Abbott, Abbott Park, Ill.), hBNP 5-13 (AnaSpec, San Jose, Calif.), hBNP 1-32 (Peptide Institute, Osaka, Japan) peptides or a 0 peptide control were allowed to react with the AM1 mAb for one hour. The plates were washed and an acridinylated hBNP (1-32 cyclic) conjugate (Abbott ADD, Abbott Park, Ill.) was added. The plates were once again incubated and washed. The Relative Luminescence Units (RLUs) were obtained from the chemiluminescence signal generated as the serially-layered pre-trigger/trigger combination (Abbott, Abbott Park, Ill.) on the Microbeta Jet (Perkin-Elmer, Turku, Finland). Anti-BNP 106.3 AM1 mAb was found to be reactive to the free hBNP fragments amino acids 1-26 and amino acids 5-13 as demonstrated by >85% signal displacement in the microtiter assay.

Fine Epitope Mapping of Engineered Chimeric 106.3 Variants

Anti-BNP 106.3 AM1 Alanine Peptide Mapping EIA

The binding site of the 106.3 AM1 mAb was identified using an alanine mutagenesis screening procedure with a cyclic hBNP 1-32 alanine substituted peptide panel. Single amino acids of the hBNP peptide were replaced with an alanine amino acid (except at positions 10 and 26). The 106.3 AM1 mAb was evaluated for its ability to bind the unlabelled alanine substituted peptides versus labeled hBNP 1-32 peptide. The mAb at a constant concentration is incubated on the solid phase coated with an anti-species antibody, then the unbound sample is washed away. The bound antibody is allowed to react with the 2900 nM unlabeled peptides. Following incubation, a wash is used to eliminate any unbound free peptide. Next, the biotinylated hBNP 1-32 cyclic peptide (Abbott GPRD, Abbott Park, Ill.) at 2.9 nM is allowed to react with any unbound sites on the anti-BNP 106.3 AM1 mAb. Unbound peptide is washed away prior to the addition of strepavidin-HRPO (Invitrogen, Carlsbad, Calif.). The OPD substrate system (Abbott, Abbott Park, Ill.) was used for color development and signals read on a Titertek MAP EIA workstation (Titertek Instruments, Huntsville, Ala.).

Figure 19:
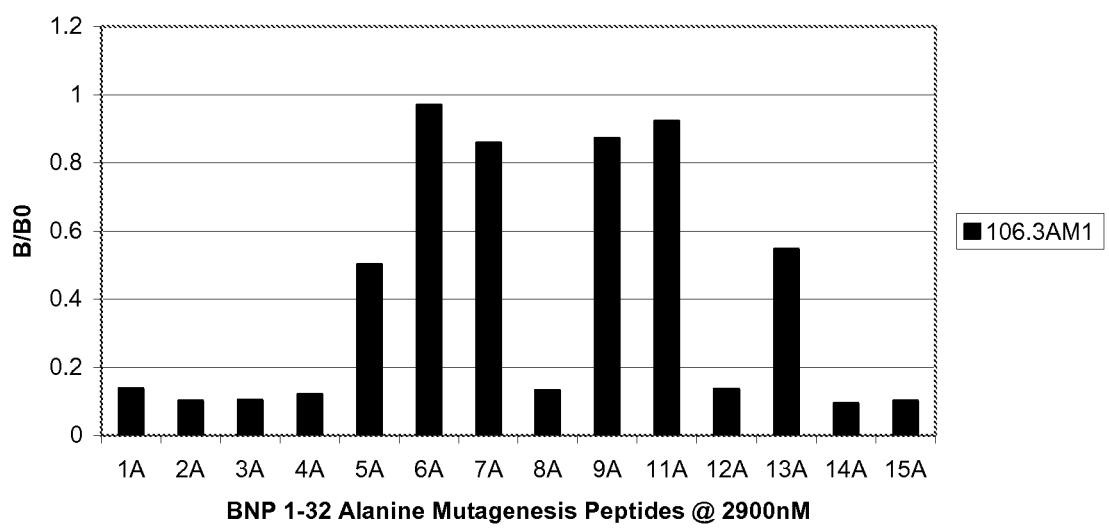
FIG. 19 shows the alanine peptide mapping of antibody 106.3 AM1 using EIA.
Figure 20:
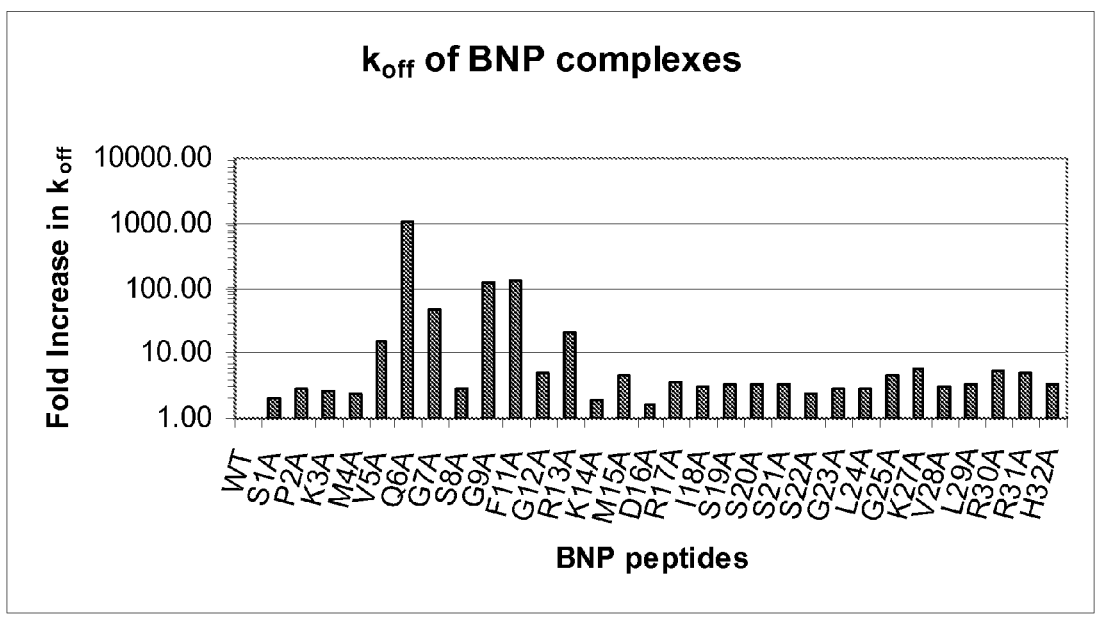
FIG. 20 shows the alanine peptide mapping of antibody 106.3 AM1 using BIAcore. The fold increase in $k_{off}$ of BNP complexes comprising various BNP peptides are displayed.

This signal displacement EIA assay was used as a tool to determine the fine epitope mapping profile of the 106.3 AM1 mAb. The free peptide concentration was 2-log over that of the labeled peptide to ensure that inhibition occurs. The bar graph in FIG. 19 shows the bound over unbound (B/BO) ratio of the AM1 antibody binding signal of free peptide versus labeled peptide. If an amino acid residue is critical for AM1 mAb binding to hBNP, partial to no displacement of signal is detected. In this example, if a B/Bo ratio of >0.4 is obtained, the specific amino acid is considered critical for mAb binding. The 106.3AM1 mAb functional epitope is identified as V5, Q6, G7, G9, F11, and R13 in bold in the sequence below.

(SEQ ID NO: 5)
NH2-SPKMVQGSGCFGRKMDRISSSSGLGCKVLRRH-COOH

Anti-BNP 106.sc128 L1 B24H2 288 AM1Alanine Peptide Mapping with BIAcore

A high density Goat Anti-human Fc (GAHFc) antibody (Jackson ImmunoResearch Laboratories, West Grove, Pa.) (an antispecies antibody) surface plasma resonance (SPR) biosensor was prepared by immobilizing GAHFc to a preconditioned BIAcore CM5 chip (Uppsala, Sweden) by amine coupling as described above.

At 25° C., 60 ul of the anti-BNP AM1 cAb are injected at 10 μL/min onto individual SPR flow cells with one flow cell left blank as a reference control. After loading each cAb onto the biosensor, all flow cells are allowed to equilibrate for 10 minutes with SPR running buffer at a flow rate of 100 μL/min. 200 μL of BNP peptide or BNP single alanine substituted peptides (alanine substituted at each position except 10 and 26) at 10 nM was flowed over the AM1 surface at 100 μL/min. Dissociation was allowed to take place and monitored for 1800 seconds. The surface is then regenerated as previously described herein.

Figure 15:
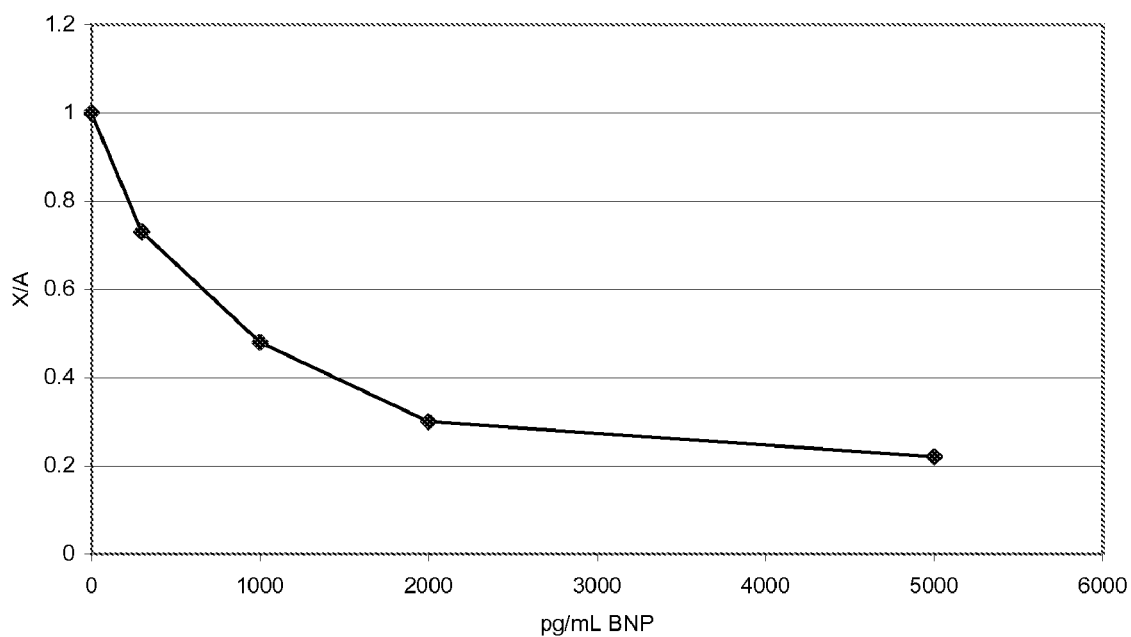
FIG. 15 shows the results of testing to determine antibody 106.3AM1's ability to bind to human cyclic BNP 1-32 in a single antibody assay format as described in Example 3 (X signal generated with given concentration of unlabelled human cyclic BNP 1-32; A signal generated with no unlabelled human cyclic BNP 1-32; X/A=ratio of these two signals).

The data was double-referenced corrected (the sample data was corrected by subtracting the reference data and then subtracting blank buffer data). Off-rates were determined from the dissociation phase of sensograms. Results indicate that amino acids V5, Q6, G7, G9, F11, and R13 are important for stability of the anti-BNP AM1/WT BNP complex. When these residues are individually mutated into alanine, the off-rate increases by at least one order of magnitude. This suggests that the anti-BNP AM1 cAb binding epitope for BNP contains the following BNP residues V5, Q6, G7, G9, F11, and R13A, in accordance with the EIA findings noted above (See FIG. 20).

EXAMPLE 2

A.T.C.C. Deposit Information

Chinese Hamster Ovary cell line for BNP106.3sc128 am1CHO1162-236 (also referred to herein as "106.3 AM1") was deposited with the American Type Culture Collection (hereinafter referred to as "A.T.C.C."), 10801 University Blvd., Manassas, Va. 20110-2209, on Sep. 20, 2005 and assigned A.T.C.C. Accession No. PTA-6987.

EXAMPLE 3

Competitive Immunoassay Using a Single Antibody Format

The antibody produced by CHO cell line 106.3 AM1 ("antibody 106.3 AM1") described above in Examples 1 and 2 was purified and tested to determine the antibody's ability to bind human cyclic BNP 1-32 in a single antibody format on the ARCHITECT® instrument (Abbott Laboratories, Abbott Park, Ill. This instrument is described in U.S. Pat. No. 5,468,646). This single antibody format encompasses the use of only one analyte specific antibody in the testing reaction.

Paramagnetic microparticles (hereinafter "microparticles", Polymer Labs, Amherst, Mass.) were washed and then reacted with serially diluted Goat anti-human antibody (Jackson ImmunoResearch, West Grove, Pa.). The Goat anti-human antibody was coated onto the paramagnetic microparticles using the techniques described in U.S. Pat. No. 6,162,902. Specifically, EDAC coupling was used (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl)carbodiimide, hydrochloride. EDAC is commercially available from Sigma-Aldrich, St. Louis, Mo.). After incubating, the microparticles were washed and overcoated with BSA. These Goat anti-human coated microparticles were then reacted with serially diluted antibody 106.3 AM1, incubated and washed.

These coated microparticles were then tested on the ARCHITECT® instrument (Abbott Laboratories, Abbott Park, Ill.) for reactivity to human cyclic BNP 1-32. An aliquot containing human cyclic BNP 1-32 was delivered to the same well of the reaction vessel as the microparticles to form a reaction mixture. The reaction mixture was incubated for approximately 18 minutes. After incubation, the microparticles were washed with the ARCHITECT® Line Diluent to remove any of the human cyclic BNP 1-32 that was not captured. The ARCHITECT® Line Diluent is commercially available from Abbott Laboratories, Abbott Park, Ill. Next, human cyclic BNP 1-32 linked to acridinium (hereinafter "tracer") was dispensed into the reaction vessel and allowed to react with the microparticles for about 4 minutes, after which the microparticles were washed with the ARCHITECT® Line Diluent to remove the unbound materials. The tracer was diluted to about 5-25 ng/mL. A solution of hydrogen peroxide and then sodium hydroxide was added to the reaction vessel and the chemiluminescent signal was measured by the chemiluminescent microparticle immunoassay (CMIA) optical assembly of the ARCHITECT® instrument. As shown in FIG. 15, in this assay format, the antibody 106.3 AM1 showed reactivity to the unlabelled human cyclic BNP 1-32 in a concentration dependent manner.

EXAMPLE 4

Sandwich Assays Using Antibodies Produced by CHO Cell Line 106.3 AM1

For the modified ARCHITECT®-hBNP assay (hereinafter referred to as "Arch-BNP") paramagnetic particles were coated with monoclonal antibody ("mAb") 3-631-436. This mAb binds to an amino acid sequence containing amino acids 13-18 on the hBNP peptide. (Monoclonal antibodies produced by hybridoma cell line 3-631-436 are described in U.S. patent application Ser. No. 11/135,050, filed on May 25, 2005, the contents of which are herein incorporated by reference. Monoclonal antibodies produced by hybridoma cell line 3-631-436 are also referred interchangeably herein as "monoclonal antibody 3-631-436" and "3-631-436". Additionally, murine hybridoma cell line 3-631-436 was deposited with the A.T.C.C. on Dec. 21, 2004 and assigned A.T.C.C. Accession No. PTA-6476). Monoclonal antibody 3-631-436 was coated onto a paramagnetic particle (Polymer Laboratories, Amherst, Mass.) using the techniques described in U.S. Pat. No. 6,162,902. Specifically, EDAC coupling was used (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl)carbodiimide, hydrochloride. EDAC is commercially available from Sigma-Aldrich, St. Louis, Mo.). Particles were washed and overcoated with BSA. These particles were used to capture BNP peptide in the assay during the first (1$^{st}$) incubation with specimens.

Alternatively, monoclonal antibody 3-631-436 was biotinylated using NHS-PEO$_4$-biotin (Pierce Biotechnology, Inc., Rockford, Ill.) and captured on streptavidin-coated superparamagnetic Dynabeads (Dynal Biotech LLC, Brown Deer, Wis.). These particles were also used to capture BNP peptide in the assay during the first (1$^{st}$) incubation with specimens.

Antibody 106.3 AM1 (See Examples 1 and 2) was conjugated to acridinium (Abbott Laboratories, Abbott Park, Ill.) and is used in the assay during the second (2$^{nd}$) incubation to detect the particle-bound hBNP peptide. The conjugation occurred by reaction of antibody AM1 with an activated acridinium-carboxamide ester.

In a complimentary modified Arch-BNP assay to that described above, capture particles were prepared by coating antibody 106.3 AM1 onto paramagnetic particles (Polymer Laboratories, Amherst, Mass.) utilizing EDAC chemistry or by biotinylation of antibody 106.3 AM1 and capture on streptavidin coated superparamagnetic Dynabeads (Invitrogen, Carlsbad, Calif.). The procedures were identical to those described above for preparation of monoclonal antibody 3-631-436 particles. These particles were also used to capture hBNP peptide in the assay during the first (1$^{st}$) incubation with specimens. Monoclonal antibody 3-631-436 was conjugated to acridinium the same way antibody AM1 was conjugated to acridinium and is used in the assay during the 2nd incubation to detect the particle-bound hBNP peptide.

BNP immunoassays were performed on an ARCHITECT® instrument (this instrument is described in U.S. Pat. No. 5,468,646).

An aliquot containing a calibrator solution was delivered to the same well of the reaction vessel as the microparticles to form a reaction mixture. The calibrator solution contained hBNP full-length peptide. The microparticles coated with the capture antibody in a Tris/BSA diluent were pipetted by the sampling probe into the appropriate wells of the reaction vessel in the sampling center. The reaction mixture was incubated for approximately 4 minutes (18 min for streptavidin based particles) at a temperature of about 37° C. After the incubation, the reaction mixture was washed with the ARCHITECT® Line Diluent to remove any of the calibrator that was not captured. The ARCHITECT® Line Diluent is commercially available from Abbott Laboratories, Abbott Park, Ill.

The mAb-Acridinium-conjugates at about 50-100 ng/mL were dispensed into the reaction vessel and incubated for approximately 4 minutes at a temperature of about 37° C. After the incubation, the reaction vessel was washed with the ARCHITECT® Line Diluent to remove the unbound materials.

A solution of hydrogen peroxide and then sodium hydroxide was added to the reaction vessel and the chemiluminescent signal was measured by the chemiluminescent microparticle immunoassay (CMIA) optical assembly of the ARCHITECT® instrument.

Figure 16:
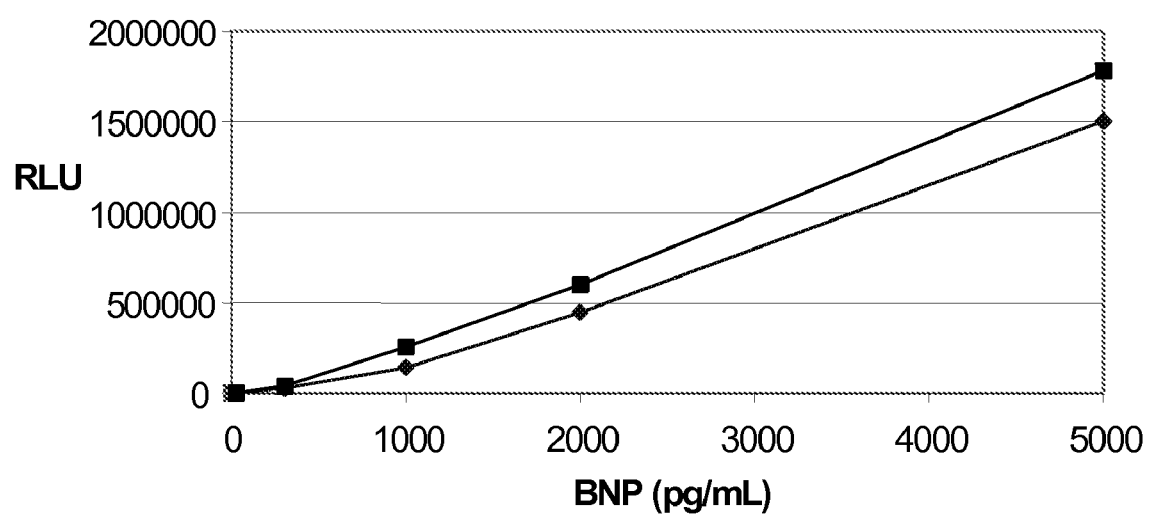
FIG. 16 shows an anti-hBNP antibody pair evaluation using streptavidin microparticles using antibody 106.3 AM1 and 3-631-436 as described in Example 4. In essence, the following were employed: M280 Streptavidin particles at 0.05% solids, 65 ng/mL conjugates, 100 μL sample volume, and a 2-step (18/4) sandwich format. Symbols & Abbreviations: diamonds, anti-BNP(106.3AM1)SA μP/anti-BNP(3-631-436)CPSP; squares, anti-BNP(3-631-436)SA μP/anti-BNP(106.3AM1)CPSP; RLU, Relative Light Units.
Figure 17:
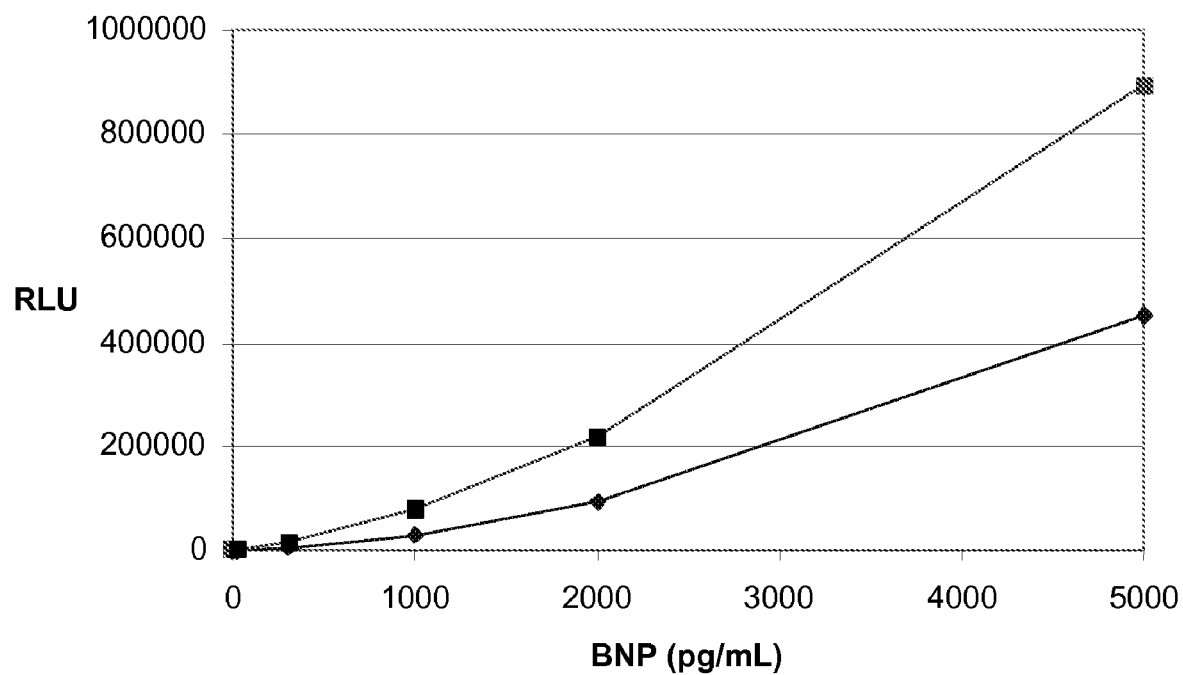
FIG. 17 shows anti-hBNP antibody pair evaluation using paramagnetic microparticles (from Polymer Labs) using antibody 106.3 AM1 and 3-631-436 as described in Example 4. Symbols & Abbreviations: diamonds, anti-BNP(106.3AM1) SA μP/anti-BNP(3-631-436)CPSP; squares, anti-BNP(3-631-436)SA μP/anti-BNP(106.3AM1)CPSP; RLU, Relative Light Units.

The ARCHITECT® system measures the acridinium signals which are typically measured in relative light units (hereinafter "rlu's"). Measurements were made in triplicate. The results shown in Table 3 below and in FIGS. 16 and 17 show the mean of the triplicate values. Specifically, the results in Table 3 and FIGS. 16 and 17 are shown in pg/mL BNP calibrator.

TABLE 3

|  |  | uP mAb clone | | | |
| --- | --- | --- | --- | --- | --- |
|  |  | 106.3AM1 | 3-631-436 | 106.3AM1 | 3-631-436 |
|  |  | Conj mAb clone | | | |
| BNP (pg/mL) |  | 3-631-436 | 106.3AM1 | 3-631-436 | 106.3AM1 |
|  | Sample | | | | |
| 0 | Cal A | 1132 | 1275 | 706 | 528 |
| 30 | Cal B | 1784 | 2386 | 671 | 1291 |
| 300 | Cal C | 19819 | 35445 | 3907 | 12618 |
| 1000 | Cal D | 142648 | 250363 | 28612 | 76400 |
| 2000 | Cal E | 446152 | 600661 | 93326 | 216220 |
| 5000 | Cal F | 1502213 | 1780437 | 451856 | 893368 |
|  | Ratio | | | | |
|  | A/A | 1.0 | 1.0 | 1.0 | 1.0 |
|  | B/A | 1.6 | 1.9 | 1.0 | 2.4 |
|  | C/A | 17.5 | 27.8 | 5.5 | 23.9 |
|  | D/A | 126.0 | 196.4 | 40.5 | 144.6 |
|  | E/A | 394.0 | 471.1 | 132.2 | 409.2 |

In addition, the immunoassays can be used to monitor patients receiving therapeutic doses of hBNP or fragments of hBNP and anti-hBNP treatments.

EXAMPLE 5

Identification of Immunoglobulin Genes

Messenger RNA was isolated from subcloned anti-BNP 3-631-436 hybridoma cells (hybridoma cell line 3-631-436 (A.T.C.C. Accession No. PTA-6476) as described in U.S. Patent Publication 2006/0183154 published on Aug. 17, 2006). 3-631-436 mRNA was utilized in a reverse transcriptase-polymerase chain reaction using a mouse Ig primer set kit purchased from Novagen (Novagen (which is an Affiliate of Merck KGaA, Darmstadt, Germany), Cat No. 69831-3) with immunoglobulin gene specific primers contained in the kit. The resulting PCR products were sequenced and thus the immunoglobulin variable heavy chain gene was identified (See, FIGS. 23, 24 and 25A and 25B)).

Alternatively the N-terminal amino acid sequence of the 3-631-436 light chain was determined using a LC-MS-MS technique subsequently used to isolate the light chain gene. The antibody heavy and light chain were separated on a SDS-PAGE gel, trypsin digested and analyzed by LC-MS-MS. The N-terminus amino acid sequence was determined using a database search to be DVVMTQTPLTLSVTTGQPA-SISC (SEQ ID NO: 152). A degenerate 5' nucleotide primer (5' GAYGTNGTNATGACNCARACNCCN 3' where N=A, G, C, T; Y=C,T; R=A,G) (SEQ ID NO: 153) and reverse kappa chain primer supplied with the Novagen kit (above) was used to amplify the 3-631-436 kappa light chain from mRNA. The resulting PCR product was sequenced to identify the complete light chain variable gene (See FIGS. 25A and 25B).

Cloning 3-631-436 Variable Region Genes into pYD41 Vector

Figure 21:
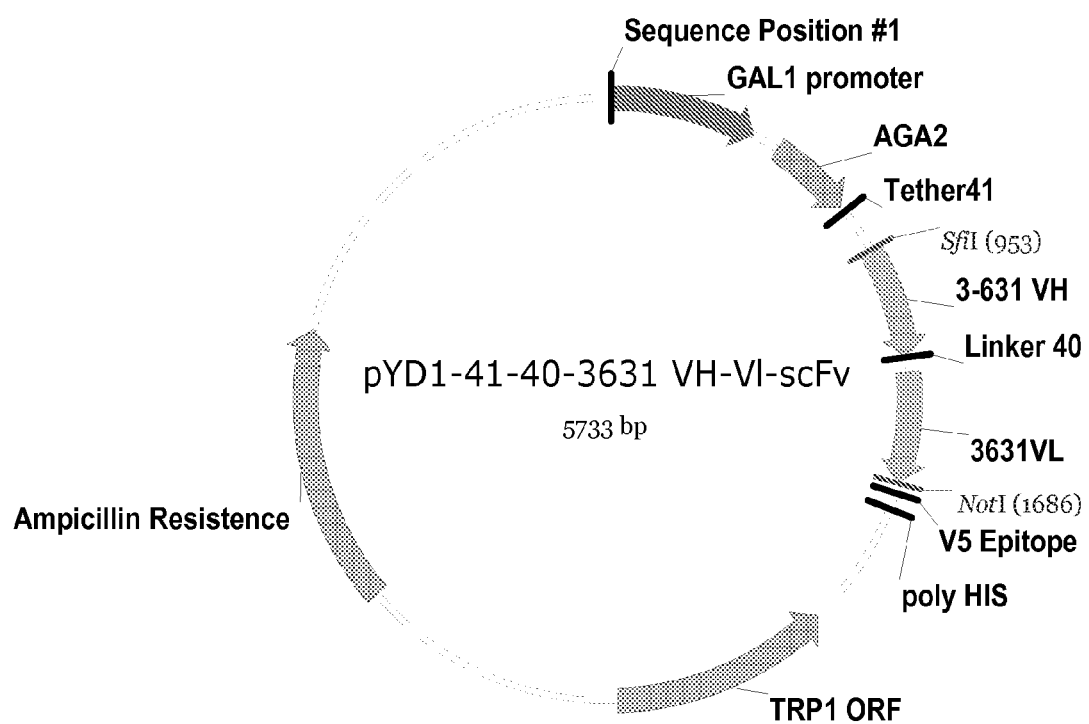
FIG. 21 is a plasmid map for vector pYD1-41-40-3631 containing the 3-631-436 single-chain variable fragment shown in FIG. 23.

A yeast display system was used to express unmutated anti-BNP proteins (described herein infra) and a library of anti-BNP proteins on the yeast surface as a fusion to the yeast protein AGA2. A yeast display vector called pYD (Invitrogen, Carlsbad, Calif.), was used as it allows for cloning of the anti-BNP gene at the C-terminus of the AGA2 gene, a yeast mating factor (See, Boder and Wittrup, *Nature Biotechnology*, 15:553-557 (June 1997). Other critical features of the pYD vector include a galactose inducible promoter and an epitope tag, V5, on the C-terminus of the inserted anti-BNP gene (See, FIG. 21 and FIGS. 25A-25B).

The yeast display platform utilizes an antibody format known as the single-chain variable fragment. In the scFv format, the variable heavy domain is connected to the variable light domain through a flexible linker (variable heavy domain—Linker GPAKELTPLKEAKVS (SEQ ID NO:4)—variable light domain).

Figure 23:
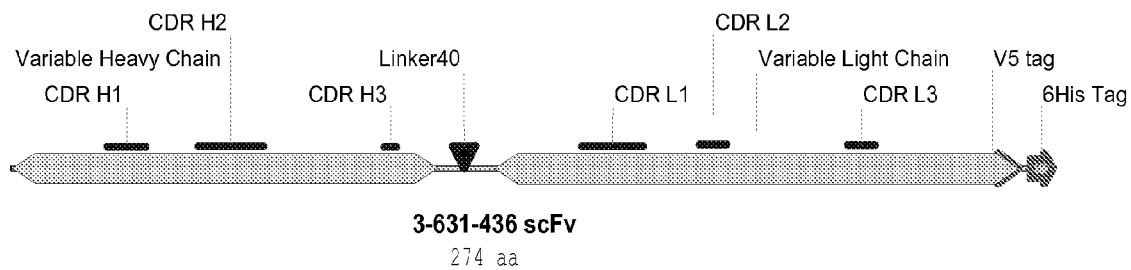
FIG. 23 is a diagram of the 3-631-436 scFv. Six His tag disclosed as SEQ ID NO: 156.

PCR single overlap extension (SOE) was used to combine the variable heavy (VH) and the variable light genes (VL) for the 3-631-436 scFv construct (See, e.g., FIG. 23 and FIGS. 25A and 25B). The 3-631-436 scFv DNA was cloned into the yeast display vector pYD41 using vector restriction sites SfiI and NotI. The pYD41-3-631-436 scFv vector was transformed into DH5α *E. coli*. Plasmid DNA was then isolated from the *E. coli* and the 3-631-436 scFv insert was sequenced to ensure the scFv was cloned in frame with the AGA2 protein.

The cloning site for the scFv into the yeast display vector pYD41 is in an ORF that includes the following genes: AGA2-tether linker 41-X press epitope tag-3-631-436 variable heavy chain-Linker 40-3-631-436 variable light chain-V5 epitope tag —Six His tag (SEQ ID NO: 156). In addition, the yeast strain EBY100 is a tryptophan auxotroph and the pYD41 vector encodes for tryptophan as the system's selectable marker.

Transformation into *Saccharomyces cerevisiae* Strain EBY100

Yeast display plasmid, pYD41-3-631-436 scFv, was transformed into *S. cerevisiae* EBY100 using Gietz and Schiestl Method (See, Schiestl and Gietz, *Current Genetics*, 16(5-6): 339-46 (December 1989)). Dilutions of the transformation reaction were plated on selective glucose plates (2% glucose (0.67% yeast nitrogen base, 0.105% HSM -trp—ura, 1.8% bacterial agar, 18.2% sorbitol, 0.86% $NaH_2PO_4.H_2O$, 1.02% $Na_2HPO_4.7H_2O$)) and incubated at 30° C. for 48-72 hours. Selective glucose media was inoculated with individual colonies and grown shaking at 30° C. for 16-20 hours. Protein expression was induced in colonies by transferring 0.5 OD600 of cells/mL (1e7cells/0.50D/mL) to selective galactose media. Colonies were shaken at 20° C. for 16-24 hours and then analyzed by the FACS Aria flow cytometer for binding to cyclic BNP (referred to as "1-32c") (SEQ ID NO:5) and anti-V5. For flow cytometry assays, yeast cells expressing 3-631-436 scFv were incubated with biotinylated: cyclic BNP (1-32c) (SEQ ID NO:5) or anti-V5 antibody followed by streptavidin: phycoerythrin (SA:PE, BD Pharmingen) or FITC labeled goat anti-mouse immunoglobulin—(GAM: FITC, Molecular Probes (which is an Affiliate of Invitrogen, Carlsbad, Calif.)). The flow cytometry histograms as shown in FIGS. 26A and 26B illustrate full-length surface expression of 3-631-436 scFv (Ab Expressionbinding) and binding of 3-631-436 scFv to cyclic BNP (1-32c) (Ag binding) (SEQ ID NO:5).

Off-rate Analysis for 3-631-436 scFv and 3-631-436 Variants on Yeast.

Figure 27:
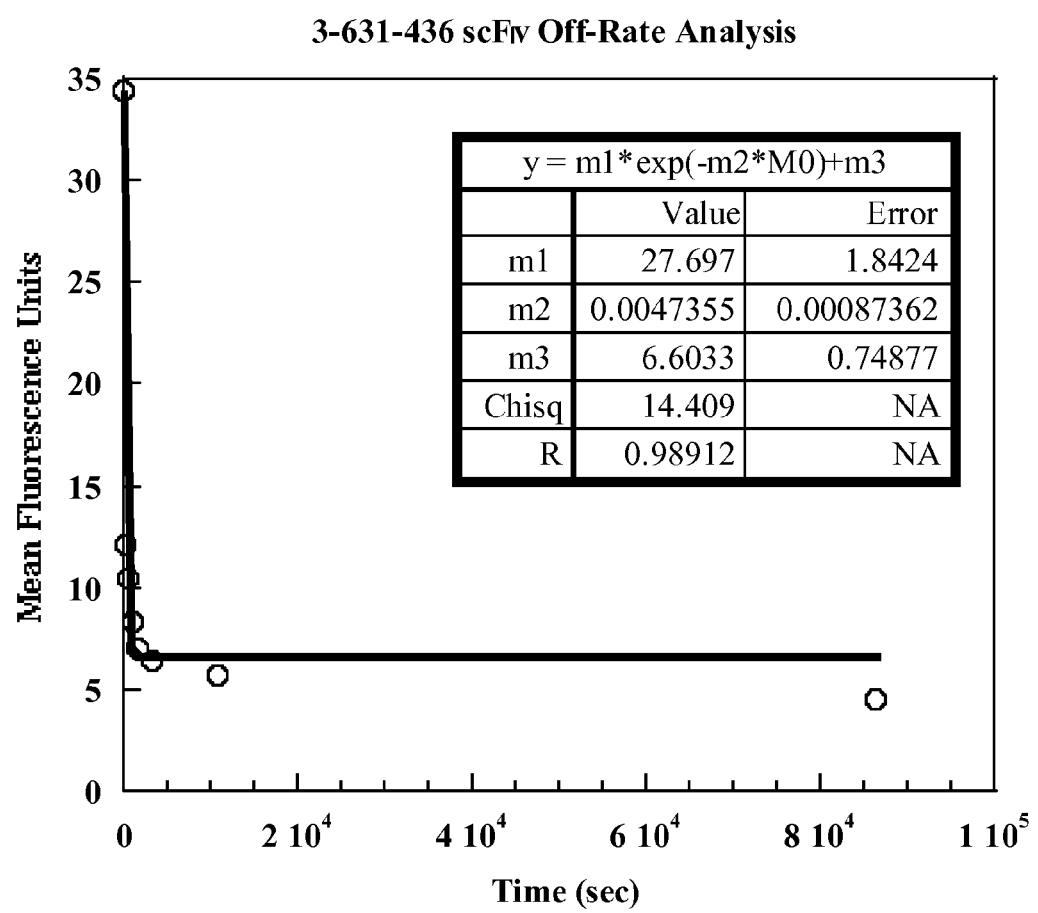
FIG. 27 shows the 3-631-436 scFv off-rate measurement. More specifically, yeast expressing 3-631-436 scFv were incubated with a saturating concentration of biotinylated cyclic BNP (1-32c) (SEQ ID NO:5). Cells were then washed and incubated with a saturating concentration of unlabelled BNP 1-32c (SEQ ID NO:5). At each time point, cells were transferred to ice, washed and incubated with SA:PE. After 30 minutes, cells were washed again and analyzed on the flow cytometer. A first order decay equation was used to fit the individual time points where m1 was the theoretical maximum mean fluorescence units ("MFU") at time 0, m2 was the off-rate ("koff"), m3 was the background MFU due to autofluorescence, and M0 was the time x (the x being the time that is being measured) that measurements are taken. The half-life ($t_{1/2}$) of 3-631-436 scFv binding to cyclic BNP (1-32c) was calculated using: $t_{1/2}=\ln 2/k_{off}$. Three to five times the half-life was the time used to sort the 3-631-436 CDR mutagenic libraries.

Off-rate measurements of 3-631-436 scFv and 3-631-436 variants on yeast were measured by incubating 0.05 OD yeast ($1\times10^6$ cells) with 100-fold molar excess of biotinylated-cyclic BNP 1-32c (~0.3 µM) (SEQ ID NO:5) and anti-V5 antibody (2.5 µg/mL) for 30-60 minutes at room temperature. Cells were then washed twice with blocking buffer containing phosphate buffered saline with 1% bovine serum albumin (PBS/BSA) and incubated at room temperature with 100-fold molar excess unlabelled cyclic BNP 1-32c (SEQ ID NO:5) for varying amounts of time (0, 5 min, 15 min, 30 min, 60 min, 120 min, 180 min, 240 min (See FIG. 27)). At each individual time point, yeast cells were transferred to ice to halt the reaction. Cells were then washed twice with PBS/BSA and suspended in secondary staining reagents, specifically, SA:PE and GAM:FITC. Cells were incubated on ice for 30 minutes, washed twice and then analyzed on the FACS Aria flow cytometer. FIG. 27 shows the off-rate data plotted as mean fluorescence units ("MFU") versus time (in seconds). A first order decay equation was used to fit the data. The off-rate, m2 in the equation shown in FIG. 27, was fitted to $4.7\times10^{-3}$ $sec^{-1}$ with and R value of 0.98912. The 3-631-436 scFv half-life ($t_{1/2}$) was 2.4 minutes ($t_{1/2}$=ln $2/k_{off}$).

An off-rate sorting strategy was one sorting pressure used to identify off-rate improved 3-631-436 variants from mutagenic libraries. Therefore, the 3-631-436 scFv, unmutated or wildtype ("wt"), half-life was used to determine the appropriate time to sort the mutagenic libraries. 3-631-436 mutagenic libraries were sorted approximately 10-12 min after the addition of unlabelled cyclic BNP (1-32c) (SEQ ID NO:5) with the same assay conditions described for wt 3-631-436 scFv.

Generation of 3-631-436 CDR Directed Libraries

Mutagenesis was directed to the three heavy and three light chain complementary determining regions (CDR) of antibody 3-631-436 (See, e.g., FIGS. 22A-22D and 25A and 25B and SEQ ID NOS:90-92) since these loops are the major antigen contact sites. CDR loop lengths and numbering were defined using Kabat nomenclature. Individual libraries were composed that randomly mutated three amino acid positions of the CDR in a single library with the mutagenic window shifted by one amino acid per library (See, FIG. 9). The library diversity for an individual library totaled $20^3$ or 8,000 possible variants with every amino acid sampled at every CDR position. For 3-631-436 scFv, a total of 50 libraries were generated 24 variable heavy and 26 variable light libraries.

Libraries were generated by combining linearized gapped pYD41-3-631-436 vector and single stranded oligonucleotides with chemically competent EBY100 yeast (See, FIG. 10). The gapped pYD41 vector is a vector created by PCR that lacks a specific region of each CDR that is replaced in library construction by the single stranded degenerate oligonucleotide. Degenerate single-stranded oligonucleotides are 90-105 nucleotides long with 39-43 nucleotides of homology to the pYD41-3-631-436 scFv vector on each side of the nine degenerate nucleotide window. The oligonucleotides for each library, 50 total, were synthesized (See FIGS. 31A-31F and SEQ ID NOS:93-142). Gapped vector (1 µg) and the degenerate oligonucleotide (16 µg) were combined with EBY100 yeast (3e8 cells) and transformed using the Gietz and Schiestl library transformation protocol (Schiestl and Gietz, *Current Genetics,* 16(5-6):339-46 (December 1989)). The degenerate oligonucleotide and the pYD41-3-631-436 scFv gapped vector cyclize during transformation due to homologous recombination facilitated by the nucleotide overlap and the mechanism of yeast endogenous gap repair. Libraries were grown at 30° C. for 48-72 hours in selective glucose media and passed again in selective glucose media. Individual libraries were pooled according to their CDR as follows: H1 (1-8), H2 (1-8), H2 (9-15), L1 (1-8), L1 (9-14), L2 (1-5), L3 (1-7) prior to induction of protein expression for library sorting.

3-631-436 Mutagenic CDR Libraries 3-631-436 libraries were sorted based on an off-rate sorting strategy, an equilibrium sorting strategy, and an on-rate/off-rate sorting strategy. 3-631-436 CDR mutagenic libraries were induced in galactose expression media at 20° C. for 18-24 hours. For off-rate sorting, at room temperature, 3-631-436 mutagenic libraries were washed with PBS/BSA, incubated with saturating concentrations of biotinylated cyclic BNP (1-32c) (SEQ ID NO:5) and anti-V5 antibody, washed twice and incubated with unlabelled cyclic BNP (1-32c) (SEQ ID NO:5). After 10-12 minutes, mutagenic libraries were washed twice and incubated on ice with SA-PE (1:200 dilution) and GAM-IgG2a AlexaFluor 488 (1:150 dilution) for 20-30 minutes. Finally, cells were washed, analyzed and sorted on the FACS Aria. Sort gates were set based on unmutated 3-631-436 binding under the same assay conditions with a gate set to sort full-length BNP binding clones. Each sort collected the top 0.1-0.2% of the BNP binding population. Sorted cells were grown in selective glucose media and grown 18-24 hours at 30° C. Sort 1 cells were induced and sorting was repeated for two additional rounds.

For equilibrium sorting, at room temperature, 3-631-436 mutagenic libraries were washed with PBS/BSA and incubated with 26 pM biotinylated cyclic BNP (1-32c) (SEQ ID NO:5) and anti-V5 antibody. The concentration of biotinylated BNP was 10-fold lower than the KD of the 3-631-436 wt scFv(~260 µM). After one to two hours, libraries were transferred to ice, washed twice and incubated with anti-V5 antibody for 30 minutes followed by two washes and incubation with SA:PE and GAM-IgG2a AlexaFluor488 for 30 minutes. Cells were washed and analyzed on FACS aria with sort gates established based on 3-631-436 wt binding under assay conditions. Each sort collected the top 0.1-0.2% of the BNP binding population. Sorted cells were grown and sorting was repeated two additional rounds.

For on-rate/off-rate sorting, light chain library pools and heavy chain library pools were combined into a VL library or VH libraries respectively. The first round of sorting utilized the off-rate approach described above with the exception of incubating for 12.5 minutes with competitor unlabelled BNP. In the second and third sort rounds, the libraries were incubated with 50 pM biotinylated BNP and allowed to reach 90% scFv saturation at ~14 minutes prior to performing the off rate assay format described above. For the fourth and final sort round, the libraries were incubated with 50 pM biotinylated BNP and allowed to reach 80% scFv saturation at ~10 minutes prior to performing the off-rate rate assay format.

After the last sort, sorted cells were plated onto selective glucose plates and placed at 30° C. for 72 hours. One library showed improvements relative to wt 3-631-436 scFv:light chain library L2 (1-7 pool). Individual yeast colonies from these libraries were inoculated in selective glucose media, cryopreserved and induced in selective galactose media. Individual colonies were then characterized and ranked in an off-rate assay.

Analysis of Selected 3-631-436 Variants

Selected clones were initially characterized in the off-rate assay described above for wt 3-631-436 scFv. FIG. 28 shows the off-rate values determined from a first order decay curve for each improved 3-631-436 scFv variant evaluated. Overall, clones exhibited improvements in off-rate better than 2-fold that of the 3-631-436 scFv wt clone.

Selected 3-631-436 scFv variants were sequenced to determine the amino acid mutations being expressed. Initially, plasmid DNA was isolated from yeast suspension cultures using a yeast mini-prep kit (Cat No. D2001, Zymo Research Orange, Calif.). In order to obtain sequencing grade plasmid DNA, plasmid from the yeast mini-prep kit was transformed into DH5α *E. coli*, and then purified from culture using *E. coli* mini-prep kits (Qiagen). Pure plasmid DNA was then sequenced using pYD41 vector specific primers (pYD41 for—TAGCATGACTGGTGGACAGC (SEQ ID NO:79) and pYD41rev-CGTAGAATCGAGACCGAG (SEQ ID NO:80)). Nucleotide and amino acid sequence data for 3-631-436 scFv variants is shown in FIG. 29. Position numbers refers to amino acid position given by numbering using the Kabat numbering system.

A convergence of mutations was identified in the CDR L2 from Val/Val/Ser at positions 50-52 to tryptophan/threonine-methionine-/aspartate-asparagine-threonine.

Cloning and Soluble Expression of 3-631-436 Chimeric Antibodies in a Transient or Stable Expression System Selected 3-631-436 variants were converted to chimeric mouse $IgG_{2b}$/kappa antibodies through cloning of the 3-631-436 variable domains into the transient expression vector system called pBOS (Abbott Bioresearch Center, Worcester, Mass.). More specifically, PCR was used to amplify the variable heavy and variable light chain genes with restriction sites for cloning into separate pBOS vectors (Mizushima and Nagata, *Nucleic Acids Research,* 18:5322, (1990)). The variable heavy and variable light genes were ligated in digested/dephosphorylated vector and transformed into DH5α *E. coli*. Plasmid DNA was purified from *E. coli* and transfected into 293H cells using lipofectamine (Invitrogen, Carlsbad, Calif.). Transient antibody was expressed for the following 3-631-436 variants: wt chimeric called 3-631-436 AM1 and AM2, AM3, AM4, 3-631-436 AM5, AM6, and 3-631-436 AM8 chimeric. Clones were assigned AM or "affinity matured" name designation as in FIG. 30 prior to cloning.

Using the pBOS-3-631-436 heavy and light vectors, a stable CHO cell line plasmid was created in a two step cloning procedure. First, variable heavy chain and variable light genes were ligated in frame to the mouse constant genes in pBV and pJV plasmids (Abbott Bioresearch Center, Worcester, Mass.), respectively, using the restriction enzymes SrfI/NotI. Ligation reactions were transformed into DH5α *E. coli* and plasmid DNA was subsequently isolated from individual colonies. The pBV-3-631-436 mouse variable heavy—IgG2b IgG$_{2b}$ and pJV-3-631-436 mouse variable light—kappa were sequenced at the cloning sites.

The second cloning step involved combining the heavy chain IgG$_{2b}$ gene and the light chain kappa gene into a single stable cell line vector. The pBV-3-631-436 and pJV-3-631-436 vectors were digested with AscI/PacI. The VL-mouse kappa constant and the VH-mouse IgG2b constant DNA fragments were gel purified and ligated to produce the stable cell line vector called pBJ-3-631-436. The pBJ-3-631-436 heavy/light chimeric plasmid was transformed into CHO cells using calcium phosphate protocol. Stable cell lines were subcloned from initial transformation. A stable CHO cell line has been developed for the clone 3-631-436 AM5 (also referred to as "BNP3-631-436AM5CHO893-214" and "BNP3-631-436AM8CHO974-211") and deposited with the A.T.C.C. as described in Example 6 herein.

BIAcore Characterization of Engineered Chimeric 3-631-436 variants

A goat Anti-mouse Fc (GAMFc) antibody (Jackson ImmunoResearch Laboratories, West Grove, Pa.) (an antispecies antibody) surface plasma resonance (SPR) biosensor was prepared by immobilizing GAM:Fc to a preconditioned BIAcore CM5 chip (Uppsala, Sweden) by amine coupling (amino coupling is well known in the art, for example, see Nordin, H et al., *Analytical Biochemist y*, 340:359-368 (2005)). The carboxymethyl-dextran biosensor is activated with a 1:1 mixture of 0.4 M EDC and 0.1 NHS at 20 µL/minute. GAMFc in 10 mM sodium acetate (pH 5.0) is coupled to the activated surface with a 10 minute injection. The surface is then deactivated with 1 M ethanolamine pH 8.5 for 8 minutes followed by another 10 minute injection of GAMFc. This is followed with a biosensor conditioning of ten 60 second injections of 150 mM H$_3$PO$_4$ at a flow rate of 30 µL/min. ~14 kRU, resonance units, of GAMFc is coupled to the biosensor in each flow cell.

Purified anti-BNP antibodies: 3-631-436 wt, 3-631-436 AM1, 3-631-436 AM2, 3-631-436 AM3, 3-631-436 AM4, 3-631-436 AM5, 3-631-436 AM6 and 3-631-436 AM8, (described above), are diluted into supplemented SPR Running Buffer (BIAcore, Uppsala, Sweden) (degassed/vacuum-filtered HBS-EP (BIAcore, Sweden) to a concentration of 10-25 µg/mL of purified antibody. A frozen (−80° C.) aliquot of BNP in dH$_2$O at 100 µM is diluted into SPR Running Buffer to a concentration of 1 uM, 50 nM and/or 3-fold serial dilutions from 100 nM.

At 25° C., 55-60 µL of each anti-BNP Abs are injected at 5 µL/min onto individual SPR flow cells with one flow cell left blank as a reference control. After loading each Ab onto the biosensor, all flow cells are allowed to equilibrate for 5-6 minutes with SPR running buffer at a flow rate of 75 µL/min before a 150 µL injection of BNP or running buffer followed by 360 seconds of dissociation time. Subsequently, the flow rate is changed to 30-100 µL/min and the surface is then regenerated with three 33-60 second pulses of 100-150 mM phosphoric acid at a flow rate of 30-100 µL/min.

The data was double-referenced corrected (the BNP sample data was corrected by subtracting the reference data and then subtracting blank buffer data) and fitted to a 1:1 Langmuir Binding model (See, *BIA Evaluation 3 Software Handbook*, edition November 1999 (version AD) Copyright 1997-1999, Biacore AB) with considerations for mass transport and linear drift with BIAevaluation software (version 3.2).

Using BIAcore SPR, the equilibrium dissociation constant (K$_D$) of the wild-type 3-631-436 mAb was determined to be $3.8 \times 10^{-10}$M with an on-rate of $6.7 \times 10^6$ M$^{-1}$sec$^{-1}$ and an off-rate of $2.5 \times 10^{-3}$sec$^{-1}$. The equilibrium dissociation constant (K$_D$) of the 3-631-436 AM2 cAb was determined to be $1.6 \times 10^{-10}$M with an on-rate of $3.6 \times 10^6$ M$^{-1}$sec$^{-1}$ and an off-rate of $5.6 \times 10^4$ sec$^{-1}$. The equilibrium dissociation constant (K$_D$) of the 3-631-436 AM3 cAb was determined to be $2.1 \times 10^{-10}$M with an on-rate of $5.8 \times 10^6$ M$^{-1}$sec$^{-1}$ and an off-rate of $1.6 \times 10^3$ sec$^{-1}$. The equilibrium dissociation constant (K$_D$) of the 3-631-436 AM4 cAb was determined to be $3.7 \times 10^{-10}$M with an on-rate of $1.6 \times 10^6$ M$^{-1}$sec$^{-1}$ and an off-rate of $6 \times 10^4$ sec$^{-1}$. The equilibrium dissociation constant (K$_D$) of the 3-631-436 AM5 cAb was determined to be $1.4 \times 10^{-10}$M with an on-rate of $7.9 \times 10^6$ M$^{-1}$sec$^{-1}$ and an off-rate of $1.1 \times 10^3$ sec$^{-1}$. The equilibrium dissociation constant (K$_D$) of the 3-631-436 AM6 cAb was determined to be $2.8 \times 10^{-10}$M with an on-rate of $1.5 \times 10^6$ M$^{-1}$sec$^{-1}$ and an off-rate of $4.1 \times 10^4$ sec$^{-1}$. The equilibrium dissociation constant (K$_D$) of the 3-631-436 AM8 cAb was determined to be $1.0 \times 10^{-10}$M with an on-rate of $8.1 \times 10^6$ M$^{-1}$sec$^{-1}$ and an off-rate of $8.2 \times 10^{-4}$sec$^{-1}$. Sapidyne's KinExA instrument was also used to determine K$_D$ values in a solution phase measurement (Sapidyne, Boise, Id.) as stated in FIG. 30.

EXAMPLE 6

A.T.C.C. Deposit Information

Chinese Hamster Ovary cell line for BNP3-631-436AM5CHO893-214 (also referred to herein as "3-631-436 AM5") was deposited with the American Type Culture Collection (hereinafter referred to as "A.T.C.C."), 10801 University Blvd., Manassas, Va. 20110-2209, on Apr. 24, 2007 and assigned A.T.C.C. Accession No. PTA-8369.

Chinese Hamster Ovary cell line for BNP3-631-436AM8CHO974-211 (also referred to herein as "3-631-436 AM8") was deposited with the American Type Culture Collection (hereinafter referred to as "A.T.C.C."), 10801 University Blvd., Manassas, Va. 20110-2209, on Apr. 24, 2007 and assigned A.T.C.C. Accession No. PTA-8368.

EXAMPLE 7

Sandwich Assays Using 3-631-436 AM Antibodies

For the modified ARCHITECT®-hBNP assay (hereinafter referred to as "Arch-BNP") paramagnetic particles were coated with monoclonal antibody ("mAb") 3-631-436 or 3-631-436 affinity matured "AM" mutants. The 3-631-436 Abs binds to an amino acid sequence containing amino acids 13-18 on the hBNP peptide (monoclonal antibodies produced by hybridoma cell line 3-631-436 are described in U.S. patent application Ser. No. 11/135,050, filed on May 25, 2005, the contents of which are herein incorporated by reference). Monoclonal antibodies produced by hybridoma cell line 3-631-436 are also referred interchangeably herein as "monoclonal antibody 3-631-436" and "3-631-436". Additionally, murine hybridoma cell line 3-631-436 was deposited with the A.T.C.C. on Dec. 21, 2004 and assigned A.T.C.C. Accession No. PTA-6476). Monoclonal antibody 3-631-436 or recombinant 3-631-436 AMx antibodies, where x is a number that denotes the affinity matured variant, were coated onto paramagnetic particles (Polymer Laboratories, Amherst, Mass.) using the techniques described in U.S. Pat. No. 6,162,902.

Specifically, EDAC coupling was used (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl)carbodiimide, hydrochloride. EDAC is commercially available from Sigma-Aldrich, St. Louis, Mo.). Particles were washed and overcoated with BSA. These particles were used to capture BNP peptide in the assay during the first ($1^{st}$) incubation with Architect BNP calibrators or specimens.

Antibody 106.3 AM1 (See Examples 1 and 2) was conjugated to acridinium (Abbott Laboratories, Abbott Park, Ill.) and is used in the assay during the second ($2^{nd}$) incubation to detect the particle-bound hBNP peptide. The conjugation occurred by reaction of antibody 106.3 AM1 with an activated acridinium-carboxamide ester.

BNP immunoassays were performed on an ARCHITECT® instrument (this instrument is described in U.S. Pat. No. 5,468,646).

An aliquot containing a calibrator solution was delivered to the same well of the reaction vessel as the microparticles to form a reaction mixture. The calibrator solution contained hBNP full-length peptide. The microparticles coated with the capture antibody in a Tris/BSA diluent were pipetted by the sampling probe into the appropriate wells of the reaction vessel in the sampling center. The reaction mixture was incubated for approximately 184 minutes at a temperature of about 37° C. After the incubation, the reaction mixture was washed with the ARCHITECT® Line Diluent to remove any of the calibrator that was not captured. The ARCHITECT® Line Diluent is commercially available from Abbott Laboratories, Abbott Park, Ill.

The mAb-Acridinium-conjugates at about 100 ng/mL were dispensed into the reaction vessel and incubated for approximately 4 minutes at a temperature of about 37° C. After the incubation, the reaction vessel was washed with the ARCHITECT® Line Diluent to remove the unbound materials.

A solution of hydrogen peroxide and then sodium hydroxide was added to the reaction vessel and the chemiluminescent signal was measured by the chemiluminescent microparticle immunoassay (CMIA) optical assembly of the ARCHITECT® instrument.

Figure 32:
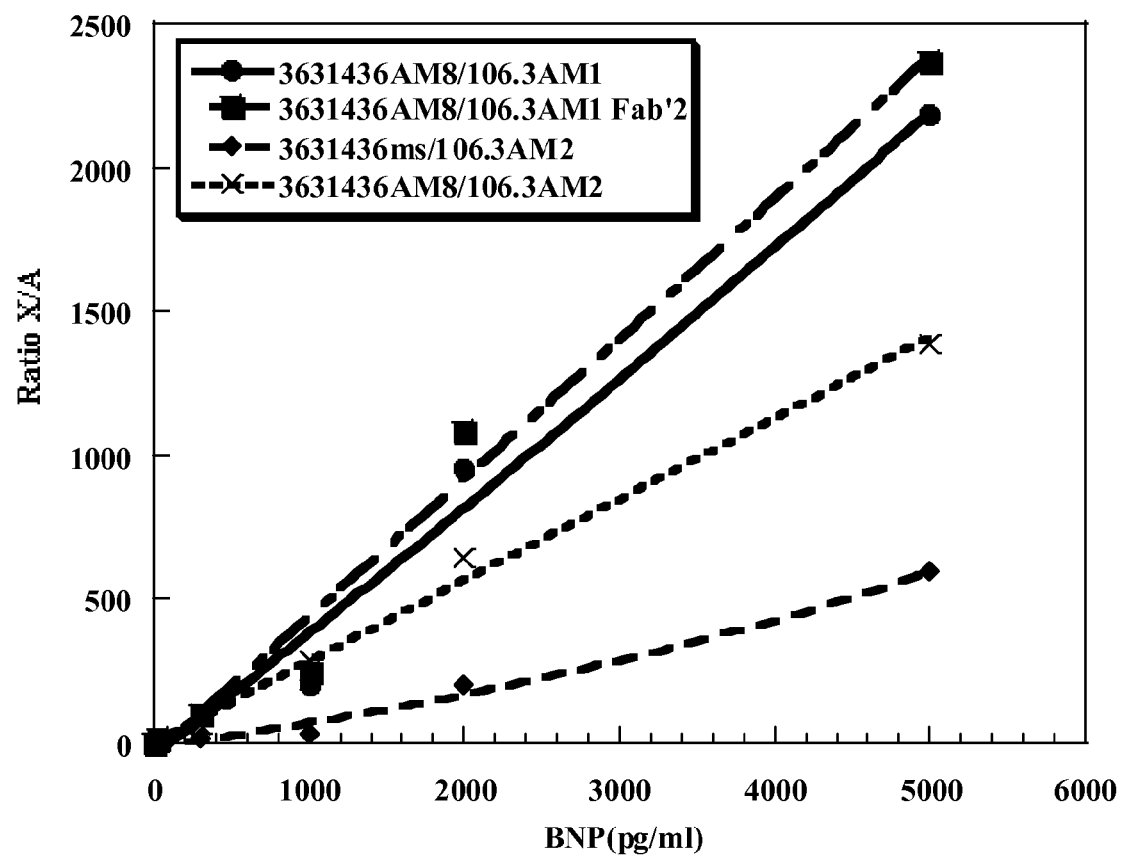
FIG. 32 shows anti-hBNP antibody pair evaluation using paramagnetic microparticles (from Polymer Labs) using antibody 3-631-436 AM8, antibody 106.3 AM1, antibody 106.3 AM1 Fab'2, antibody 106.3 AM2 and 3-631-436 as described in Example 7. Symbols & Abbreviations: circles anti-BNP(3-631-436 AM8) μP/anti-BNP(106.3AM1-Acrydinium); squares, anti-BNP(3-631-436 AM8) μP/anti-BNP (106.3AM1 Fab'2-Acrydinium); diamonds, anti-BNP (ms) μP/anti-BNP(106.3AM2-Acrydinium); "X's", anti-BNP(3-631-436AM8) μP/anti-BNP(106.3AM2-Acrydinium); RLU, Relative Light Units.

The ARCHITECT® system measures the acridinium signals which are typically measured in relative light units (hereinafter "rlu's"). Measurements were made in triplicate. The results shown in Tables 4 and 5 below and in FIG. 32 shows the mean of the triplicate values. Specifically, the results in Table 4 and FIG. 32 are shown in pg/mL BNP calibrator.

In addition, the immunoassays can be used to monitor patients receiving therapeutic doses of hBNP or fragments of hBNP and anti-hBNP treatments.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLE 4

| Microparticle<br>Conjugate | 3631436AM8<br>106.3 AM2 | 3631436 ms<br>106.3AM2 | 3631436AM8<br>106.3AM1 | 3631436AM8<br>106.3 AM1<br>Fab'2 |
|---|---|---|---|---|
| Cal A (0 pg/mL) | 2176 | 1096 | 527 | 634 |
| Cal B (30 pg/mL) | 9321 | 3004 | 7455 | 10305 |
| Cal C (300 pg/mL) | 131587 | 15681 | 47327 | 65486 |
| Cal D (1000 pg/mL) | 631930 | 35461 | 108478 | 159603 |
| Cal E (2000 pg/mL) | 1405322 | 217211 | 500753 | 688275 |
| Cal F (5000 pg/mL) | 3023686 | 652218 | 1152358 | 1502446 |
| Ratio A/A | 1.0 | 1.0 | 1.0 | 1.0 |
| Ratio B/A | 4.3 | 2.7 | 14.1 | 16.3 |
| Ratio C/A | 60.5 | 14.3 | 89.8 | 103.3 |
| Ratio D/A | 290.4 | 32.4 | 205.8 | 251.7 |
| Ratio E/A | 645.8 | 198.2 | 950.2 | 1085.6 |
| Ratio F/A | 1389.6 | 595.1 | 2186.6 | 2369.8 |

SEQUENCE LISTING

<160> NUMBER OF SEQ ID NOS: 169

<210> SEQ ID NO 1
<211> LENGTH: 5745
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

| | | | | | |
|---|---|---|---|---|---|
| acggattaga | agccgccgag | cgggtgacag | ccctccgaag | gaagactctc | ctccgtgcgt | 60 |
| cctcgtcctc | accggtcgcg | ttcctgaaac | gcagatgtgc | ctcgcgccgc | actgctccga | 120 |
| acaataaaga | ttctacaata | ctagctttta | tggttatgaa | gaggaaaaat | tggcagtaac | 180 |
| ctggccccac | aaaccttcaa | atgaacgaat | caaattaaca | accataggat | gataatgcga | 240 |
| ttagtttttt | agccttattt | ctggggtaat | taatcagcga | agcgatgatt | tttgatctat | 300 |
| taacagatat | ataaatgcaa | aaactgcatt | aaccacttta | actaatactt | tcaacatttt | 360 |
| cggtttgtat | tacttcttat | tcaaatgtaa | taaaagtatc | aacaaaaaat | tgttaatata | 420 |
| cctctatact | ttaacgtcaa | ggagaaaaaa | ccccggatcg | gactactagc | agctgtaata | 480 |
| cgactcacta | tagggaatat | taagctaatt | ctacttcata | cattttcaat | taagatgcag | 540 |
| ttacttcgct | gtttttcaat | attttctgtt | attgcttcag | ttttagcaca | ggaactgaca | 600 |
| actatatgcg | agcaaatccc | ctcaccaact | ttagaatcga | cgccgtactc | tttgtcaacg | 660 |
| actactattt | tggccaacgg | gaaggcaatg | caaggagttt | ttgaatatta | caaatcagta | 720 |
| acgtttgtca | gtaattgcgg | ttctcacccc | tcaacaacta | gcaaaggcag | ccccataaac | 780 |
| acacagtatg | tttttaagct | tctgcaggct | agtggtgaga | caaggtgga | gtacgcgccg | 840 |
| gcgttgatgg | ccttgtctgc | tagcatgact | ggtggacagc | aaatgggtcg | gatctgtac | 900 |
| gacgatgacg | ataaggtacc | aggatccagt | gtggtggaat | tcgcggccca | gccggccatg | 960 |
| gcccagatcc | agttggtgca | gtctggacct | gagctgagga | agcctggaga | gacagtcaag | 1020 |
| atctcctgca | agggttctgg | atataccttc | acacactatg | gaataaactg | ggtgaagcag | 1080 |
| actccaagaa | aggatttaaa | gtggatgggc | tggataaaca | cccatactgg | agagccaata | 1140 |
| tatgctgatg | acttcaaggg | acggtttgcc | ttctctttgg | aaacctctgc | caacactgcc | 1200 |
| tatttgcaaa | tcaacaacct | caacaatgga | gacatgggta | catatttctg | tacaagaagt | 1260 |
| caccggtttg | gtttggacta | ctggggtcaa | ggtacctcag | tcaccgtctc | gtcaggtccc | 1320 |
| gccaaggagt | tgacgcccct | gaaggaggcg | aaggtctctg | acaatgtgct | gacccaatct | 1380 |
| ccaccttctt | tggctgtgtc | tctagggcag | agggccacca | tctcctgcaa | ggccagccaa | 1440 |
| agtgttgatt | ataatggtga | tagttatctg | aactggtacc | aacagaagcc | aggacagcca | 1500 |
| cccaaattcc | tcatctatgc | tgcatccaat | ctagaatctg | ggatcccagc | caggtttagt | 1560 |
| ggcagtgggt | ctgggacaga | cttcaacctc | aacatccatc | ctgtggagga | ggaggatgct | 1620 |
| gcaacctatt | actgtcagca | aagtaatgag | gatccattca | cgttcggctc | ggggacaaag | 1680 |
| ttggaaataa | aacgggcggc | cgccctcgag | tctagagggc | ccttcgaagg | taagcctatc | 1740 |
| cctaaccctc | tcctcggtct | cgattctacg | cgtaccggtc | atcatcacca | tcaccattga | 1800 |
| gtttaaaccc | gctgatctga | taacaacagt | gtagatgtaa | caaaatcgac | tttgttccca | 1860 |
| ctgtactttt | agctcgtaca | aaatacaata | tactttcat | ttctccgtaa | caacatgtt | 1920 |
| ttcccatgta | atatccttt | ctattttcg | ttccgttacc | aactttacac | atactttata | 1980 |

```
tagctattca cttctataca ctaaaaaact aagacaattt taattttgct gcctgccata    2040
tttcaatttg ttataaattc ctataattta tcctattagt agctaaaaaa agatgaatgt    2100
gaatcgaatc ctaagagaat tgggcaagtg cacaaacaat acttaaataa atactactca    2160
gtaataacct atttcttagc atttttgacg aaatttgcta ttttgttaga gtcttttaca    2220
ccatttgtct ccacacctcc gcttacatca acaccaataa cgccatttaa tctaagcgca    2280
tcaccaacat tttctggcgt cagtccacca gctaacataa aatgtaagct ctcggggctc    2340
tcttgccttc caacccagtc agaaatcgag ttccaatcca aaagttcacc tgtcccacct    2400
gcttctgaat caaacaaggg aataaacgaa tgaggtttct gtgaagctgc actgagtagt    2460
atgttgcagt cttttggaaa tacgagtctt ttaataactg gcaaaccgag gaactcttgg    2520
tattcttgcc acgactcatc tccgtgcagt tggacgatat caatgccgta atcattgacc    2580
agagccaaaa catcctcctt aggttgatta cgaaacacgc caaccaagta tttcggagtg    2640
cctgaactat ttttatatgc ttttacaaga cttgaaattt tccttgcaat aaccgggtca    2700
attgttctct ttctattggg cacacatata atacccagca agtcagcatc ggaatctaga    2760
gcacattctg cggcctctgt gctctgcaag ccgcaaactt tcaccaatgg accagaacta    2820
cctgtgaaat taataacaga catactccaa gctgcctttg tgtgcttaat cacgtatact    2880
cacgtgctca atagtcacca atgccctccc tcttggccct ctccttttct tttttcgacc    2940
gaatttcttg aagacgaaag ggcctcgtga tacgcctatt tttataggtt aatgtcatga    3000
taataatggt ttcttaggac ggatcgcttg cctgtaactt acgcgcgcct cgtatctttt    3060
aatgatggaa taatttggga atttactctg tgtttattta tttttatgtt ttgtatttgg    3120
attttagaaa gtaaataaag aaggtagaag agttacggaa tgaagaaaaa aaaataaaca    3180
aaggtttaaa aaatttcaac aaaaagcgta ctttacatat atatttatta gacaagaaaa    3240
gcagattaaa tagatataca ttcgattaac gataagtaaa atgtaaaatc acaggatttt    3300
cgtgtgtggt cttctacaca gacaagatga aacaattcgg cattaatacc tgagagcagg    3360
aagagcaaga taaaaggtag tatttgttgg cgatcccccct agagtctttt acatcttcgg    3420
aaaacaaaaa ctatttttc tttaatttct tttttttactt tctatttta atttatatat    3480 ttatattaaa aaatttaaat tataattatt tttatagcac gtgatgaaaa ggacccaggt    3540
ggcacttttc ggggaaatgt gcgcggaacc cctatttgtt tattttttcta aatacattca    3600 aatatgtatc cgctcatgag acaataaccc tgataaatgc ttcaataata ttgaaaaagg    3660
aagagtatga gtattcaaca tttccgtgtc gcccttattc ccttttttgc ggcatttttgc    3720 cttcctgttt ttgctcaccc agaaacgctg gtgaaagtaa aagatgctga agatcagttg    3780
ggtgcacgag tgggttacat cgaactggat ctcaacagcg gtaagatcct tgagagtttt    3840
cgccccgaag aacgtttttcc aatgatgagc acttttaaag ttctgctatg tggcgcggta    3900
ttatcccgtg ttgacgccgg gcaagagcaa ctcggtcgcc gcatacacta ttctcagaat    3960
gacttggttg agtactcacc agtcacagaa aagcatctta cggatggcat gacagtaaga    4020
gaattatgca gtgctgccat aaccatgagt gataacactg cggccaactt acttctgaca    4080
acgatcggag gaccgaagga gctaaccgct ttttttgcaca acatggggga tcatgtaact    4140
cgccttgatc gttgggaacc ggagctgaat gaagccatac caaacgacga gcgtgacacc    4200
acgatgcctg tagcaatggc aacaacgttg cgcaaactat taactggcga actacttact    4260
ctagcttccc ggcaacaatt aatagactgg atggaggcgg ataaagttgc aggaccactt    4320
ctgcgctcgg cccttccggc tggctggttt attgctgata aatctggagc cggtgagcgt    4380
```

```
gggtctcgcg gtatcattgc agcactgggg ccagatggta agccctcccg tatcgtagtt    4440
atctacacga cgggcagtca ggcaactatg gatgaacgaa atagacagat cgctgagata    4500
ggtgcctcac tgattaagca ttggtaactg tcagaccaag tttactcata tatactttag    4560
attgatttaa aacttcattt ttaatttaaa aggatctagg tgaagatcct ttttgataat    4620
ctcatgacca aaatccctta acgtgagttt tcgttccact gagcgtcaga ccccgtagaa    4680
aagatcaaag gatcttcttg agatcctttt tttctgcgcg taatctgctg cttgcaaaca    4740 aaaaaccac cgctaccagc ggtggtttgt ttgccggatc aagagctacc aactctttt    4800 ccgaaggtaa ctggcttcag cagagcgcag ataccaaata ctgtccttct agtgtagccg    4860
tagttaggcc accacttcaa gaactctgta gcaccgccta catacctcgc tctgctaatc    4920
ctgttaccag tggctgctgc cagtggcgat aagtcgtgtc ttaccgggtt ggactcaaga    4980
cgatagttac cggataaggc gcagcggtcg ggctgaacgg ggggttcgtg cacacagccc    5040
agcttggagc gaacgaccta caccgaactg agatacctac agcgtgagca ttgagaaagc    5100
gccacgcttc ccgaagggag aaaggcggac aggtatccgg taagcggcag ggtcggaaca    5160
ggagagcgca cgagggagct tccagggggg aacgcctggt atctttatag tcctgtcggg    5220
tttcgccacc tctgacttga gcgtcgattt ttgtgatgct cgtcaggggg gcggagccta    5280
tggaaaaacg ccagcaacgc ggccttttta cggttcctgg ccttttgctg gccttttgct    5340
cacatgttct ttcctgcgtt atcccctgat tctgtggata accgtattac cgcctttgag    5400
tgagctgata ccgctcgccg cagccgaacg accgagcgca gcgagtcagt gagcgaggaa    5460
gcggaagagc gcccaatacg caaaccgcct ctccccgcgc gttggccgat tcattaatgc    5520
agctggcacg acaggtttcc cgactggaaa gcgggcagtg agcgcaacgc aattaatgtg    5580
agttacctca ctcattaggc accccaggct ttacacttta tgcttccggc tcctatgttg    5640
tgtggaattg tgagcggata acaatttcac acaggaaaca gctatgacca tgattacgcc    5700
aagctcggaa ttaaccctca ctaaagggaa caaaagctgg ctagt              5745
```

<210> SEQ ID NO 2
<211> LENGTH: 837
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gtctaggtca accacgtcag acctggactc gactccttcg gacctctctg tcagttctag     60
aggacgttcc caagacctat atggaagtgt gtgataccct atttgaccca cttcgtctga    120
ggttctttcc taaatttcac ctacccgacc tatttgtggg tatgacctct cggttatata    180
cgactactga agttccctgc caaacggaag agaaacctt ggagacggtt gtgacggata    240
aacgtttagt tgttggagtt gttacctctg tacccatgta taaagacatg ttcttcagtg    300
gccaaaccaa acctgatgac cccagttcca tggagtcagt ggcagagcag tccagggcgg    360
ttcctcaact gcgggactt cctccgcttc cagagactgt tacacgactg ggttagaggt    420
ggaagaaacc gacacagaga tcccgtctcc cggtggtaga ggacgttccg gtcggtttca    480
caactaatat taccactatc aatagacttg accatggttg tcttcggtcc tgtcggtggg    540
tttaaggagt agatacgacg taggttagat cttagaccct agggtcggtc caaatcaccg    600
tcacccagac cctgtctgaa gttggagttg taggtaggac acctcctcct cctacgacgt    660
```

```
tggataatga cagtcgtttc attactccta ggtaagtgca agccgagccc ctgtttcaac    720
ctttattttg cccgccggcg ggagctcaga tctcccggga agcttccatt cggataggga    780
ttgggagagg agccagagct aagatgcgca tggccagtag tagtggtagt ggtaact       837
```

<210> SEQ ID NO 3
<211> LENGTH: 276
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 3

```
Gln Leu Val Gln Ser Gly Pro Glu Leu Arg Lys Pro Gly Glu Thr Val
1               5                   10                  15

Lys Ile Ser Cys Lys Gly Ser Gly Tyr Thr Phe Thr His Tyr Gly Ile
            20                  25                  30

Asn Trp Val Lys Gln Thr Pro Arg Lys Asp Leu Lys Trp Met Gly Trp
        35                  40                  45

Ile Asn Thr His Thr Gly Glu Pro Ile Tyr Ala Asp Asp Phe Lys Gly
    50                  55                  60

Arg Phe Ala Phe Ser Leu Glu Thr Ser Ala Asn Thr Ala Tyr Leu Gln
65                  70                  75                  80

Ile Asn Asn Leu Asn Asn Gly Asp Met Gly Thr Tyr Phe Cys Thr Arg
                85                  90                  95

Ser His Arg Phe Gly Leu Asp Tyr Trp Gly Gln Gly Thr Ser Val Thr
            100                 105                 110

Val Ser Ser Gly Pro Ala Lys Glu Leu Thr Pro Leu Lys Glu Ala Lys
        115                 120                 125

Val Ser Asp Asn Val Leu Thr Gln Ser Pro Pro Ser Leu Ala Val Ser
    130                 135                 140

Leu Gly Gln Arg Ala Thr Ile Ser Cys Lys Ala Ser Gln Ser Val Asp
145                 150                 155                 160

Tyr Asn Gly Asp Ser Tyr Leu Asn Trp Tyr Gln Gln Lys Pro Gly Gln
                165                 170                 175

Pro Pro Lys Phe Leu Ile Tyr Ala Ala Ser Asn Leu Glu Ser Gly Ile
            180                 185                 190

Pro Ala Arg Phe Ser Gly Ser Gly Ser Gly Thr Asp Phe Asn Leu Asn
        195                 200                 205

Ile His Pro Val Glu Glu Glu Asp Ala Ala Thr Tyr Tyr Cys Gln Gln
    210                 215                 220

Ser Asn Glu Asp Pro Phe Thr Phe Gly Ser Gly Thr Lys Leu Glu Ile
225                 230                 235                 240

Lys Arg Ala Ala Ala Leu Glu Ser Arg Gly Pro Phe Glu Gly Lys Pro
                245                 250                 255

Ile Pro Asn Pro Leu Leu Gly Leu Asp Ser Thr Arg Thr Gly His His
            260                 265                 270

His His His His
        275
```

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
   peptide -continued

```
<400> SEQUENCE: 4

Gly Pro Ala Lys Glu Leu Thr Pro Leu Lys Glu Ala Lys Val Ser
1               5                   10                  15

<210> SEQ ID NO 5
<211> LENGTH: 32
<212> TYPE: PRT
<213> ORGANISM: Homo sapiens

<400> SEQUENCE: 5

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Thr Phe Thr His Tyr Gly Ile Asn
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ile Asn Thr His Thr Gly Glu Pro Ile Tyr Ala Asp Asp Phe Lys
1               5                   10                  15

Gly

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser His Arg Phe Gly Leu Asp Tyr
1               5

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Ala Ser Gln Ser Val Asp Tyr Asn Gly Asp Ser Tyr Leu Asn
1               5                   10                  15
```

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Ala Ser Asn Leu Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gln Ser Asn Glu Asp Pro Phe Thr
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (10)..(10)
<223> OTHER INFORMATION: Ile or Tyr

<400> SEQUENCE: 12

Trp Ile Asn Thr His Thr Gly Glu Xaa Xaa Tyr Ala Asp Asp Phe Lys
1               5                   10                  15

Gly

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Ala, Asn, Gln, Tyr, Thr or Arg
<220> FEATURE:
<221> NAME/KEY: MOD_RES
<222> LOCATION: (4)..(4)
<223> OTHER INFORMATION: Gln, Tyr, Trp, Ala or Phe
<220> FEATURE:
<221> NAME/KEY: MOD_RES
<222> LOCATION: (5)..(5)
<223> OTHER INFORMATION: Ser, Gly, Pro, Ala or Asp

<400> SEQUENCE: 13

Lys Ala Xaa Xaa Xaa Val Asp Tyr Asn Gly Asp Ser Tyr Leu Asn
1               5                   10                  15
```

```
<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn or Cys
<220> FEATURE:
<221> NAME/KEY: MOD_RES
<222> LOCATION: (5)..(5)
<223> OTHER INFORMATION: Leu, Gly or Ala
<220> FEATURE:
<221> NAME/KEY: MOD_RES
<222> LOCATION: (6)..(6)
<223> OTHER INFORMATION: Glu, Trp or Pro

<400> SEQUENCE: 14

Ala Ala Ser Xaa Xaa Xaa Ser
1               5

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ile Asn Thr His Thr Gly Glu Ala Tyr Tyr Ala Asp Asp Phe Lys
1               5                   10                  15

Gly

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Ala Gln Phe Ala Val Asp Tyr Asn Gly Asp Ser Tyr Leu Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ala Tyr Ala Ser Val Asp Tyr Asn Gly Asp Ser Tyr Leu Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Lys Ala Gln Trp Gly Val Asp Tyr Asn Gly Asp Ser Tyr Leu Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Thr Trp Asp Val Asp Tyr Asn Gly Asp Ser Tyr Leu Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ala Arg Trp Pro Val Asp Tyr Asn Gly Asp Ser Tyr Leu Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ala Ala Tyr Gly Val Asp Tyr Asn Gly Asp Ser Tyr Leu Asn
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Asn Trp Pro Val Asp Tyr Asn Gly Asp Ser Tyr Leu Asn
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser Cys Gly Trp Ser
1               5

<210> SEQ ID NO 24
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 24

Ala Ala Ser Cys Ala Pro Ser
1               5

<210> SEQ ID NO 25
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 25
aacctcaaca atggagacat gggtacatat ttctgtacaa gannsnnsnn stttggtttg       60
gactactggg gtcaaggtac ctcagtcacc gtctcgtcag gtccc                     105

<210> SEQ ID NO 26
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 26
aacctcaaca atggagacat gggtacatat ttctgtacaa gaagtnnsnn snnsggtttg       60
gactactggg gtcaaggtac ctcagtcacc gtctcgtcag gtccc                     105

<210> SEQ ID NO 27
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
```

```
<220> FEATURE:
<221> NAME/KEY: modified_base
<222> LOCATION: (55)..(56)
<223> OTHER INFORMATION: a, c, t or g

<400> SEQUENCE: 27
aacctcaaca atggagacat gggtacatat ttctgtacaa gaagtcacnn snnsnnsttg      60
gactactggg gtcaaggtac ctcagtcacc gtctcgtcag gtccc                    105

<210> SEQ ID NO 28
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 28
aacctcaaca atggagacat gggtacatat ttctgtacaa gaagtcaccg gnnsnnsnns      60
gactactggg gtcaaggtac ctcagtcacc gtctcgtcag gtccc                    105

<210> SEQ ID NO 29
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 29
aacctcaaca atggagacat gggtacatat ttctgtacaa gaagtcaccg gtttnnsnns      60
nnstactggg gtcaaggtac ctcagtcacc gtctcgtcag gtccc                    105

<210> SEQ ID NO 30
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
```

-continued

```
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 30
gacatgggta catatttctg tacaagaagt caccggtttg gtnnsnnsnn stggggtcaa      60
ggtacctcag tcaccgtctc gtcaggtccc gccgccaag                            99

<210> SEQ ID NO 31
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 31
tgggtgaagc agactccaag aaaggattta aagtggatgg gcnnsnnsnn sacccatact      60
ggagagccaa tatatgctga tgacttcaag ggacggtttg ccttc                     105

<210> SEQ ID NO 32
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 32
tgggtgaagc agactccaag aaaggattta aagtggatgg gctggnnsnn snnscatact     60
ggagagccaa tatatgctga tgacttcaag ggacggtttg ccttc                    105

<210> SEQ ID NO 33
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 33
tgggtgaagc agactccaag aaaggattta aagtggatgg gctggatann snnsnnsact    60
ggagagccaa tatatgctga tgacttcaag ggacggtttg ccttc                  105

<210> SEQ ID NO 34
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 34
tgggtgaagc agactccaag aaaggattta aagtggatgg gctggataaa cnnsnnsnns    60
ggagagccaa tatatgctga tgacttcaag ggacggtttg ccttc                  105

<210> SEQ ID NO 35
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 35
tgggtgaagc agactccaag aaaggattta aagtggatgg gctggataaa caccnnsnns    60
nnsgagccaa tatatgctga tgacttcaag ggacggtttg ccttc                  105

<210> SEQ ID NO 36
<211> LENGTH: 105
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 36
ccaagaaagg atttaaagtg gatgggctgg ataaacaccc atnnsnnsnn sccaatatat    60
gctgatgact tcaagggacg gtttgccttc tctttggaaa cctct                  105

<210> SEQ ID NO 37
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 37
ccaagaaagg atttaaagtg gatgggctgg ataaacaccc atactnnsnn snnsatatat    60
gctgatgact tcaagggacg gtttgccttc tctttggaaa cctct                  105

<210> SEQ ID NO 38
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 38
ccaagaaagg atttaaagtg gatgggctgg ataaacaccc atactggann snnsnnstat    60
gctgatgact tcaagggacg gtttgccttc tctttggaaa cctct                  105
```

```
<210> SEQ ID NO 39
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 39
ccaagaaagg atttaaagtg gatgggctgg ataaacaccc atactggaga gnnsnnsnns      60
gctgatgact tcaagggacg gtttgccttc tctttggaaa cctct                    105

<210> SEQ ID NO 40
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 40
ccaagaaagg atttaaagtg gatgggctgg ataaacaccc atactggaga gccannsnns      60
nnsgatgact tcaagggacg gtttgccttc tctttggaaa cctct                    105

<210> SEQ ID NO 41
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 41
aagtggatgg gctggataaa cacccatact ggagagccaa tannsnnsnn sgacttcaag      60
ggacggtttg ccttctcttt ggaaacctct gccaacactg cctat                    105
```

```
<210> SEQ ID NO 42
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 42
aagtggatgg gctggataaa cacccatact ggagagccaa tatatnnsnn snnsttcaag      60
ggacggtttg ccttctcttt ggaaacctct gccaacactg cctat                    105

<210> SEQ ID NO 43
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 43
aagtggatgg gctggataaa cacccatact ggagagccaa tatatgctnn snnsnnsaag      60
ggacggtttg ccttctcttt ggaaacctct gccaacactg cctat                    105

<210> SEQ ID NO 44
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 44
aagtggatgg gctggataaa cacccatact ggagagccaa tatatgctga tnnsnnsnns      60
ggacggtttg ccttctcttt ggaaacctct gccaacactg cctat                    105
```

```
<210> SEQ ID NO 45
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 45
aagtggatgg gctggataaa cacccatact ggagagccaa tatatgctga tgacnnsnns      60
nnscggtttg ccttctcttt ggaaacctct gccaacactg cctat                    105

<210> SEQ ID NO 46
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 46
aggaagcctg gagagacagt caagatctcc tgcaagggtt ctnnsnnsnn sttcacacac      60
tatggaataa actgggtgaa gcagactcca agaaaggatt taaag                    105

<210> SEQ ID NO 47
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 47
aggaagcctg gagagacagt caagatctcc tgcaagggtt ctggannsnn snnsacacac      60
tatggaataa actgggtgaa gcagactcca agaaaggatt taaag                    105
```

```
<210> SEQ ID NO 48
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 48
aggaagcctg gagagacagt caagatctcc tgcaagggtt ctggatatnn snnsnnscac      60
tatggaataa actgggtgaa gcagactcca agaaaggatt taaag                    105

<210> SEQ ID NO 49
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 49
aggaagcctg gagagacagt caagatctcc tgcaagggtt ctggatatac cnnsnnsnns      60
tatggaataa actgggtgaa gcagactcca agaaaggatt taaag                    105

<210> SEQ ID NO 50
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 50
aggaagcctg gagagacagt caagatctcc tgcaagggtt ctggatatac cttcnnsnns      60
nnsggaataa actgggtgaa gcagactcca agaaaggatt taaag                    105
```

```
<210> SEQ ID NO 51
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 51
acagtcaaga tctcctgcaa gggttctgga tataccttca cannsnnsnn sataaactgg    60
gtgaagcaga ctccaagaaa ggatttaaag tggatgggc                          99

<210> SEQ ID NO 52
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 52
acagtcaaga tctcctgcaa gggttctgga tataccttca cacacnnsnn snnsaactgg    60
gtgaagcaga ctccaagaaa ggatttaaag tggatgggc                          99

<210> SEQ ID NO 53
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 53
acagtcaaga tctcctgcaa gggttctgga tataccttca cacactatnn snnsnnstgg    60
gtgaagcaga ctccaagaaa ggatttaaag tggatgggc                          99
```

```
<210> SEQ ID NO 54
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 54
ttggctgtgt ctctagggca gagggccacc atctcctgcn nsnnsnnsca aagtgttgat      60
tataatggtg atagttatct gaactggtac caacagaag                            99

<210> SEQ ID NO 55
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 55
ttggctgtgt ctctagggca gagggccacc atctcctgca agnnsnnsnn sagtgttgat      60
tataatggtg atagttatct gaactggtac caacagaag                            99

<210> SEQ ID NO 56
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 56
ttggctgtgt ctctagggca gagggccacc atctcctgca aggccnnsnn snnsgttgat      60
tataatggtg atagttatct gaactggtac caacagaag                            99
```

```
<210> SEQ ID NO 57
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 57
ttggctgtgt ctctagggca gagggccacc atctcctgca aggccagcnn snnsnnsgat      60
tataatggtg atagttatct gaactggtac caacagaag                            99

<210> SEQ ID NO 58
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 58
ttggctgtgt ctctagggca gagggccacc atctcctgca aggccagcca annsnnsnns      60
tataatggtg atagttatct gaactggtac caacagaag                            99

<210> SEQ ID NO 59
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 59
gggcagaggg ccaccatctc ctgcaaggcc agccaaagtn nsnnsnnsaa tggtgatagt      60
tatctgaact ggtaccaaca gaagccagga cagccaccc                            99
```

```
<210> SEQ ID NO 60
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 60
gggcagaggg ccaccatctc ctgcaaggcc agccaaagtg ttnnsnnsnn sggtgatagt      60
tatctgaact ggtaccaaca gaagccagga cagccaccc                            99

<210> SEQ ID NO 61
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 61
gggcagaggg ccaccatctc ctgcaaggcc agccaaagtg ttgatnnsnn snnsgatagt      60
tatctgaact ggtaccaaca gaagccagga cagccaccc                            99

<210> SEQ ID NO 62
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 62
gggcagaggg ccaccatctc ctgcaaggcc agccaaagtg ttgattatnn snnsnnsagt      60
tatctgaact ggtaccaaca gaagccagga cagccaccc                            99
```

```
<210> SEQ ID NO 63
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 63
gggcagaggg ccaccatctc ctgcaaggcc agccaaagtg ttgattataa tnnsnnsnns      60
tatctgaact ggtaccaaca gaagccagga cagccaccc                             99

<210> SEQ ID NO 64
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 64
atctcctgca aggccagcca aagtgttgat tataatggtn nsnnsnnsct gaactggtac      60
caacagaagc caggacagcc acccaaattc ctc                                   93

<210> SEQ ID NO 65
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 65
atctcctgca aggccagcca aagtgttgat tataatggtg atnnsnnsnn saactggtac      60
caacagaagc caggacagcc acccaaattc ctc                                   93
```

```
<210> SEQ ID NO 66
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 66
atctcctgca aggccagcca aagtgttgat tataatggtg atagtnnsnn snnstggtac      60
caacagaagc caggacagcc acccaaattc ctc                                  93

<210> SEQ ID NO 67
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 67
caacagaagc caggacagcc acccaaattc ctcatctatn nsnnsnnsaa tctagaatct      60
gggatcccag ccaggtttag tggcagtggg tctgggaca                            99

<210> SEQ ID NO 68
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 68
caacagaagc caggacagcc acccaaattc ctcatctatg ctnnsnnsnn sctagaatct      60
gggatcccag ccaggtttag tggcagtggg tctgggaca                            99
```

```
<210> SEQ ID NO 69
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 69
caacagaagc caggacagcc acccaaattc ctcatctatg ctgcannsnn snnsgaatct      60
gggatcccag ccaggtttag tggcagtggg tctgggaca                             99

<210> SEQ ID NO 70
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 70
caacagaagc caggacagcc acccaaattc ctcatctatg ctgcatccnn snnsnnstct      60
gggatcccag ccaggtttag tggcagtggg tctgggaca                             99

<210> SEQ ID NO 71
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 71
caacagaagc caggacagcc acccaaattc ctcatctatg ctgcatccaa tnnsnnsnns      60
gggatcccag ccaggtttag tggcagtggg tctgggaca                             99
```

```
<210> SEQ ID NO 72
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 72
catcctgtgg aggaggagga tgctgcaacc tattactgtn nsnnsnnsaa tgaggatcca    60
ttcacgttcg gctcggggac aaagttggaa ataaaacgg                           99

<210> SEQ ID NO 73
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 73
catcctgtgg aggaggagga tgctgcaacc tattactgtc agnnsnnsnn sgaggatcca    60
ttcacgttcg gctcggggac aaagttggaa ataaaacgg                           99

<210> SEQ ID NO 74
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 74
catcctgtgg aggaggagga tgctgcaacc tattactgtc agcaannsnn snnsgatcca    60
ttcacgttcg gctcggggac aaagttggaa ataaaacgg                           99
```

```
<210> SEQ ID NO 75
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 75
catcctgtgg aggaggagga tgctgcaacc tattactgtc agcaaagtnn snnsnnscca      60
ttcacgttcg gctcggggac aaagttggaa ataaaacgg                            99

<210> SEQ ID NO 76
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 76
catcctgtgg aggaggagga tgctgcaacc tattactgtc agcaaagtaa tnnsnnsnns      60
ttcacgttcg gctcggggac aaagttggaa ataaaacgg                            99

<210> SEQ ID NO 77
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 77
gaggatgctg caacctatta ctgtcagcaa agtaatgagn nsnnsnnsac gttcggctcg      60
gggacaaagt tggaaataaa acgggcggcc gcc                                  93
```

```
<210> SEQ ID NO 78
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 78
gaggatgctg caacctatta ctgtcagcaa agtaatgagg atnnsnnsnn sttcggctcg     60
gggacaaagt tggaaataaa acgggcggcc gcc                                 93

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tagcatgact ggtggacagc                                                20

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgtagaatcg agaccgag                                                  18

<210> SEQ ID NO 81
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tggataaaca cccatactgg agaggcgtac tatgctgatg acttcaaggg a              51

<210> SEQ ID NO 82
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
aaggccaact ggcccgttga ttataatggt gatagttatc tgaac                    45
```

```
<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Val, Gln, His, Trp or Arg
<220> FEATURE:
<221> NAME/KEY: MOD_RES
<222> LOCATION: (2)..(2)
<223> OTHER INFORMATION: Val, Asn, Thr or Met
<220> FEATURE:
<221> NAME/KEY: MOD_RES
<222> LOCATION: (3)..(3)
<223> OTHER INFORMATION: Ser, Thr, Asn or Asp
<220> FEATURE:
<221> NAME/KEY: MOD_RES
<222> LOCATION: (4)..(4)
<223> OTHER INFORMATION: Lys or Ile
<220> FEATURE:
<223> OTHER INFORMATION: See specification as filed for detailed
      description of substitutions and preferred embodiments

<400> SEQUENCE: 83

Xaa Xaa Xaa Xaa Leu Glu Ser
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Tyr Thr Phe Thr Ser Tyr Trp Met Asn
1               5                   10

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ile Asp Pro Tyr Asp Ser Glu Thr His Tyr Asn Gln Lys Phe Lys
1               5                   10                  15

Asp

<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Gly Tyr
1
```

```
<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys Ser Ser Gln Ser Leu Leu Asp Ser Asp Gly Lys Thr Tyr Leu Asn
1               5                   10                  15

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Val Ser Lys Leu Glu Ser
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Gln Ala Thr His Phe Pro
1               5

<210> SEQ ID NO 90
<211> LENGTH: 5733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
acggattaga agccgccgag cgggtgacag ccctccgaag gaagactctc ctccgtgcgt    60
cctcgtcctc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcatt aaccacttta actaatactt tcaacatttt   360
cggtttgtat tacttcttat tcaaatgtaa taaaagtatc aacaaaaaat tgttaatata   420
cctctatact ttaacgtcaa ggagaaaaaa ccccggatcg gactactagc agctgtaata   480
cgactcacta tagggaatat taagctaatt ctacttcata cattttcaat taagatgcag   540
ttacttcgct gttttcaat attttctgtt attgcttcag ttttagcaca ggaactgaca   600
actatatgcg agcaaatccc ctcaccaact ttagaatcga cgccgtactc tttgtcaacg   660
actactattt tggccaacgg gaaggcaatg caaggagttt ttgaatatta caatcagta    720 acgtttgtca gtaattgcgg ttctcacccc tcaacaacta gcaaaggcag ccccataaac   780
acacagtatg tttttaagct tctgcaggct agtggtgaga acaaggtgga gtacgcgccg   840
```

```
gcgttgatgg ccttgtctgc tagcatgact ggtggacagc aaatgggtcg ggatctgtac    900
gacgatgacg ataaggtacc aggatccagt gtggtggaat tcgcggccca gccggccatg    960
gcccaggtcc aactgcagca gcctggggct gagctggtga ggcctggggc ttcagtgaag   1020
ctgtcctgca aggcttctgg ctacacgttc accagttact ggatgaactg ggttaaacag   1080
aggcctgagc aaggccttga gtggattgga aggattgatc cttacgatag tgaaactcac   1140
tacaatcaaa agttcaagga caaggccatt ttgactgtag acaaatcctc cagcacagcc   1200
ttcgtgcaac tcaccagcct gacatctgag gactctgcgg tctattattg cgtctctgat   1260
ggttactggg gcgcagggac cacggtcacc gtctcctcag gtcccgccaa ggagttgacg   1320
cccctgaagg aggcgaaggt ctctgatgtt gttatgactc agacaccact cactttgtcg   1380
gttaccactg gacaaccagc ttccatctct tgcaagtcaa gtcagagcct cttagatagt   1440
gatggaaaaa cctatttaaa ttggttattc cagaggccag gcgagtctcc aaagctccta   1500
atctatgtgg tgtctaaact ggagtctgga gtccctgaca ggttcactgg cagtggatca   1560
gggacagatt tcacactgaa aatcagcaga gtggaggctg aggatttggg agtttattac   1620
tgcttgcaag ctacacattt tccgtggacg ttcggtggag gcaccaagct ggaaatcaaa   1680
cgggcggccg ccctcgagtc tagagggccc ttcgaaggta agcctatccc taaccctctc   1740
ctcggtctcg attctacgcg taccggtcat catcaccatc accattgagt ttaaacccgc   1800
tgatctgata caacagtgt agatgtaaca aaatcgactt tgttcccact gtacttttag   1860
ctcgtacaaa atacaatata cttttcattt ctccgtaaac aacatgtttt cccatgtaat   1920
atccttttct attttcgtt ccgttaccaa ctttacacat actttatata gctattcact   1980
tctatacact aaaaaactaa gacaattta atttttgctgc ctgccatatt tcaatttgtt   2040
ataaattcct ataatttatc ctattagtag ctaaaaaaag atgaatgtga atcgaatcct   2100
aagagaattg ggcaagtgca caaacaatac ttaaataaat actactcagt aataacctat   2160
ttcttagcat ttttgacgaa atttgctatt ttgttagagt cttttacacc atttgtctcc   2220
acacctccgc ttcatcaac accaataacc ccattaatc taagcgcatc accaacattt   2280
tctggcgtca gtccaccagc taacataaaa tgtaagctct cggggctctc ttgccttcca   2340
acccagtcag aaatcgagtt ccaatccaaa agttcacctg tcccacctgc ttctgaatca   2400
aacaagggaa taaacgaatg aggtttctgt gaagctgcac tgagtagtat gttgcagtct   2460
tttggaaata cgagtctttt aataactggc aaaccgagga actcttggta ttcttgccac   2520
gactcatctc cgtgcagttg gacgatatca atgccgtaat cattgaccag agccaaaaca   2580
tcctccttag gttgattacg aaacacgcca accaagtatt tcggagtgcc tgaactattt   2640
ttatatgctt ttacaagact tgaaattttc cttgcaataa ccgggtcaat tgttctcttt   2700
ctattgggca cacatataat acccagcaag tcagcatcgg aatctagagc acattctgcg   2760
gcctctgtgc tctgcaagcc gcaaactttc accaatggac cagaactacc tgtgaaatta   2820
ataacagaca tactccaagc tgcctttgtg tgcttaatca cgtatactca cgtgctcaat   2880
agtcaccaat gccctccctc ttggccctct ccttttcttt tttcgaccga atttcttgaa   2940
gacgaaaggg cctcgtgata cgcctatttt tataggttaa tgtcatgata ataatggttt   3000
cttaggacgg atcgcttgcc tgtaacttac acgcgcctcg tatcttttaa tgatggaata   3060
atttgggaat ttactctgtg tttatttatt tttatgtttt gtatttggat tttagaaagt   3120
aaataaagaa ggtagaagag ttacggaatg aagaaaaaaa ataaacaaa ggtttaaaaa   3180 atttcaacaa aaagcgtact ttacatatat atttattaga caagaaaagc agattaaata   3240
```

```
gatatacatt cgattaacga taagtaaaat gtaaaatcac aggattttcg tgtgtggtct    3300
tctacacaga caagatgaaa caattcggca ttaatacctg agagcaggaa gagcaagata    3360
aaaggtagta tttgttggcg atcccccta g agtcttttac atcttcggaa aacaaaaact   3420
atttttt ctt taatttcttt ttttactttc tattttta at ttatatattt atattaaaaa  3480
atttaaatta taattatttt tatagcacgt gatgaaaagg acccaggtgg cactttt cgg   3540
ggaaatgtgc gcggaacccc tatttgttta tttttctaaa tacattcaaa tatgtatccg    3600
ctcatgagac aataaccctg ataaatgctt caataatatt gaaaaggaa gagtatgagt     3660
attcaacatt tccgtgtcgc ccttattccc ttttttgcgg cattttgcct tcctgttttt    3720
gctcacccag aaacgctggt gaaagtaaaa gatgctgaag atcagttggg tgcacgagtg    3780
ggttacatcg aactggatct caacagcggt aagatcct tg agttttt cg ccccgaagaa    3840
cgttttccaa tgatgagcac ttttaaagtt ctgctatgtg gcgcggtatt atcccgtgtt    3900
gacgccgggc aagagcaact cggtcgccgc atacactatt ctcagaatga cttggttgag    3960
tactcaccag tcacagaaaa gcatcttacg gatggcatga cagtaagaga attatgcagt    4020
gctgccataa ccatgagtga taacactgcg gccaacttac ttctgacaac gatcggagga    4080
ccgaaggagc taaccgcttt tttgcacaac atgggggatc atgtaactcg ccttgatcgt    4140
tgggaaccgg agctgaatga agccatacca aacgacgagc gtgacaccac gatgcctgta    4200
gcaatggcaa caacgttgcg caaactatta actggcgaac tacttactct agcttcccgg    4260
caacaattaa tagactggat ggaggcggat aaagttgcag gaccacttct gcgctcggcc    4320
cttccggctg gctggtttat tgctgataaa tctggagccg gtgagcgtgg gtctcgcggt    4380
atcattgcag cactggggcc agatggtaag ccctcccgta tcgtagttat ctacacgacg    4440
ggcagtcagg caactatgga tgaacgaaat agacagatcg ctgagatagg tgcctcactg    4500
attaagcatt ggtaactgtc agaccaagtt tactcatata tactttagat tgatttaaaa    4560
cttcattttt aatttaaaag gatctaggtg aagatccttt ttgataatct catgaccaaa    4620
atcccttaac gtgagttttc gttccactga gcgtcagacc ccgtagaaaa gatcaaagga    4680
tcttcttgag atcctttttt tctgcgcgta atctgctgct tgcaaacaaa aaaaccaccg    4740
ctaccagcgg tggtttgttt gccggatcaa gagctaccaa ctctttttcc gaaggtaact    4800
ggcttcagca gagcgcagat accaaatact gtccttctag tgtagccgta gttaggccac    4860
cacttcaaga actctgtagc accgcctaca tacctcgctc tgctaatcct gttaccagtg    4920
gctgctgcca gtggcgataa gtcgtgtctt accgggttgg actcaagacg atagttaccg    4980
gataaggcgc agcggtcggg ctgaacgggg ggttcgtgca cacagcccag cttggagcga    5040
acgacctaca ccgaactgag atacctacag cgtgagcatt gagaaagcgc cacgcttccc    5100
gaagggagaa aggcggacag gtatccggta agcggcaggg tcggaacagg agagcgcacg    5160
agggagcttc caggggggaa cgcctggtat ctttatagtc ctgtcgggtt tcgccacctc    5220
tgacttgagc gtcgattttt gtgatgctcg tcagggggc gagcctatg gaaaaacgcc     5280
agcaacgcgg cctttttacg gttcctggcc ttttgctggc cttttgctca catgttcttt    5340
cctgcgttat cccctgattc tgtggataac cgtattaccg cctttgagtg agctgatacc    5400
gctcgccgca gccgaacgac cgagcgcagc gagtcagtga gcgaggaagc ggaagagcgc    5460
ccaatacgca aaccgcctct ccccgcgcgt tggccgattc attaatgcag ctggcacgac    5520
aggtttcccg actggaaagc gggcagtgag cgcaacgcaa ttaatgtgag ttacctcact    5580
cattaggcac cccaggcttt acactttatg cttccggctc ctatgttgtg tggaattgtg    5640
```

```
agcggataac aatttcacac aggaaacagc tatgaccatg attacgccaa gctcggaatt    5700
aaccctcact aaagggaaca aaagctggct agt                                 5733
```

<210> SEQ ID NO 91
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Gln Val Gln Leu Gln Gln Pro Gly Ala Glu Leu Val Arg Pro Gly Ala
1               5                  10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Glu Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Thr Ala Phe
65                  70                  75                  80

Val Gln Leu Thr Ser Leu Thr Ser Glu Asp Ser Ala Val Tyr Tyr Cys
                85                  90                  95

Val Ser Asp Gly Tyr Trp Gly Ala Gly Thr Thr Val Thr Val Ser Ser
            100                 105                 110

Gly Pro Ala Lys Glu Leu Thr Pro Leu Lys Glu Ala Lys Val Ser Asp
        115                 120                 125

Val Val Met Thr Gln Thr Pro Leu Thr Leu Ser Val Thr Thr Gly Gln
    130                 135                 140

Pro Ala Ser Ile Ser Cys Lys Ser Ser Gln Ser Leu Leu Asp Ser Asp
145                 150                 155                 160

Gly Lys Thr Tyr Leu Asn Trp Leu Phe Gln Arg Pro Gly Glu Ser Pro
                165                 170                 175

Lys Leu Leu Ile Tyr Val Val Ser Lys Leu Glu Ser Gly Val Pro Asp
            180                 185                 190

Arg Phe Thr Gly Ser Gly Ser Gly Thr Asp Phe Thr Leu Lys Ile Ser
        195                 200                 205

Arg Val Glu Ala Glu Asp Leu Gly Val Tyr Tyr Cys Leu Gln Ala Thr
    210                 215                 220

His Phe Pro Trp Thr Phe Gly Gly Gly Thr Lys Leu Glu Ile Lys Arg
225                 230                 235                 240

Ala Ala Ala Leu Glu Ser Arg Gly Pro Phe Glu Gly Lys Pro Ile Pro
                245                 250                 255

Asn Pro Leu Leu Gly Leu Asp Ser Thr Arg Thr Gly His His His
            260                 265                 270

His His
```

<210> SEQ ID NO 92
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
ggcccagccg gccatggccc aggtccaact gcagcagcct ggggctgagc tggtgaggcc     60
tggggcttca gtgaagctgt cctgcaaggc ttctggctac acgttcacca gttactggat    120
gaactgggtt aaacagaggc ctgagcaagg ccttgagtgg attggaagga ttgatcctta    180
cgatagtgaa actcactaca atcaaaagtt caaggacaag gccattttga ctgtagacaa    240
atcctccagc acagccttcg tgcaactcac cagcctgaca tctgaggact ctgcggtcta    300
ttattgcgtc tctgatggtt actggggcgc agggaccacg gtcaccgtct cctcaggtcc    360
cgccaaggag ttgacgcccc tgaaggaggc gaaggtctct gatgttgtta tgactcagac    420
accactcact tgtcggtta ccactggaca accagcttcc atctcttgca agtcaagtca     480
gagcctctta gatagtgatg gaaaaaccta tttaaattgg ttattccaga ggccaggcga    540
gtctccaaag ctcctaatct atgtggtgtc taaactggag tctggagtcc ctgacaggtt    600
cactggcagt ggatcaggga cagatttcac actgaaaatc agcagagtgg aggctgagga    660
tttgggagtt tattactgct tgcaagctac acattttccg tggacgttcg gtggaggcac    720
caagctggaa atcaaacggg cggccgccct cgagtctaga gggcccttcg aaggtaagcc    780
tatccctaac cctctcctcg gtctcgattc tacgcgtacc ggtcatcatc accatcacca    840
t                                                                    841
```

<210> SEQ ID NO 93
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

<400> SEQUENCE: 93

```
cctggggctt cagtgaagct gtcctgcaag gcttctnnsn nsnnsttcac cagttactgg     60
atgaactggg ttaaacagag gcctgagcaa ggccttgagt gg                       102
```

<210> SEQ ID NO 94
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g -continued

<400> SEQUENCE: 94
cctggggctt cagtgaagct gtcctgcaag gcttctggcn nsnnsnnsac cagttactgg    60
atgaactggg ttaaacagag gcctgagcaa ggccttgagt gg                     102

<210> SEQ ID NO 95
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 95
cctggggctt cagtgaagct gtcctgcaag gcttctggct acnnsnnsnn sagttactgg    60
atgaactggg ttaaacagag gcctgagcaa ggccttgagt gg                     102

<210> SEQ ID NO 96
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 96
cctggggctt cagtgaagct gtcctgcaag gcttctggct acacgnnsnn snnstactgg    60
atgaactggg ttaaacagag gcctgagcaa ggccttgagt gg                     102

<210> SEQ ID NO 97
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g -continued

```
<400> SEQUENCE: 97
cctggggctt cagtgaagct gtcctgcaag gcttctggct acacgttcnn snnsnnstgg      60
atgaactggg ttaaacagag gcctgagcaa ggccttgagt gg                       102

<210> SEQ ID NO 98
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(58)
<223> OTHER INFORMATION: a, c, t or g

<400> SEQUENCE: 98
cctggggctt cagtgaagct gtcctgcaag gcttctggct acacgttcac cnnsnnsnss      60
atgaactggg ttaaacagag gcctgagcaa ggccttgagt gg                       102

<210> SEQ ID NO 99
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 99
cctggggctt cagtgaagct gtcctgcaag gcttctggct acacgttcac cagtnnsnns      60
nnsaactggg ttaaacagag gcctgagcaa ggccttgagt gg                       102

<210> SEQ ID NO 100
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g
<220> FEATURE:
<221> NAME/KEY: modified_base
<222> LOCATION: (64)..(65)
<223> OTHER INFORMATION: a, c, t or g
```

-continued

<400> SEQUENCE: 100
cctggggctt cagtgaagct gtcctgcaag gcttctggct acacgttcac cagttacnns      60
nnsnnstggg ttaaacagag gcctgagcaa ggccttgagt gg                        102

<210> SEQ ID NO 101
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

<400> SEQUENCE: 101
aaacagaggc ctgagcaagg ccttgagtgg attggannsn nsnnscctta cgatagtgaa      60
actcactaca atcaaaagtt caaggacaag gccatttttga ct                       102

<210> SEQ ID NO 102
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 102
aaacagaggc ctgagcaagg ccttgagtgg attggaaggn nsnnsnnsta cgatagtgaa      60
actcactaca atcaaaagtt caaggacaag gccatttttga ct                       102

<210> SEQ ID NO 103
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

```
<400> SEQUENCE: 103
aaacagaggc ctgagcaagg ccttgagtgg attggaagga ttnnsnnsnn sgatagtgaa      60
actcactaca atcaaaagtt caaggacaag gccattttga ct                        102

<210> SEQ ID NO 104
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 104
aaacagaggc ctgagcaagg ccttgagtgg attggaagga ttgatnnsnn snnsagtgaa      60
actcactaca atcaaaagtt caaggacaag gccattttga ct                        102

<210> SEQ ID NO 105
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 105
aaacagaggc ctgagcaagg ccttgagtgg attggaagga ttgatcctnn snnsnnsgaa      60
actcactaca atcaaaagtt caaggacaag gccattttga ct                        102

<210> SEQ ID NO 106
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
```

<400> SEQUENCE: 106
aaacagaggc ctgagcaagg ccttgagtgg attggaagga ttgatcctta cnnsnnsnns    60
actcactaca atcaaaagtt caaggacaag gccattttga ct                      102

<210> SEQ ID NO 107
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 107
aaacagaggc ctgagcaagg ccttgagtgg attggaagga ttgatcctta cgatnnsnns    60
nnscactaca atcaaaagtt caaggacaag gccattttga ct                      102

<210> SEQ ID NO 108
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g
<220> FEATURE:
<221> NAME/KEY: modified_base
<222> LOCATION: (64)..(65)
<223> OTHER INFORMATION: a, c, t or g

<400> SEQUENCE: 108
aaacagaggc ctgagcaagg ccttgagtgg attggaagga ttgatcctta cgatagtnns    60
nnsnnstaca atcaaaagtt caaggacaag gccattttga ct                      102

<210> SEQ ID NO 109
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

```
-continued

<400> SEQUENCE: 109
gagtggattg gaaggattga tccttacgat agtgaannsn nsnnsaatca aaagttcaag      60
gacaaggcca ttttgactgt agacaaatcc tccagcaca                            99

<210> SEQ ID NO 110
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 110
gagtggattg gaaggattga tccttacgat agtgaaactn nsnnsnnsca aaagttcaag      60
gacaaggcca ttttgactgt agacaaatcc tccagcaca                            99

<210> SEQ ID NO 111
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 111
gagtggattg gaaggattga tccttacgat agtgaaactc acnnsnnsnn saagttcaag      60
gacaaggcca ttttgactgt agacaaatcc tccagcaca                            99

<210> SEQ ID NO 112
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
```

-continued

```
<400> SEQUENCE: 112
gagtggattg gaaggattga tccttacgat agtgaaactc actacnnsnn snnsttcaag      60
gacaaggcca ttttgactgt agacaaatcc tccagcaca                            99

<210> SEQ ID NO 113
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 113
gagtggattg gaaggattga tccttacgat agtgaaactc actacaatnn snnsnnsaag     60
gacaaggcca ttttgactgt agacaaatcc tccagcaca                            99

<210> SEQ ID NO 114
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 114
gagtggattg gaaggattga tccttacgat agtgaaactc actacaatca annsnnsnns     60
gacaaggcca ttttgactgt agacaaatcc tccagcaca                            99

<210> SEQ ID NO 115
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g
```

```
<400> SEQUENCE: 115
gagtggattg gaaggattga tccttacgat agtgaaactc actacaatca aaagnnsnns      60
nnsaaggcca ttttgactgt agacaaatcc tccagcaca                             99

<210> SEQ ID NO 116
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 116
agcctgacat ctgaggactc tgcggtctat tattgcgtct ctnnsnnsnn stggggcgca      60
gggaccacgg tcaccgtctc ctcaggtccc gcc                                   93

<210> SEQ ID NO 117
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

<400> SEQUENCE: 117
tcggttacca ctggacaacc agcttccatc tcttgcnnsn nsnnscagag cctcttagat      60
agtgatggaa aaacctattt aaattggtta ttccagaggc ca                        102

<210> SEQ ID NO 118
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
```

-continued

```
<400> SEQUENCE: 118
tcggttacca ctggacaacc agcttccatc tcttgcaagn nsnnsnnsag cctcttagat      60
agtgatggaa aaacctattt aaattggtta ttccagaggc ca                       102

<210> SEQ ID NO 119
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 119
tcggttacca ctggacaacc agcttccatc tcttgcaagt cannsnnsnn sctcttagat      60
agtgatggaa aaacctattt aaattggtta ttccagaggc ca                       102

<210> SEQ ID NO 120
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 120
tcggttacca ctggacaacc agcttccatc tcttgcaagt caagtnnsnn snnsttagat      60
agtgatggaa aaacctattt aaattggtta ttccagaggc ca                       102

<210> SEQ ID NO 121
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
```

```
<400> SEQUENCE: 121
tcggttacca ctggacaacc agcttccatc tcttgcaagt caagtcagnn snnsnnsgat      60
agtgatggaa aaacctattt aaattggtta ttccagaggc ca                       102

<210> SEQ ID NO 122
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 122
tcggttacca ctggacaacc agcttccatc tcttgcaagt caagtcagag cnnsnnsnns      60
agtgatggaa aaacctattt aaattggtta ttccagaggc ca                       102

<210> SEQ ID NO 123
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g

<400> SEQUENCE: 123
tcggttacca ctggacaacc agcttccatc tcttgcaagt caagtcagag cctcnnsnns      60
nnsgatggaa aaacctattt aaattggtta ttccagaggc ca                       102

<210> SEQ ID NO 124
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g
<220> FEATURE:
<221> NAME/KEY: modified_base
<222> LOCATION: (64)..(65)
<223> OTHER INFORMATION: a, c, t or g
```

-continued

```
<400> SEQUENCE: 124
tcggttacca ctggacaacc agcttccatc tcttgcaagt caagtcagag cctcttanns      60
nnsnnsggaa aaacctattt aaattggtta ttccagaggc ca                        102

<210> SEQ ID NO 125
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

<400> SEQUENCE: 125
tccatctctt gcaagtcaag tcagagcctc ttagatnnsn nsnnsaaaac ctatttaaat      60
tggttattcc agaggccagg cgagtctcca aagctc                               96

<210> SEQ ID NO 126
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 126
tccatctctt gcaagtcaag tcagagcctc ttagatagtn nsnnsnnsac ctatttaaat      60
tggttattcc agaggccagg cgagtctcca aagctc                               96

<210> SEQ ID NO 127
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
```

```
<400> SEQUENCE: 127
tccatctctt gcaagtcaag tcagagcctc ttagatagtg atnnsnnsnn statttaaat      60
tggttattcc agaggccagg cgagtctcca aagctc                               96

<210> SEQ ID NO 128
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 128
tccatctctt gcaagtcaag tcagagcctc ttagatagtg atggannsnn snnsttaaat     60
tggttattcc agaggccagg cgagtctcca aagctc                               96

<210> SEQ ID NO 129
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 129
tccatctctt gcaagtcaag tcagagcctc ttagatagtg atggaaaann snnsnnsaat     60
tggttattcc agaggccagg cgagtctcca aagctc                               96

<210> SEQ ID NO 130
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
```

-continued

<400> SEQUENCE: 130
tccatctctt gcaagtcaag tcagagcctc ttagatagtg atggaaaaac cnnsnnsnns    60
tggttattcc agaggccagg cgagtctcca aagctc                             96

<210> SEQ ID NO 131
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

<400> SEQUENCE: 131
cagaggccag gcgagtctcc aaagctccta atctatnnsn nsnnsaaact ggagtctgga    60
gtccctgaca ggttcactgg cagtggatca ggg                                93

<210> SEQ ID NO 132
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 132
cagaggccag gcgagtctcc aaagctccta atctatgtgn nsnnsnnsct ggagtctgga    60
gtccctgaca ggttcactgg cagtggatca ggg                                93

<210> SEQ ID NO 133
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g -continued

```
<400> SEQUENCE: 133
cagaggccag gcgagtctcc aaagctccta atctatgtgg tgnnsnnsnn sgagtctgga      60
gtccctgaca ggttcactgg cagtggatca ggg                                  93

<210> SEQ ID NO 134
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g

<400> SEQUENCE: 134
cagaggccag gcgagtctcc aaagctccta atctatgtgg tgtctnnsnn snnstctgga      60
gtccctgaca ggttcactgg cagtggatca ggg                                  93

<210> SEQ ID NO 135
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 135
cagaggccag gcgagtctcc aaagctccta atctatgtgg tgtctaaann snnsnnsgga      60
gtccctgaca ggttcactgg cagtggatca ggg                                  93

<210> SEQ ID NO 136
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
```

<400> SEQUENCE: 136
agagtggagg ctgaggattt gggagtttat tactgcnnsn nsnnsacaca ttttccgtgg    60
acgttcggtg gaggcaccaa gctggaaatc aaacgggcg                          99

<210> SEQ ID NO 137
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 137
agagtggagg ctgaggattt gggagtttat tactgcttgn nsnnsnnsca ttttccgtgg    60
acgttcggtg gaggcaccaa gctggaaatc aaacgggcg                          99

<210> SEQ ID NO 138
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 138
agagtggagg ctgaggattt gggagtttat tactgcttgc aannsnnsnn stttccgtgg    60
acgttcggtg gaggcaccaa gctggaaatc aaacgggcg                          99

<210> SEQ ID NO 139
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g -continued

<400> SEQUENCE: 139
agagtggagg ctgaggattt gggagtttat tactgcttgc aagctnnsnn snnsccgtgg    60
acgttcggtg gaggcaccaa gctggaaatc aaacgggcg                          99

<210> SEQ ID NO 140
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t or g
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g

<400> SEQUENCE: 140
agagtggagg ctgaggattt gggagtttat tactgcttgc aagctacann snnsnnstgg    60
acgttcggtg gaggcaccaa gctggaaatc aaacgggcg                          99

<210> SEQ ID NO 141
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (52)..(53)
<223> OTHER INFORMATION: a, c, t or g
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g

<400> SEQUENCE: 141
agagtggagg ctgaggattt gggagtttat tactgcttgc aagctacaca tnnsnnsnns    60
acgttcggtg gaggcaccaa gctggaaatc aaacgggcg                          99

<210> SEQ ID NO 142
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (55)..(56)
<223> OTHER INFORMATION: a, c, t or g
<220> FEATURE:
<221> NAME/KEY: modified_base
<222> LOCATION: (58)..(59)
<223> OTHER INFORMATION: a, c, t or g
<220> FEATURE:
<221> NAME/KEY: modified_base
<222> LOCATION: (61)..(62)
<223> OTHER INFORMATION: a, c, t or g -continued

```
<400> SEQUENCE: 142
agagtggagg ctgaggattt gggagtttat tactgcttgc aagctacaca ttttnnsnns      60
nnsttcggtg gaggcaccaa gctggaaatc aaacgggcg                             99

<210> SEQ ID NO 143
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Asn Thr Lys
1

<210> SEQ ID NO 144
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His Thr Thr Lys
1

<210> SEQ ID NO 145
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Met Thr Lys
1

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Trp Met Asn Lys
1

<210> SEQ ID NO 147
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Thr Asp Lys
1
```

```
<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Thr Asn Lys
1

<210> SEQ ID NO 149
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Trp Met Asp Lys
1

<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Trp Thr Thr Lys
1

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Thr Asp Ile
1

<210> SEQ ID NO 152
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Val Val Met Thr Gln Thr Pro Leu Thr Leu Ser Val Thr Thr Gly
1               5                   10                  15

Gln Pro Ala Ser Ile Ser Cys
            20

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (6)..(6)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (15)..(15)
<223> OTHER INFORMATION: a, c, t or g
<220> FEATURE:
<221> NAME/KEY: modified_base
<222> LOCATION: (21)..(21)
<223> OTHER INFORMATION: a, c, t or g
<220> FEATURE:
<221> NAME/KEY: modified_base
<222> LOCATION: (24)..(24)
<223> OTHER INFORMATION: a, c, t or g

<400> SEQUENCE: 153
gaygtngtna tgacncarac nccn                                              24

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gtggtgtcta aactggagtc t                                                 21

<210> SEQ ID NO 155
<211> LENGTH: 32
<212> TYPE: PRT
<213> ORGANISM: Homo sapiens

<400> SEQUENCE: 155

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 156

His His His His His His
1               5

<210> SEQ ID NO 157
<211> LENGTH: 837
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
cagatccagt tggtgcagtc tggacctgag ctgaggaagc ctggagagac agtcaagatc       60
tcctgcaagg gttctggata taccttcaca cactatggaa taaactgggt gaagcagact      120
```

-continued

```
ccaagaaagg atttaaagtg gatgggctgg ataaacaccc atactggaga gccaatatat    180
gctgatgact tcaagggacg gtttgccttc tctttggaaa cctctgccaa cactgcctat    240
ttgcaaatca acaacctcaa caatggagac atgggtacat atttctgtac aagaagtcac    300
cggtttggtt tggactactg gggtcaaggt acctcagtca ccgtctcgtc aggtcccgcc    360
aaggagttga cgcccctgaa ggaggcgaag gtctctgaca atgtgctgac ccaatctcca    420
ccttctttgg ctgtgtctct agggcagagg gccaccatct cctgcaaggc cagccaaagt    480
gttgattata atggtgatag ttatctgaac tggtaccaac agaagccagg acagccaccc    540
aaattcctca tctatgctgc atccaatcta gaatctggga tcccagccag gtttagtggc    600
agtgggtctg ggacagactt caacctcaac atccatcctg tggaggagga ggatgctgca    660
acctattact gtcagcaaag taatgaggat ccattcacgt tcggctcggg gacaaagttg    720
gaaataaaac gggcggccgc cctcgagtct agagggccct tcgaaggtaa gcctatccct    780
aaccctctcc tcggtctcga ttctacgcgt accggtcatc atcaccatca ccattga      837
```

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Val Ser Lys
1

<210> SEQ ID NO 159
<211> LENGTH: 6
<212> TYPE: PRT
<213> ORGANISM: Homo sapiens

<400> SEQUENCE: 159

Lys Val Leu Arg Arg His
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Tyr Ser Gln Ser Asn Leu Glu
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Pro Ile Gln Phe Ala Asn Leu Glu
1               5

```
<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Pro Ile Tyr Ala Ser Asn Leu Glu
1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Pro Ile Gln Trp Gly Asn Leu Glu
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Pro Ile Thr Trp Asp Asn Leu Glu
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Pro Ile Arg Trp Pro Asn Leu Glu
1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Ile Ala Tyr Gly Asn Leu Glu
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 167

Pro Ile Asn Trp Pro Asn Leu Glu
1               5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Pro Ile Ser Gln Ser Cys Gly Trp
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Pro Ile Ser Gln Ser Cys Ala Pro
1               5
```

What is claimed is:

1. Chinese hamster ovary ("CHO") cell line 3-631-436 AM5 having A.T.C.C. Accession No. PTA-8369.

2. An antibody which immunospecifically binds hBNP made from DNA extracted from the CHO cell line 3-631-436 AM5 having A.T.C.C. Accession No. PTA-8369.

3. A chimeric antibody or a hBNP-epitope binding fragment thereof produced by CHO cell line 3-631-436 AM5, wherein said cell line has A.T.C.C. Accession No. PTA-8369.

4. Chinese hamster ovary ("CHO") cell line 3-631-436 AM8 having A.T.C.C. Accession No. PTA-8368.

5. An antibody which immunospecifically binds hBNP made from DNA extracted from the CHO cell line 3-631-436 AM8 having A.T.C.C. Accession No. PTA-8368.

6. A chimeric antibody or a hBNP-epitope binding fragment thereof produced by CHO cell line 3-631-436 AM8, wherein said cell line has A.T.C.C. Accession No. PTA-8368.

7. An isolated antibody which immunospecifically binds to hBNP, wherein said antibody has a variable heavy domain and a variable light domain, the variable heavy domain comprising a heavy chain complementarity determining region ("CDR") 1, a heavy chain CDR 2 and a heavy chain CDR 3, the variable light domain comprising a light chain CDR 1, a light chain CDR 2 and a light chain CDR 3, wherein (a) Heavy Chain CDR 1 having the amino acid sequence of:

(SEQ ID NO: 84)
Gly-Tyr-Thr-Phe-Thr-Ser-Tyr-Trp-Met-Asn;

(b) Heavy Chain CDR 2 having the amino acid sequence of:

(SEQ ID NO: 85)
Arg-Ile-Asp-Pro-Tyr-Asp-Ser-Glu-Thr-His-Tyr-Asn-Gln-Lys-Phe-Lys-Asp;

(c) Heavy Chain CDR 3 having the amino acid sequence of:

(SEQ ID NO: 86)
Asp-Gly-Tyr;

(d) Light Chain CDR 1 having the amino acid sequence of:

(SEQ ID NO: 87)
Lys-Ser-Ser-Gln-Ser-Leu-Leu-Asp-Ser-Asp-Gly-Lys-Thr-Tyr-Leu-Asn;

(e) Light Chain CDR 2 having the amino acid sequence having the formula of:

(SEQ ID NO: 83)
$Xaa_9$-$Xaa_{10}$-$Xaa_{11}$-$Xaa_{12}$-Leu-Glu-Ser;

where $Xaa_9$ is selected from the group consisting of valine, glutamine, histidine, tryptophan and arginine;

where $Xaa_{10}$ is selected from the group consisting of valine, asparagine, threonine and methionine;

where $Xaa_{11}$ is selected from the group consisting of serine, threonine, asparagine and aspartic acid;

where $Xaa_{12}$ is selected from the group consisting of lysine and isoleucine;

provided that $Xaa_9$ is other than valine if $Xaa_{10}$ is Valine, $Xaa_{11}$ is serine and $Xaa_{12}$ is Lysine; and (f) Light Chain CDR 3 having the amino acid sequence of:

(SEQ ID NO: 89)
Leu-Gln-Ala-Thr-His-Phe-Pro.

8. The antibody of claim 7, wherein:
$Xaa_9$ is Glutamine;
$Xaa_{10}$ is Asparagine;
$Xaa_{11}$ is Threonine; and
$Xaa_{12}$ is Lysine.

9. The antibody of claim 7, wherein:
$Xaa_9$ is Histidine;
$Xaa_{10}$ is Threonine;
$Xaa_{11}$ is Threonine; and
$Xaa_{12}$ is Lysine.

10. The antibody of claim 7, wherein:
$Xaa_9$ is Tryptophan;
$Xaa_{10}$ is Methionine;
$Xaa_{11}$ is Threonine; and
$Xaa_{12}$ is Lysine.

11. The antibody of claim 7, wherein:
$Xaa_9$ is Tryptophan;
$Xaa_{10}$ is Methionine;
$Xaa_{11}$ is Asparagine; and
$Xaa_{12}$ is Lysine.

12. The antibody of claim 7, wherein:
$Xaa_9$ is Valine;
$Xaa_{10}$ is Threonine;
$Xaa_{11}$ is Aspartic Acid; and
$Xaa_{12}$ is Lysine.

13. The antibody of claim 7, wherein:
$Xaa_9$ is Arginine;
$Xaa_{10}$ is Threonine;
$Xaa_{11}$ is Asparagine; and
$Xaa_{12}$ is Lysine.

14. The antibody of claim 7, wherein:
$Xaa_9$ is Tryptophan;
$Xaa_{10}$ is Methionine;
$Xaa_{11}$ is Aspartic Acid; and
$Xaa_{12}$ is Lysine.

15. The antibody of claim 7, wherein:
$Xaa_9$ is Tryptophan;
$Xaa_{10}$ is Threonine;
$Xaa_{11}$ is Threonine; and
$Xaa_{12}$ is Lysine.

16. The antibody of claim 7, wherein:
$Xaa_9$ is Valine;
$Xaa_{10}$ is Threonine;
$Xaa_{11}$ is Aspartic Acid; and
$Xaa_{12}$ is Isoleucine.

17. The antibody of claim 7, wherein said antibody is a monoclonal antibody, a multispecific antibody, a human antibody, a fully humanized antibody, a partially humanized antibody, an animal antibody, a recombinant antibody, a chimeric antibody, a single-chain Fv, a single chain antibody, a single domain antibody, a Fab fragment, a F(ab')$_2$ fragment, a disulfide-linked Fv, an anti-idiotypic antibody, or a functionally active epitope-binding fragment thereof.

18. The antibody of claim 7, wherein said antibody immunospecifically binds to an epitope comprising amino acid residues 13 through 18 of hBNP (SEQ ID NO:155).

19. An immunoassay for hBNP or hBNP fragment, wherein said immunoassay kit comprises an antibody of claim 7.

20. The immunoassay of claim 19, wherein said immunoassay kit comprises a single antibody that immunospecifically binds to hBNP or hBNP fragment.

21. The immunoassay of claim 19, wherein said immunoassay kit further compromises an additional specific binding partner for hBNP or hBNP fragment.

22. A composition comprising an antibody of claim 7 in a pharmaceutically acceptable carrier.

* * * * *

UNITED STATES PATENT AND TRADEMARK OFFICE
CERTIFICATE OF CORRECTION

PATENT NO. : 7,939,069 B2  
APPLICATION NO. : 11/745963  
DATED : May 10, 2011  
INVENTOR(S) : Susan E. Brophy, Joan D. Tyner and Bryan C. Tieman Page 1 of 1

It is certified that error appears in the above-identified patent and that said Letters Patent is hereby corrected as shown below:

IN THE CLAIMS:

Claim 19 (column 186, line 23) add -- kit -- after "An immunoassay".

Claim 20 (column 186, line 27) add -- kit -- after "The immunoassay".

Claim 21 (column 186, line 30) add -- kit -- after "The immunoassay".

Claim 21 (column 186, line 31) change "compromises" to -- comprises -- after "immunoassay kit further".

Signed and Sealed this  
Second Day of July, 2013

Teresa Stanek Rea  
*Acting Director of the United States Patent and Trademark Office*